(12) United States Patent
Kim et al.

(10) Patent No.: US 10,193,081 B2
(45) Date of Patent: Jan. 29, 2019

(54) ORGANIC COMPOUND FOR OPTOELECTRIC DEVICE AND COMPOSITION FOR OPTOELECTRIC DEVICE AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Hyung-Sun Kim, Suwon-si (KR);
Young-Kwon Kim, Suwon-si (KR);
Dong-Wan Ryu, Suwon-si (KR);
Youn-Hwan Kim, Suwon-si (KR);
Eun-Sun Yu, Suwon-si (KR);
Sung-Hyun Jung, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 519 days.

(21) Appl. No.: 14/864,288

(22) Filed: Sep. 24, 2015

(65) Prior Publication Data

US 2016/0126477 A1    May 5, 2016

(30) Foreign Application Priority Data

Oct. 31, 2014    (KR) ........................ 10-2014-0150601

(51) Int. Cl.
*H01L 51/00*    (2006.01)
*H01L 27/32*    (2006.01)
(Continued)

(52) U.S. Cl.
CPC ........ *H01L 51/0072* (2013.01); *C07D 209/86* (2013.01); *C09K 11/025* (2013.01);
(Continued)

(58) Field of Classification Search
CPC .... C07D 209/86; C09K 11/025; C09K 11/06; C09K 2211/1007; C09K 2211/1011;
(Continued)

(56) References Cited

U.S. PATENT DOCUMENTS

2004/0124766 A1*  7/2004  Nakagawa .......... H01L 51/0064
                                                  313/504
2007/0190355 A1*  8/2007  Ikeda .................. C07D 239/26
                                                  428/690

(Continued)

FOREIGN PATENT DOCUMENTS

CN    102421868 A    4/2012
CN    103261172 A    8/2013
(Continued)

OTHER PUBLICATIONS

Machine translation for WO 2012/133652 A (publication date—Oct. 2012).*

(Continued)

*Primary Examiner* — Dawn L Garrett
(74) *Attorney, Agent, or Firm* — Lee & Morse, P.C.

(57) ABSTRACT

Disclosed are a first compound for an organic optoelectric device represented by a combination of Chemical Formula I-1 and Chemical Formula I-2 and a composition for an organic optoelectric device including the first compound for an organic optoelectric device and at least one second compound for an organic optoelectric device having a moiety represented by Chemical Formula II, and an organic optoelectric device and a display device including the same. Chemical Formula I-1, Chemical Formula I-2 and Chemical Formula II are the same as described in the detailed description.

19 Claims, 1 Drawing Sheet

(51) Int. Cl.
  *C07D 209/86* (2006.01)
  *C09K 11/02* (2006.01)
  *C09K 11/06* (2006.01)
  *H01L 51/50* (2006.01)

(52) U.S. Cl.
  CPC .......... *C09K 11/06* (2013.01); *H01L 51/0054* (2013.01); *H01L 51/0067* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/185* (2013.01); *H01L 51/0059* (2013.01); *H01L 51/0085* (2013.01); *H01L 51/5016* (2013.01); *H01L 51/5064* (2013.01); *H01L 2251/5384* (2013.01)

(58) Field of Classification Search
  CPC .... C09K 2211/1029; C09K 2211/1044; C09K 2211/1059; C09K 2211/185; H01L 2251/5384; H01L 51/0054; H01L 51/0059; H01L 51/0067; H01L 51/0072; H01L 51/0085; H01L 51/5016; H01L 51/5064
  See application file for complete search history.

(56) References Cited

U.S. PATENT DOCUMENTS

| | | | |
|---|---|---|---|
| 2011/0042654 A1 | 2/2011 | Jung et al. | |
| 2011/0288295 A1* | 11/2011 | Aihara | C07D 401/14 544/180 |
| 2012/0056171 A1* | 3/2012 | Kim | C09B 57/00 257/40 |
| 2013/0256645 A1 | 10/2013 | Min et al. | |
| 2014/0027750 A1* | 1/2014 | Yu | H01L 51/0067 257/40 |

FOREIGN PATENT DOCUMENTS

| | | | |
|---|---|---|---|
| EP | 2 431 445 A2 | | 3/2012 |
| JP | 2011-082238 A | | 4/2011 |
| JP | 2012-216819 A | * | 11/2012 |
| KR | 10-1211091 B1 | | 12/2012 |
| KR | 10-1227126 B1 | | 1/2013 |
| KR | 10-2014-0000259 A | | 1/2014 |
| KR | 10-2014-0057687 A | | 5/2014 |
| KR | 10-1433822 B1 | | 8/2014 |
| KR | 10-2015-0042650 A | | 4/2015 |
| TW | 201332995 A1 | | 8/2013 |
| WO | WO 2012/133652 A1 | * | 10/2012 |
| WO | WO 2012161382 A1 | * | 11/2012 |
| WO | WO 2014/030872 A2 | | 2/2014 |

OTHER PUBLICATIONS

Machine translation for JP 2012-216819 A (publication date—Nov. 2012).*
Extended European Search Report dated Mar. 3, 2016 in Corresponding European Patent Application No. 15191522.0.
Taiwanese Search Report dated May 25, 2016 in Corresponding Taiwanese Patent Application No. 104132908.
Shin, et al., A new N-fluorenyl carbazole host material: Synthesis, physical properties and applications for highly efficient phosphorescent organic light emitting diodes, Organic Electronics 12 (2011) 785-793.
Chinese Office Action dated Aug. 9, 2017, of the corresponding Chinese Patent Application No. 201510671555.3.

* cited by examiner

[FIG. 1]
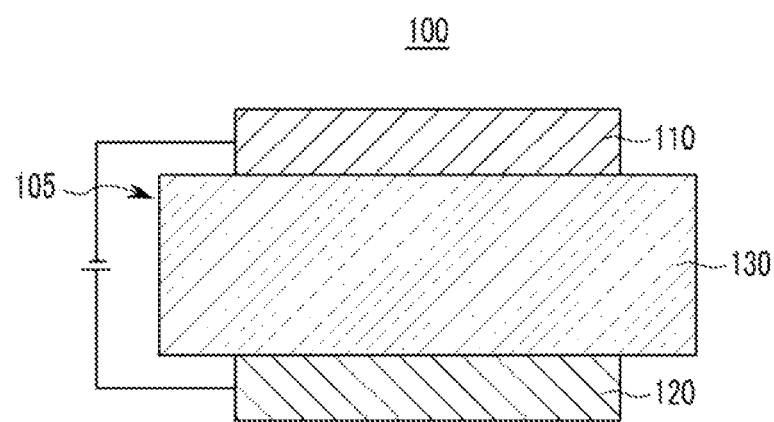
[FIG. 2]
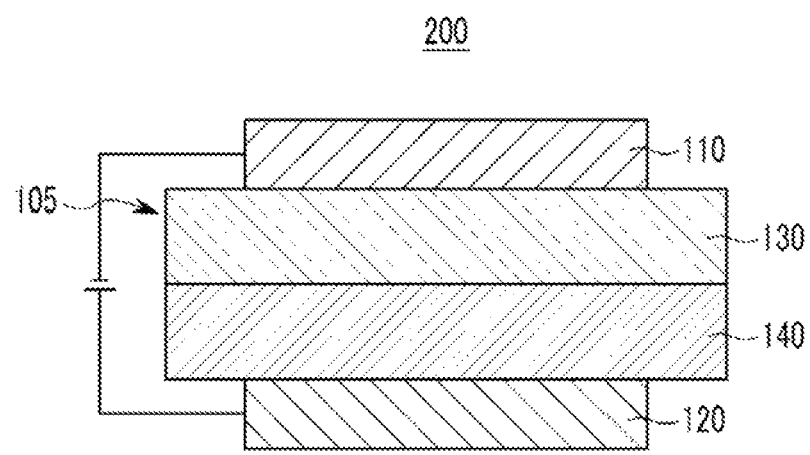

ORGANIC COMPOUND FOR OPTOELECTRIC DEVICE AND COMPOSITION FOR OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2014-0150601 filed in the Korean Intellectual Property Office on Oct. 31, 2014, the entire contents of which are incorporated herein by reference.

BACKGROUND OF THE INVENTION

1. Field of the Invention

Embodiments relate to a compound for an organic optoelectric device, a composition for an organic optoelectric device, an organic optoelectric device, and a display device.

2. Description of the Related Art

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

SUMMARY OF THE INVENTION

According to an embodiment, a compound for an organic optoelectric device represented by a combination of Chemical Formula I-1 and Chemical Formula I-2 is provided.

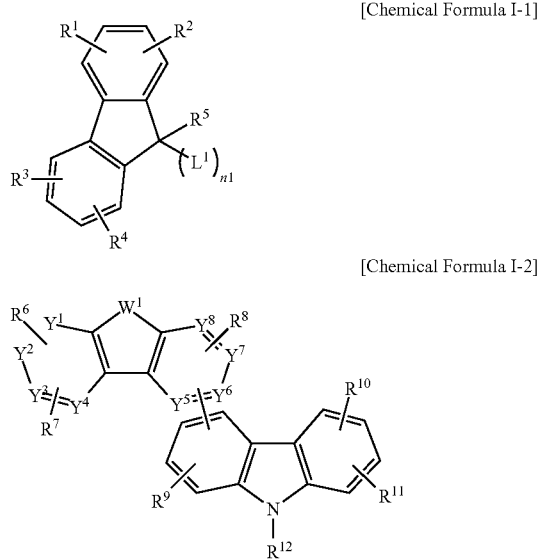

[Chemical Formula I-1]

[Chemical Formula I-2]

In Chemical Formulae I-1 and I-2,
$Y^1$ to $Y^8$ may independently be C or $CR^a$,
$W^1$ may be N or $NR^b$,
one of $Y^1$ to $Y^8$ and $W^1$ of Chemical Formula I-2 is linked to $L^1$ of Chemical Formula I-1,
$R^1$ to $R^{12}$, $R^a$ and $R^b$ may each independently be hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof,
$R^1$ to $R^4$, $R^6$ to $R^8$, $R^a$, and $R^9$ to $R^{11}$ may each independently be present or the adjacent two are linked to each other to form a fused ring,
$L^1$ may be a single bond, a substituted or unsubstituted C6 to C30 arylene group, a substituted or unsubstituted C2 to C30 heteroarylene group, or a combination thereof, and
n1 may be an integer of 1 to 3,
wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

According to another embodiment, a composition for an organic optoelectric device including a first compound for an organic optoelectric device according to an embodiment and at least one second compound for an organic optoelectric device having a moiety represented by Chemical Formula II is provided.

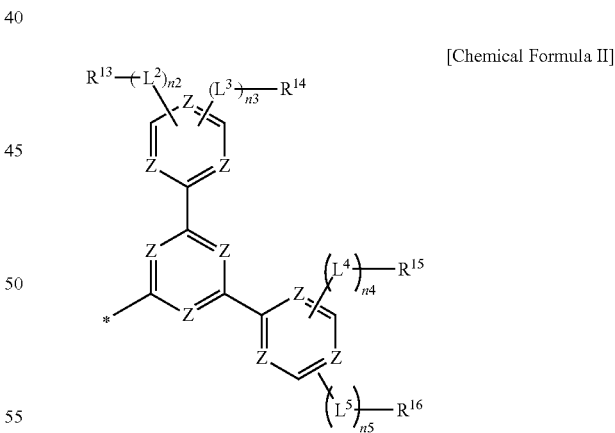

[Chemical Formula II]

In Chemical Formula II,
each Z may independently be N, C or $CR^c$,
at least one of Z may be N,
$R^{13}$ to $R^{16}$ may independently be hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $L^2$ to $L^5$ may each independently be a single bond, a substituted or unsubstituted C6 to C30 arylene group, a substituted or unsubstituted C2 to C30 heteroarylene group, or a combination thereof, n2 to n5 are each independently one of integers of 0 to 5, and

* indicates a linking point, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

According to another embodiment, an organic optoelectric device includes an anode and a cathode facing each other and at least one organic layer between the anode and the cathode, wherein the organic layer includes the compound for an organic optoelectric device or the composition for an organic optoelectric device.

According to yet another embodiment, a display device including the organic optoelectric device is provided.

BRIEF DESCRIPTION OF THE DRAWINGS

Features will become apparent to those of skill in the art by describing in detail example embodiments with reference to the attached drawings in which:

FIGS. 1 and 2 are cross-sectional views showing organic light emitting diodes according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

In the present specification, when a definition is not otherwise provided, the term "substituted" refers to one substituted with a substituent selected from deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, hydroxyl group, amino group, substituted or unsubstituted C1 to C20 amine group, nitro group, substituted or unsubstituted C3 to C40 silyl group, C1 to C30 alkyl group, C1 to C10 alkylsilyl group, C6 to C30 arylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, P, and Si, and remaining carbons in one compound or substituent.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, the term "heteroaryl group" refers to an aryl group including 1 to 3 heteroatoms selected from N, O, S, P, and Si, and remaining carbons. When the heteroaryl group is a fused ring, each ring may include 1 to 3 hetero atoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, or a combination thereof, but are not limited thereto.

In the present, the single bond may refer to direct linkage without carbon a hetero atom except carbon, and specifically when L is a single bond, a substituent linked to L directly links to core directly. That is to say, in the present specification, a single bond excludes methylene including carbon, and the like.

In the specification, hole characteristics refer to characteristics capable of donating an electron when an electric field is applied and that a hole formed in the anode is easily injected into the emission layer and transported in the emission layer due to conductive characteristics according to highest occupied molecular orbital (HOMO) level.

In addition, electron characteristics refer to characteristics capable of accepting an electron when an electric field is applied and that an electron formed in the cathode is easily injected into the emission layer and transported in the emission layer due to conductive characteristics according to lowest unoccupied molecular orbital (LUMO) level.

Hereinafter, a compound for an organic optoelectric device according to an embodiment is described.

A compound for an organic optoelectric device according to an embodiment is represented by a combination of Chemical Formula I-1 and Chemical Formula I-2.

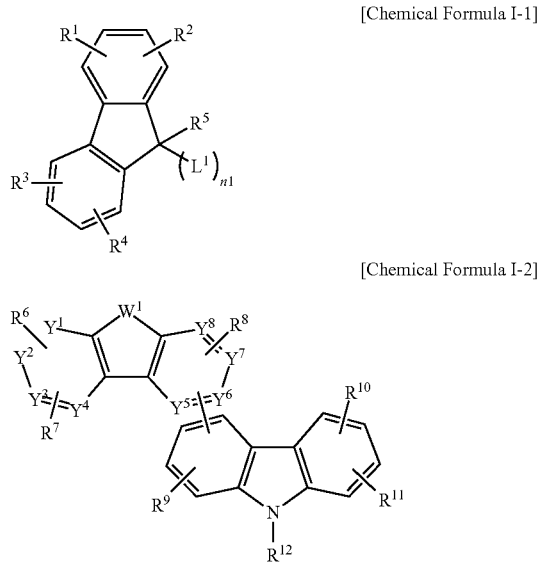

[Chemical Formula I-1]

[Chemical Formula I-2]

In the present example embodiment, in Chemical Formulae I-1 and I-2, $Y^1$ to $Y^8$ are independently C or $CR^a$, $W^1$ is N or $NR^b$, one of $Y^1$ to $Y^8$ and $W^1$ of Chemical Formula I-2 is linked to $L^1$ of Chemical Formula I-1, $R^1$ to $R^{12}$, $R^a$ and $R^b$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $R^1$ to $R^4$, $R^6$ to $R^8$, $R^a$, and $R^9$ to $R^{11}$ are each independently present or adjacent two are linked to each other to form a fused ring, $L^1$ is a single bond, a substituted or unsubstituted C6 to C30 arylene group, a substituted or unsubstituted C2 to C30 heteroarylene group, or a combination thereof, and n1 is an integer of 1 to 3, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

In the compound for an organic optoelectric device represented by a combination of Chemical Formulae I-1 and I-2, bicarbazole represented by Chemical Formula I-2 is substituted at No. 9 of fluorene represented by Chemical Formula I-1.

The compound for an organic optoelectric device may have characteristics of a lower deposition temperature but a higher glass transition temperature compared with one having a similar molecular weight and thus, may have an effect of relatively improving heat-resisting stability and process stability.

In addition, the compound includes a bicarbazole backbone that may have excellent hole transport properties in terms of operation of a device and thus, may stably inject and transport holes particularly when used for an optical auxiliary layer.

For example, when the compound is used for a hole transport auxiliary layer, luminous efficiency and life-span of a device may be increased by decreasing an energy level gap between a hole transport layer (HTL) and an emission layer and thus, injecting and transporting holes.

The compound for an organic optoelectric device may be, for example, represented by one of Chemical Formulae I-A, I-B, I-C, I-D and I-E according to a linking position of bicarbazole.

[Chemical Formula I-A]
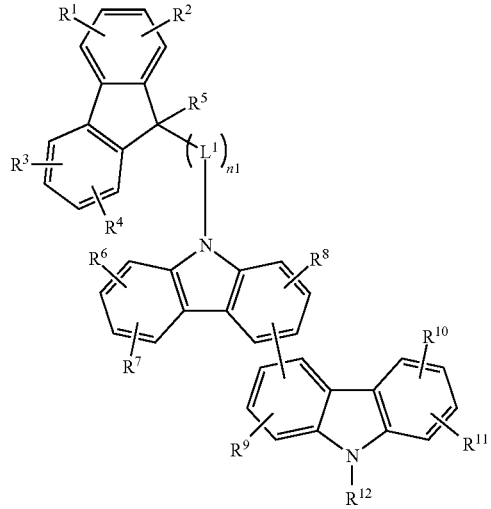
[Chemical formula I-B]
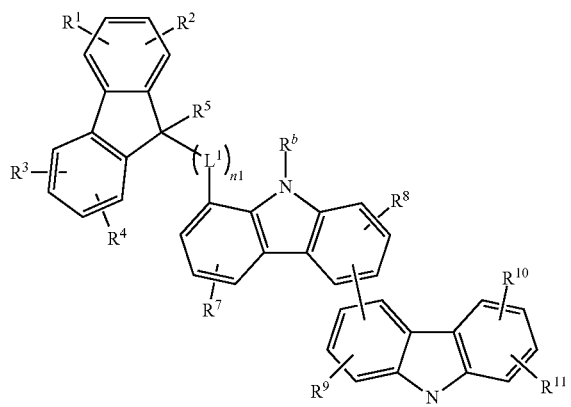
[Chemical Formula I-C]
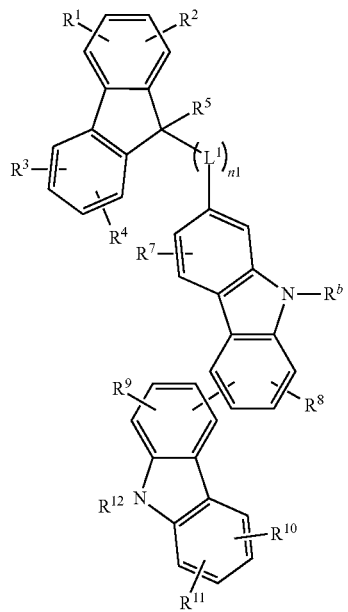
[Chemical Formula I-D]
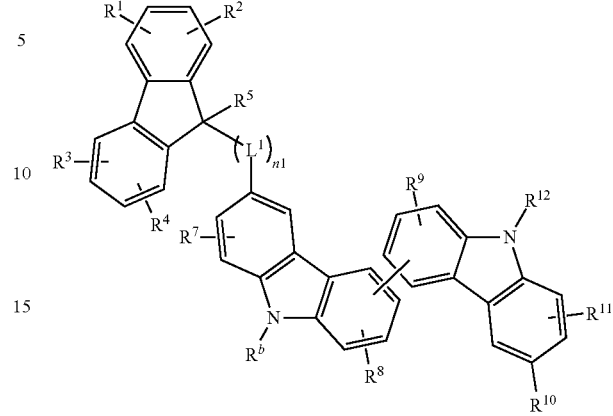
[Chemical Formula I-E]
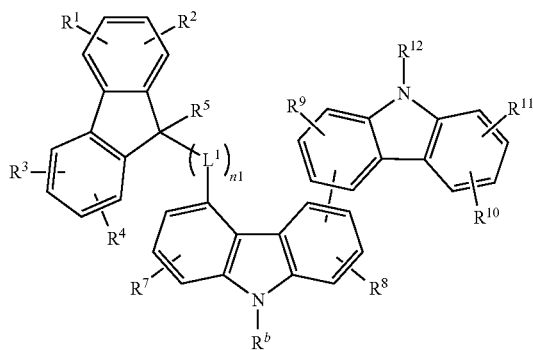
In the present example embodiment, in Chemical Formulae I-A, I-B, I-C, I-D and I-E, $R^1$ to $R^{12}$ and $R^b$, $L^1$ and n1 are the same as described above.
The Chemical Formula I-2 may be represented by one of Chemical Formulae I-2a to I-2h.
[Chemical Formula I-2a]
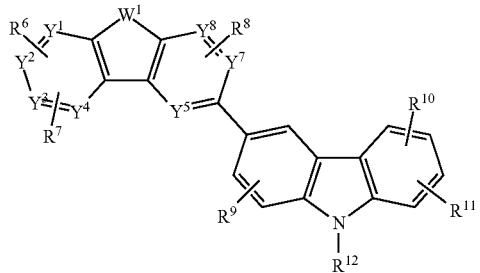
[Chemical Formula I-2b]
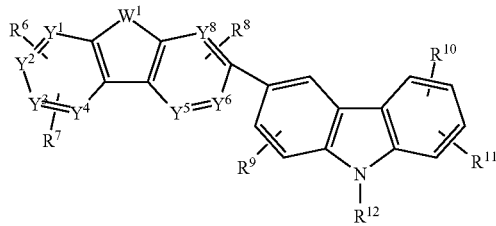

[Chemical Formula I-2c]

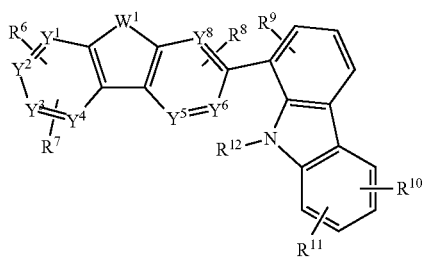

[Chemical Formula I-2d]

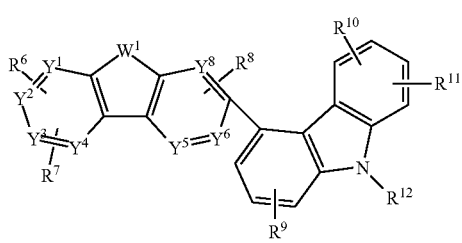

[Chemical Formula I-2e]

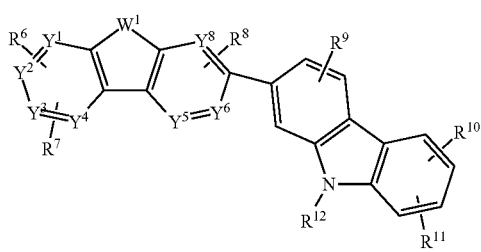

[Chemical Formula I-2f]

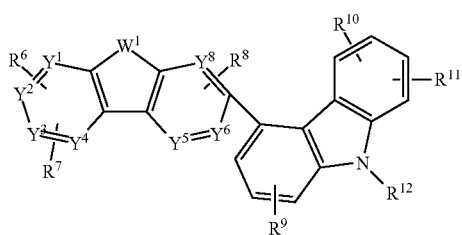

[Chemical Formula I-2g]

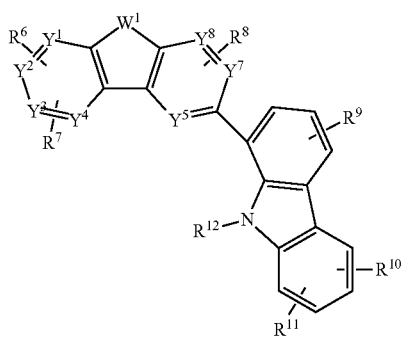

[Chemical Formula I-2h]

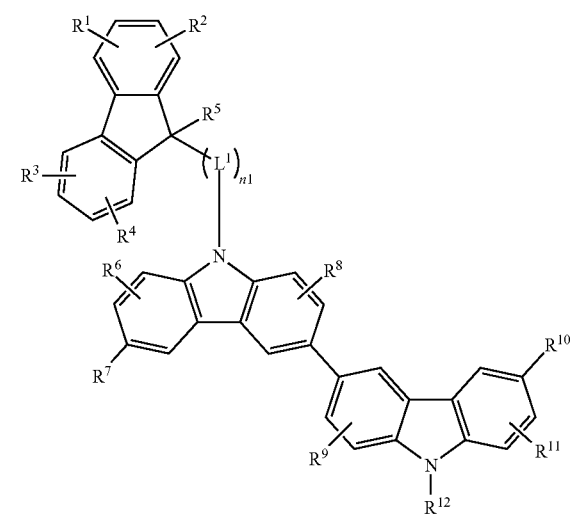

In the present example embodiment, in Chemical Formula I-2a to I-2h, $Y^1$ to $Y^8$, $W^1$, $R^6$ to $R^{12}$ are the same as described above.

The compound for an organic optoelectric device may be, for example represented by one of Chemical Formulae I a, I b, I c, I d and I e.

[Chemical Formula I a]

[Chemical Formula I b]

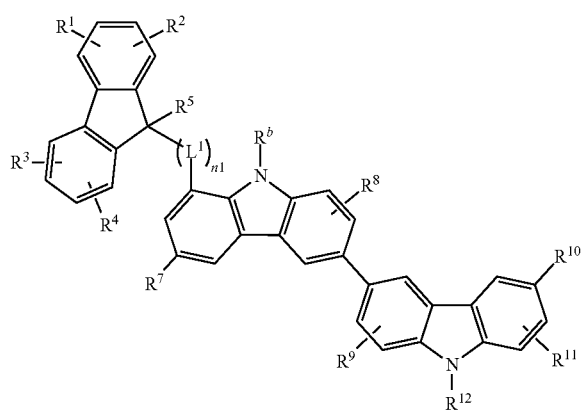

-continued

[Chemical Formula I c]

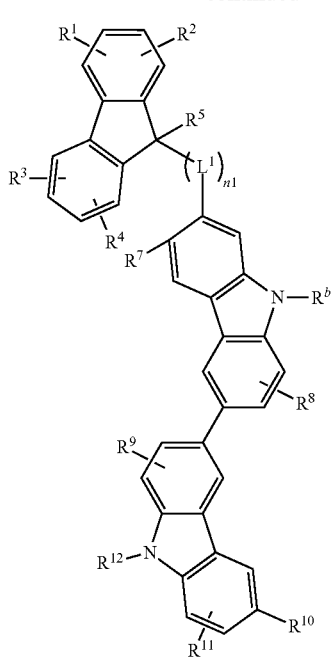

[Chemical Formula I d]

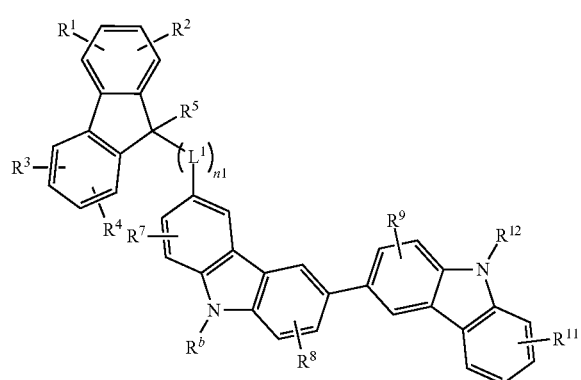

[Chemical Formula I e]

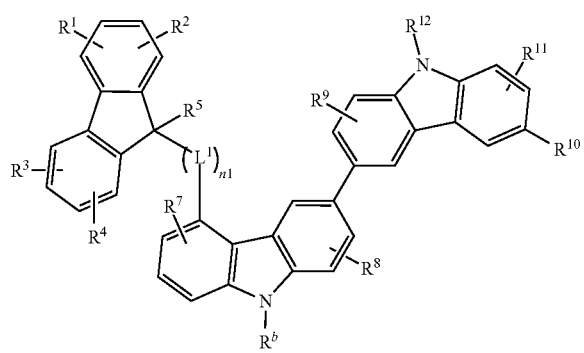

In the present example embodiment, in Chemical Formulae Ia to Ie, $R^1$ to $R^{12}$, $R^b$, $L^1$ and n1 are the same as described above.

The $R^1$ to $R^{12}$ may be each independently hydrogen, deuterium, a substituted or unsubstituted C1 to C30 alkyl group, a substituted or unsubstituted C6 to C30 aryl group, a substituted or unsubstituted C2 to C30 heteroaryl group, a substituted or unsubstituted C6 to C30 arylamine group, or a combination thereof.

In addition, the $L^1$ may be a single bond, a substituted or unsubstituted C6 to C30 arylene group, a substituted or unsubstituted C2 to C30 heteroarylene group, or a combination thereof, and the n1 may be an integer of 1 to 3. For example, the $L^1$ may be a substituted or unsubstituted phenylene listed in Group 1.

[Group 1]

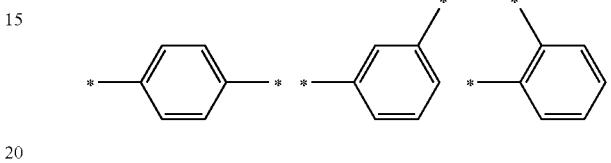

In Group 1,

\* indicates a linking point, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound for an organic optoelectric device may be, for example compounds listed in Group 2 but is not limited thereto.

Heteroatom of the compounds in group 2 is "N".

[Group 2]

[2-1]

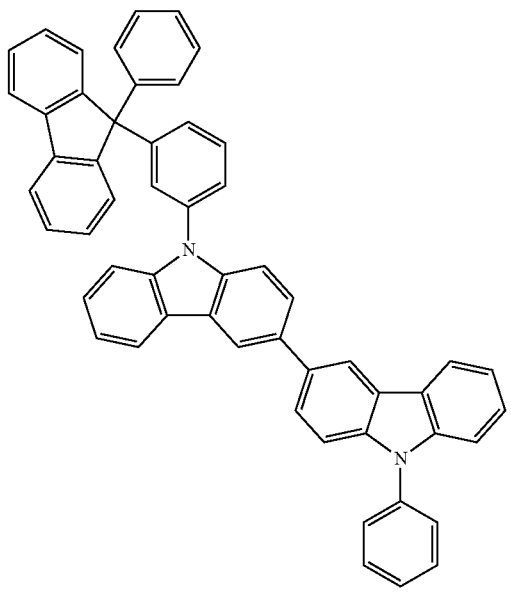

-continued
[2-2]
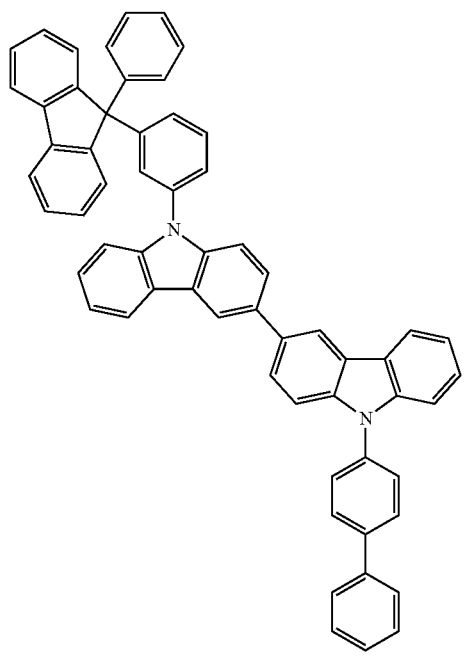
[2-4]
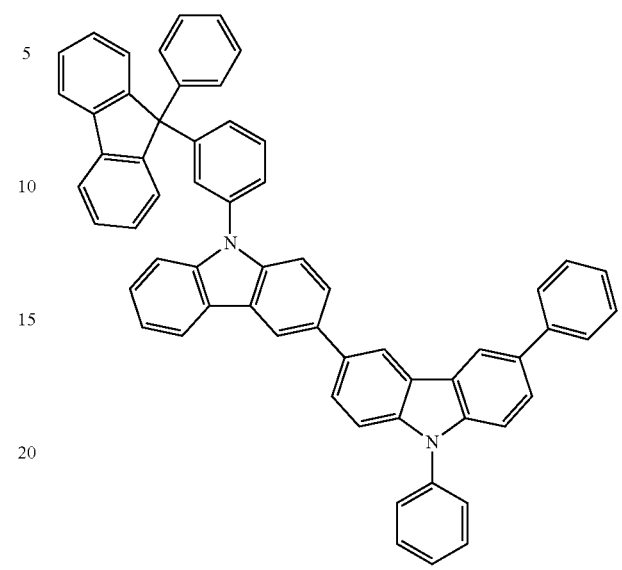
[2-3]
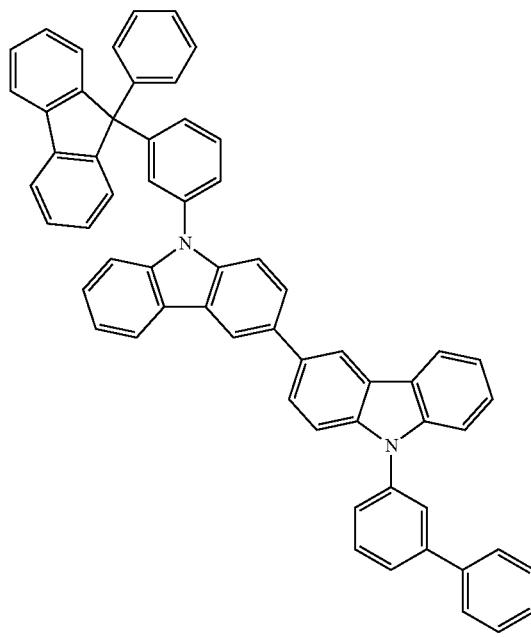
[2-5]
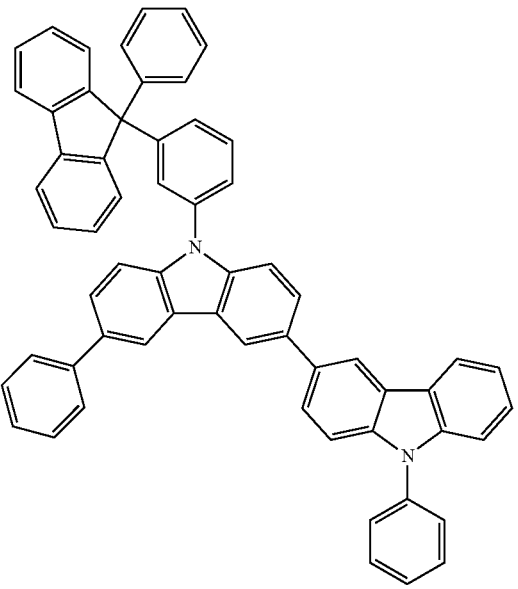

[2-6]
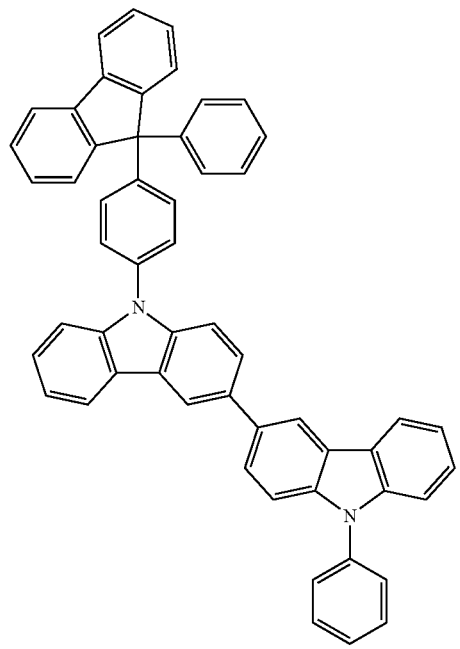
[2-7]
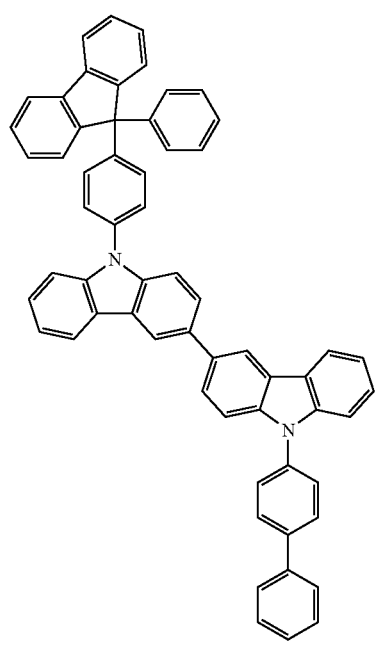
[2-8]
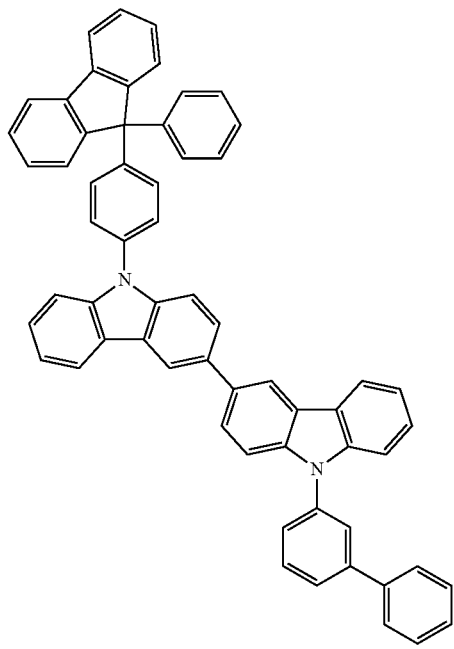
[2-9]
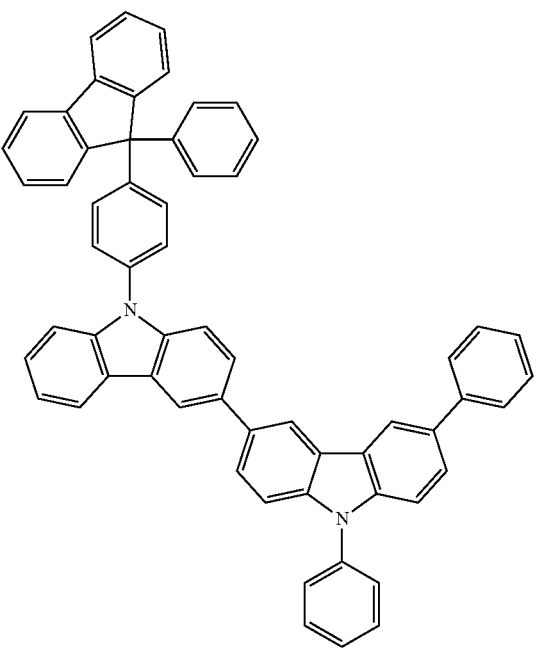

[2-10]
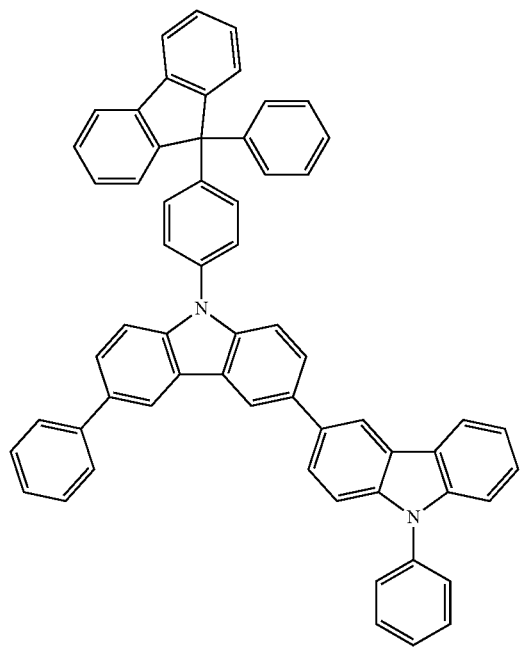
[2-11]
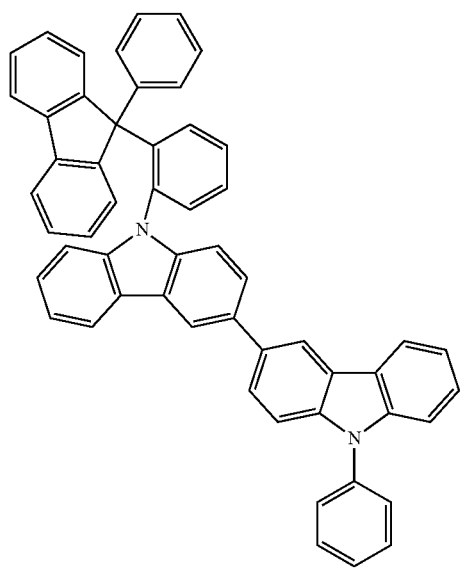
[2-12]
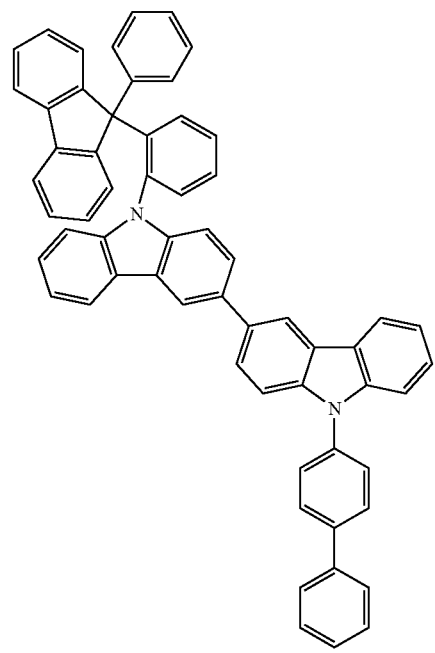
[2-13]
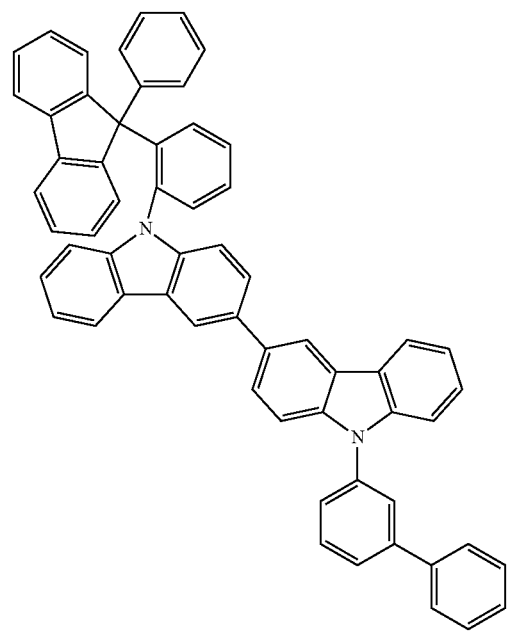

[2-14]
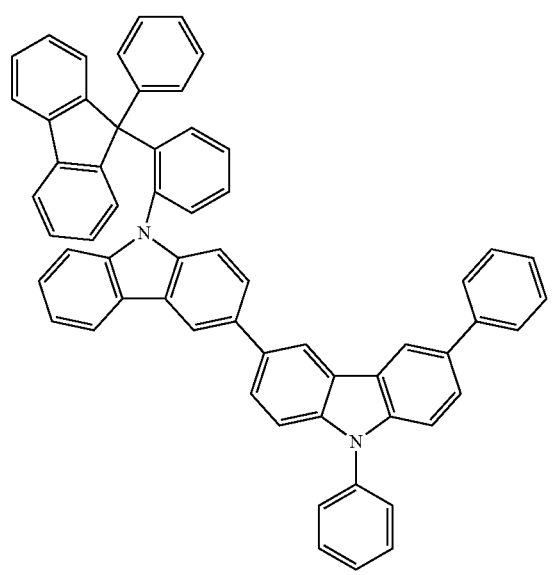
[2-15]
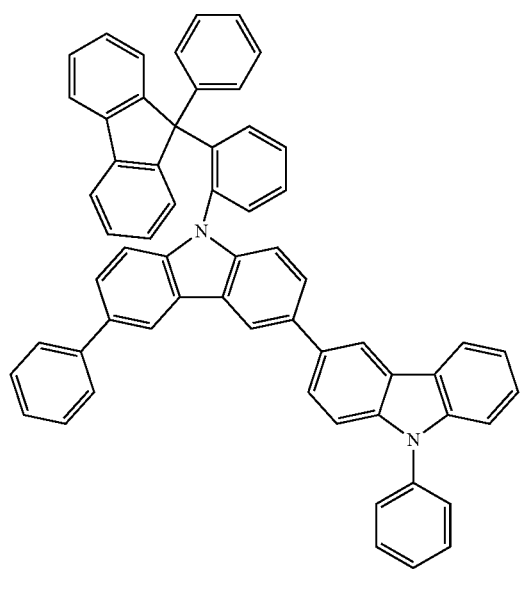
[2-16]
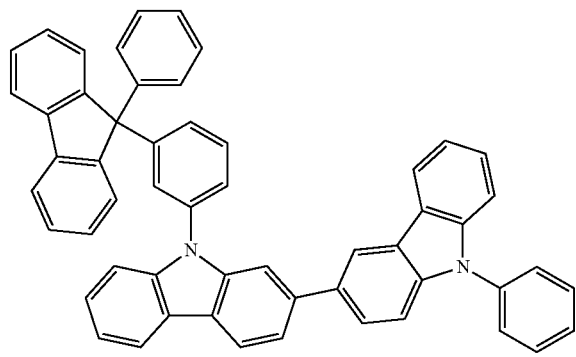
[2-17]
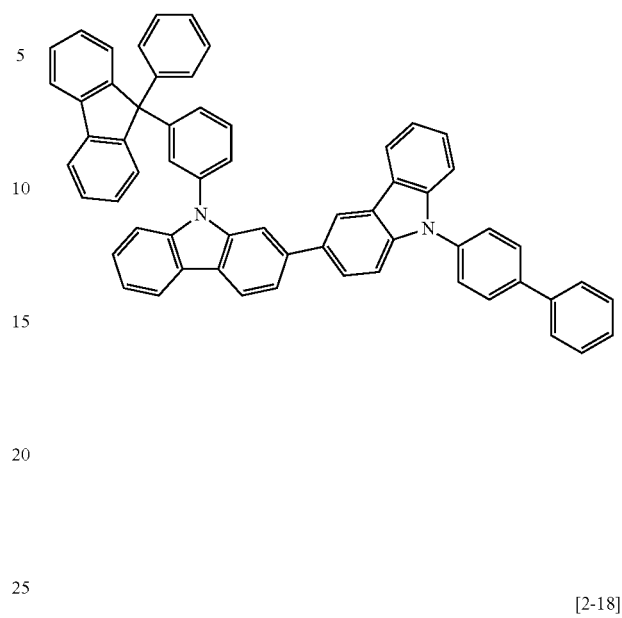
[2-18]
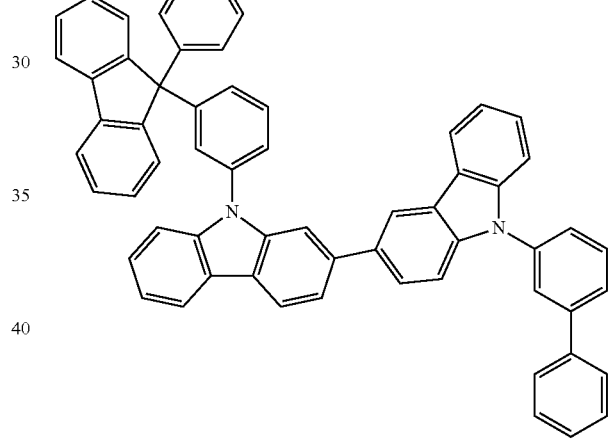
[2-19]
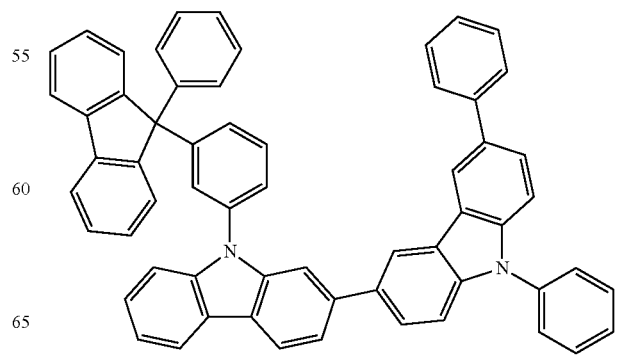

[2-20]
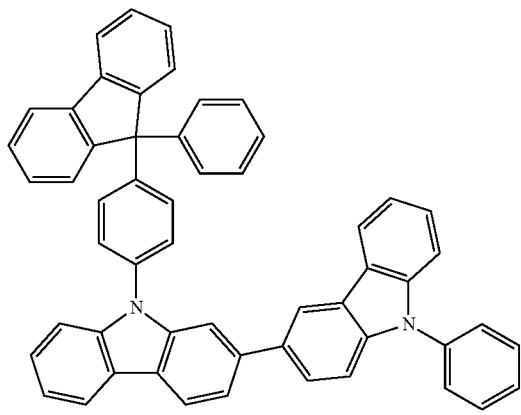
[2-23]
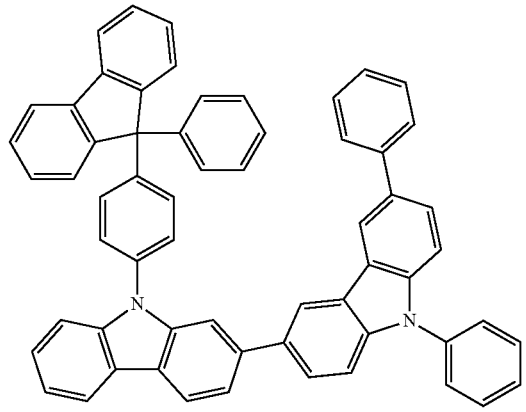
[2-21]
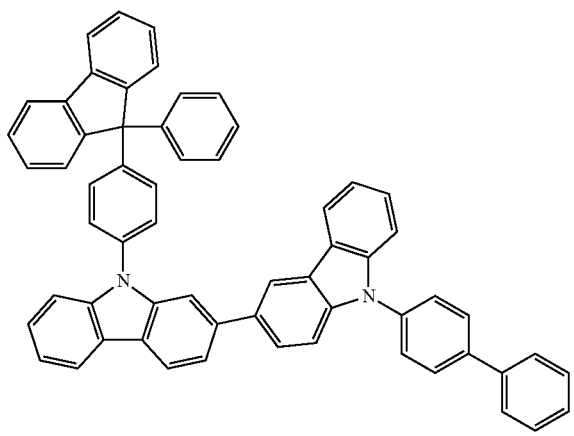
[2-24]
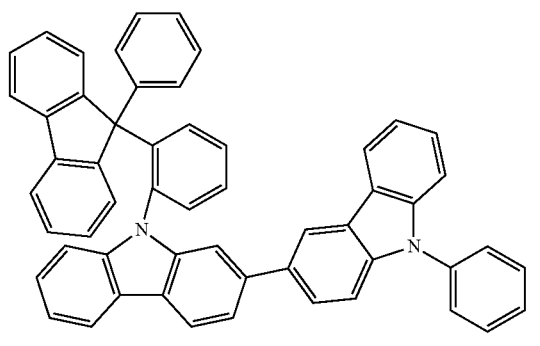
[2-25]
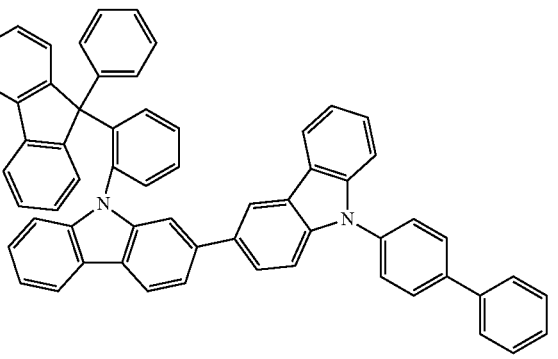
[2-22]
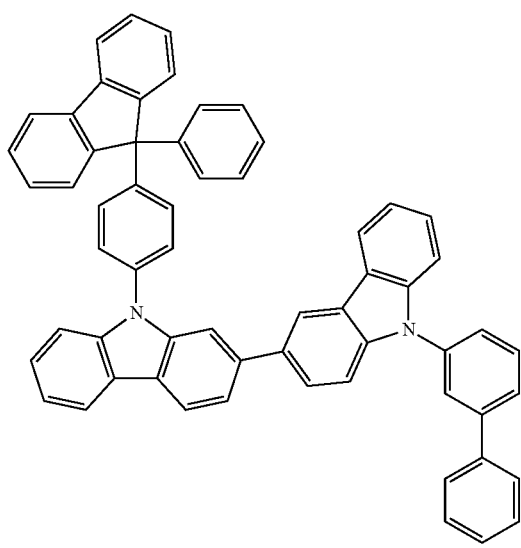
[2-26]
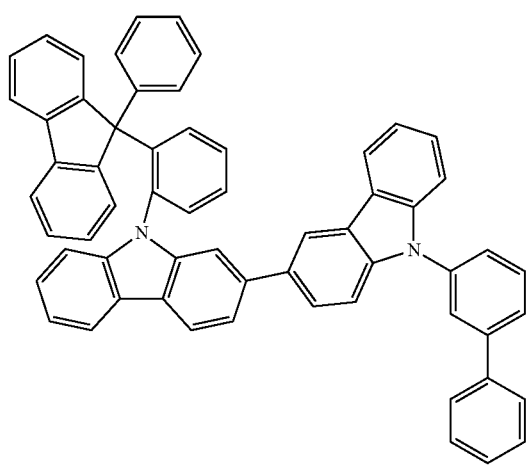

[2-27]
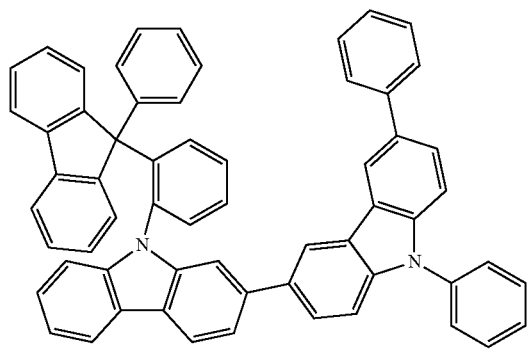
[2-28]
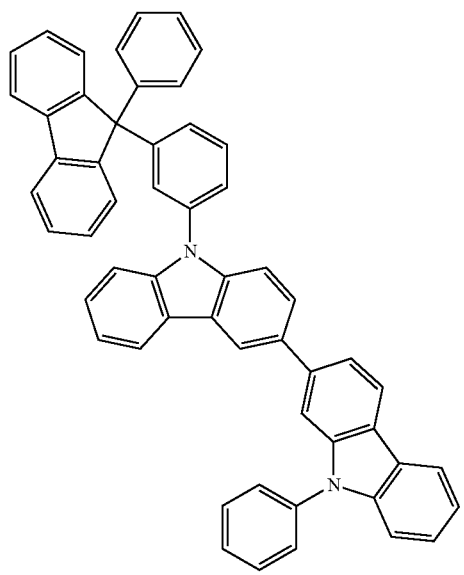
[2-29]
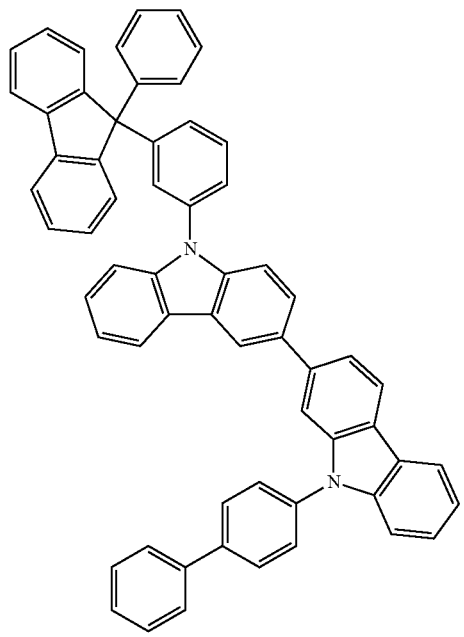
[2-30]
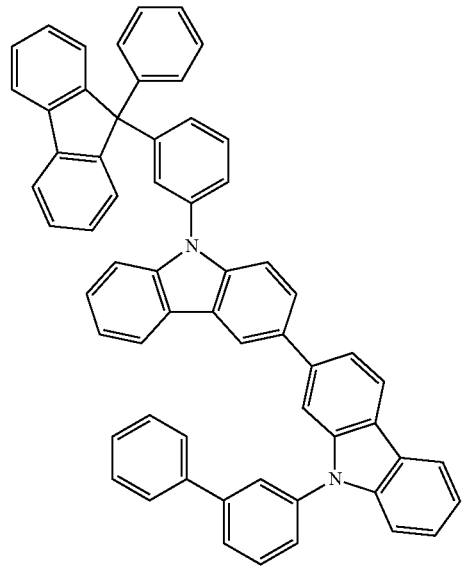
[2-31]
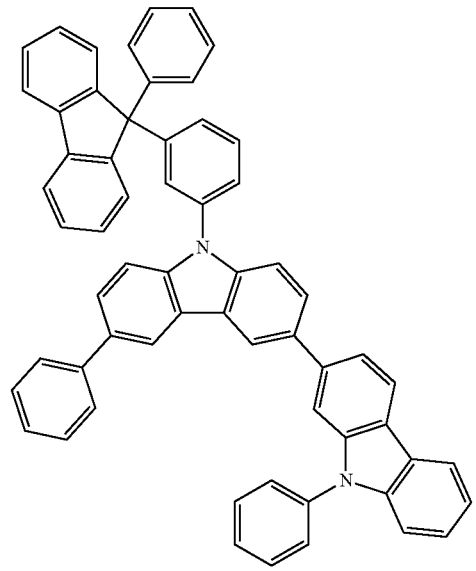

[2-32]
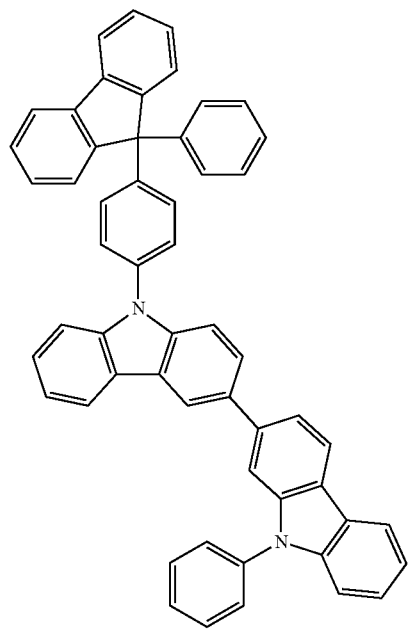
[2-33]
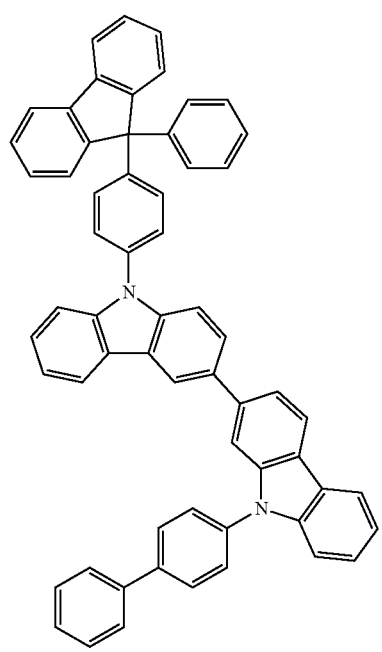
[2-34]
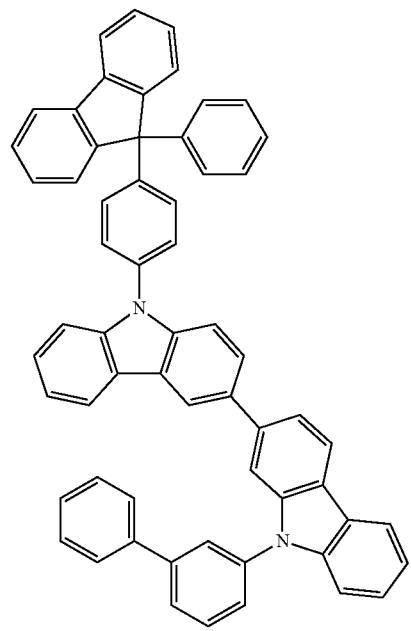
[2-35]
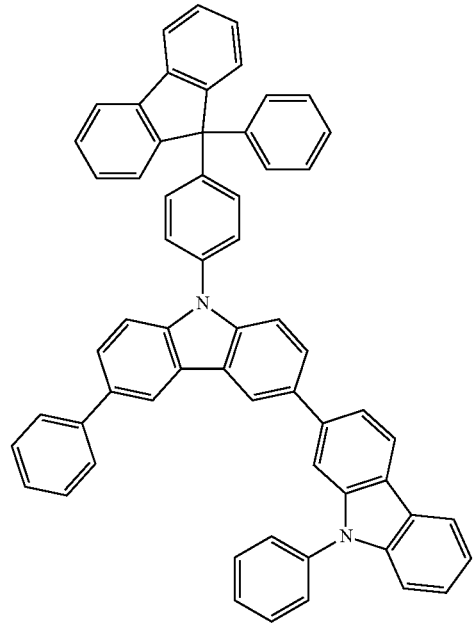

[2-36]
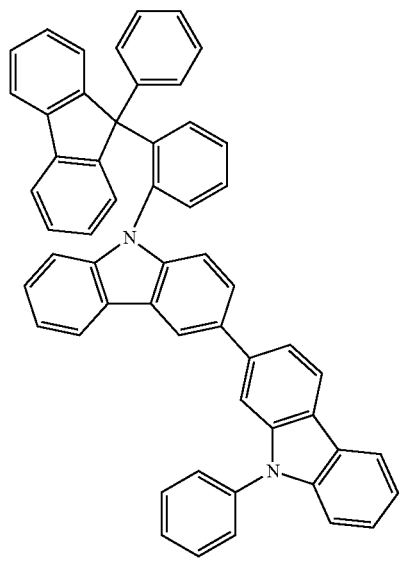
[2-38]
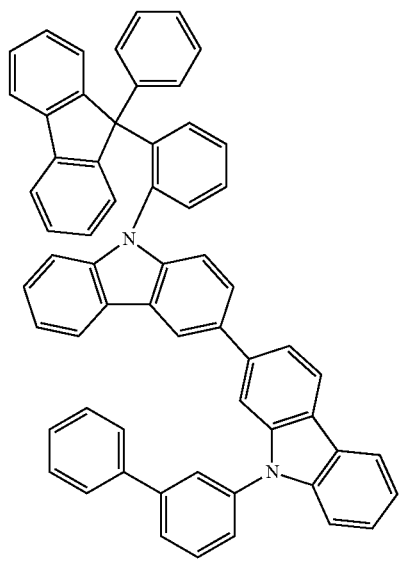
[2-37]
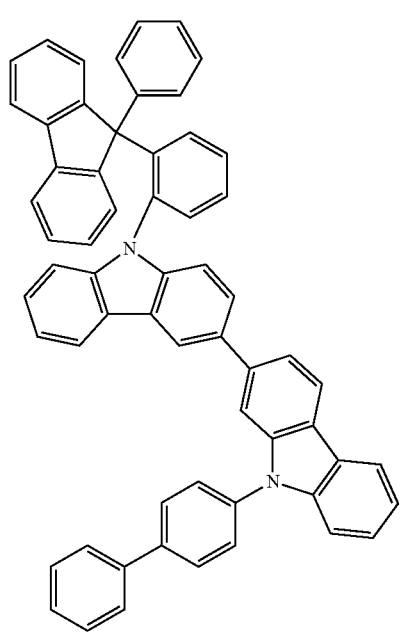
[2-39]
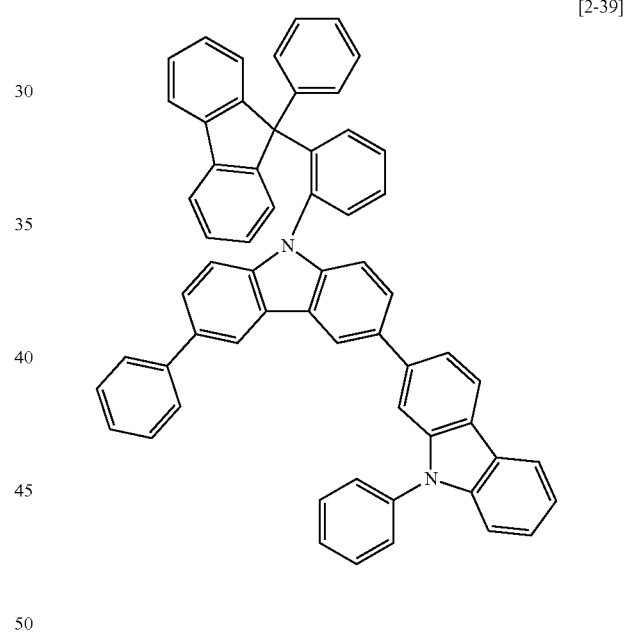
[2-40]
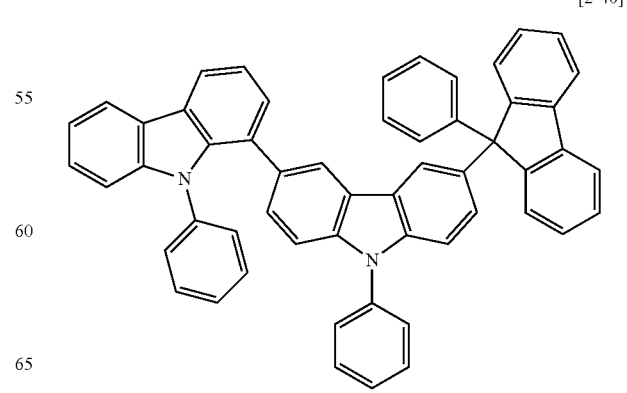

[2-41]
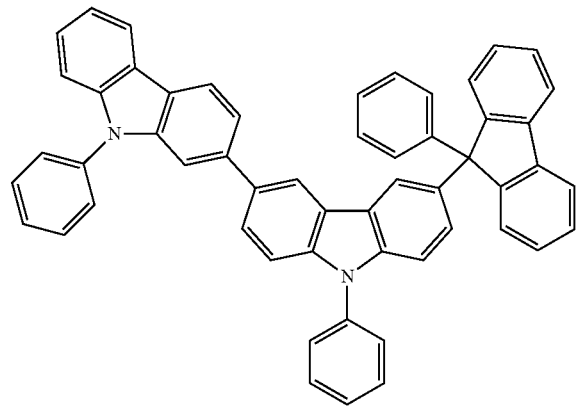
[2-42]
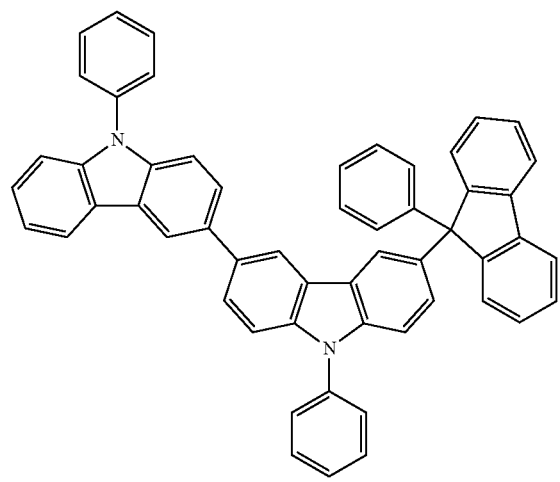
[2-43]
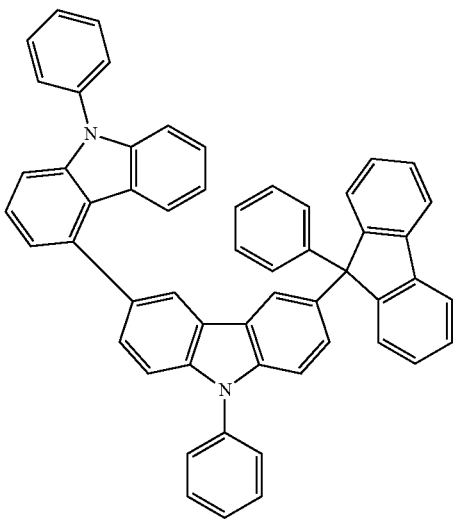
[2-44]
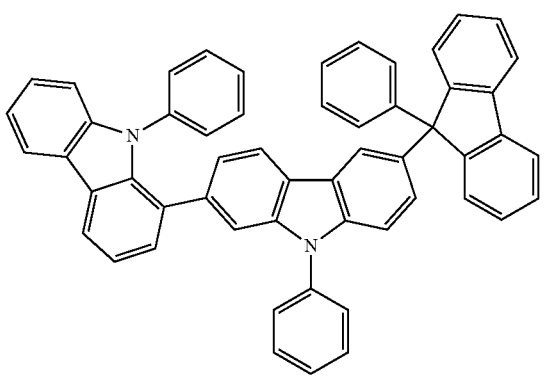
[2-45]
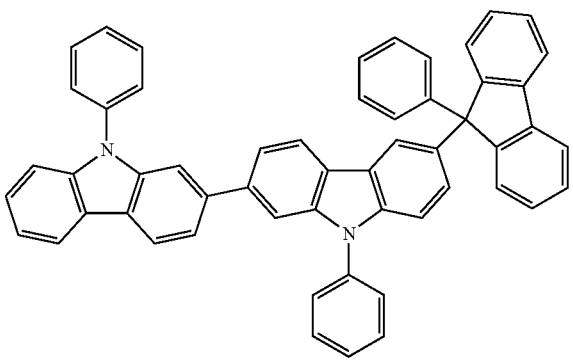
[2-46]
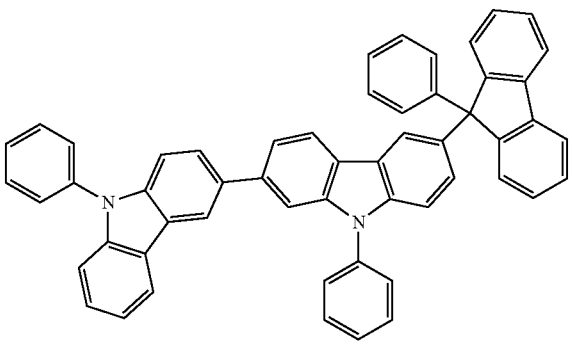
[2-47]
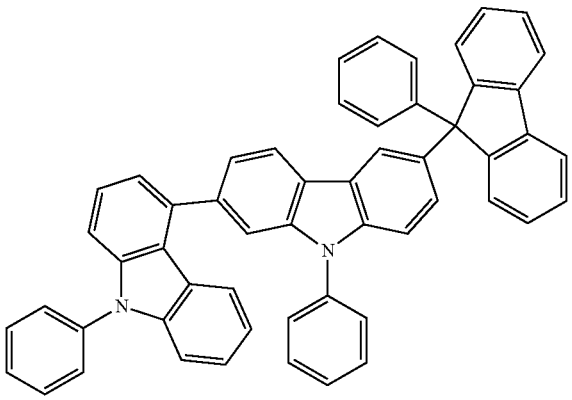

[2-48]
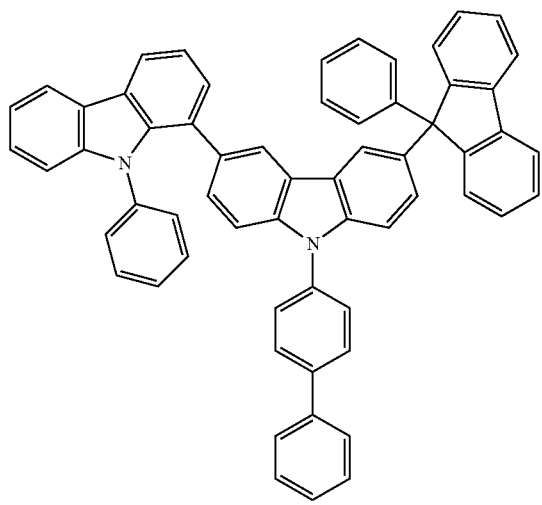
[2-50]
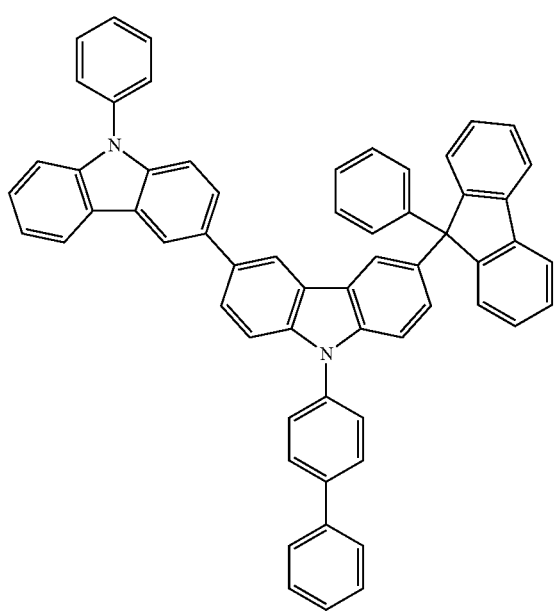
[2-49]
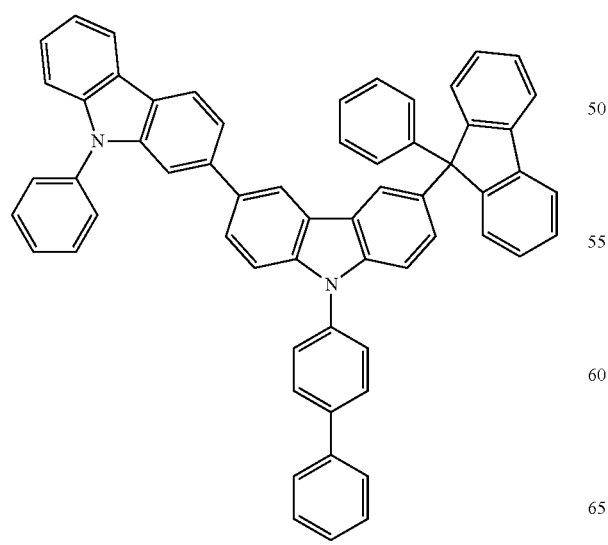
[2-51]
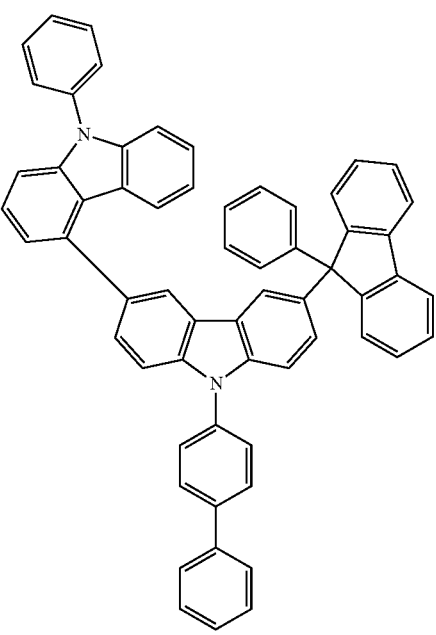

-continued
[2-52]
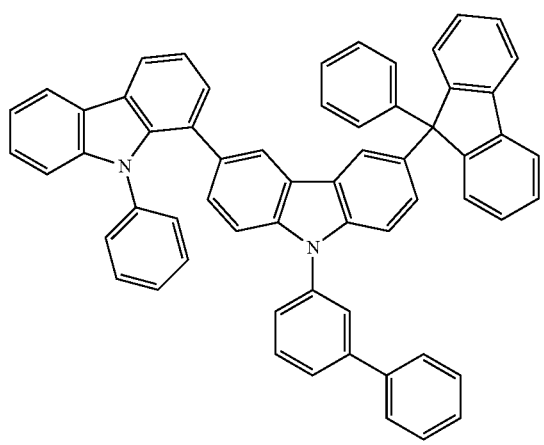
[2-55]
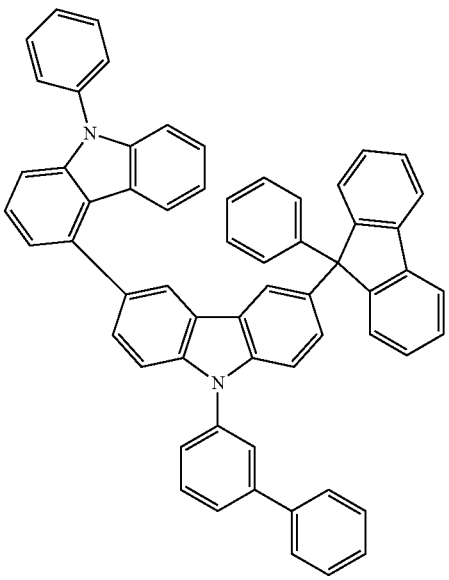
[2-53]
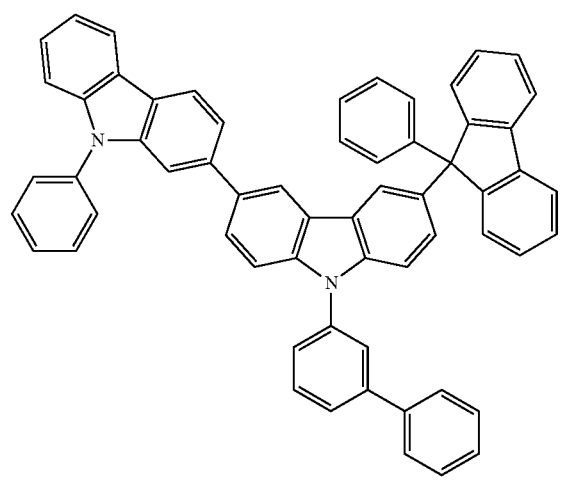
[2-56]
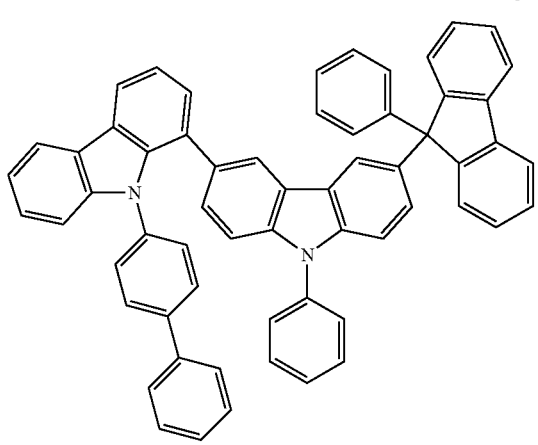
[2-54]
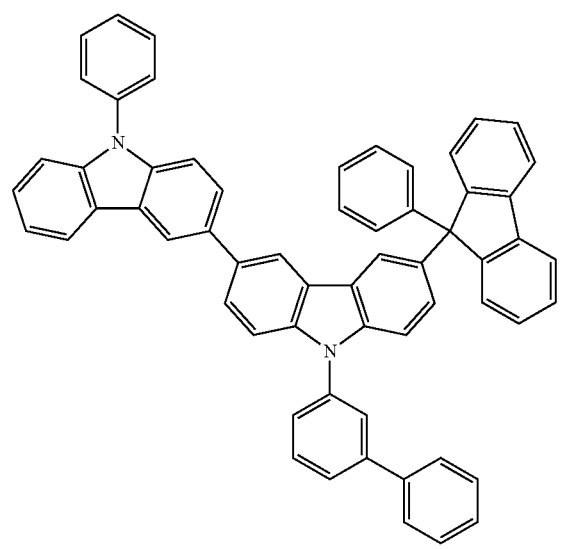
[2-57]
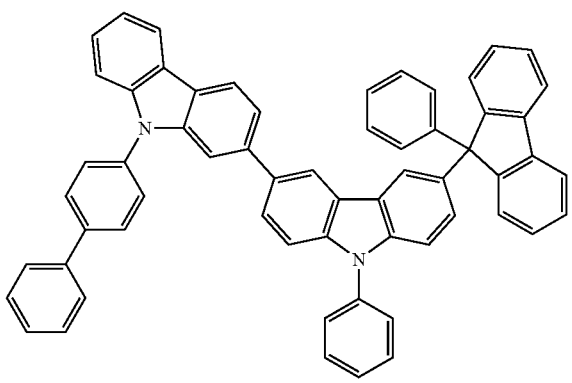

[2-58]
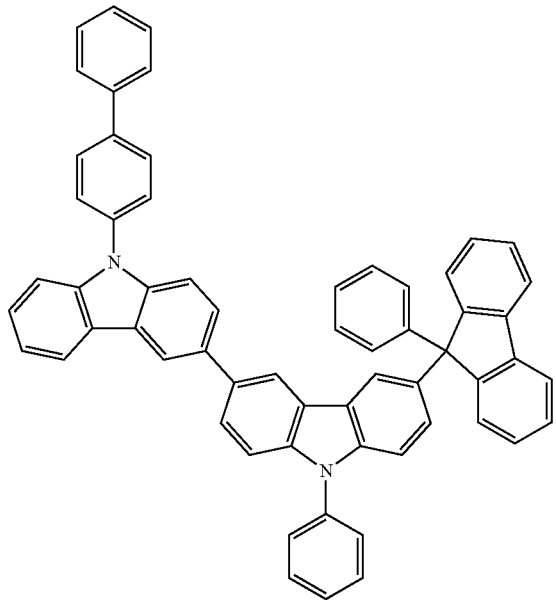
[2-61]
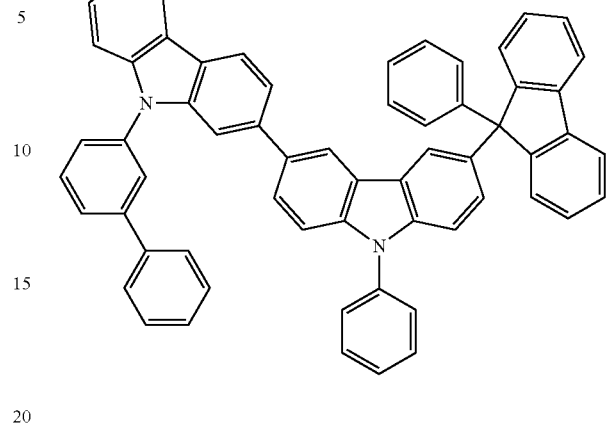
[2-59]
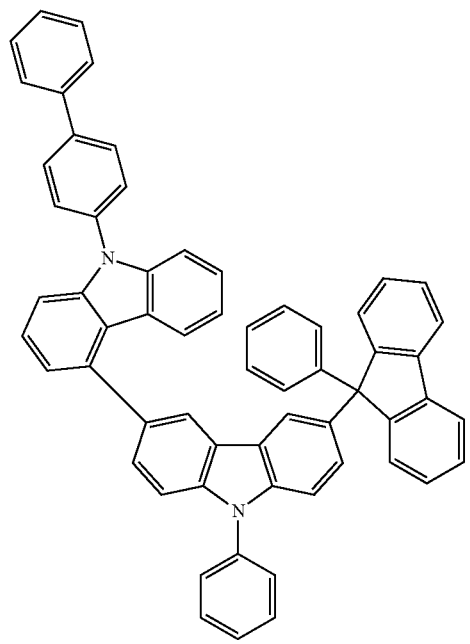
[2-62]
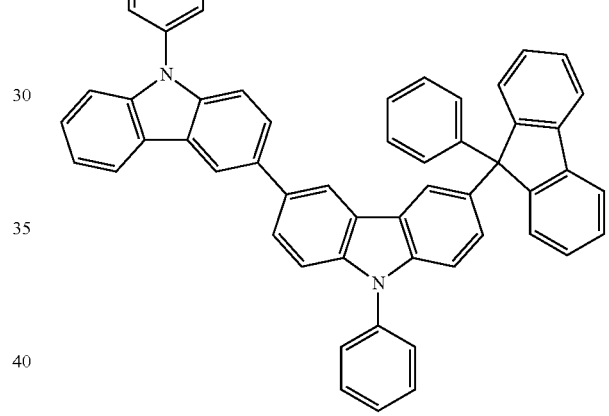
[2-60]
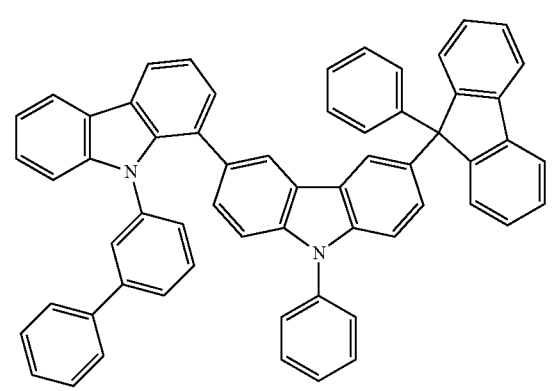
[2-63]
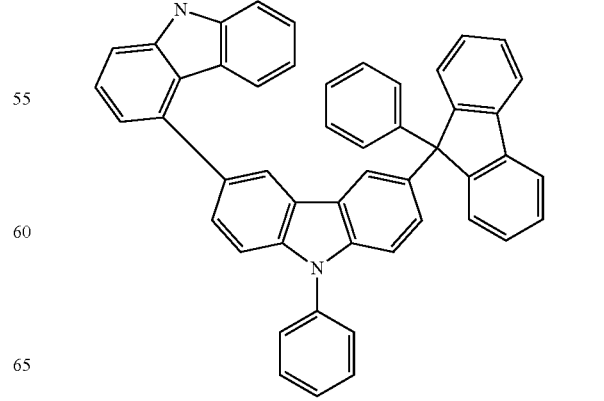

[2-64]
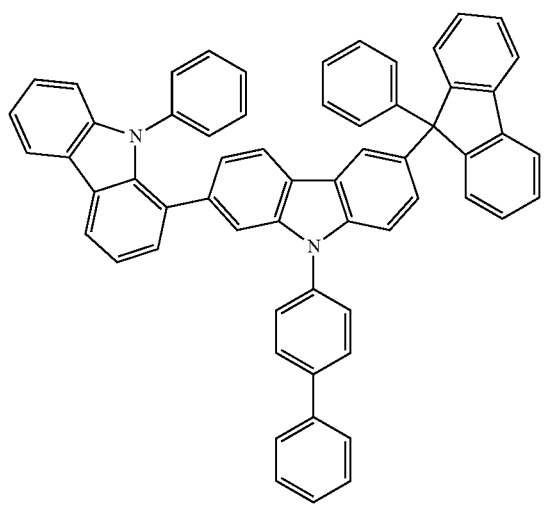
[2-65]
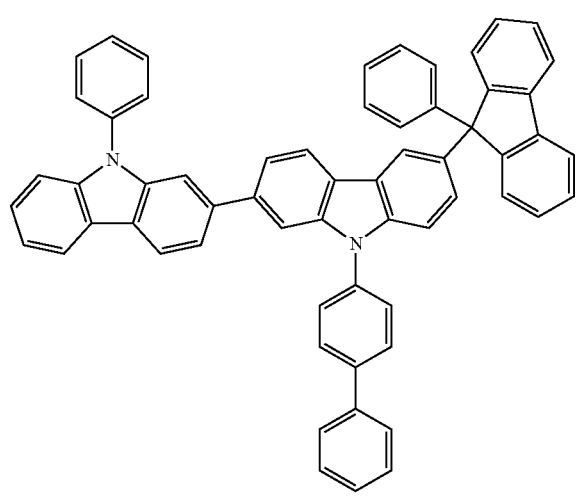
[2-66]
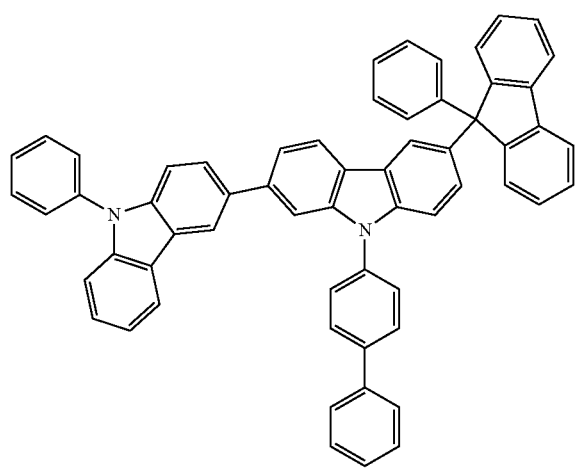
[2-67]
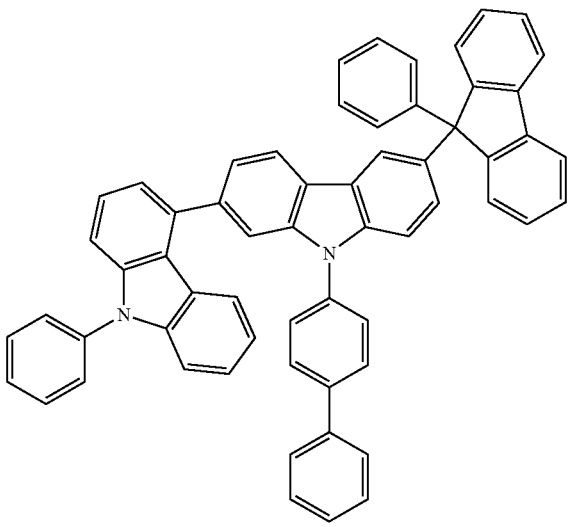
[2-68]
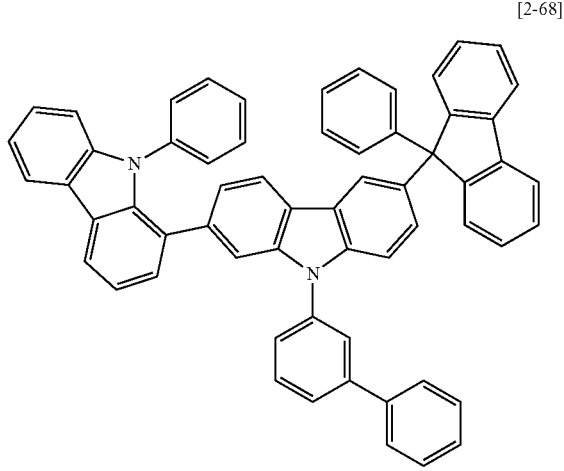
[2-69]
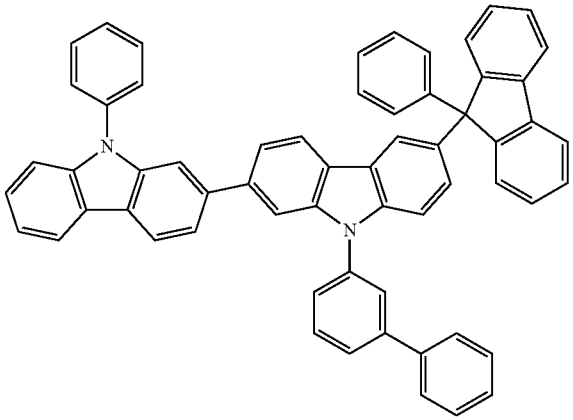

[2-70]
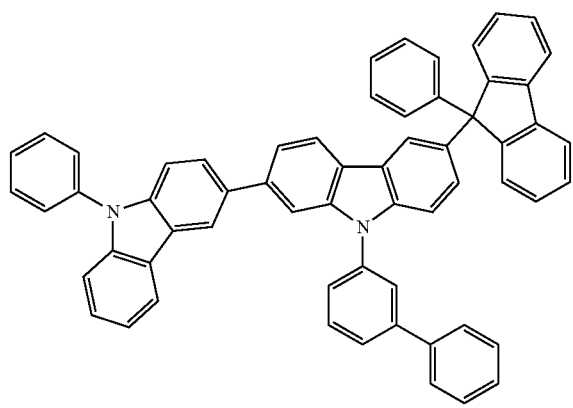
[2-73]
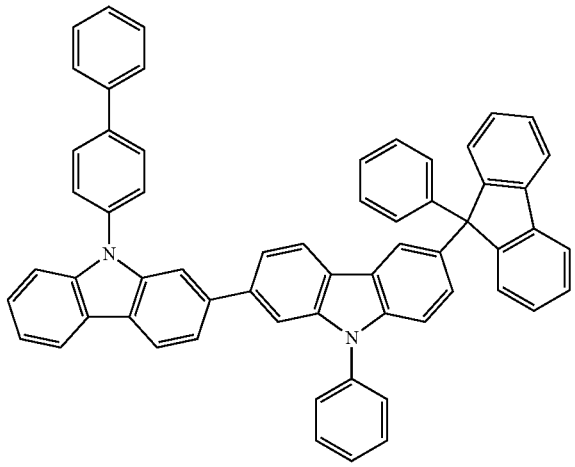
[2-71]
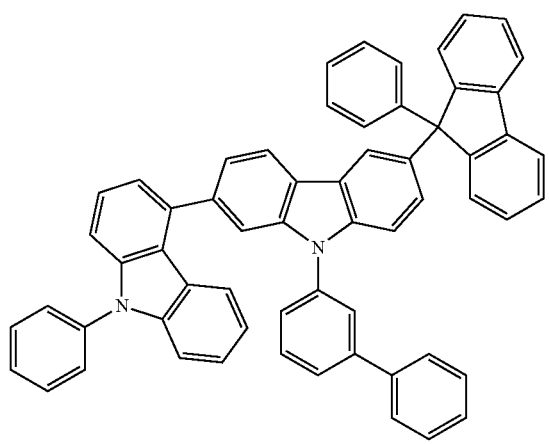
[2-74]
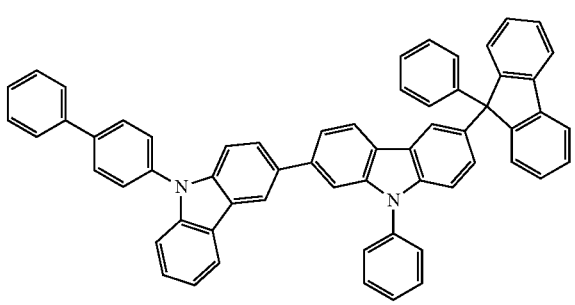
[2-72]
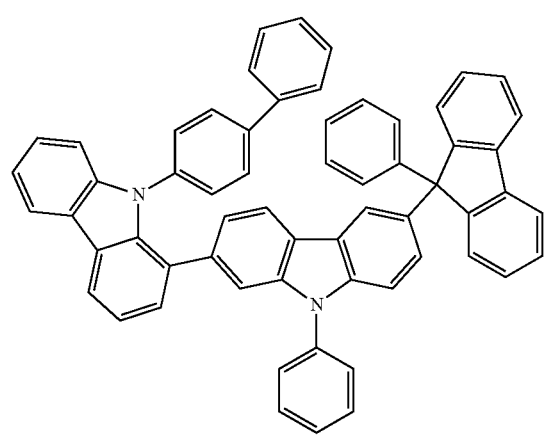
[2-75]
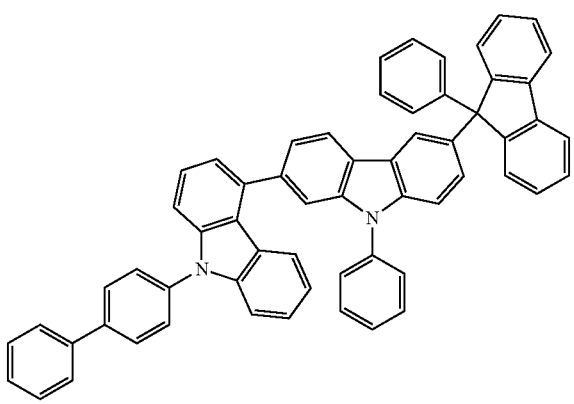

[2-76]

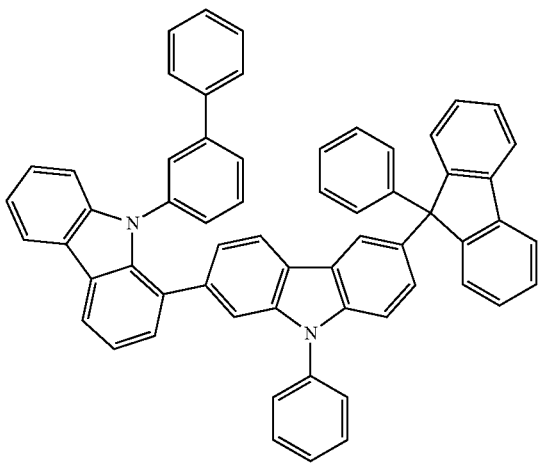

[2-77]

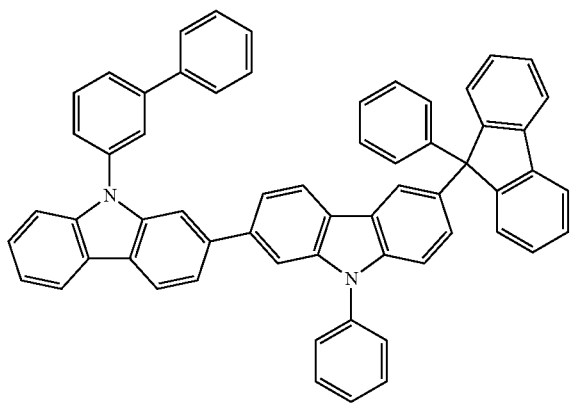

[2-78]

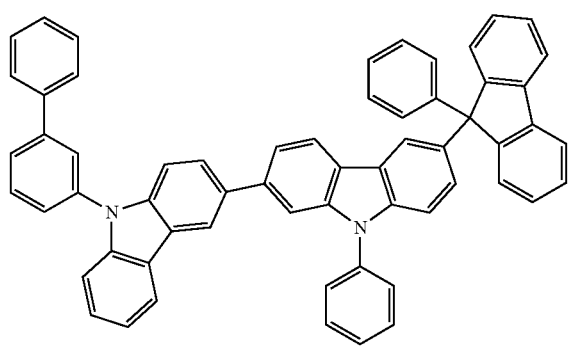

[2-79]

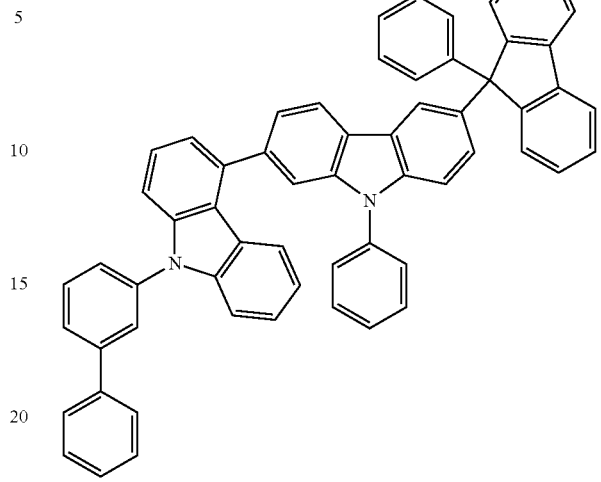

The compound for an organic optoelectric device may be applied to an organic optoelectric device.

The compound for an organic optoelectric device may be applied to an organic optoelectric device singularly or along with other compounds for an organic optoelectric device. When the compound for an organic optoelectric device is used with the other compounds for an organic optoelectric device, they may be applied as a composition.

Hereinafter, a composition for an organic optoelectric device including the compound for an organic optoelectric device is described as an example.

The composition for an organic optoelectric device may include, for example a composition including the compound for an organic optoelectric device, as described above, and at least one second compound for an organic optoelectric device having a moiety represented by Chemical Formula II.

[Chemical Formula II]

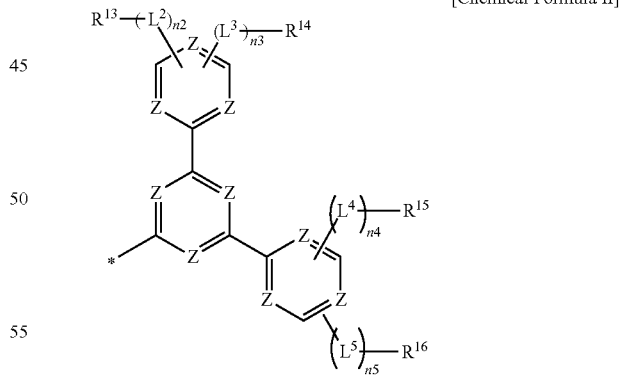

In the present example embodiment, in Chemical Formula II, each Z is independently N, C or $CR^c$, and at least one of Z is N, $R^{13}$ to $R^{16}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $L^2$ to $L^5$ are each independently a single bond, a substituted or unsubstituted C6 to C30 arylene group, a substituted or unsubstituted C2 to C30 heteroarylene group, or a combination thereof, n2 to n5 are each independently one of integers of 0 to 5, and

* indicates a linking point, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

Hereinafter, the compound for an organic optoelectric device is referred to be a 'first compound for an organic optoelectric device' and the compound having the moiety represented by Chemical Formula II is referred to be a 'second compound for an organic optoelectric device'.

The second compound for an organic optoelectric device may be, for example represented by Chemical Formula II-A, or Chemical Formula II-B.

[Chemical Formula II-B]

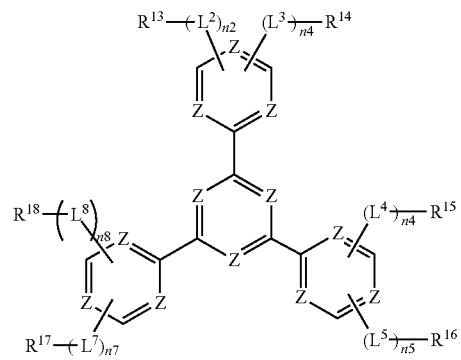

In the present example embodiment, in Chemical Formulae II-A and II-B, each Z is independently N, C or $CR^c$, and at least one of Z is N, $X^1$ to $X^{12}$ are each independently N, C or $CR^d$, $L^2$ to $L^8$ are each independently a single bond, a substituted or unsubstituted C6 to C30 arylene group, a substituted or unsubstituted C2 to C30 heteroarylene group, or a combination thereof, n2 to n8 are each independently one of integers of 0 to 5, and $R^{13}$ to $R^{18}$, $R^c$ and $R^d$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The second compound for an organic optoelectric device represented by Chemical Formula II-A may be, for example represented by Chemical Formula II-A1 or Chemical Formula II-A2.

[Chemical Formula II-A]

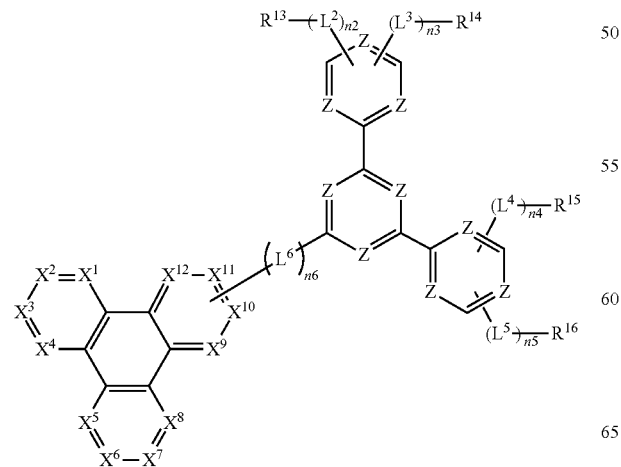

[Chemical Formula II-A1]

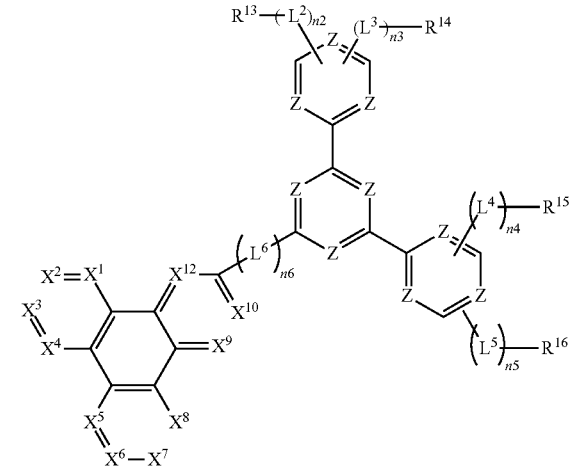

[Chemical Formula II-A2]

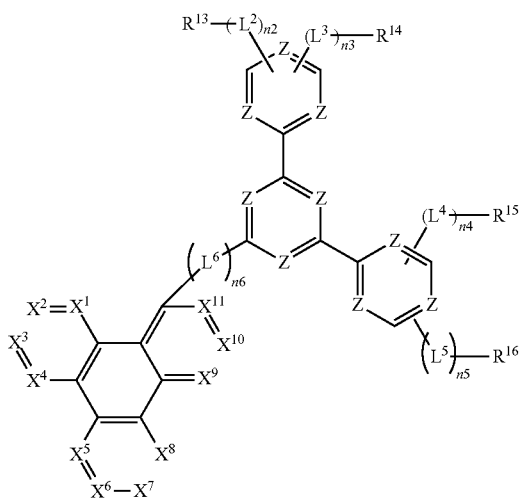

In the present example embodiment, in Chemical Formulae II-A1 and II-A2, Z, $X^1$ to $X^{12}$, $R^{13}$ to $R^{16}$, n2 to n6 and $L^2$ to $L^6$ are the same as described above.

The $L^6$ may be a substituted or unsubstituted phenylene group having a kink structure, a substituted or unsubstituted biphenylene group having a kink structure or a substituted or unsubstituted terphenylene group having a kink structure listed in Group 3.

[Group 3]

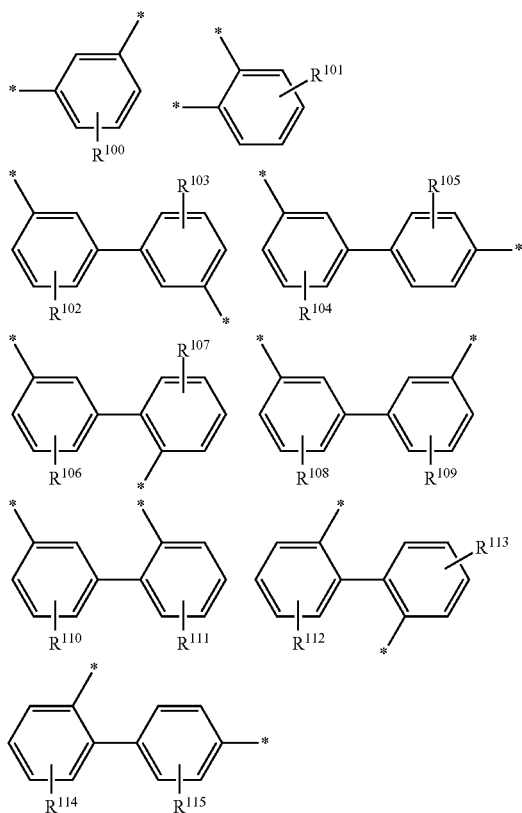

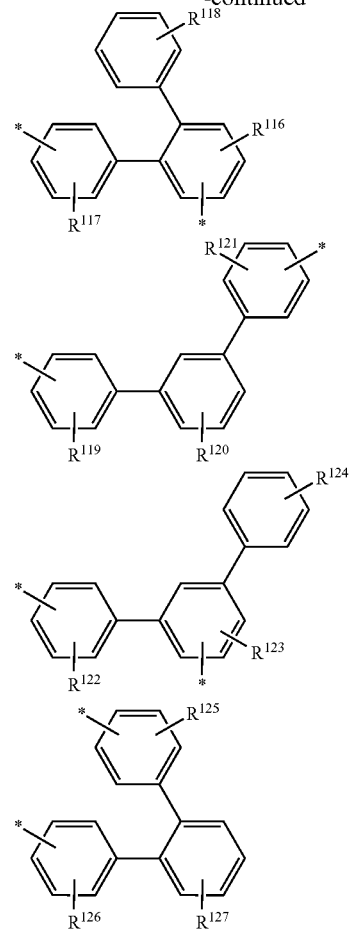

In Group 3,
$R^{100}$ to $R^{127}$ are each independently hydrogen, deuterium, a C1 to C10 alkyl group, a C3 to C30 cycloalkyl group, a C3 to C30 heterocycloalkyl group, a C6 to C30 aryl group, a C2 to C30 heteroaryl group, amine group, a C6 to C30 arylamine group, a C2 to C30 heteroarylamine group, a C1 to C30 alkoxy group, a halogen, a halogen-containing group, a cyano group, a hydroxyl group, an amino group, a nitro group, a carboxyl group, a ferrocenyl group or a combination thereof.

The second compound for an organic optoelectric device represented by Chemical Formula II-A may be represented by Chemical Formulae II-a1 to II-a20 having at least two kink structures.

[Chemical Formula II-a1]

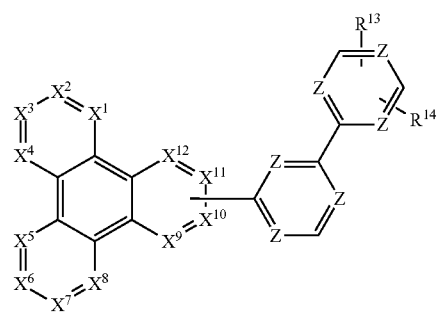

[Chemical Formula II-a2]
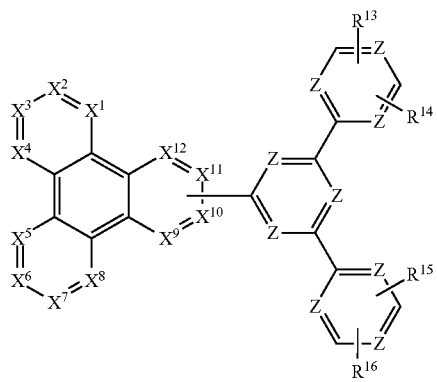
[Chemical Formula II-a3]
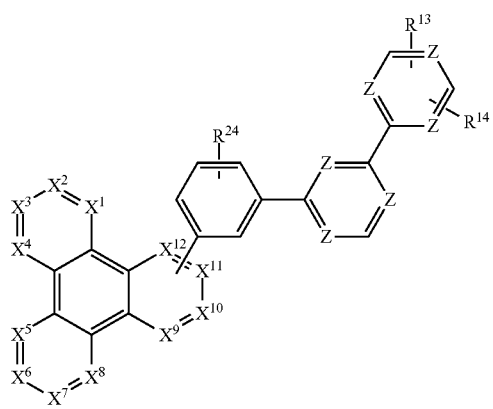
[Chemical Formula II-a4]
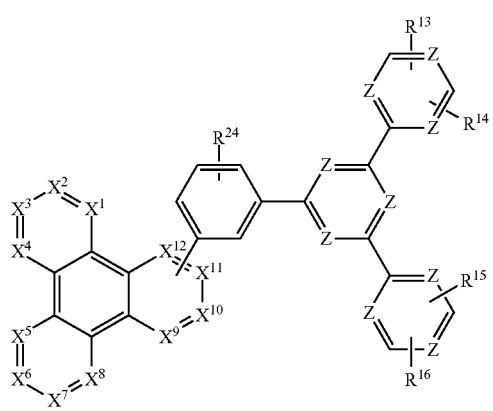
[Chemical Formula II-a5]
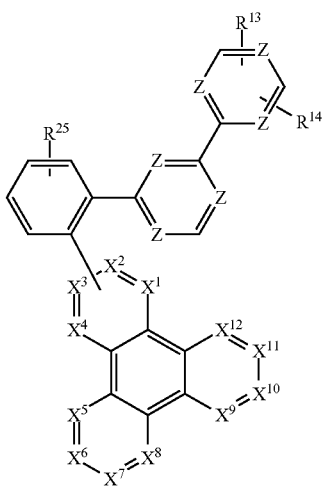
[Chemical Formula II-a6]
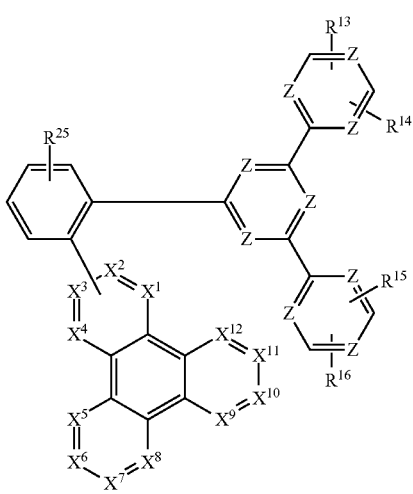
[Chemical Formula II-a7]
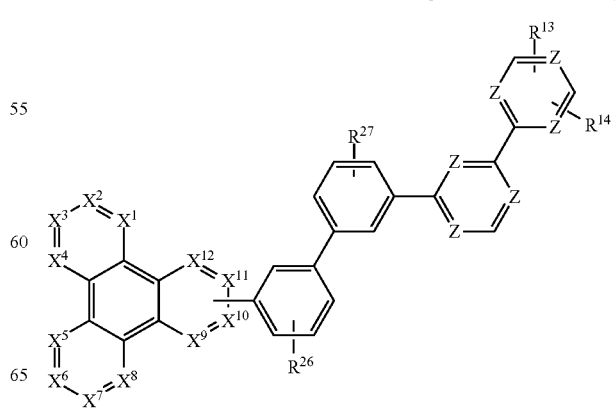

[Chemical Formula II-a8]
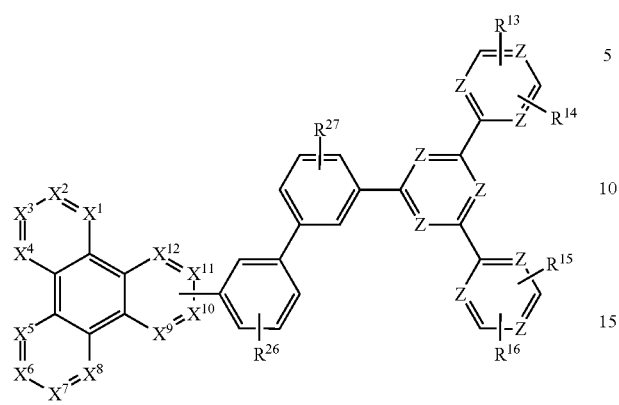
[Chemical Formula II-a9]
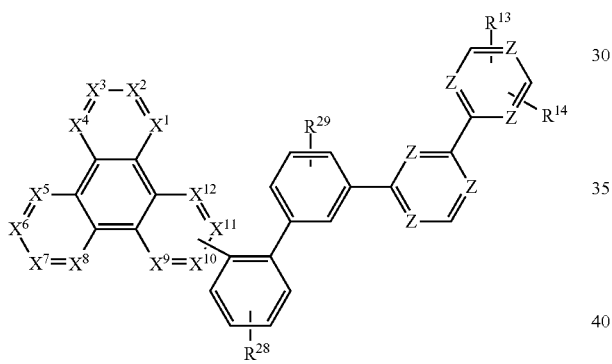
[Chemical Formula II-a10]
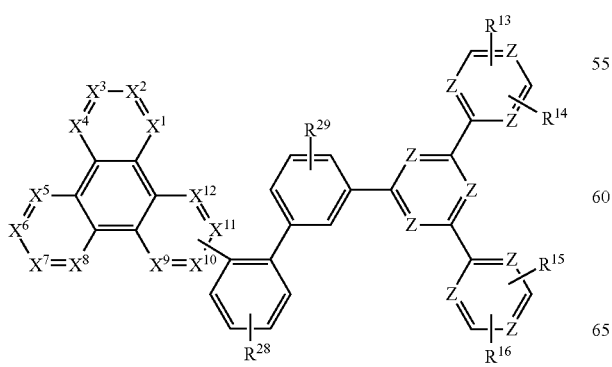
[Chemical Formula II-a11]
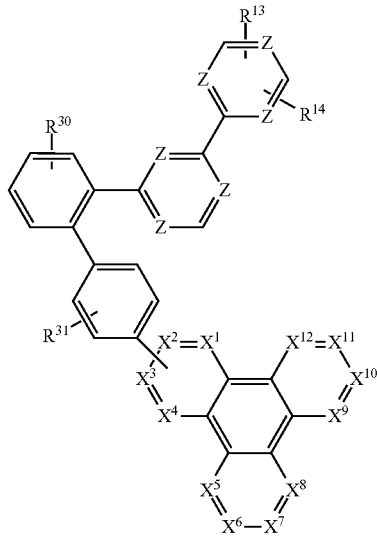
[Chemical Formula II-a12]
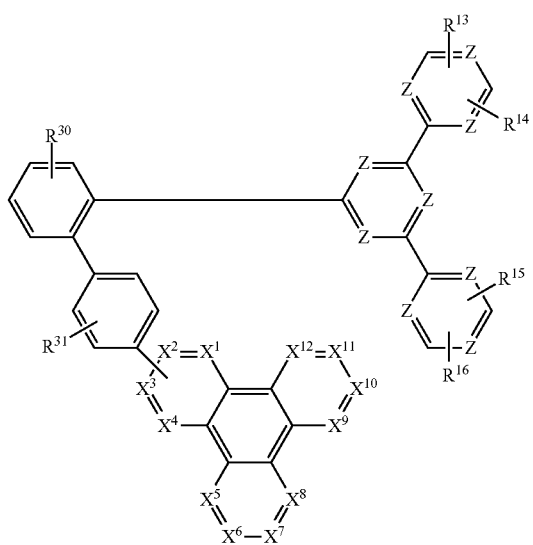

[Chemical Formula II-a13]
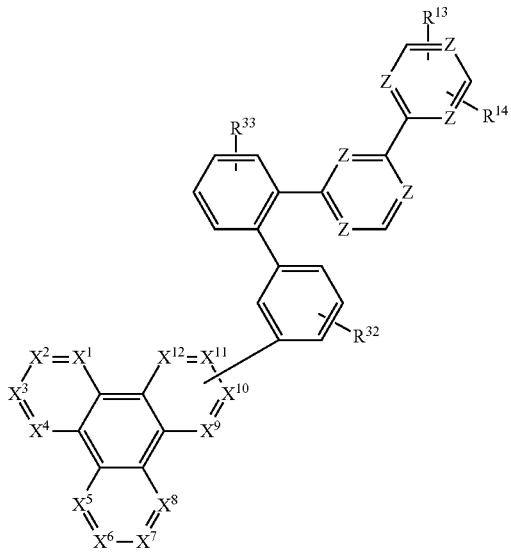
[Chemical Formula II-a14]
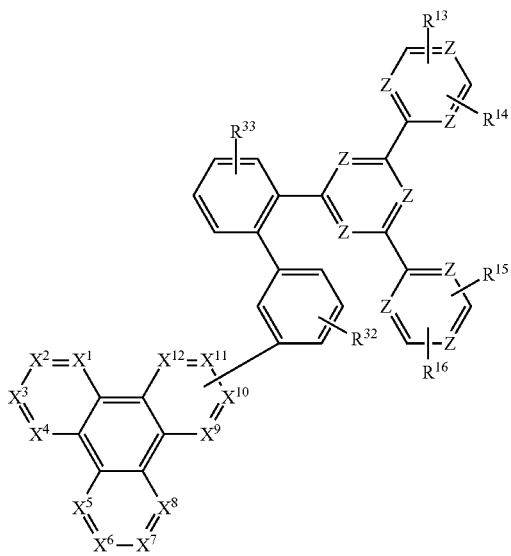
[Chemical Formula II-a15]
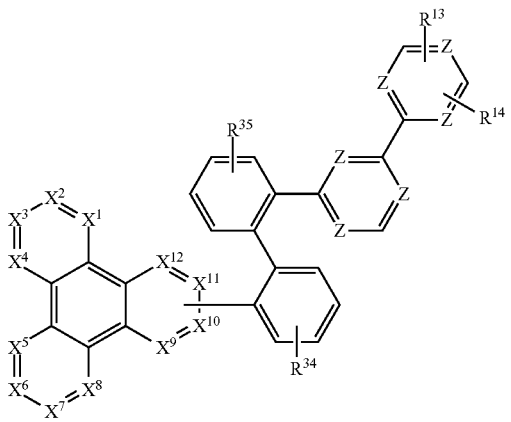
[Chemical Formula II-a16]
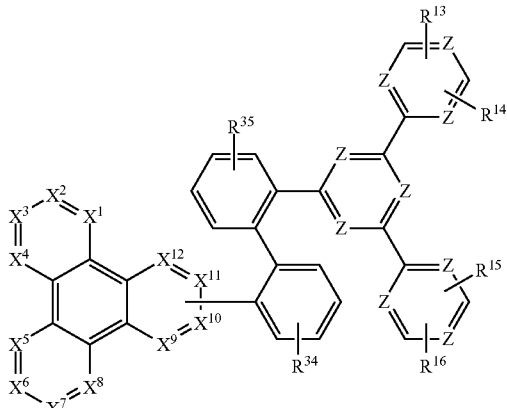
[Chemical Formula II-a17]
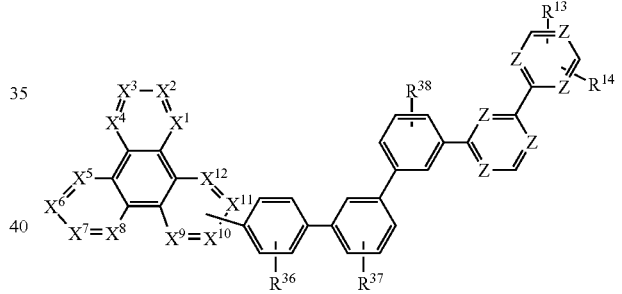
[Chemical Formula II-a18]
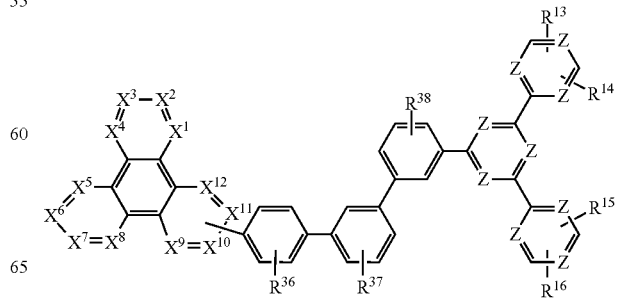

[Chemical Formula II-a19]

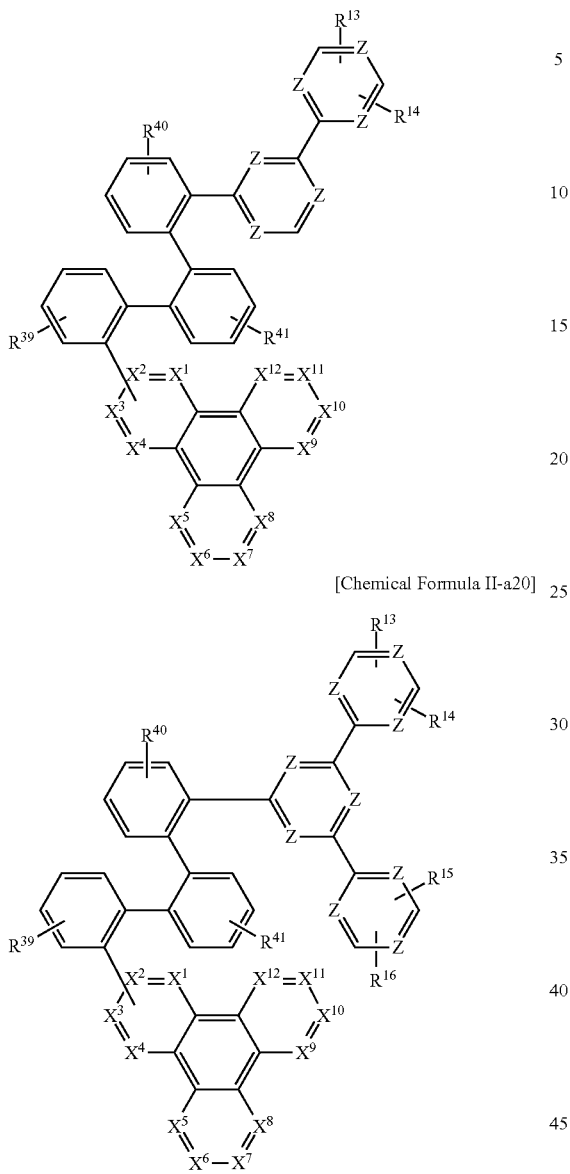

[Chemical Formula II-a20]

[Group 4]

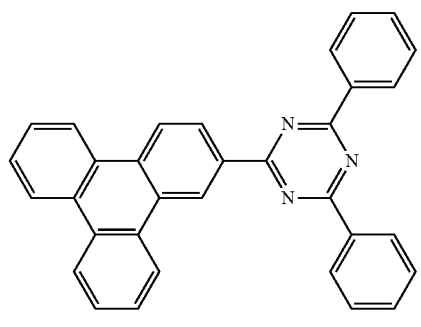

[4-1]

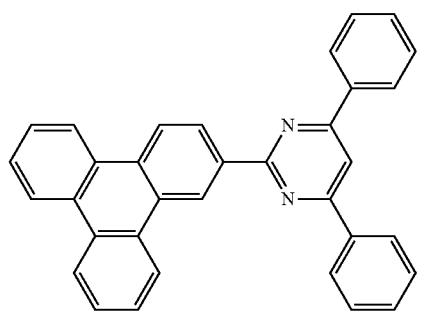

[4-2]

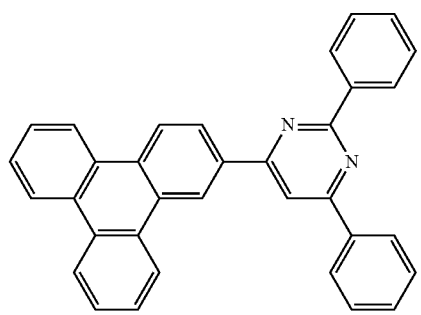

[4-3]

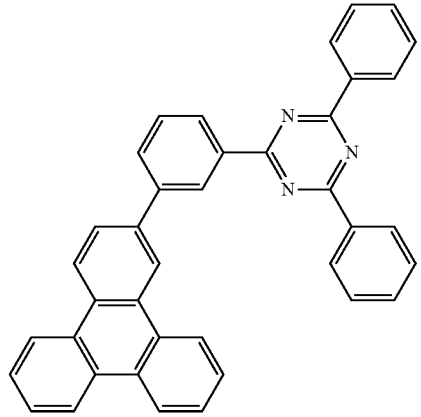

[4-4]

In the present example embodiment, in Chemical Formulae II-a1 to II-a20, Z, $X^1$ to $X^{12}$, $R^{13}$ to $R^{16}$ are the same as described above, $R^{24}$ to $R^{41}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C2 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof.

The second compound for an organic optoelectric device represented by Chemical Formula II-A may be compounds of Group 4, but is not limited thereto. In Group 4, heteroatom of the compounds is "N".

[4-5]
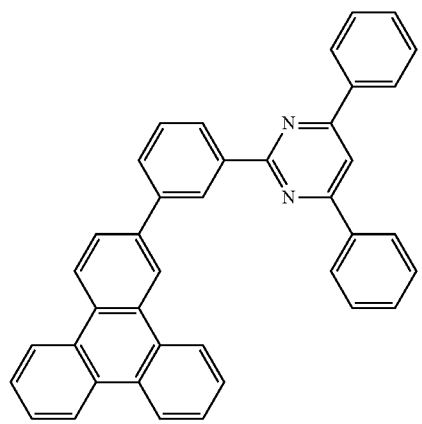
[4-8]
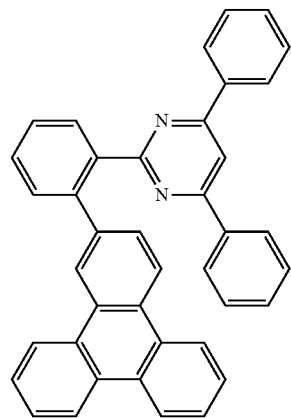
[4-6]
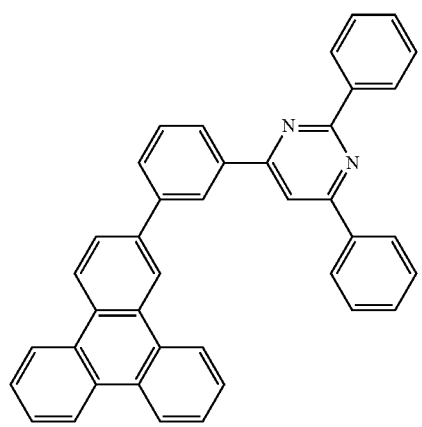
[4-9]
[4-7]
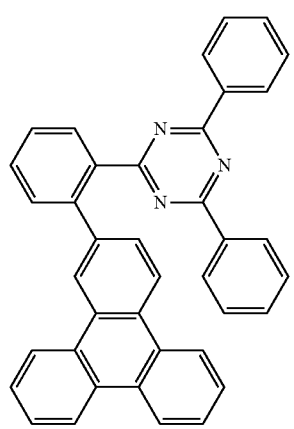
[4-10]
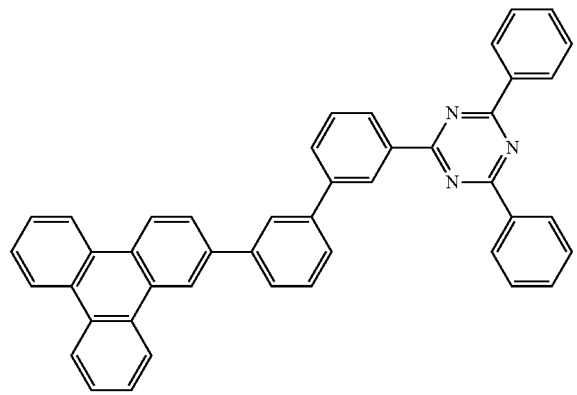

[4-11]
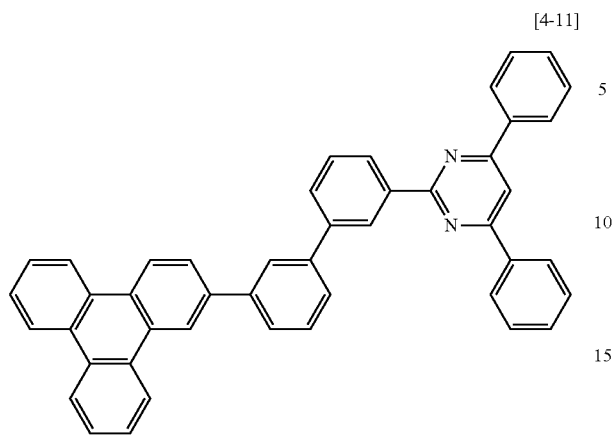
[4-15]
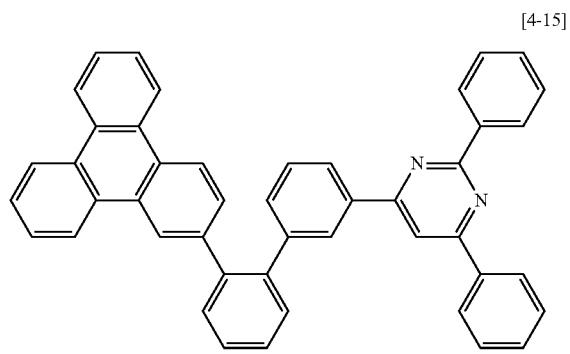
[4-12]
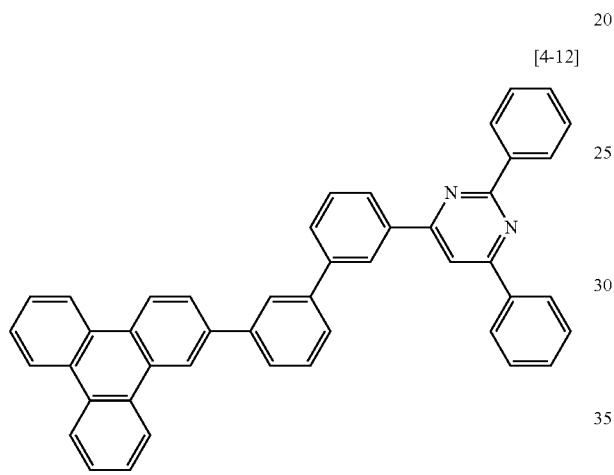
[4-16]
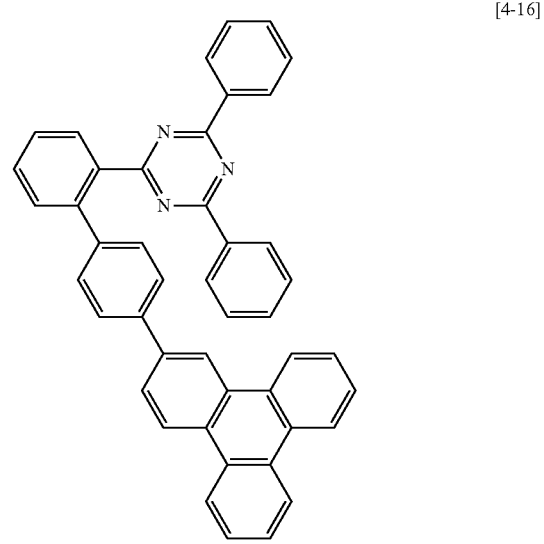
[4-13]
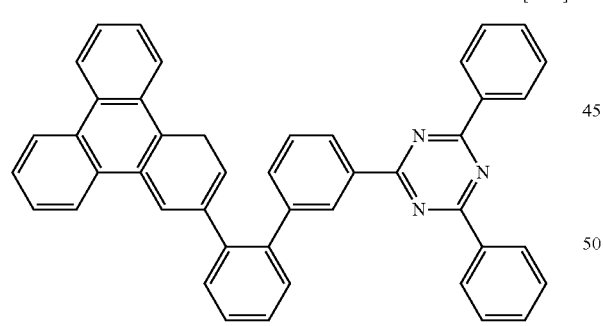
[4-17]
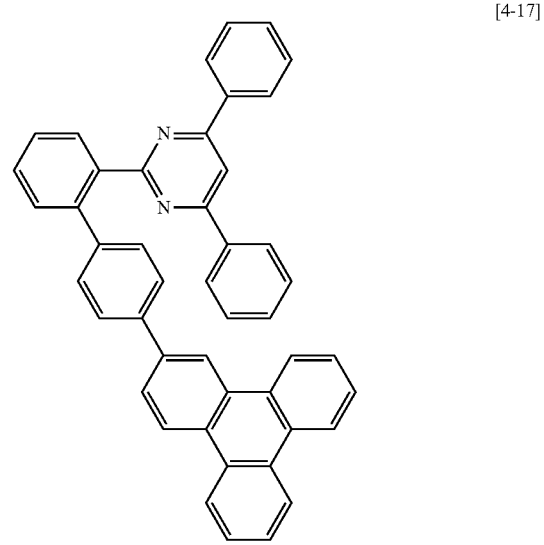
[4-14]
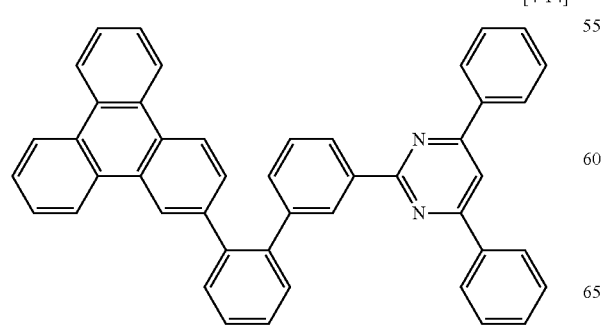

[4-18]
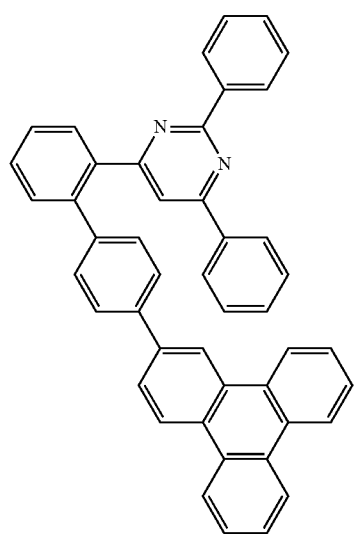
[4-19]
[4-20]
[4-21]
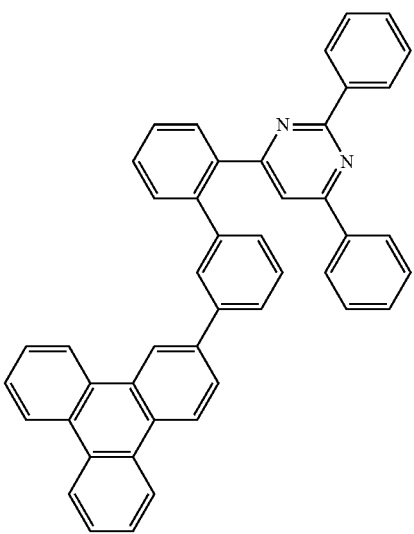
[4-22]
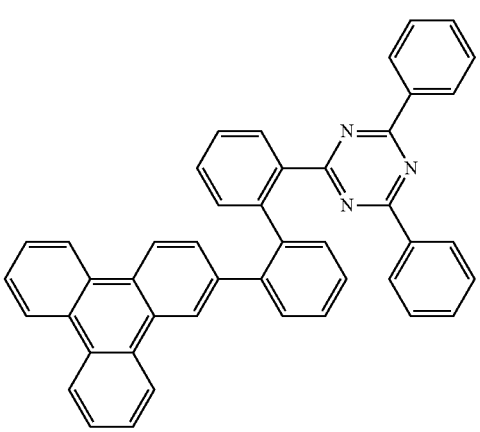
[4-23]
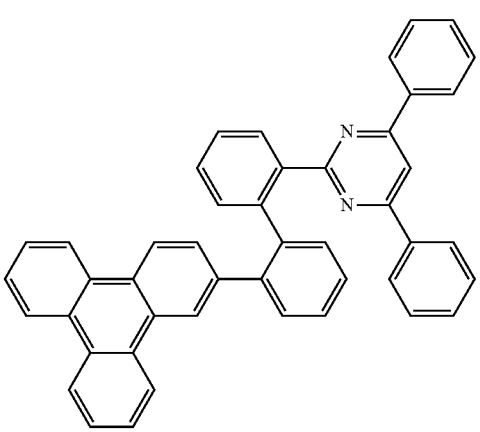

[4-24]
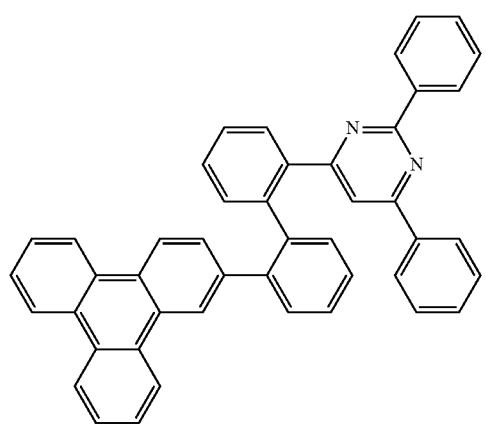
[4-25]
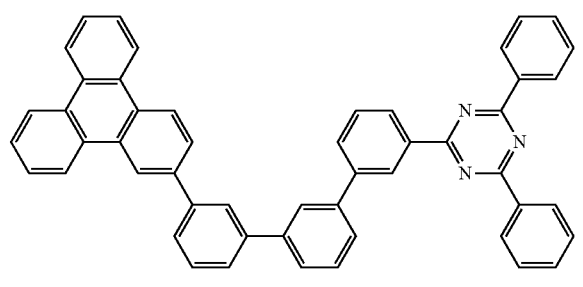
[4-26]
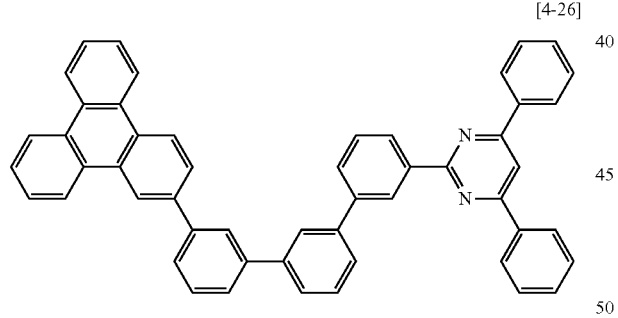
[4-27]
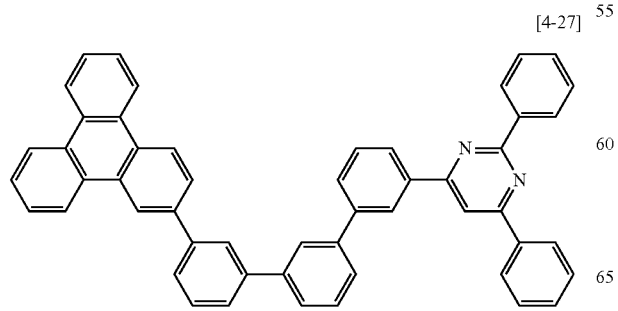
[4-28]
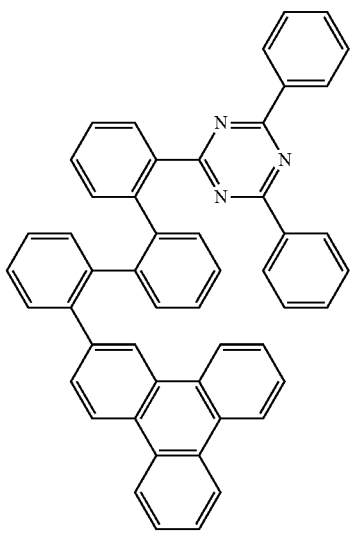
[4-29]
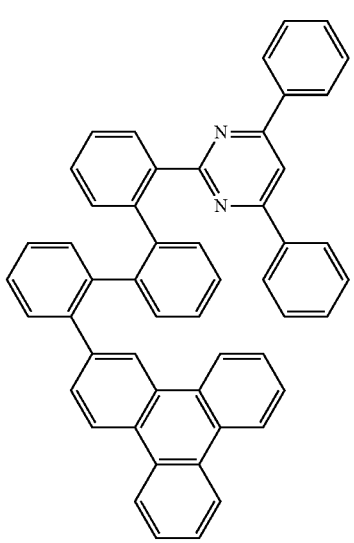
[4-30]
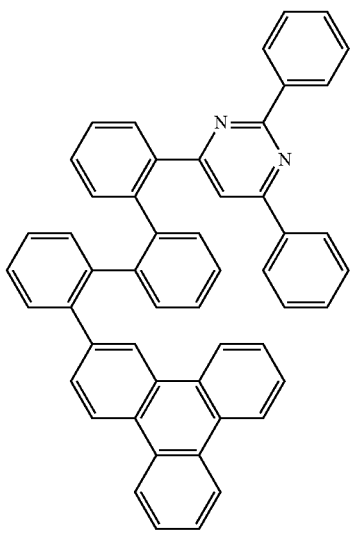

[4-31]
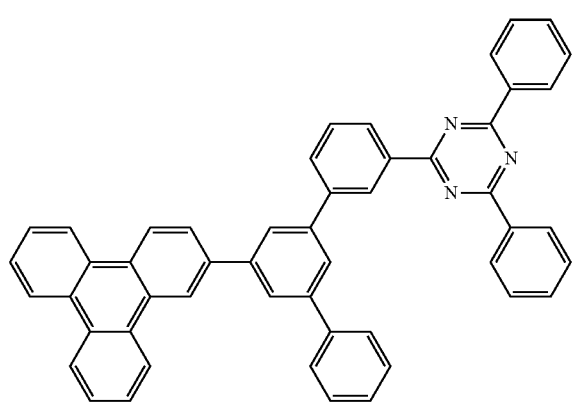
[4-32]
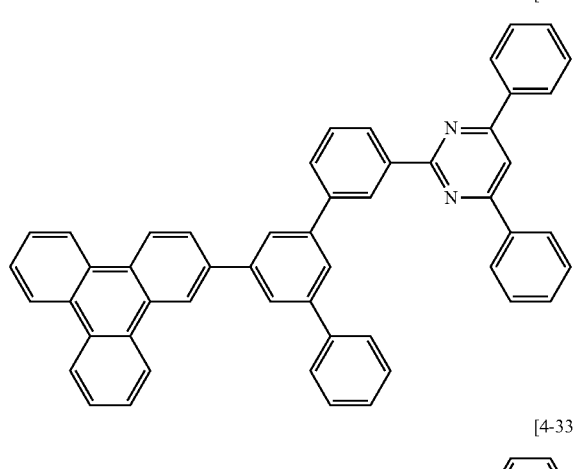
[4-33]
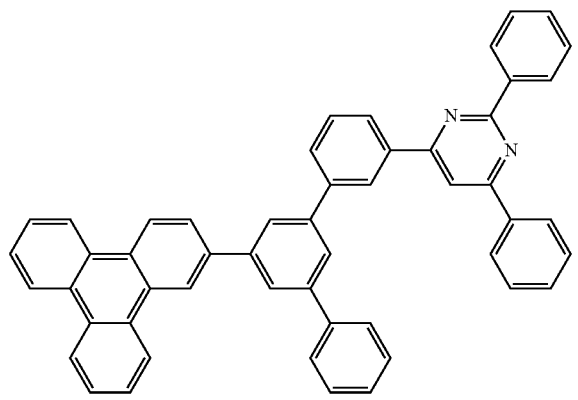
[4-34]
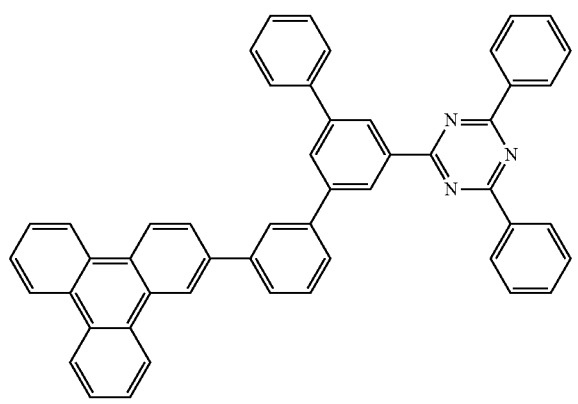
[4-35]
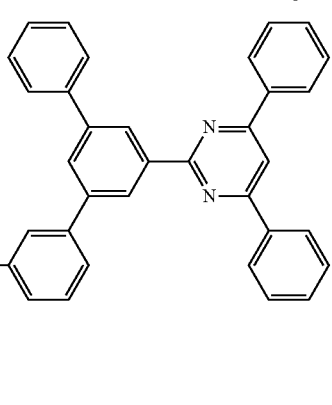
[4-36]
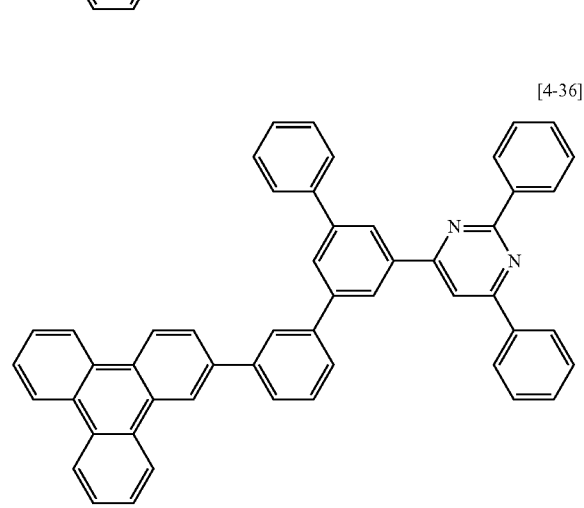
[4-37]
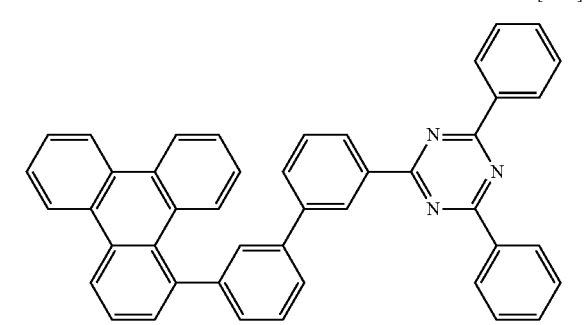
[4-38]
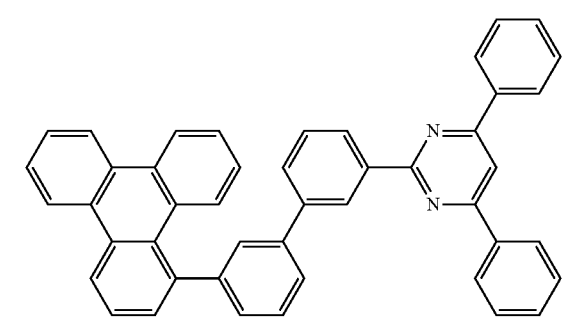

-continued

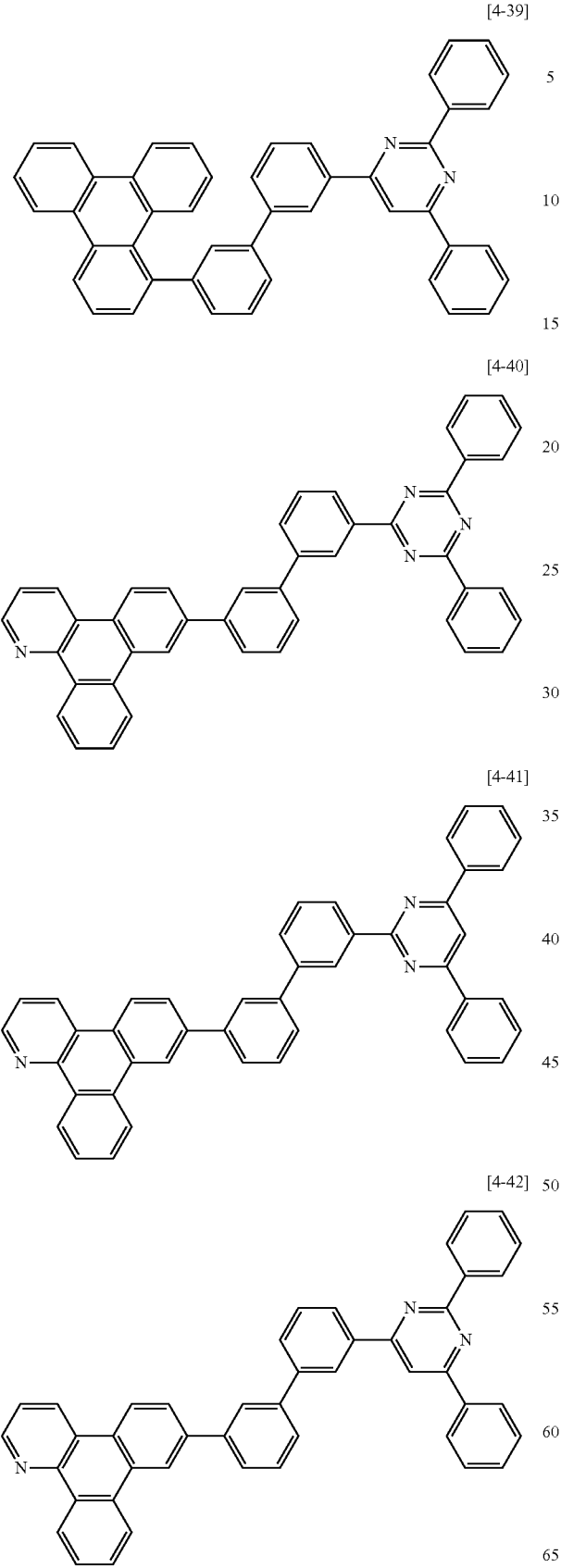

[4-39]

[4-40]

[4-41]

[4-42]

The second compound for an organic optoelectric device represented by Chemical Formula II-B may be, for example, represented by Chemical Formula II-B1 or Chemical Formula II-B2.

[Chemical Formula II-B1]

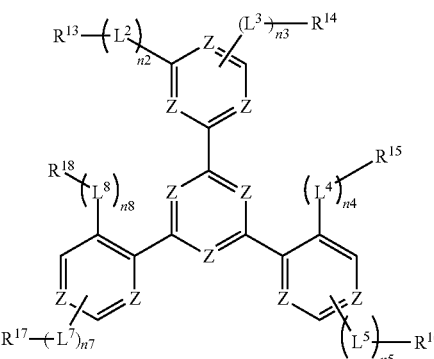

[Chemical Formula II-B2]

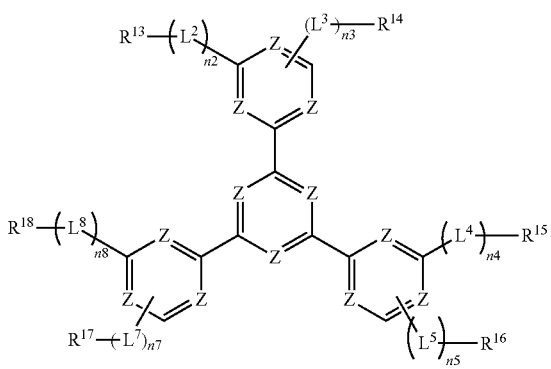

In the present example embodiment, in Chemical Formulae II-B1 and II-B2, Z, $R^{13}$ to $R^{18}$, $L^2$ to $L^5$, $L^7$, $L^8$, n2 to n5, n7 and n8 are the same as described above.

The kink structure indicates a structure that an arylene group and/or a heteroarylene group are not linked at the linking portion as a straight line. For example, as for phenylene, ortho phenylene (o-phenylene) and meta phenylene (m-phenylene) have no straight structure at the linking portion and thus, the kink structure, while para phenylene (p-phenylene) has a straight structure at the linking portion and thus, no kink structure.

$L^2$ to $L^5$, $L^7$ and $L^8$ of the second compound for an organic optoelectric device represented by Chemical Formula II-B may be a single bond, a substituted or unsubstituted phenylene group, a substituted or unsubstituted biphenylene group, a substituted or unsubstituted terphenylene group, a substituted or unsubstituted quarterphenylene group, a substituted or unsubstituted naphthalenylene group, and may be, for example one of the following linking groups.

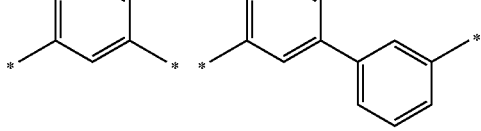

-continued
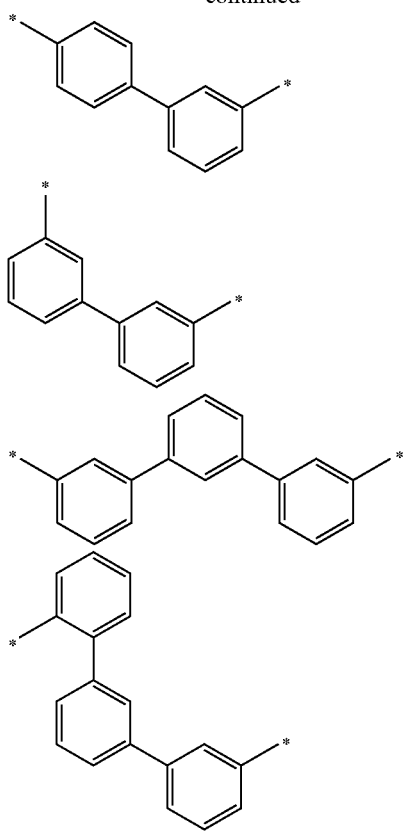
-continued
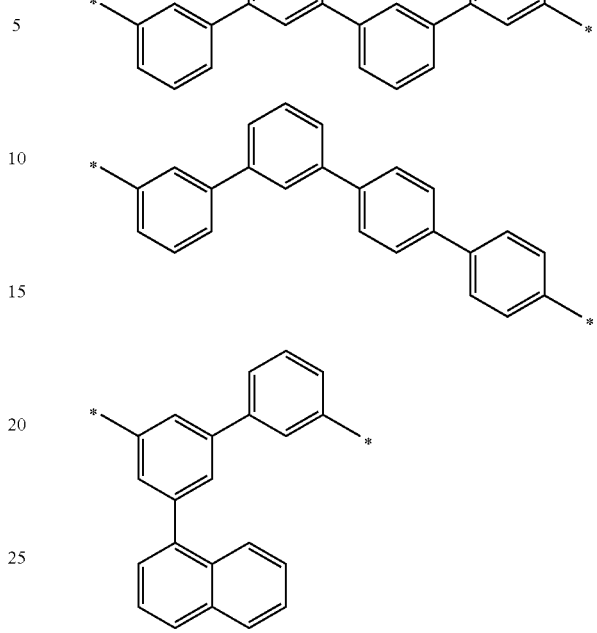
The second compound for an organic optoelectric device represented by Chemical Formula II-B may be, for example represented by at least one of Chemical Formula II-7b1 to Chemical Formula II-b7, but is not limited thereto.
[Chemical Formula II-b1]
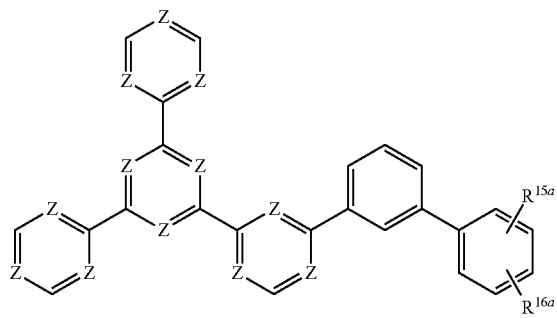
[Chemical Formula II-b2]
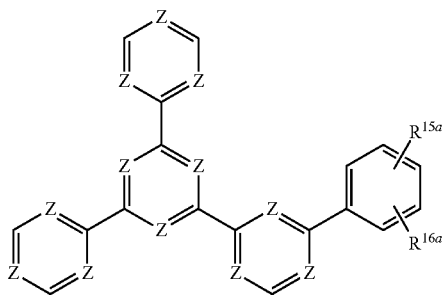
[Chemical Formula II-b3]
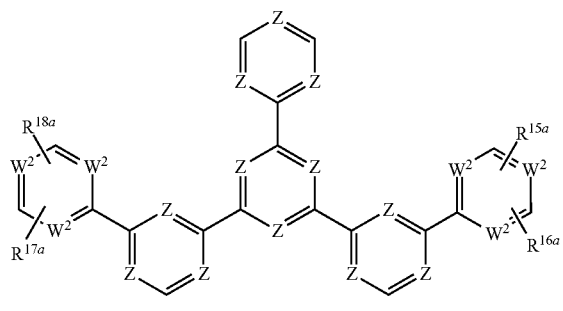
[Chemical Formula II-b4]
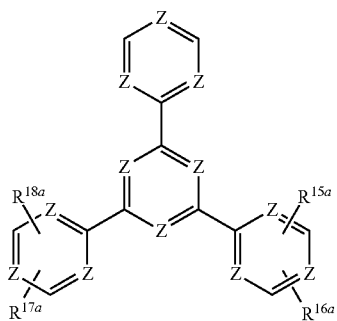

[Chemical Formula II-b5]

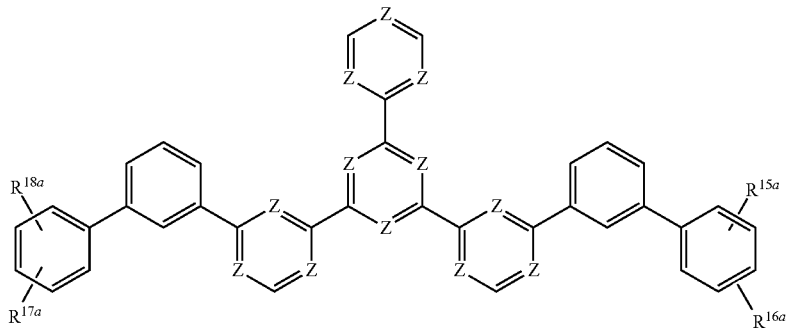

[Chemical Formula II-b6]

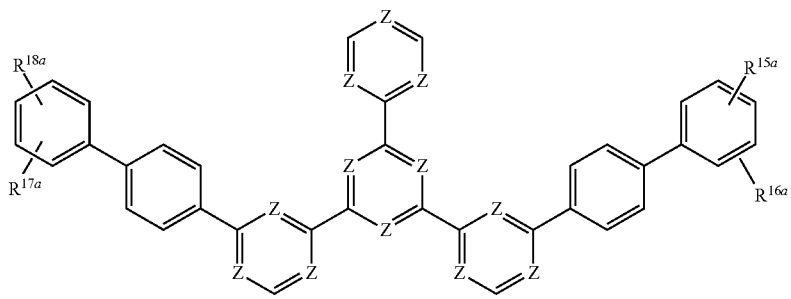

[Chemical Formula II-b7]

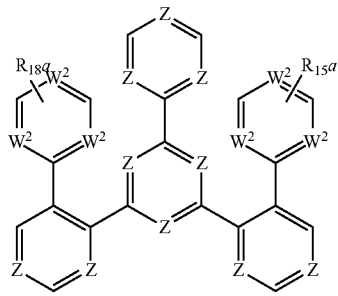

In the present example embodiment, in Chemical Formulae II-b1 to II-b7,

Z is described above, $W^2$ is each independently N, C or $CR^e$, and $R^{15a}$ to $R^{18a}$ and $R^e$ are each independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof.

$R^{15a}$ to $R^{18a}$ may be hydrogen, deuterium, a substituted or unsubstituted phenyl group, a substituted or unsubstituted biphenyl group, a substituted or unsubstituted terphenyl group, a substituted or unsubstituted quarterphenyl group, a substituted or unsubstituted naphthalene group, a substituted or unsubstituted pyridine group, a substituted or unsubstituted pyrimidine group, a substituted or unsubstituted triazine group, a substituted or unsubstituted quinolinyl group, a substituted or unsubstituted isoquinolinyl group, a substituted or unsubstituted phenanthroline, a substituted or unsubstituted quinazoline, and may be, for example selected from the substituted or unsubstituted groups of Group 5.

[Group 5]

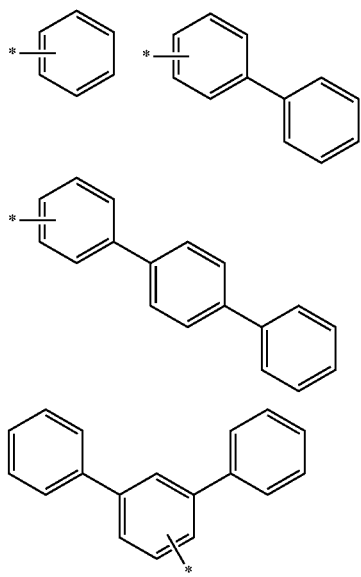

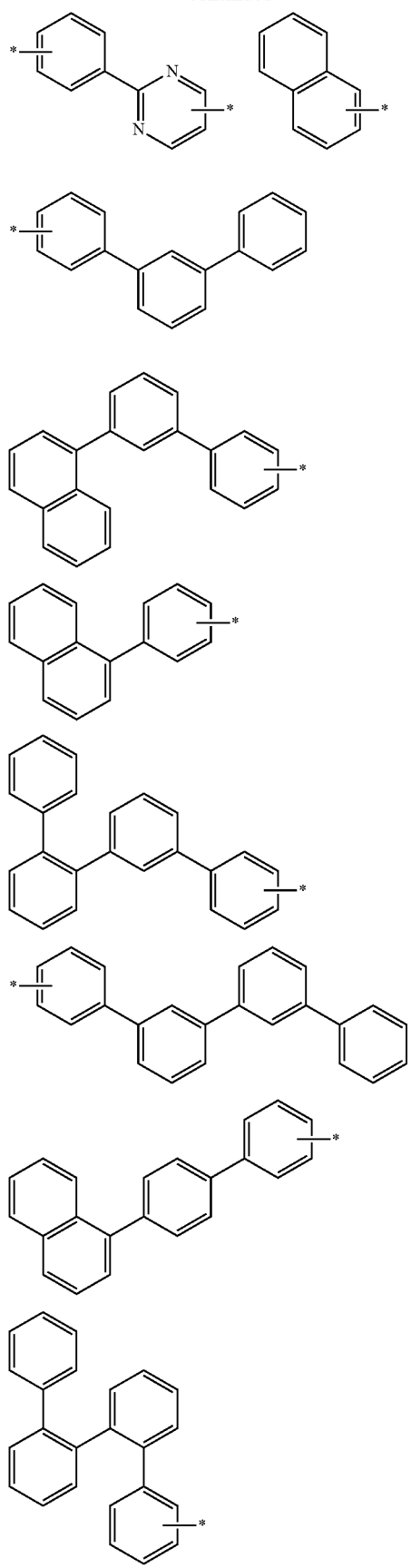
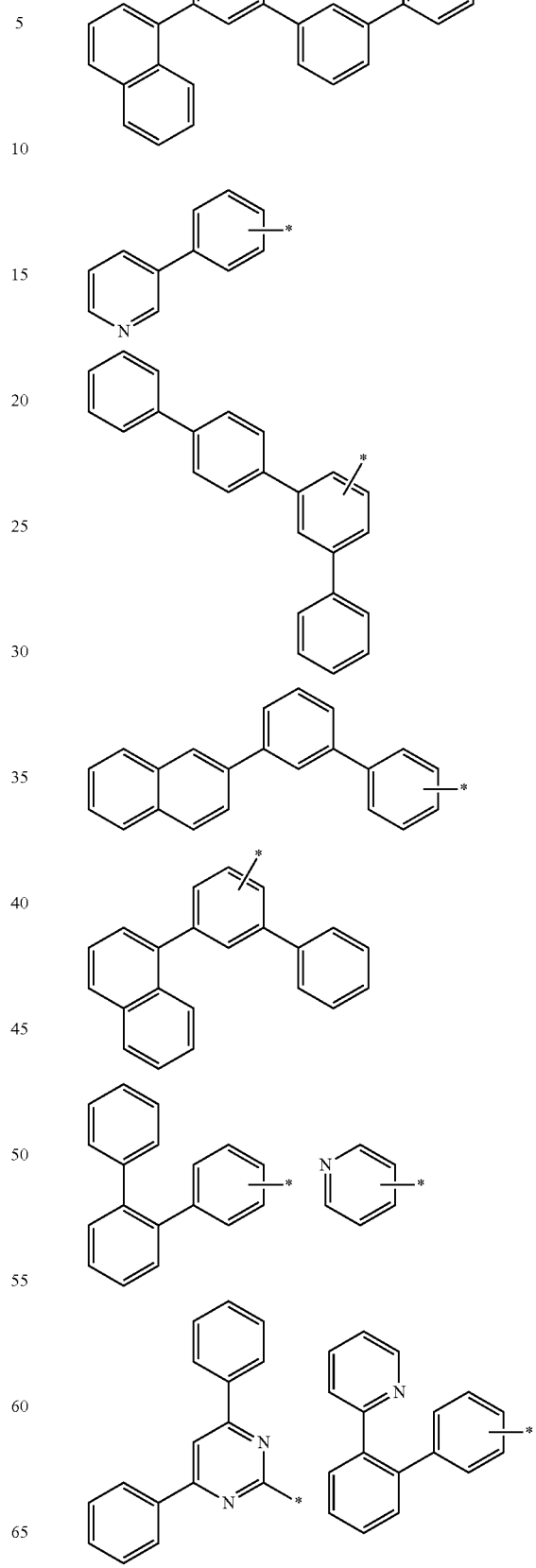

73
-continued
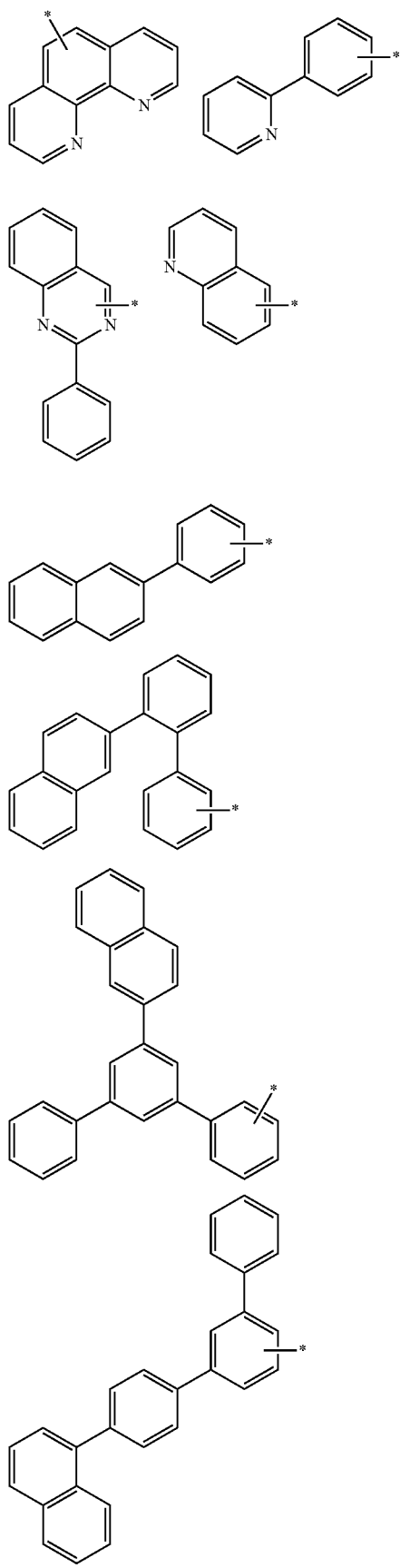
74
-continued
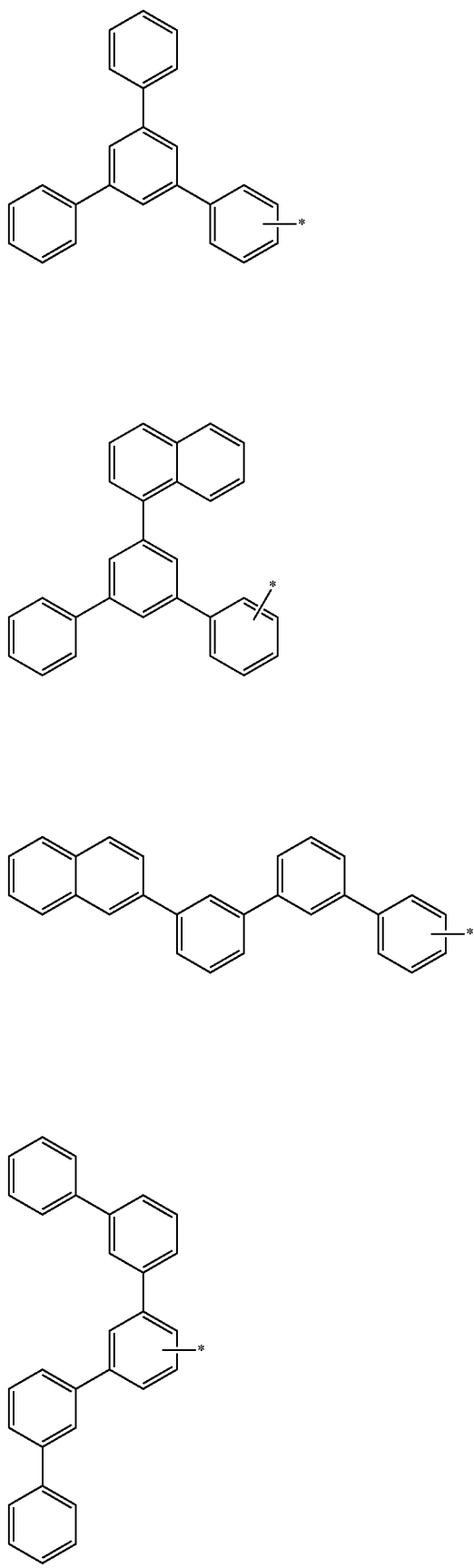

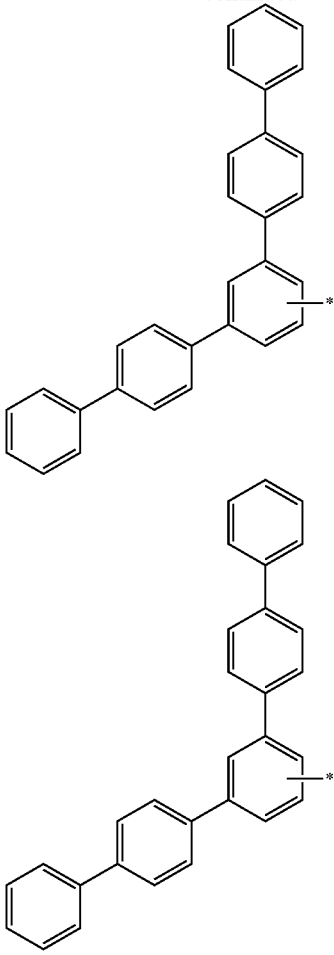
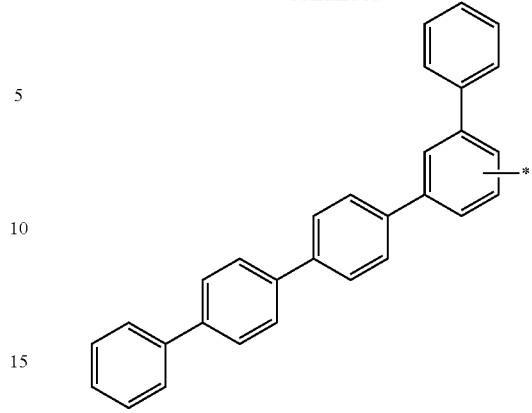

In Group 5, * indicates a linking point, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The second compound for an organic optoelectric device represented by Chemical Formula II-B may be compounds of Group 6, but is not limited thereto. In Group 6, heteroatom of the compounds is "N".

[Group 6]

[6-1]

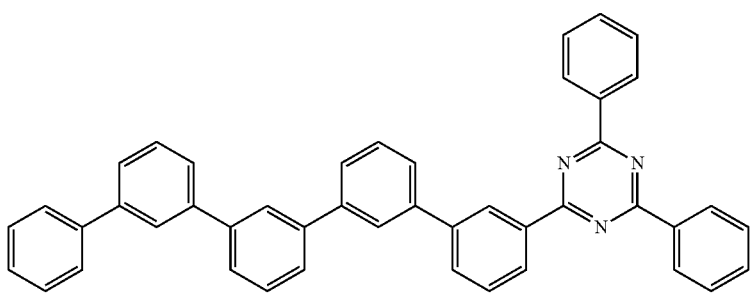

[6-2]

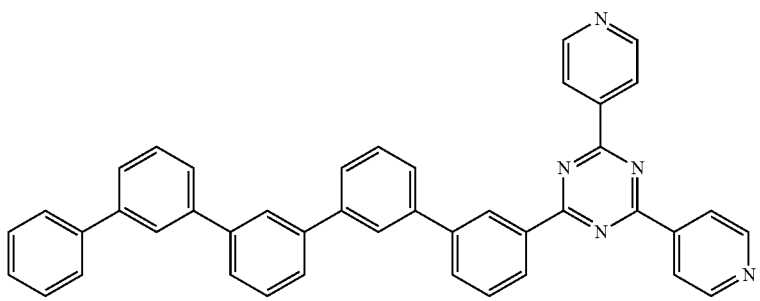

[6-3]
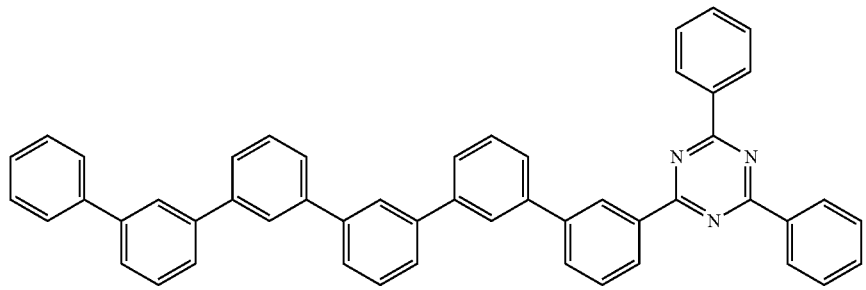
[6-4]
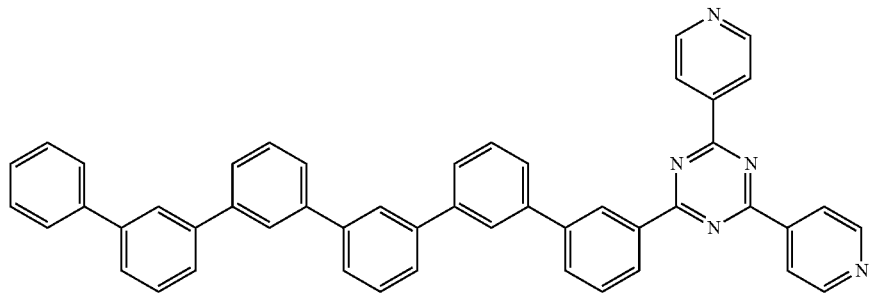
[6-5] [6-6]
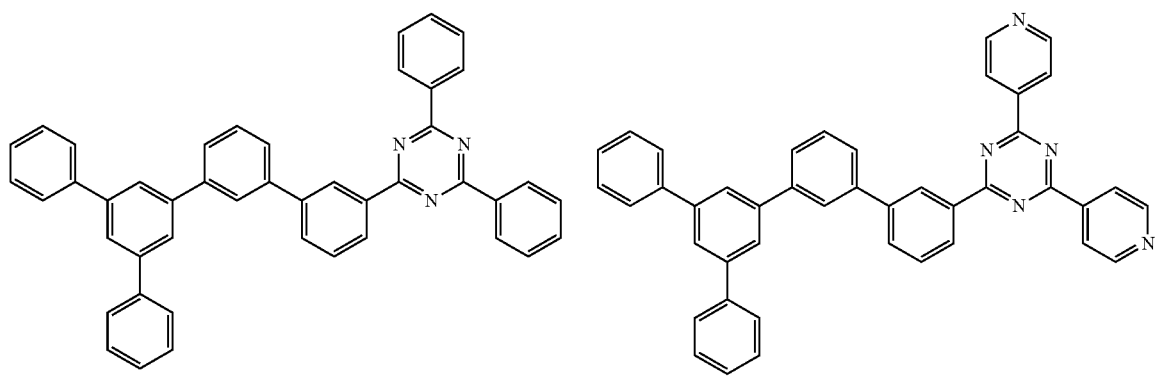
[6-7]
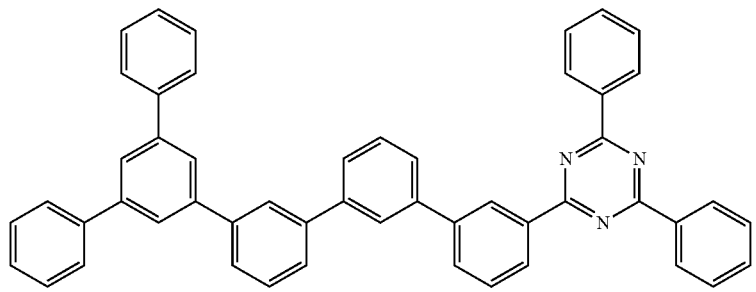
[6-8]
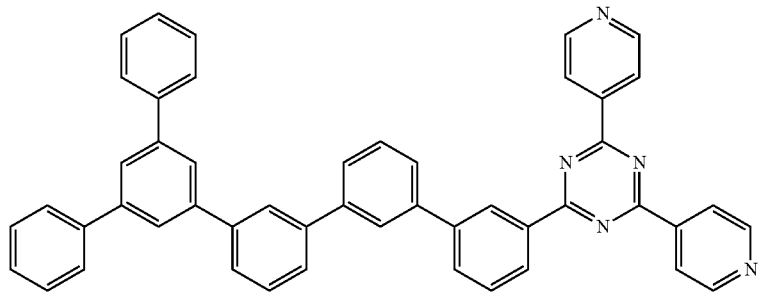

-continued
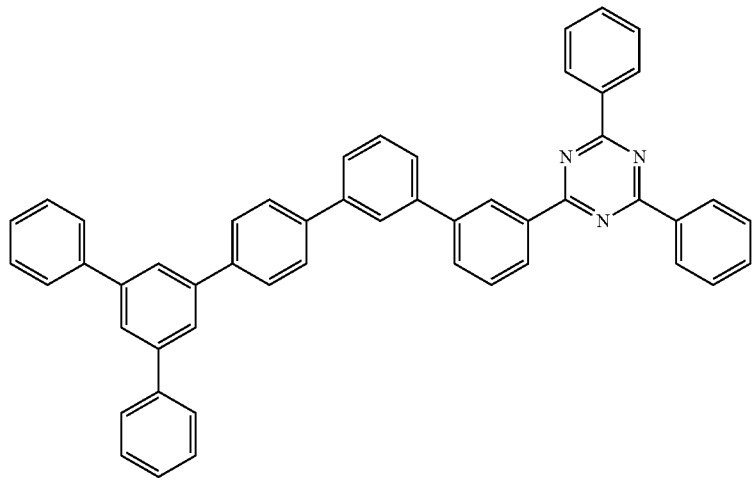
[6-9]
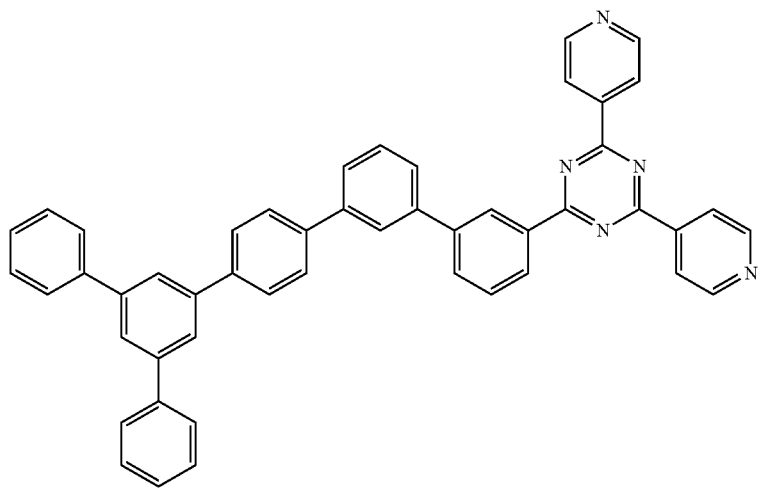
[6-10]
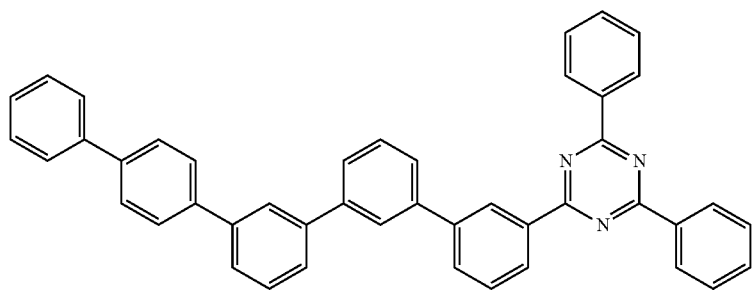
[6-11]
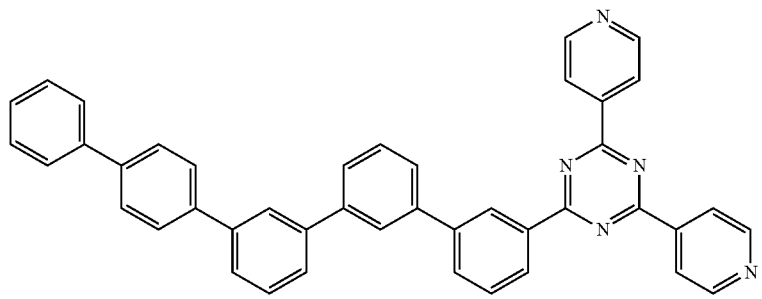
[6-12]

-continued
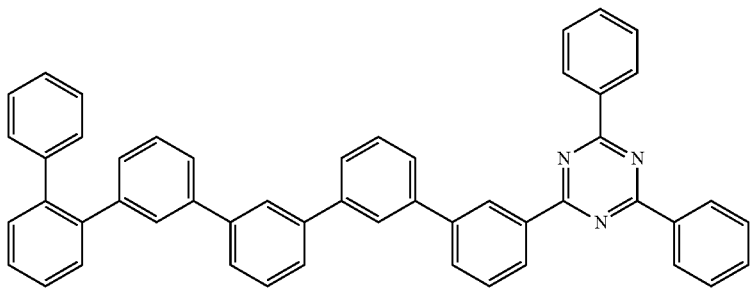
[6-13]
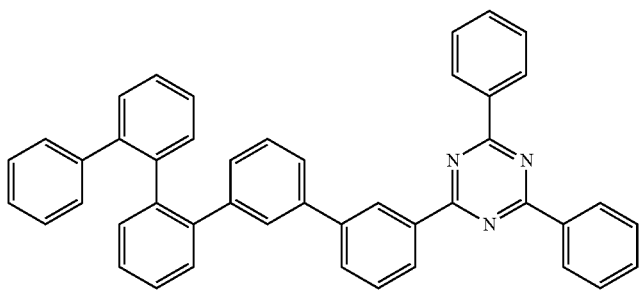
[6-14]
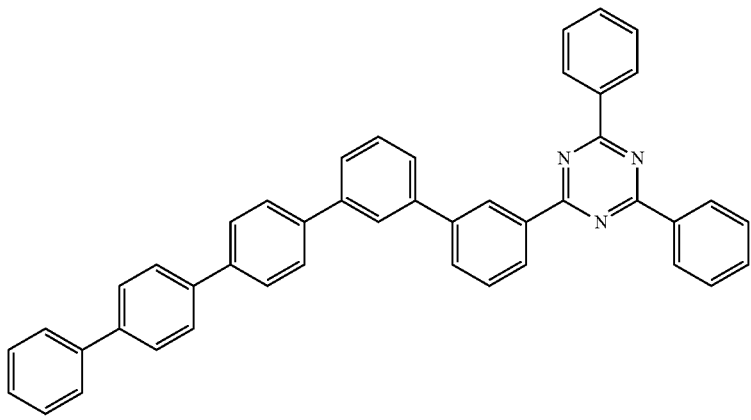
[6-15]
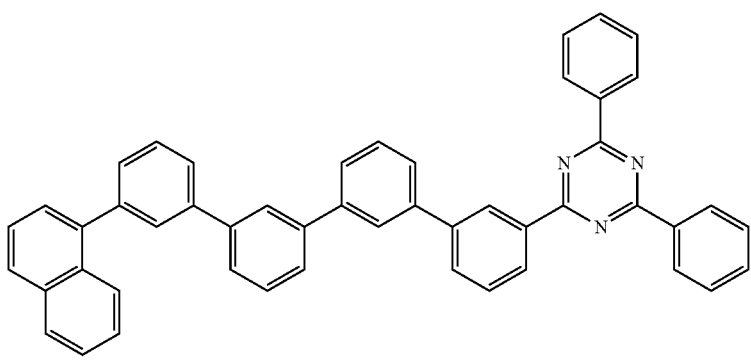
[6-16]

[6-17]

[6-18]

[6-19]

[6-20]

[6-21]

[6-22]
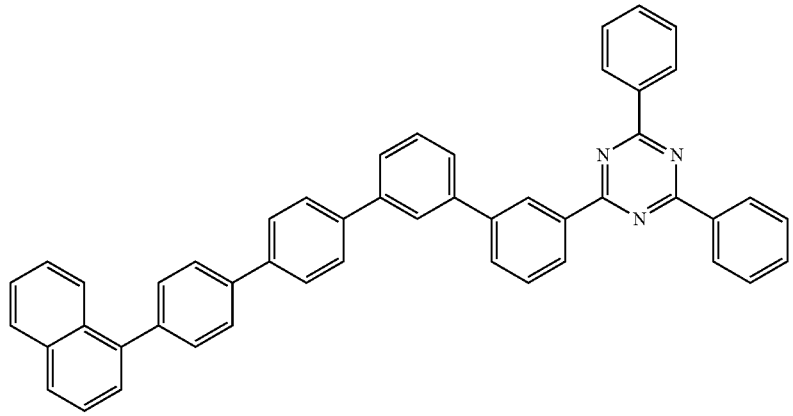
[6-23]
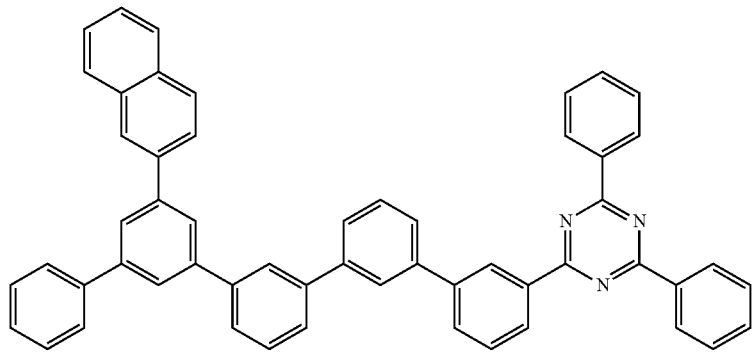
[6-24]
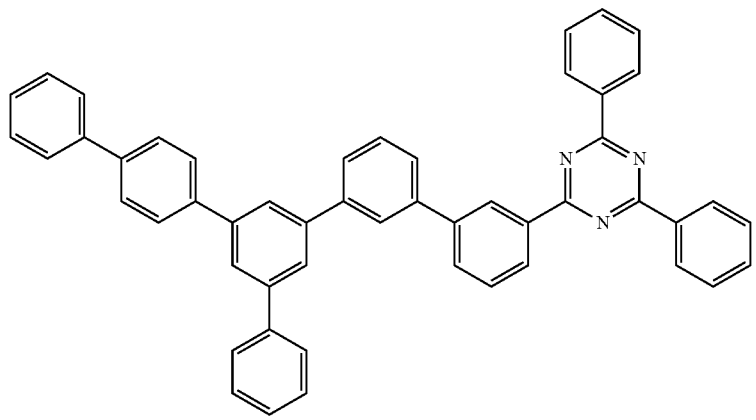
[6-25]
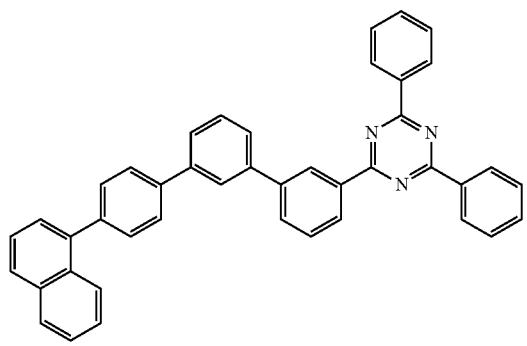
[6-26]
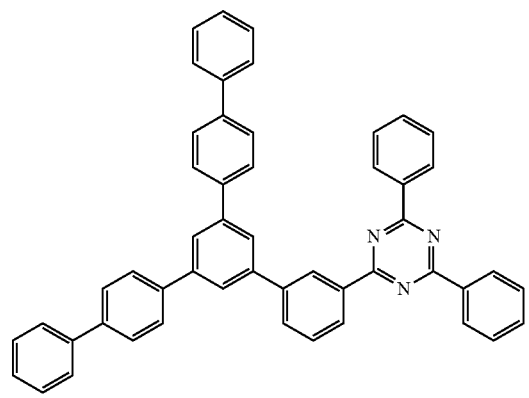

-continued
[6-27]
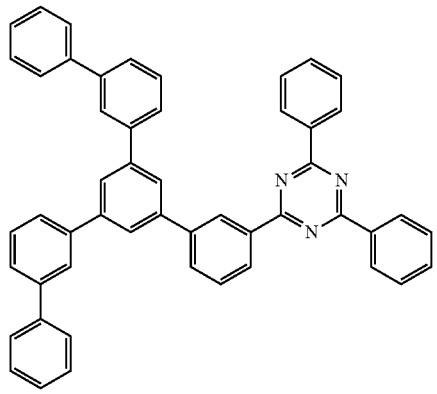
[6-28]
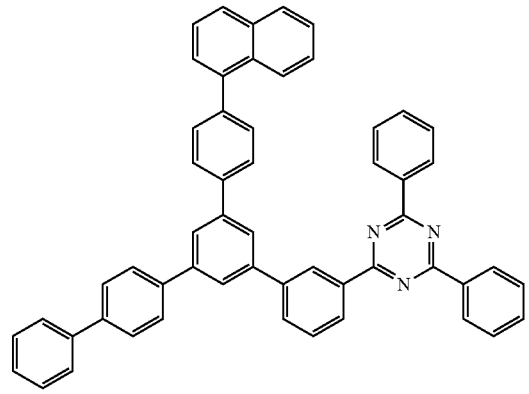
[6-29]
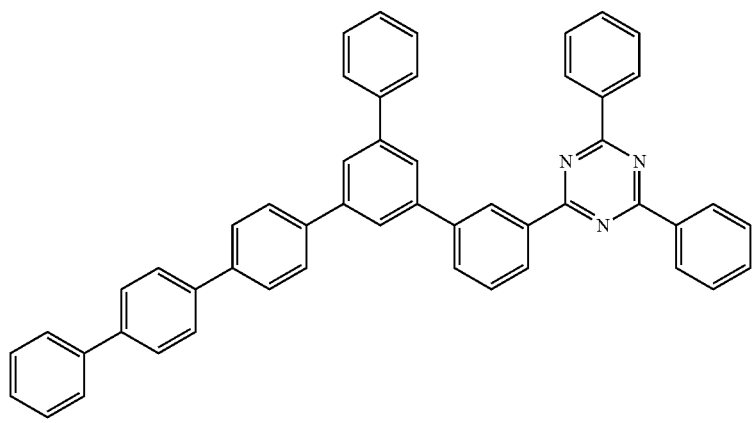
[6-30]
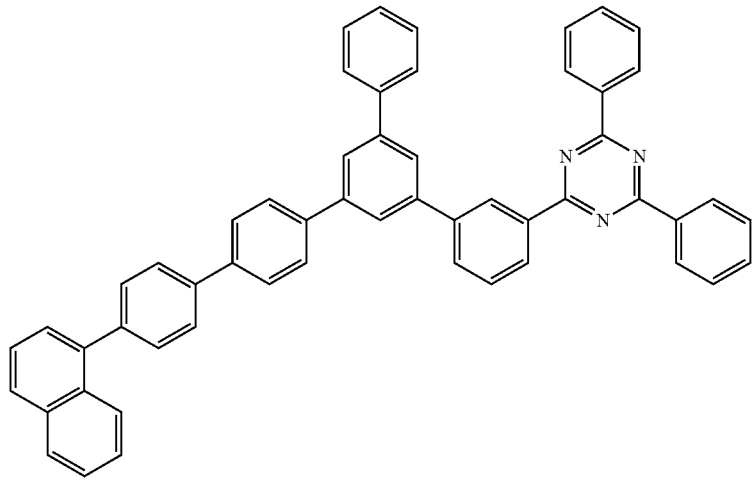
[6-31]
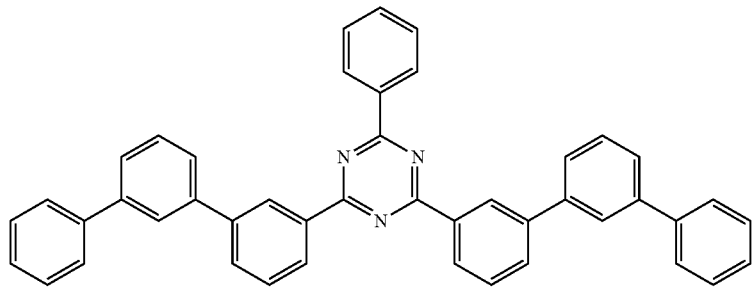

-continued
[6-32]
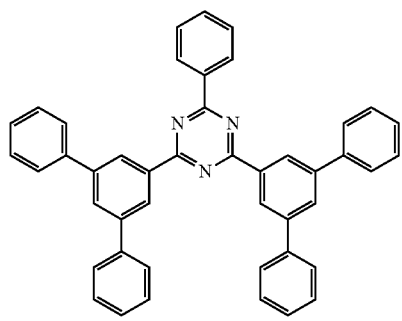
[6-33]
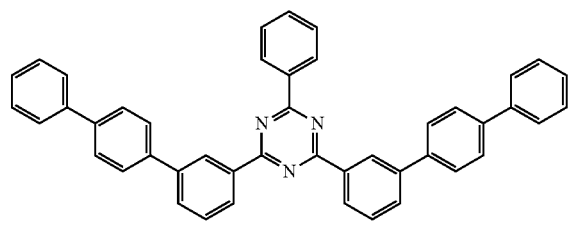
[6-34]
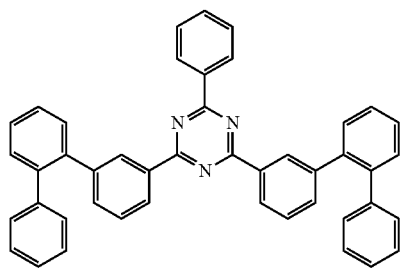
[6-35]
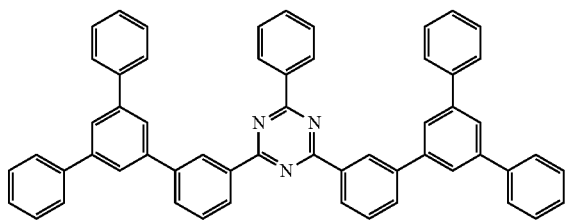
[6-36]
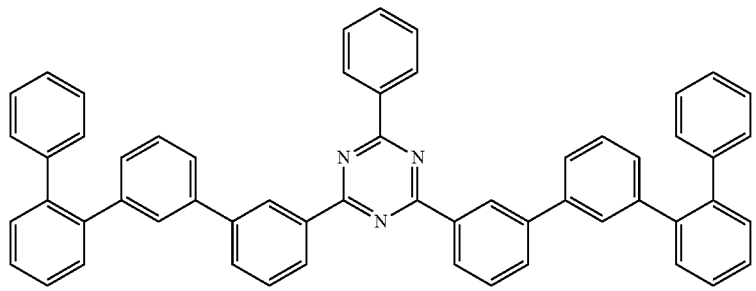
[6-37]
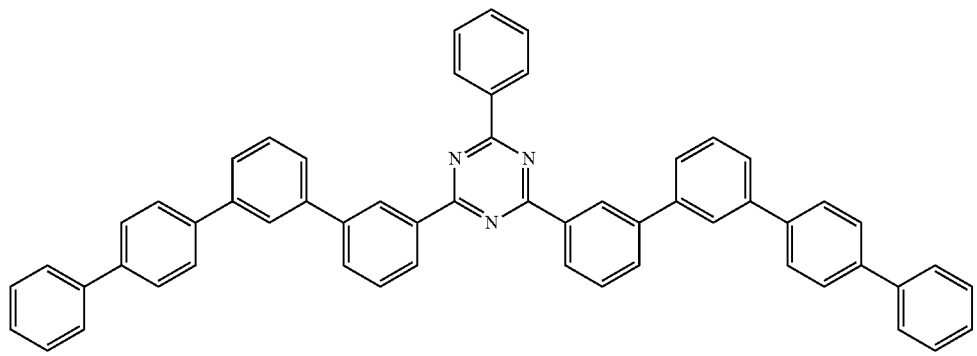

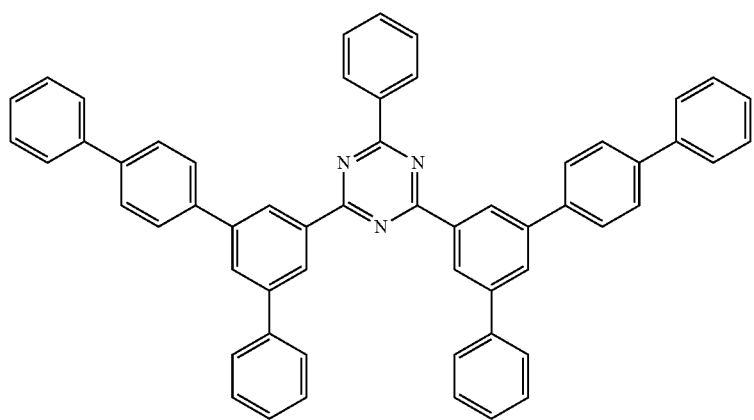
[6-38]
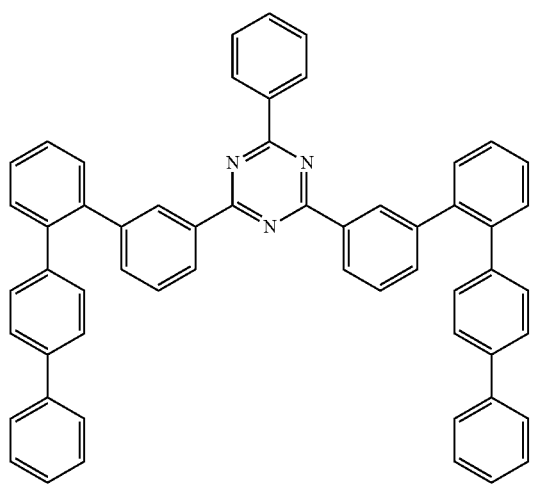
[6-39]
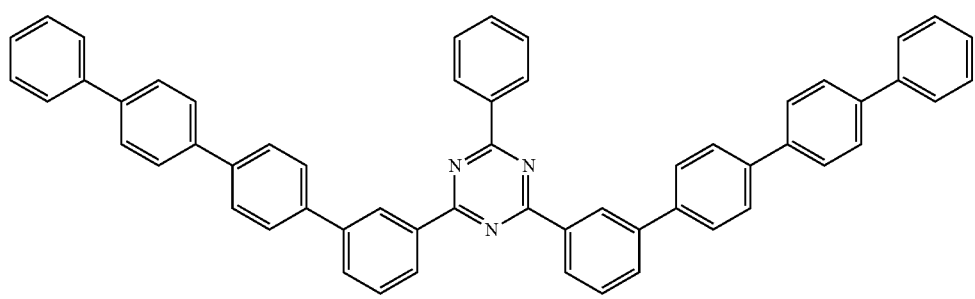
[6-40]

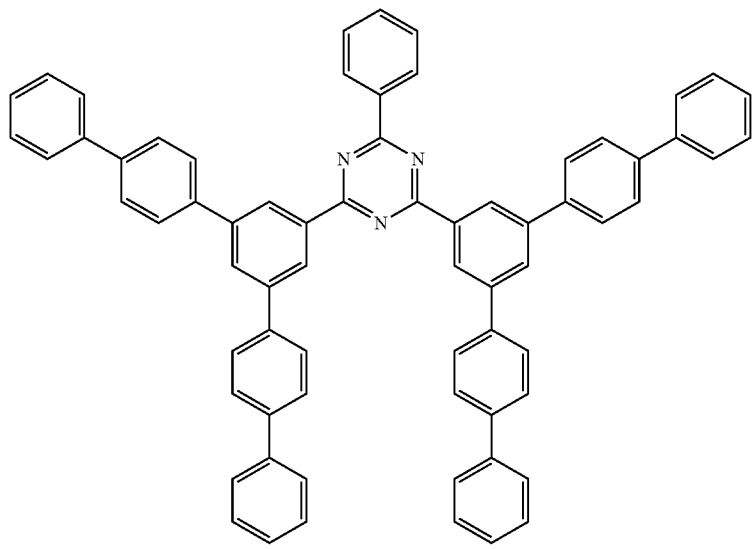
[6-41]
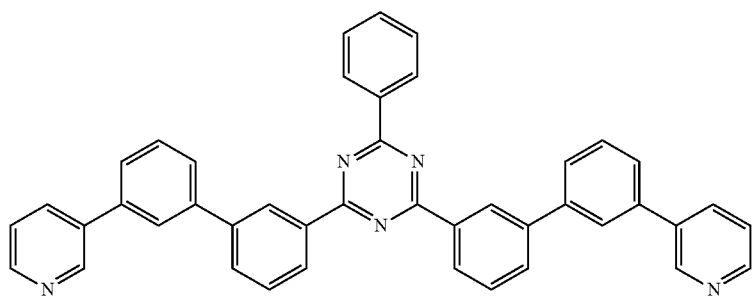
[6-42]
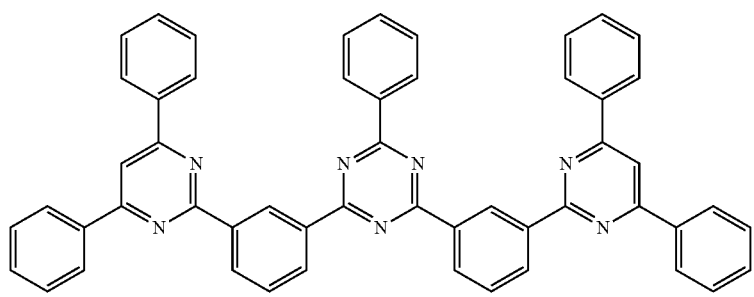
[6-43]
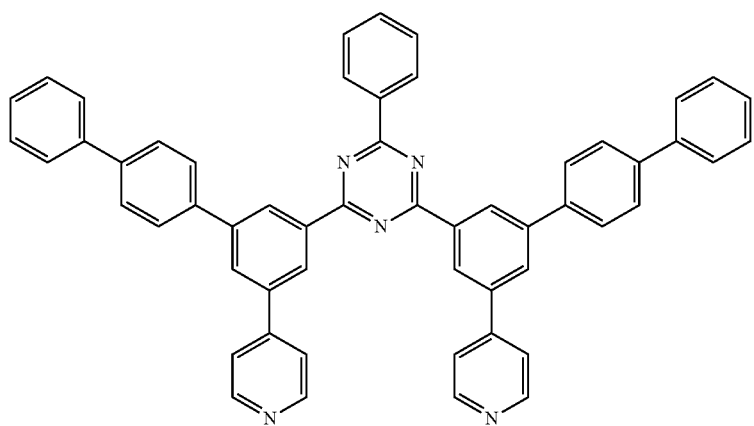
[6-44]

[6-45]
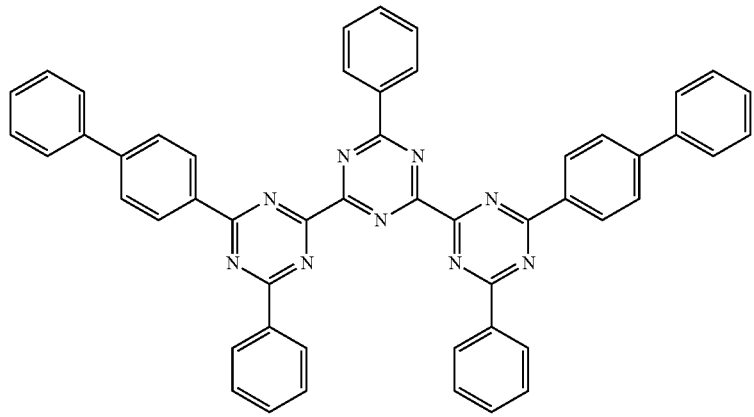
[6-46]
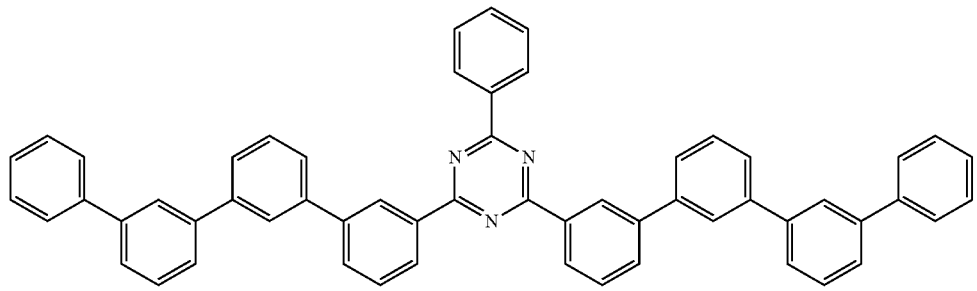
[6-47]
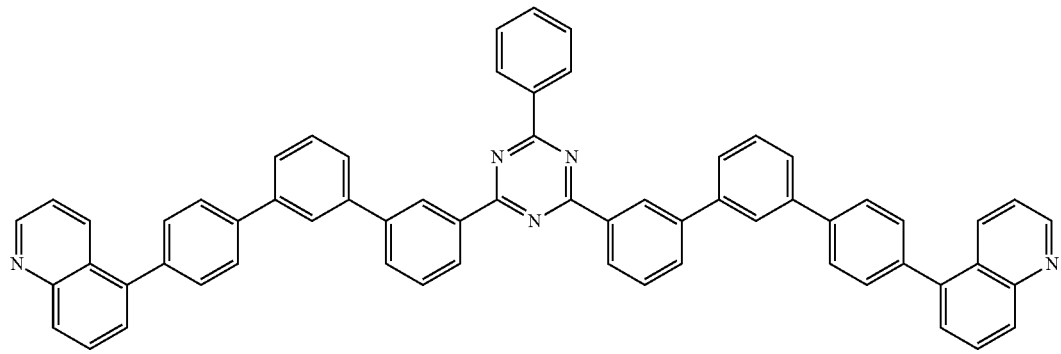
[6-48]
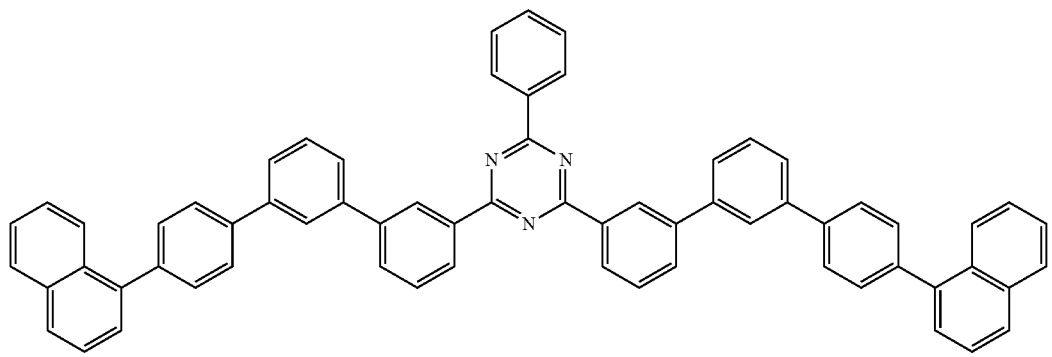

-continued
[6-49]
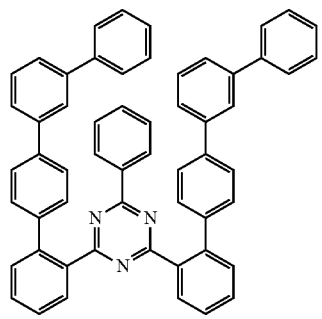
[6-50]
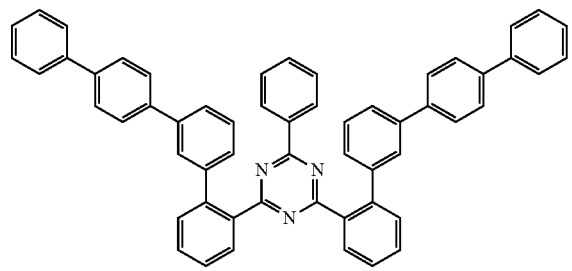
[6-51]
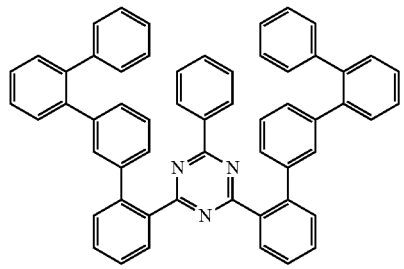
[6-52]
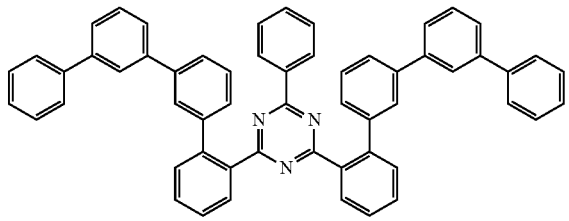
[6-53]
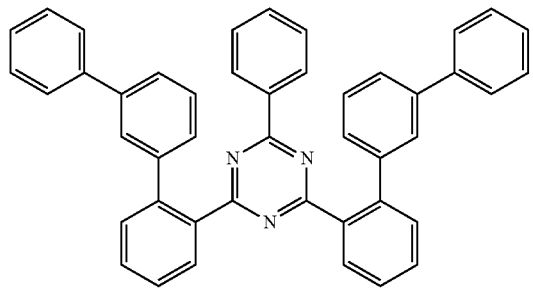
[6-54]
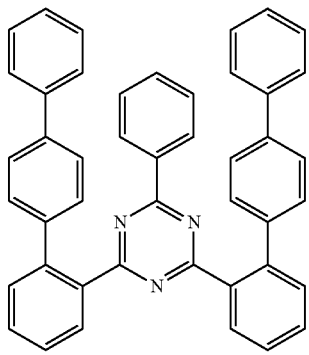
[6-55]
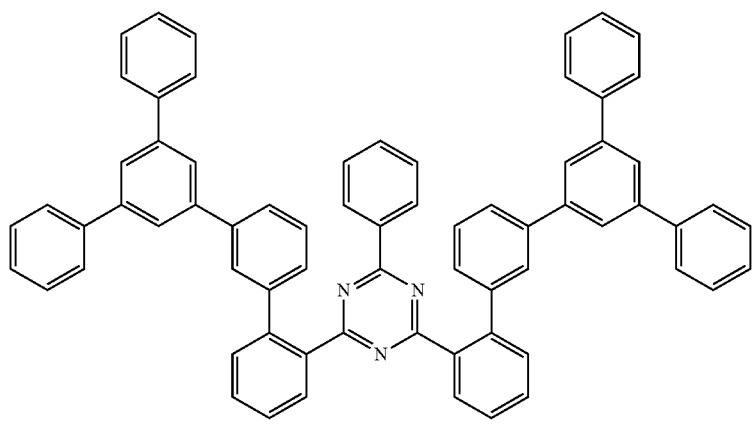

[6-56]
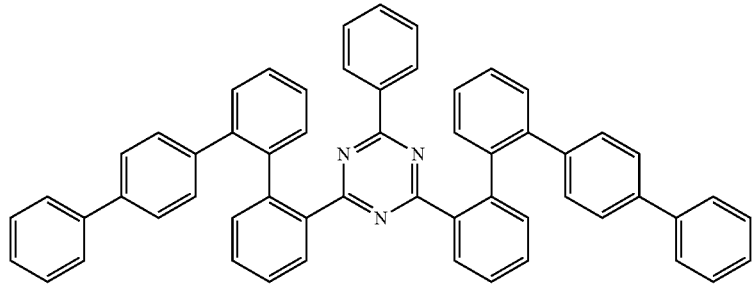
[6-57]
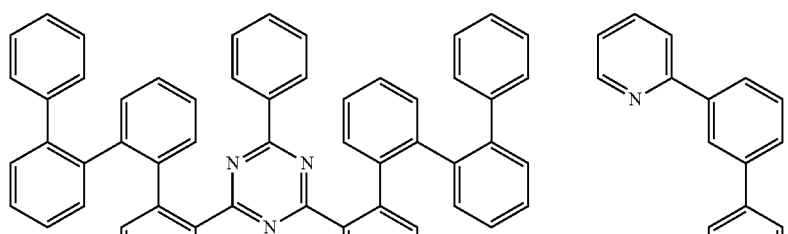
[6-58]
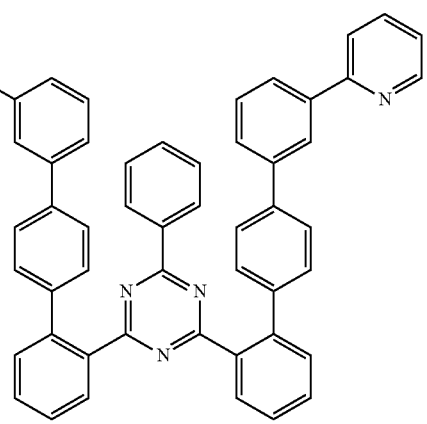
[6-59]
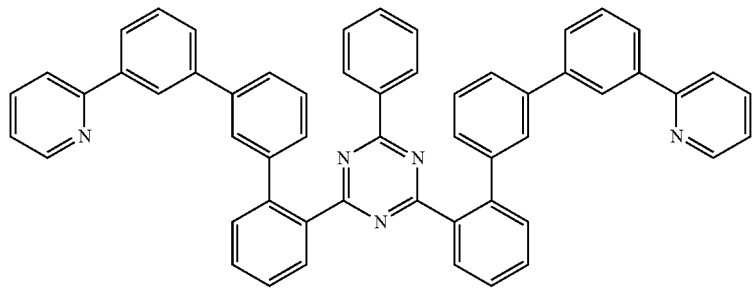
[6-60]
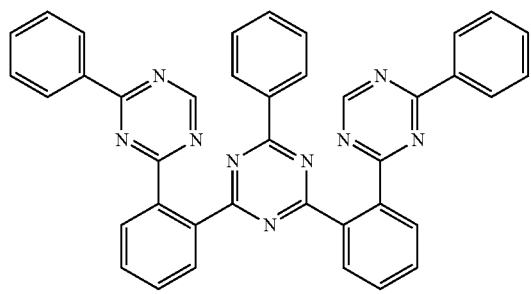
[6-61]
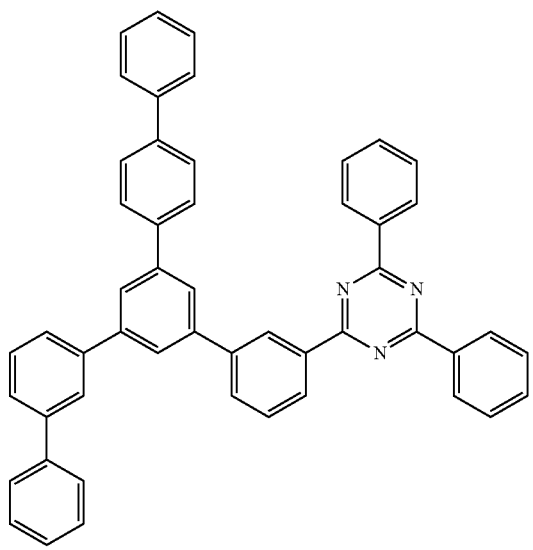

-continued
[6-62]
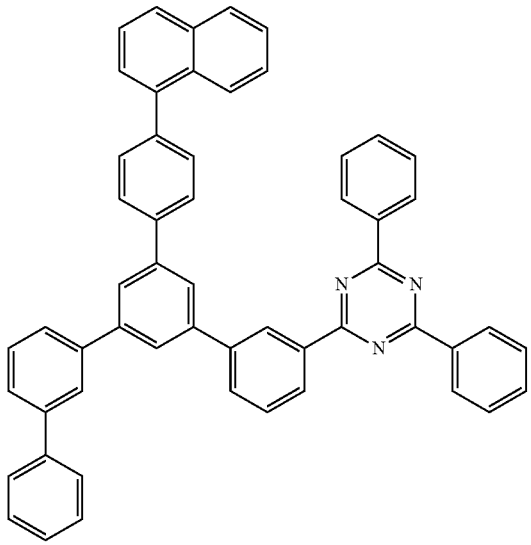
[6-63]
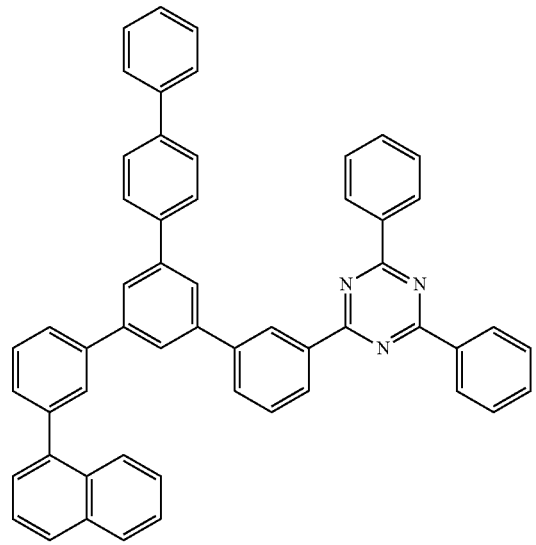
[6-64]
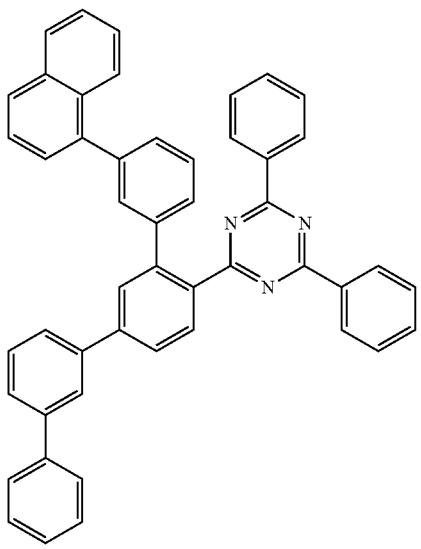
[6-65]
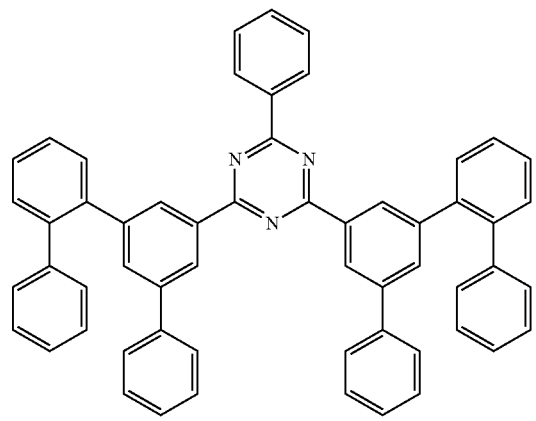
[6-66]
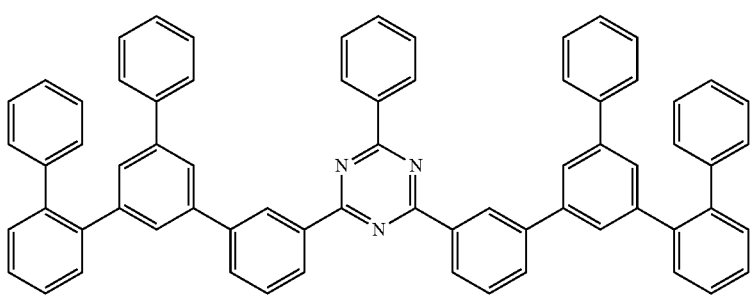

-continued
[6-67]
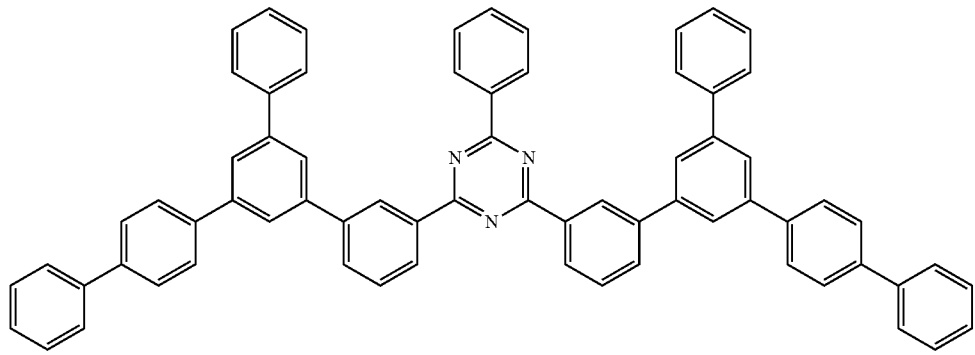
[6-68]
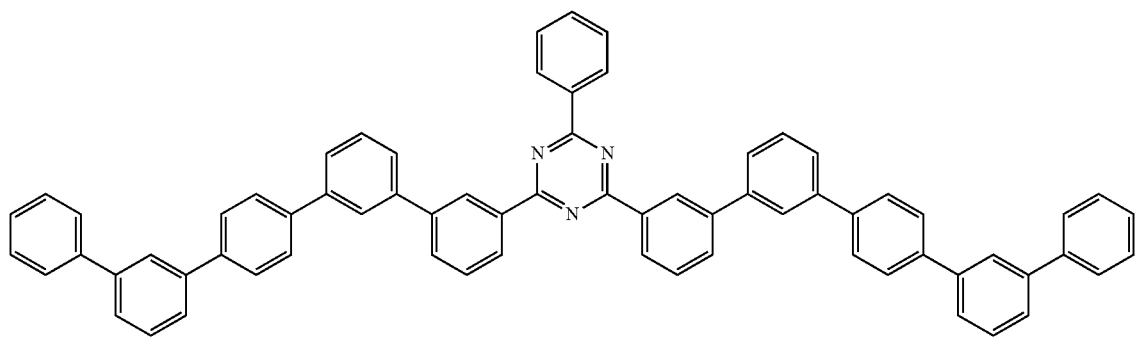
[6-69]
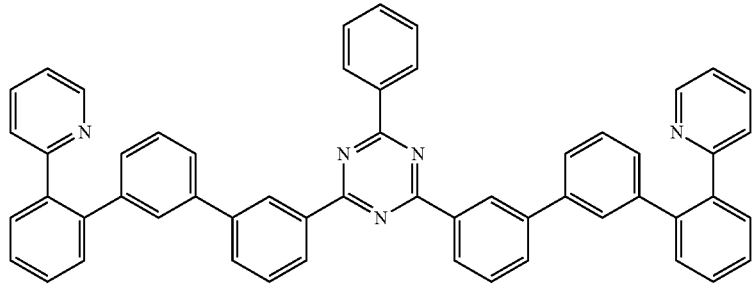
[6-70]
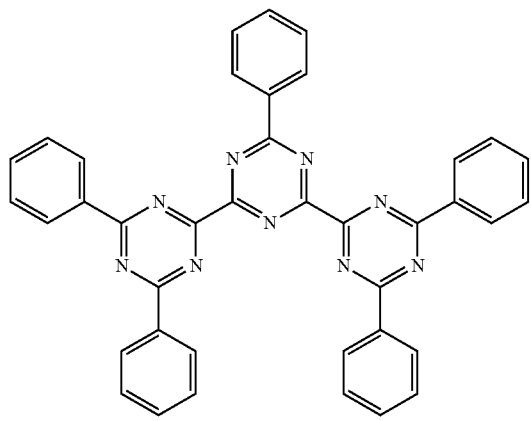

[6-71]
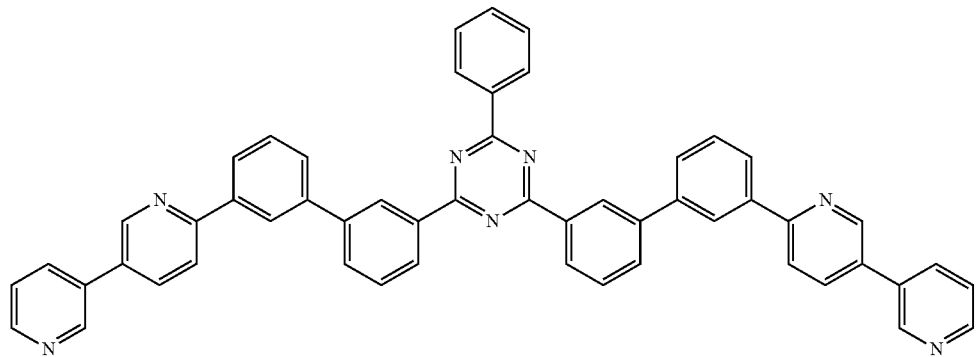
[6-72]
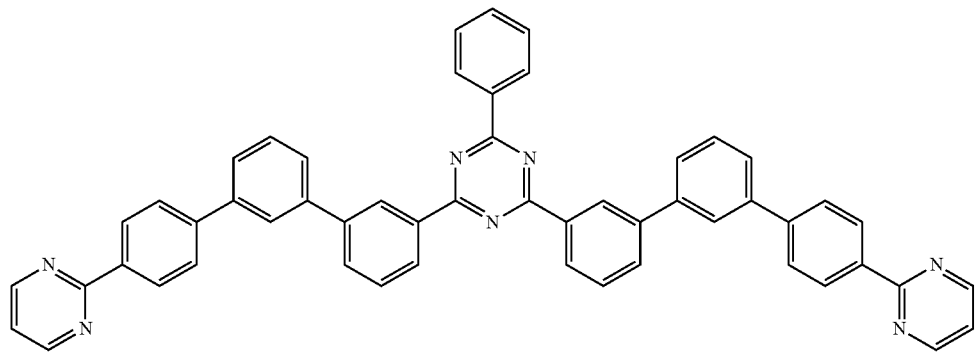
[6-73]
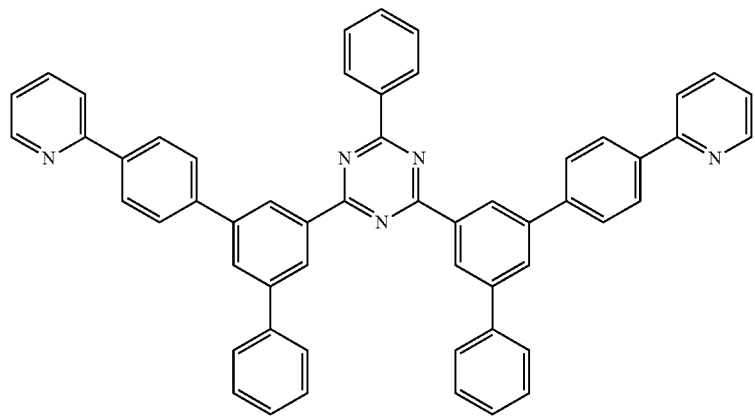
[6-74]
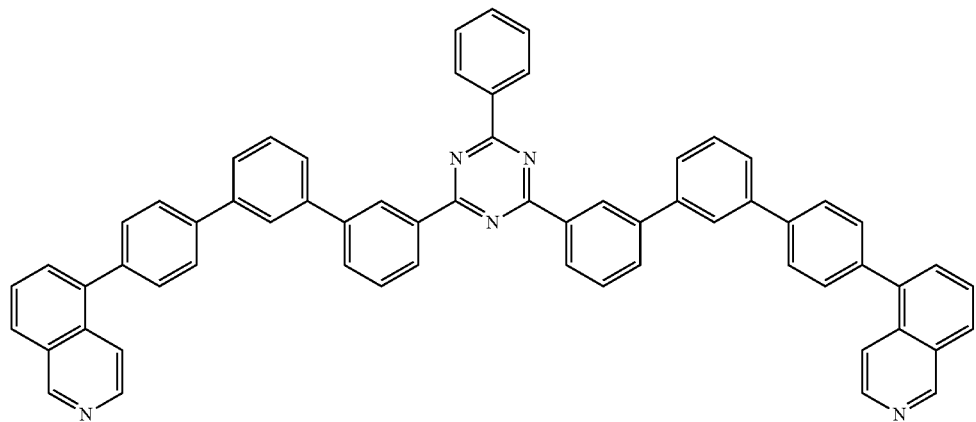

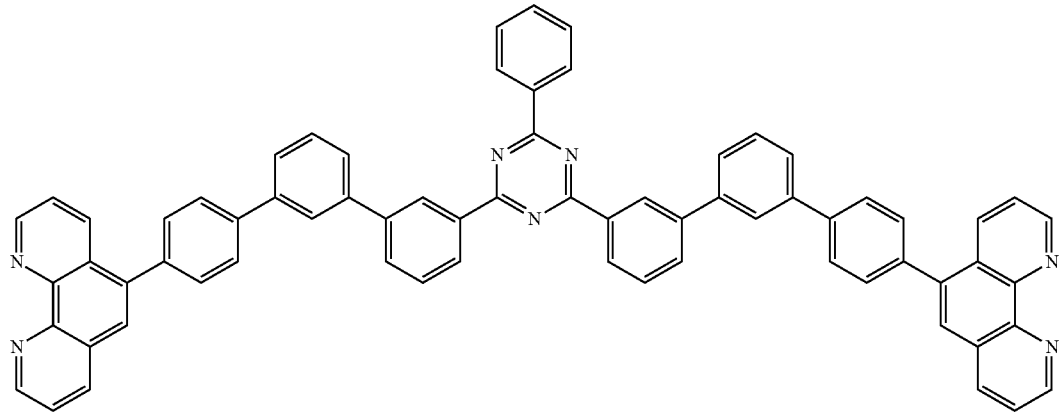
[6-75]
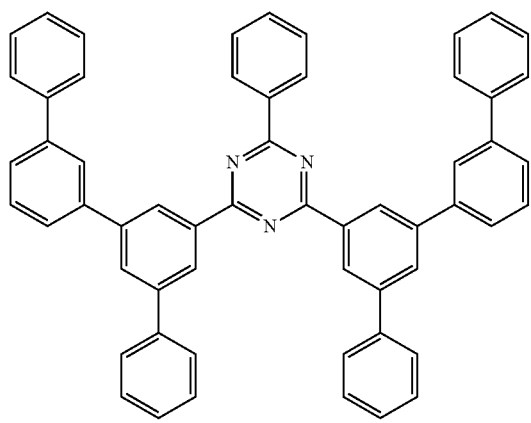
[6-76]
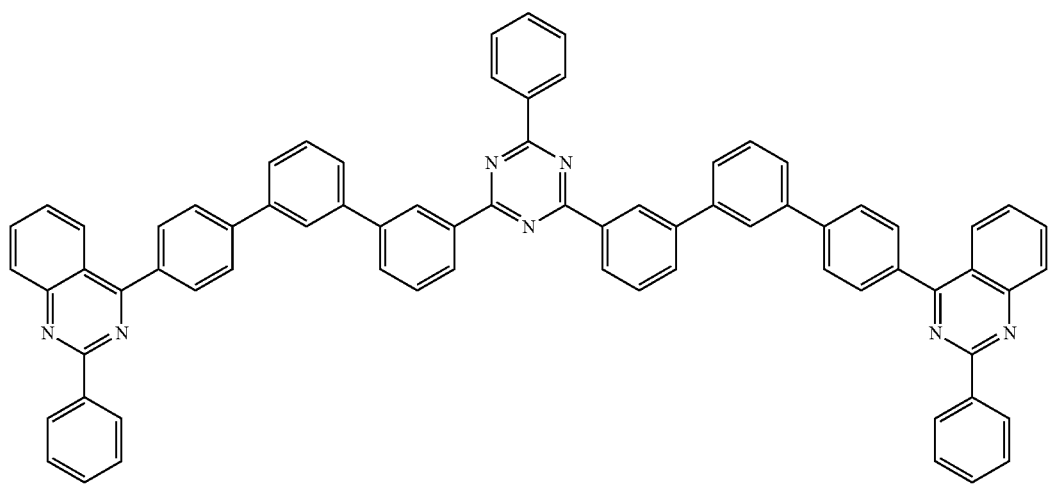
[6-77]

[6-78]
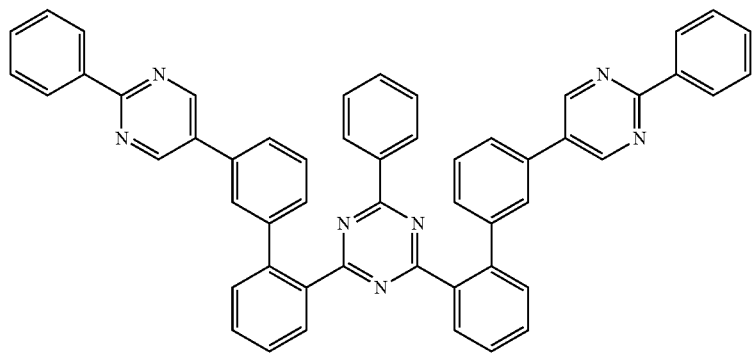
[6-79]
[6-80]
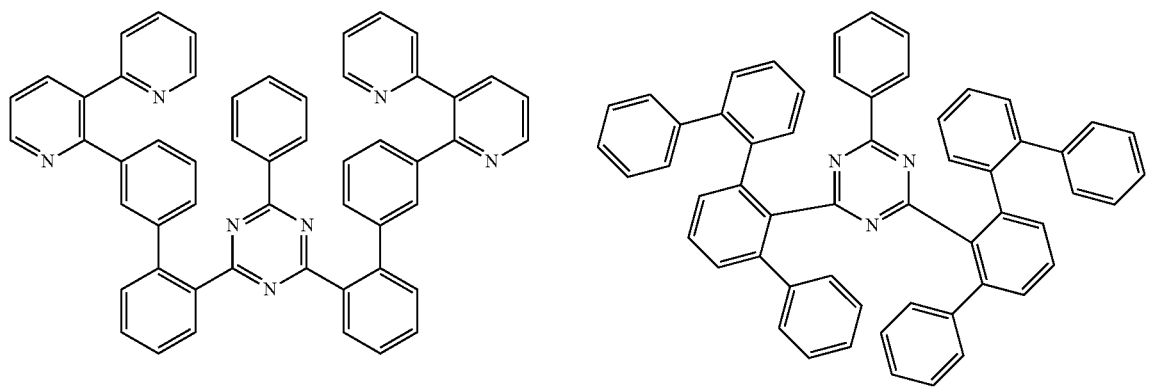
[6-81]
[6-82]
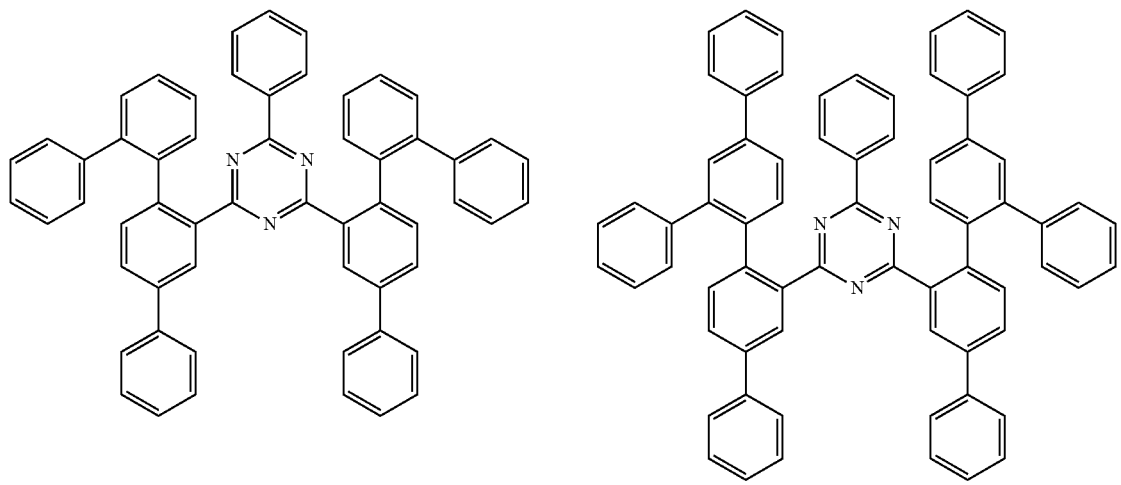

111
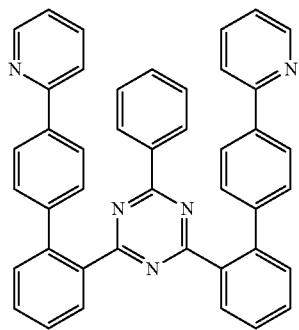
[6-83]
112
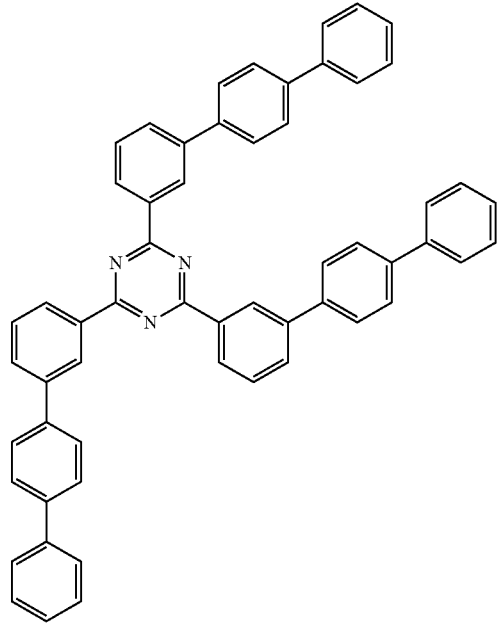
[6-84]
[6-85]
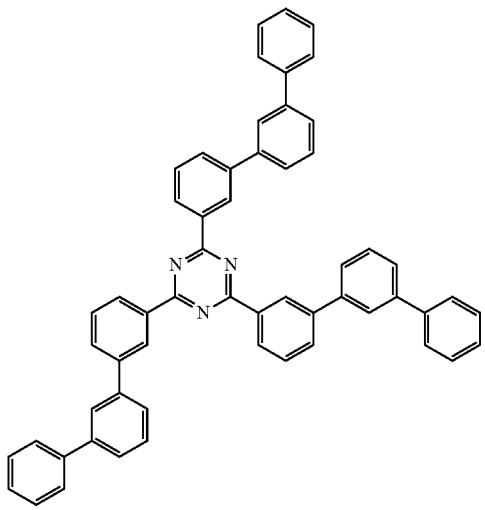
[6-86]
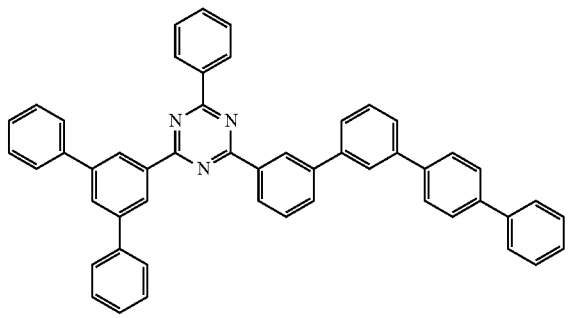
[6-87]
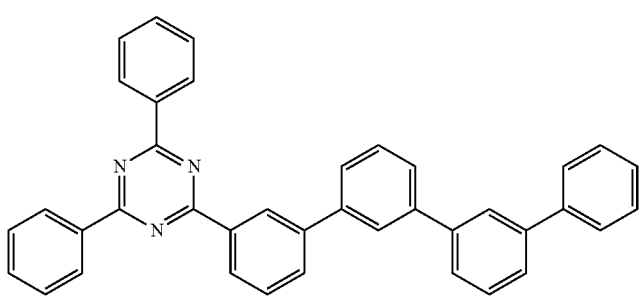

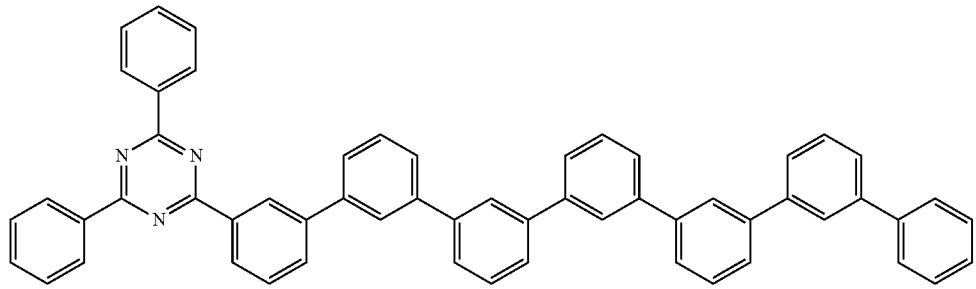
[6-88]
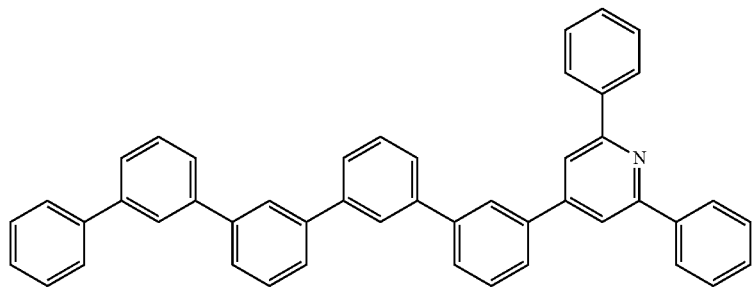
[6-89]
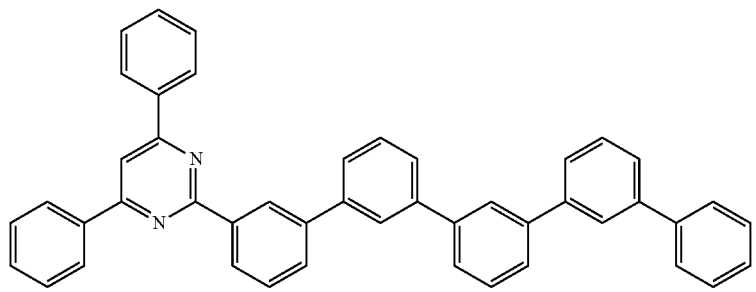
[6-90]
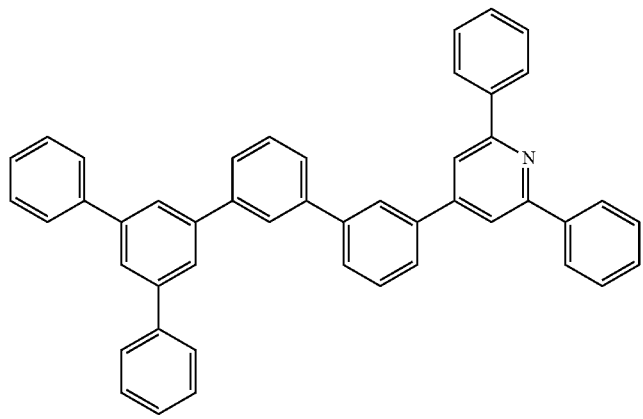
[6-91]
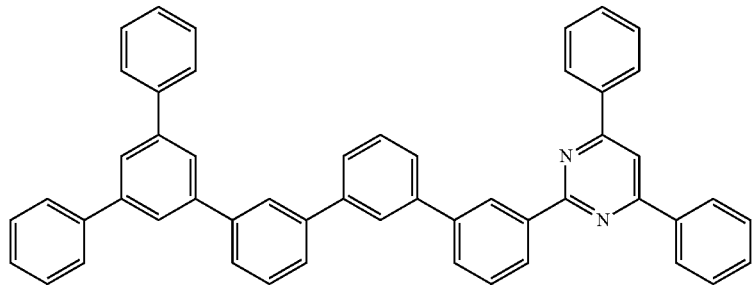
[6-92]

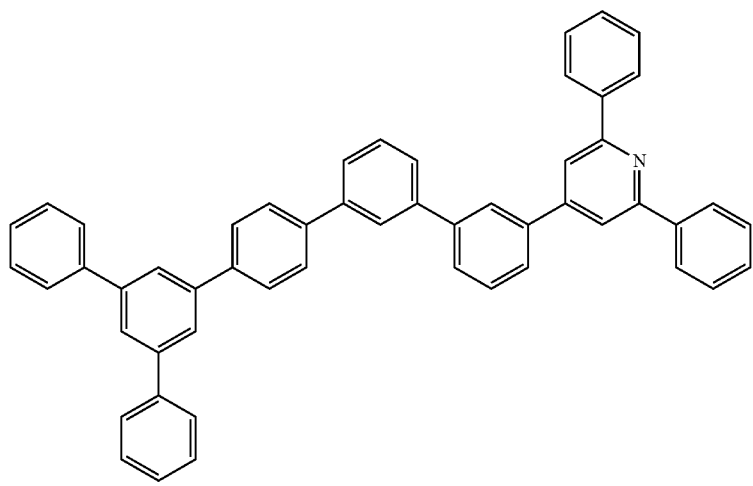
[6-93]
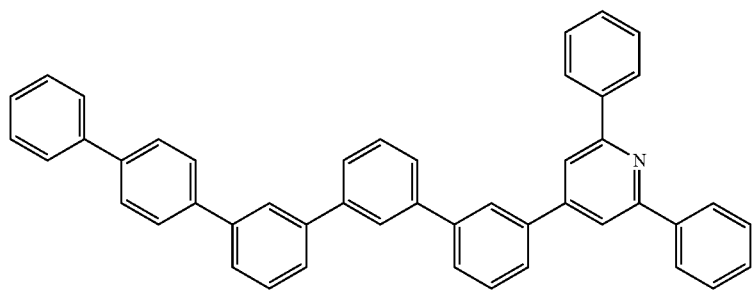
[6-94]
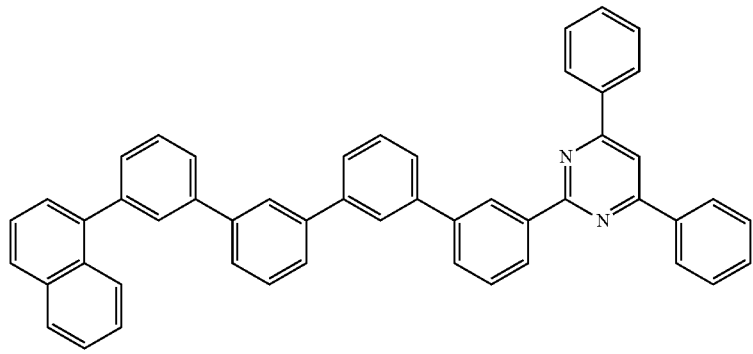
[6-95]
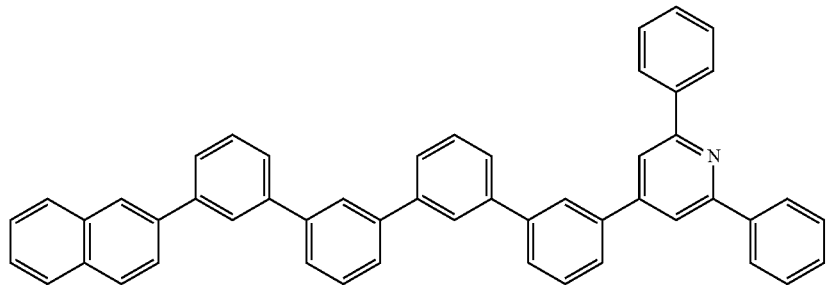
[6-96]

-continued
[6-97]
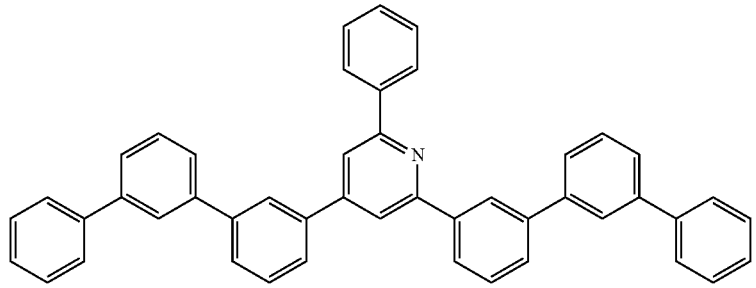
[6-98]
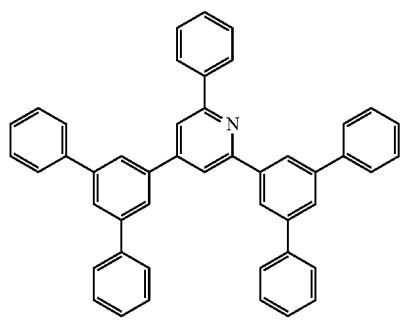
[6-99]
[6-100]
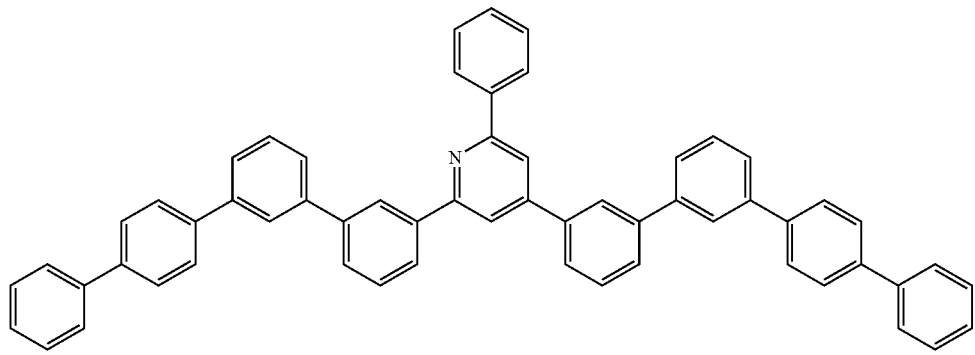
[6-101]
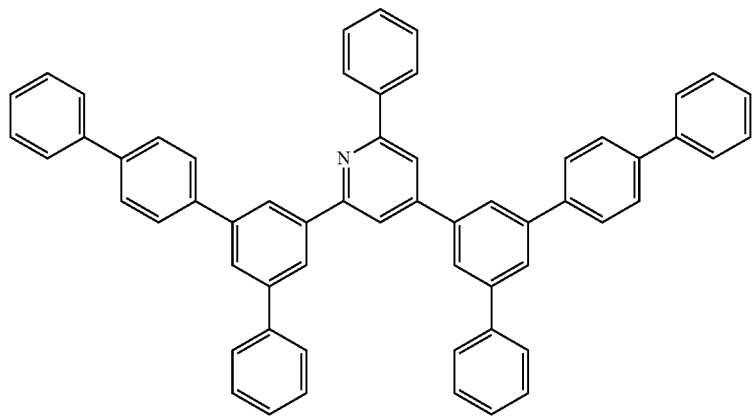

-continued
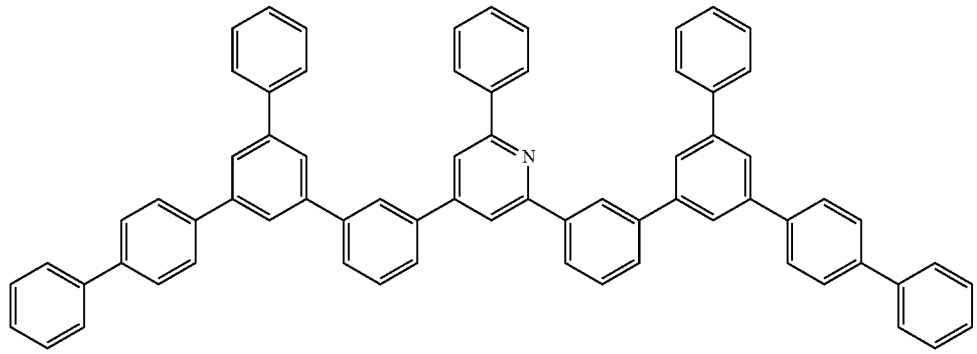
[6-102]
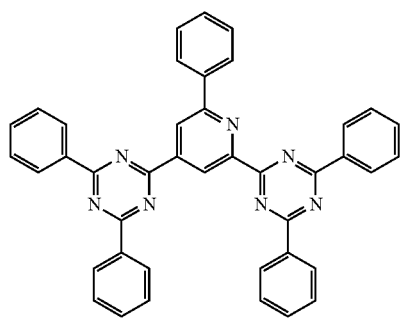
[6-103]
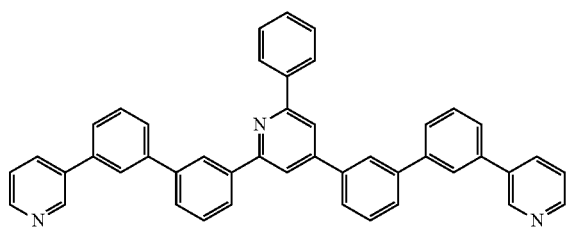
[6-104]
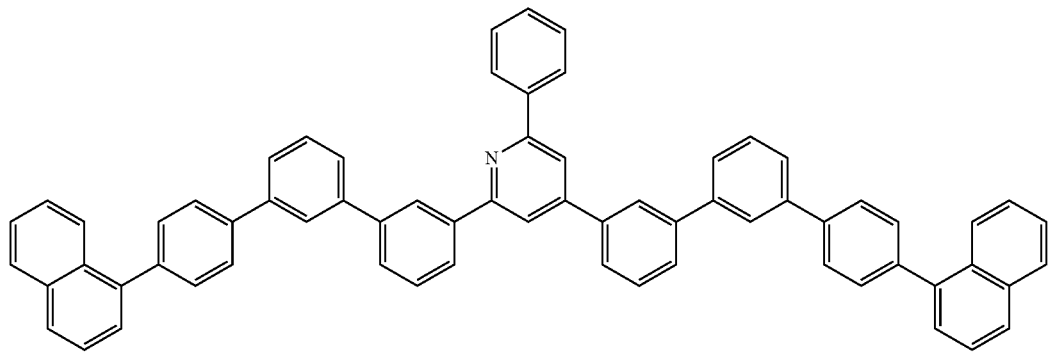
[6-105]
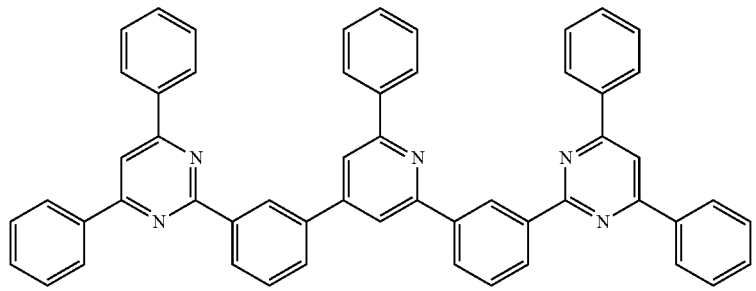
[6-106]
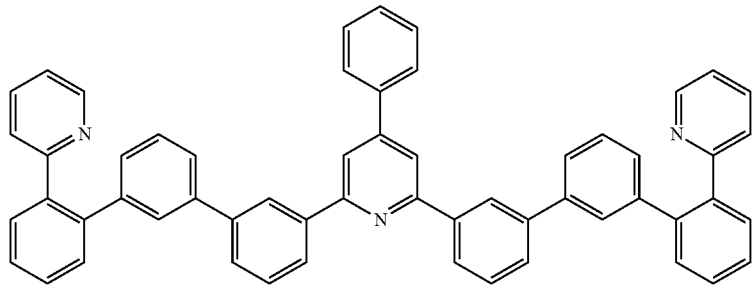
[6-107]

-continued
[6-108]
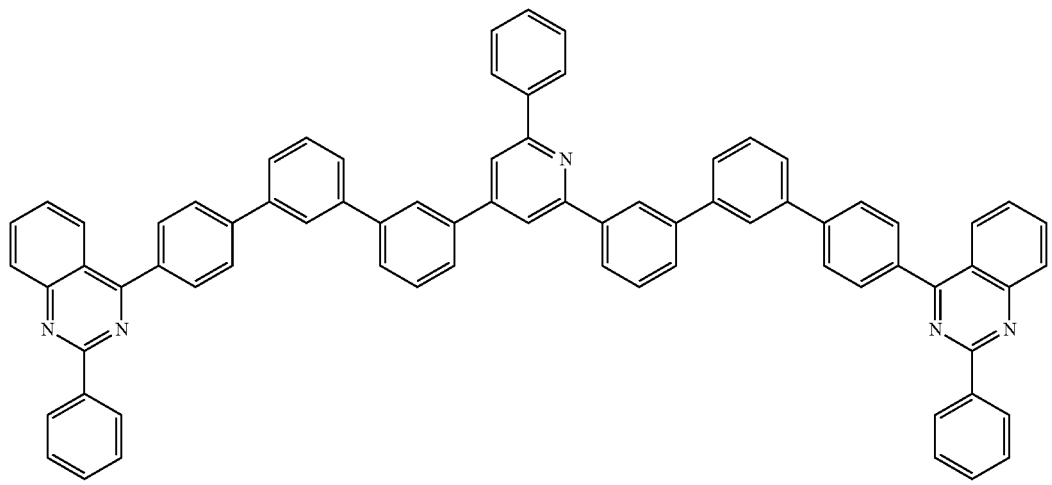
[6-109]
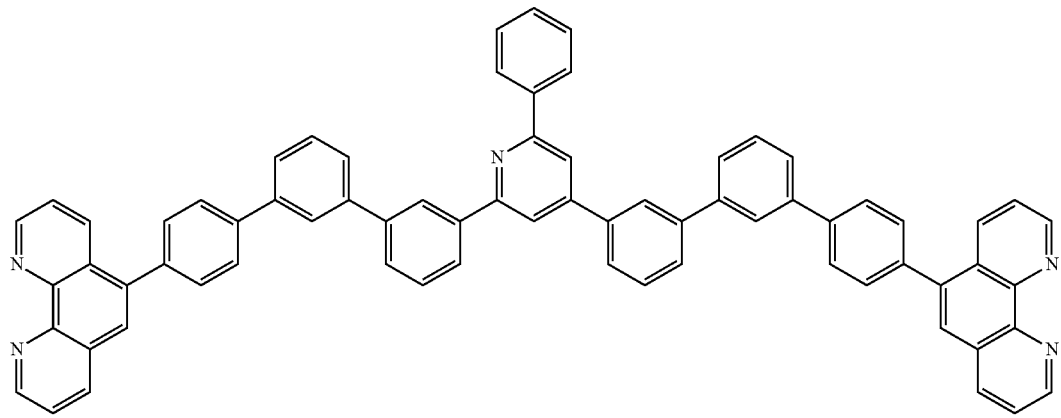
[6-110]
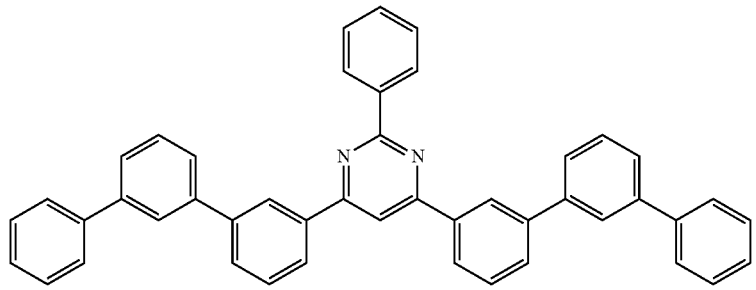
[6-111]
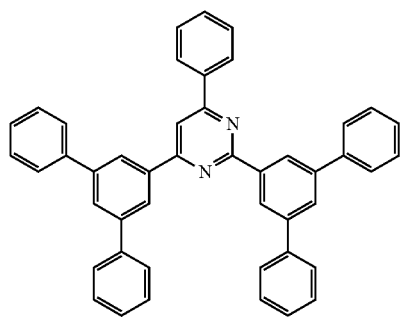
[6-112]
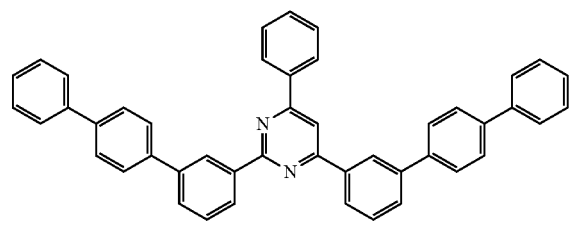

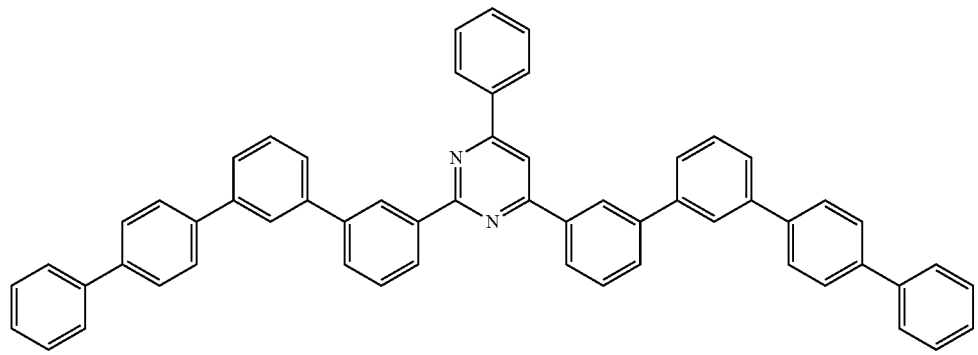
[6-113]
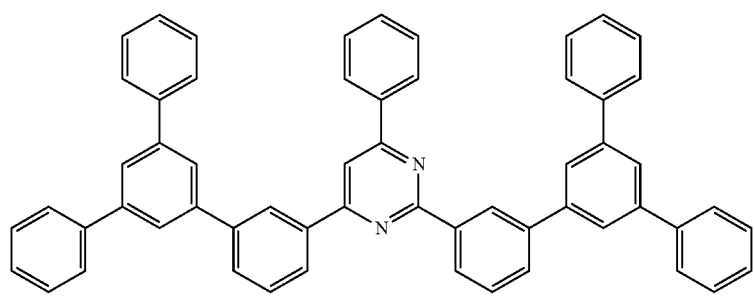
[6-114]
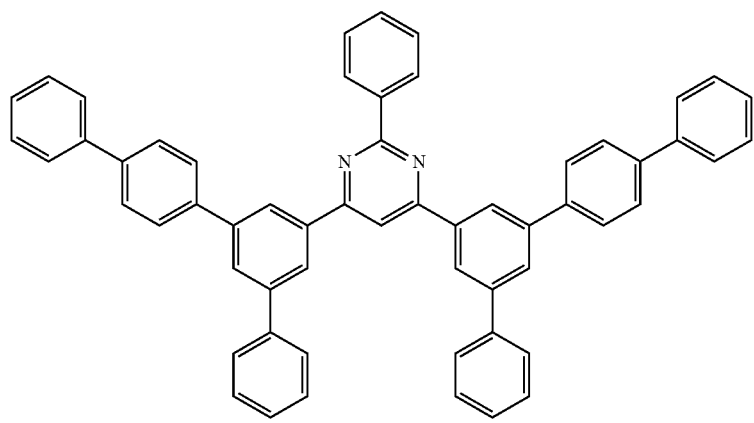
[6-115]
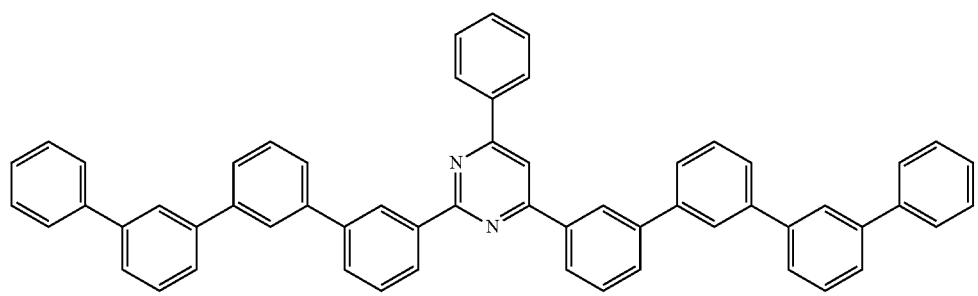
[6-116]

-continued
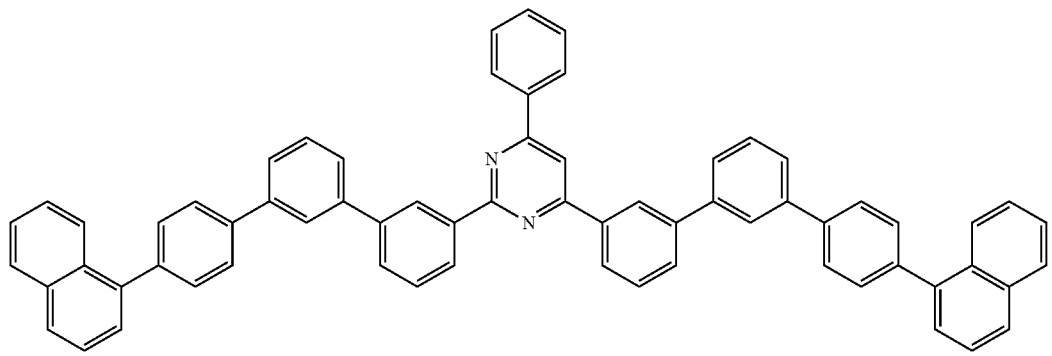
[6-117]
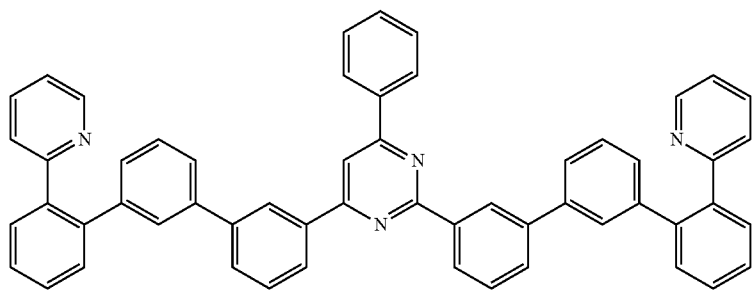
[6-118]
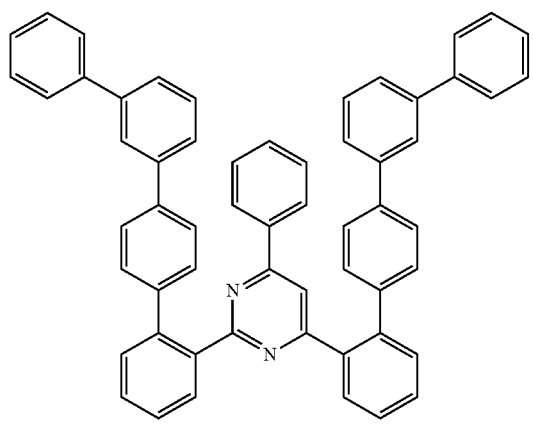
[6-119]
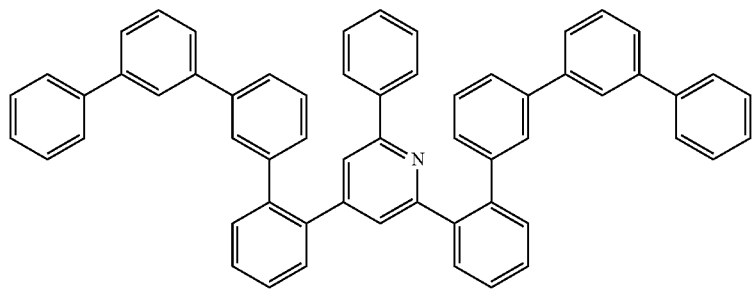
[6-120]

-continued
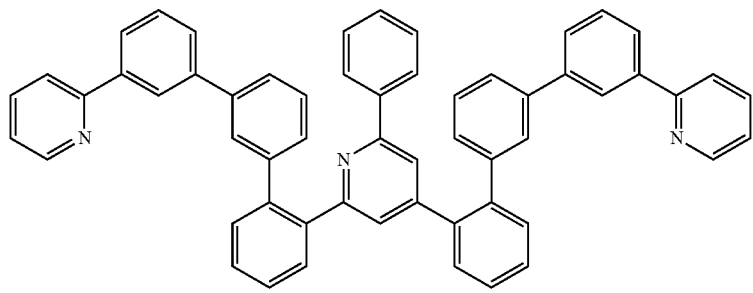
[6-121]
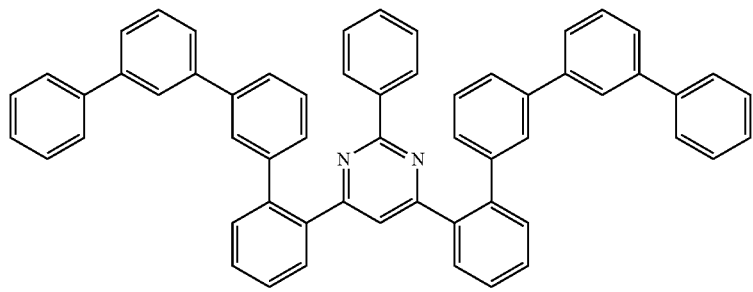
[6-122]
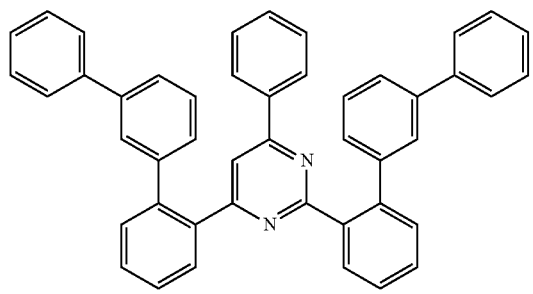
[6-123]
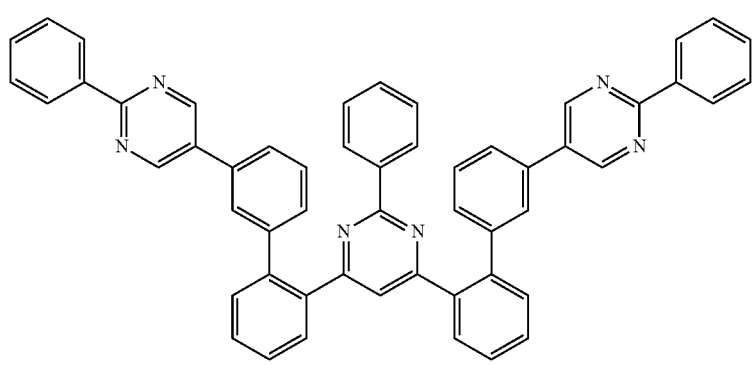
[6-124]
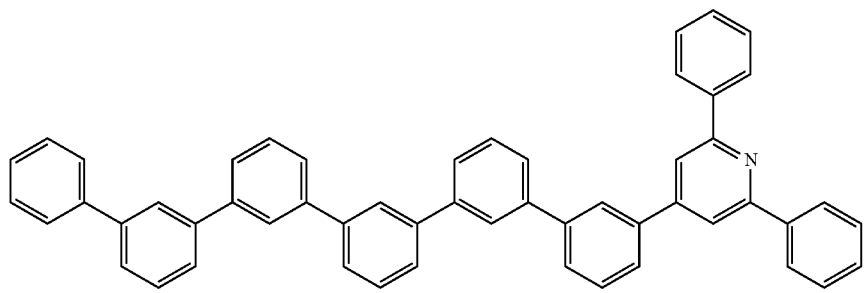
[6-125]

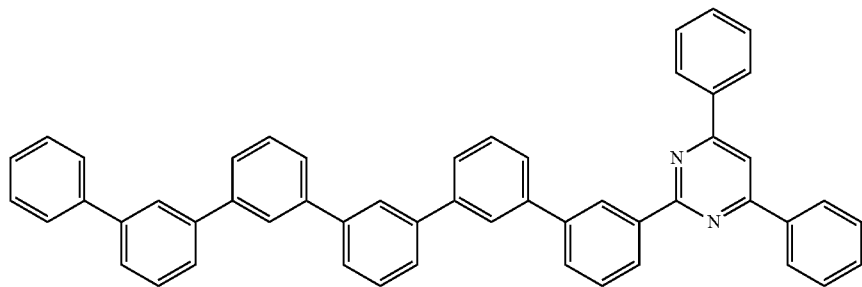
[6-126]
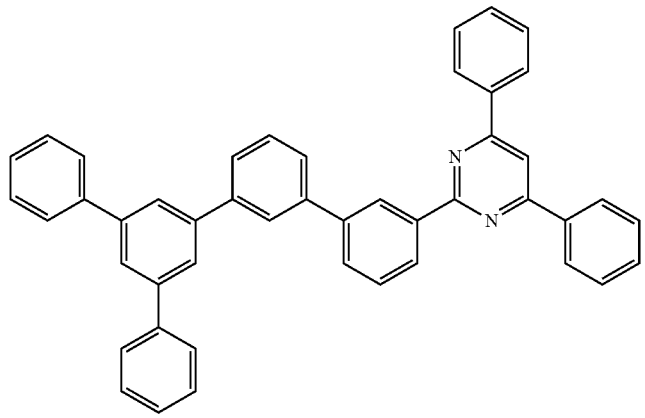
[6-127]
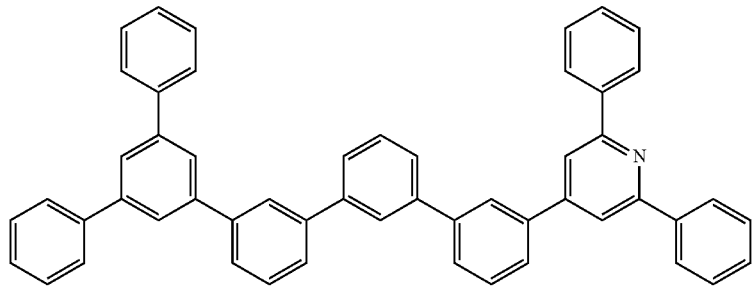
[6-128]
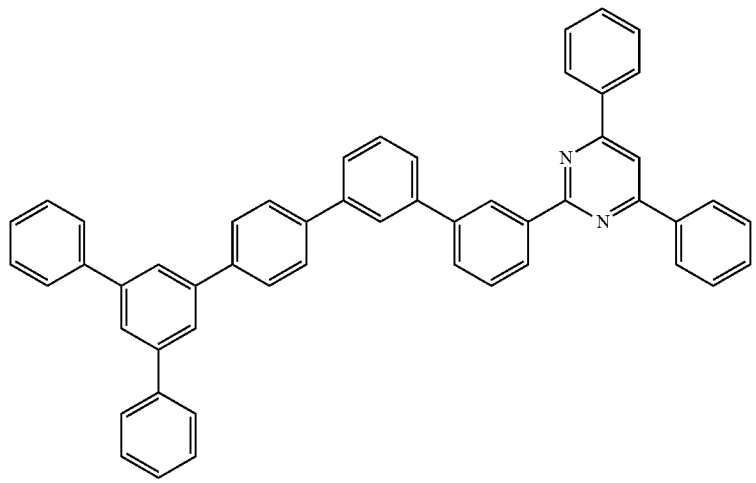
[6-129]

-continued
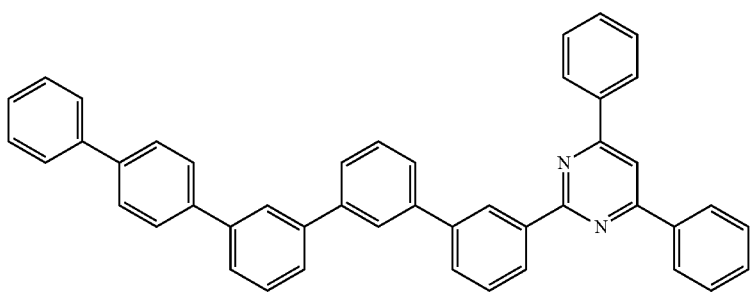
[6-130]
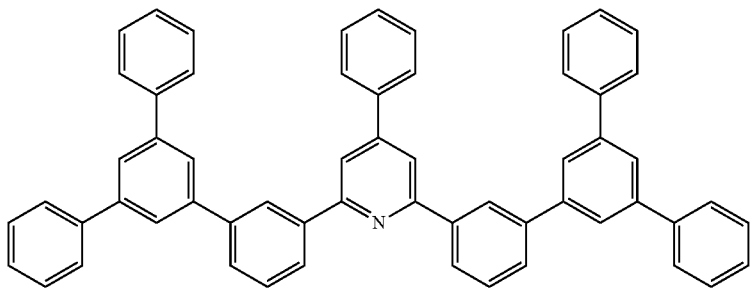
[6-131]
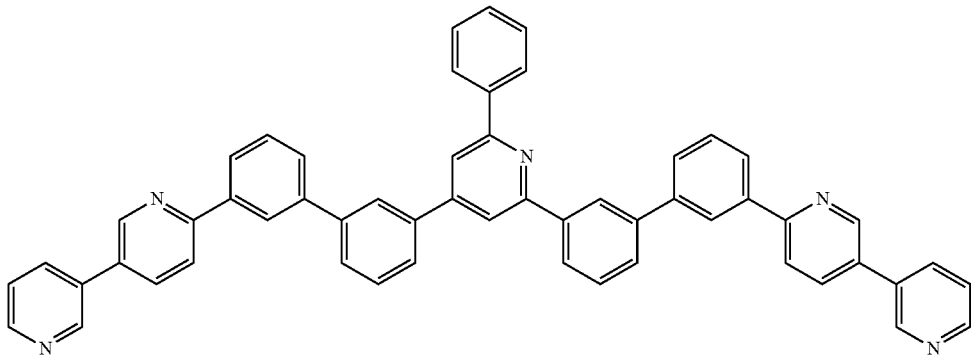
[6-132]
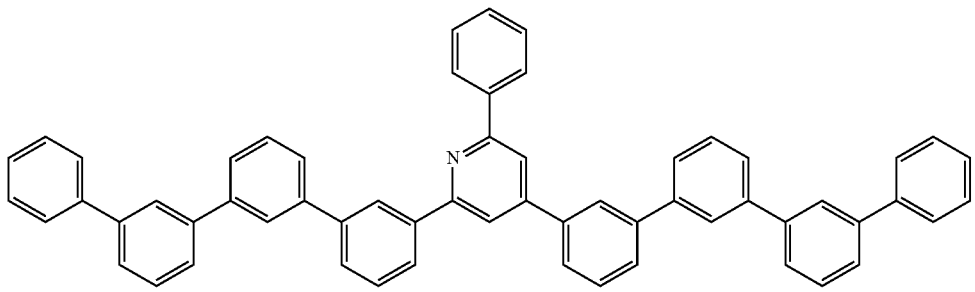
[6-133]
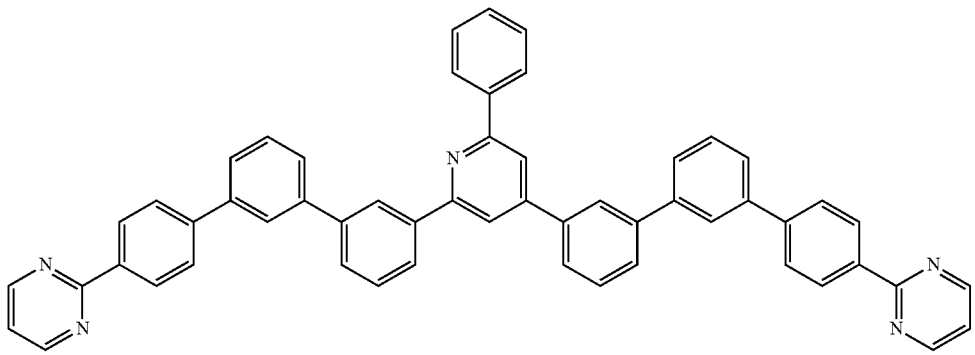
[6-134]

-continued
[6-135]
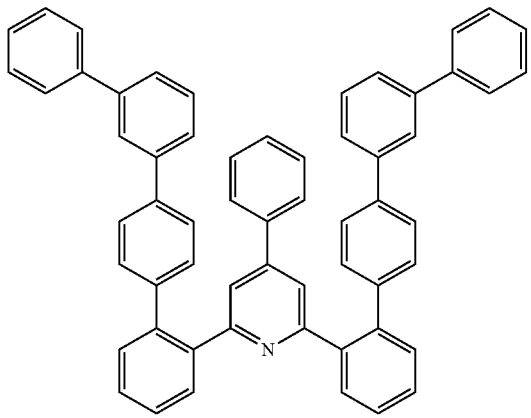
[6-136]
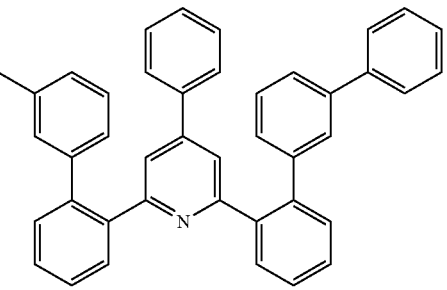
[6-137]
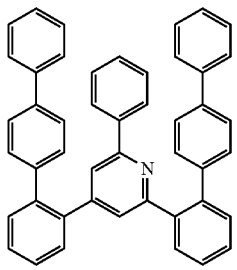
[6-138]
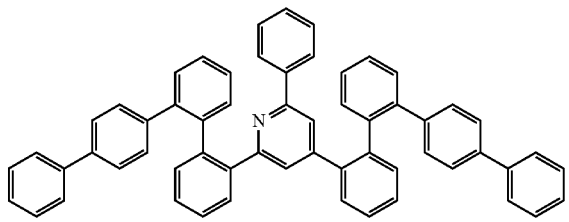
[6-139]
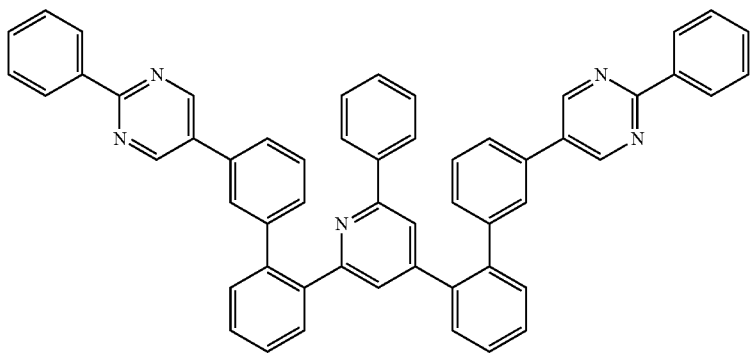
[6-140]
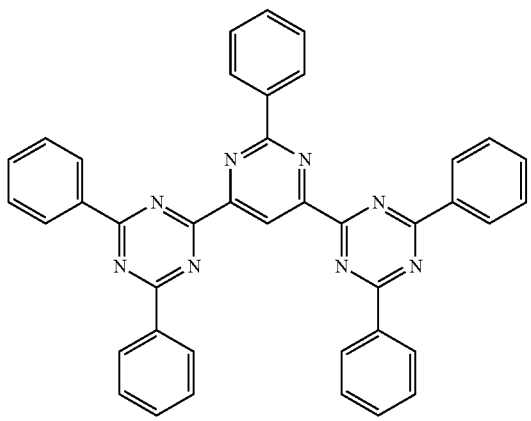

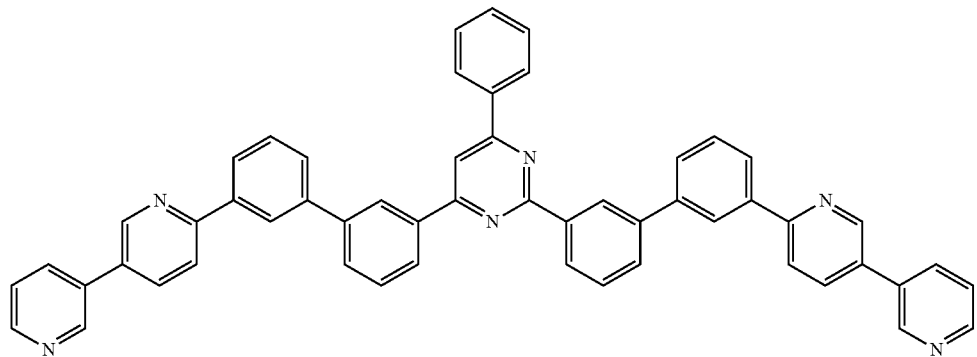
[6-141]
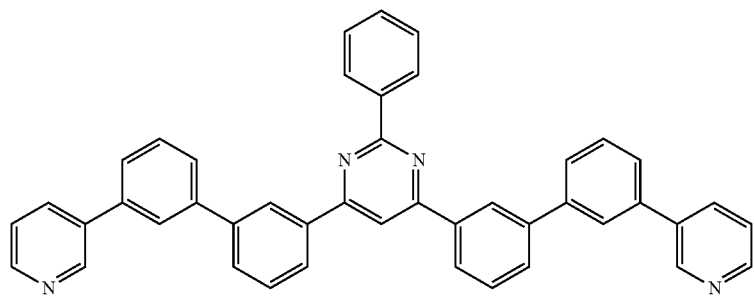
[6-142]
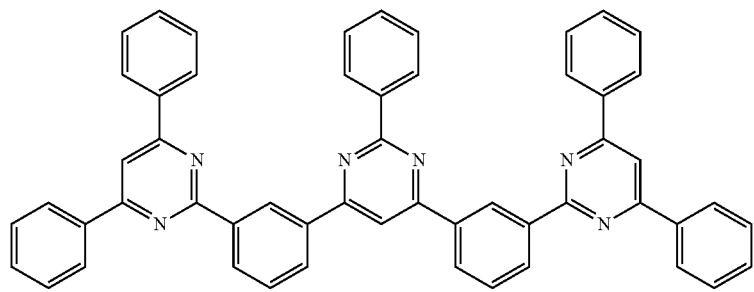
[6-143]
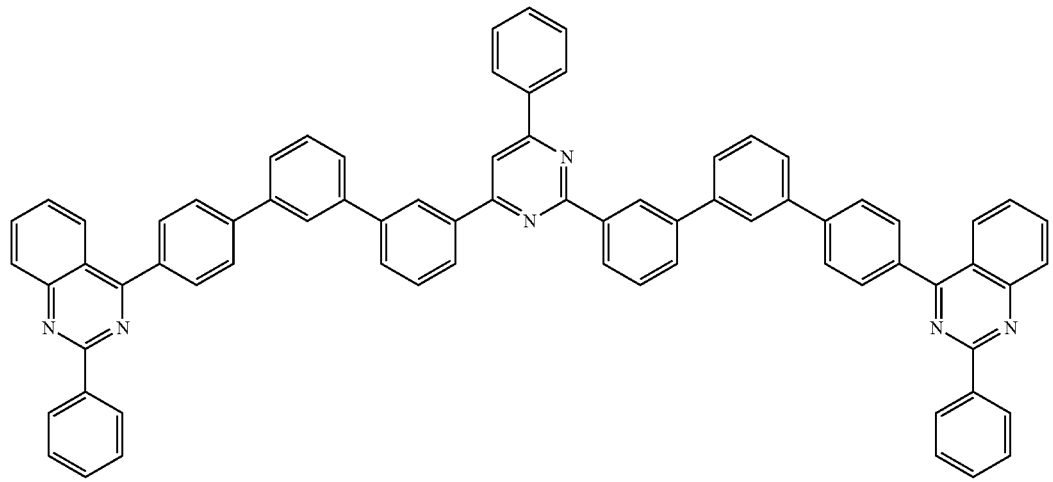
[6-144]

[6-145]
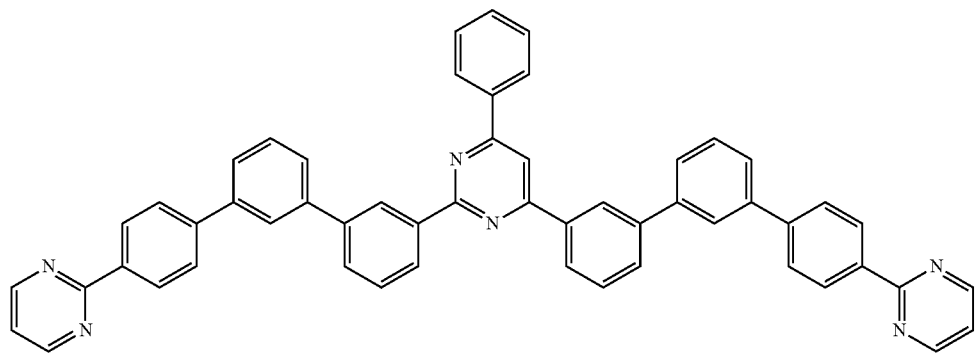
[6-146]
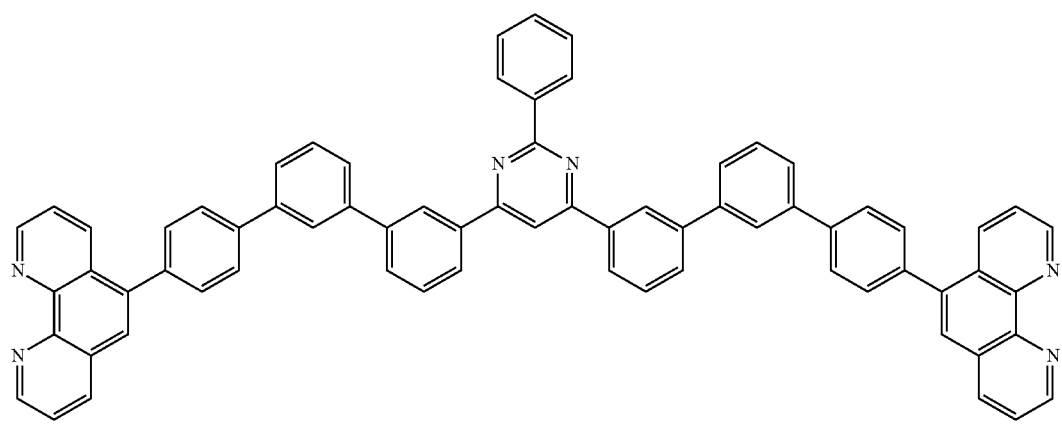
[6-147]
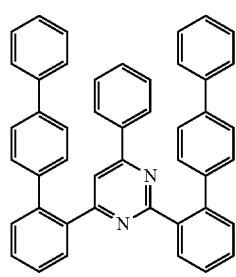
[6-148]
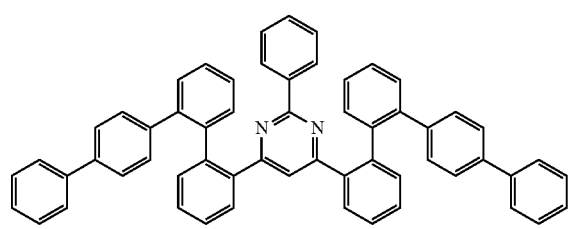
[6-149]
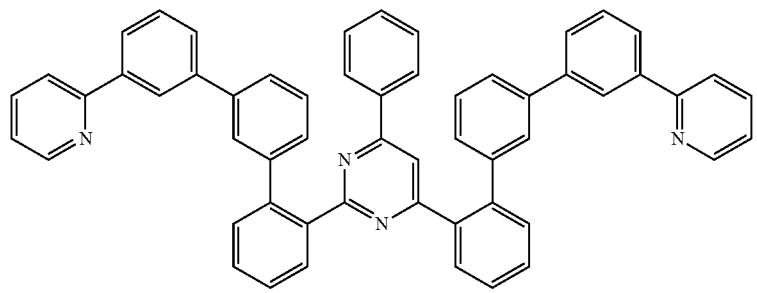

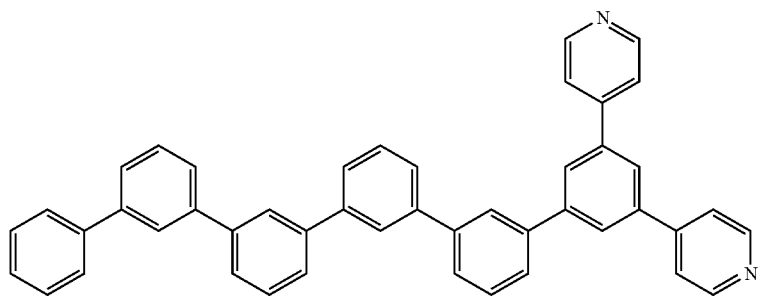
[6-150]
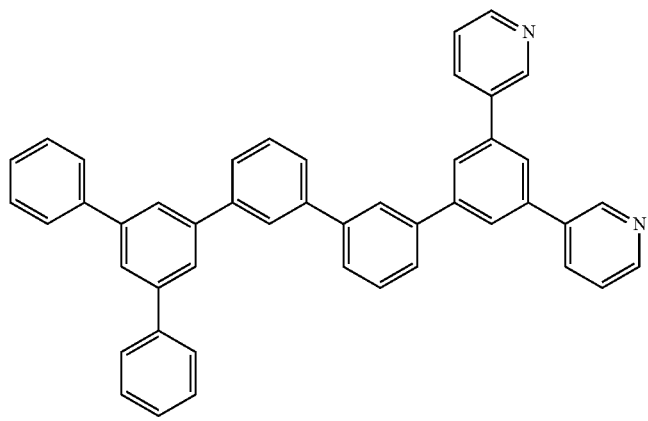
[6-151]
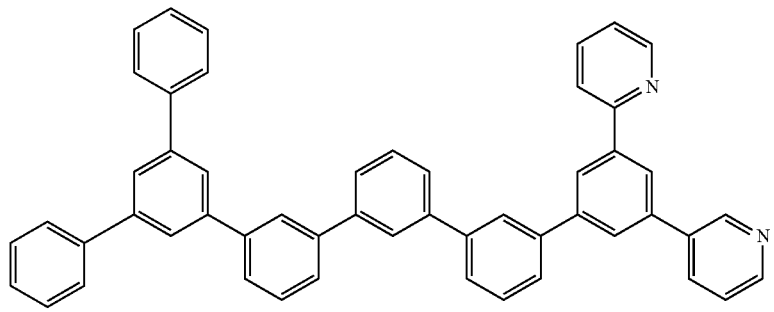
[6-152]
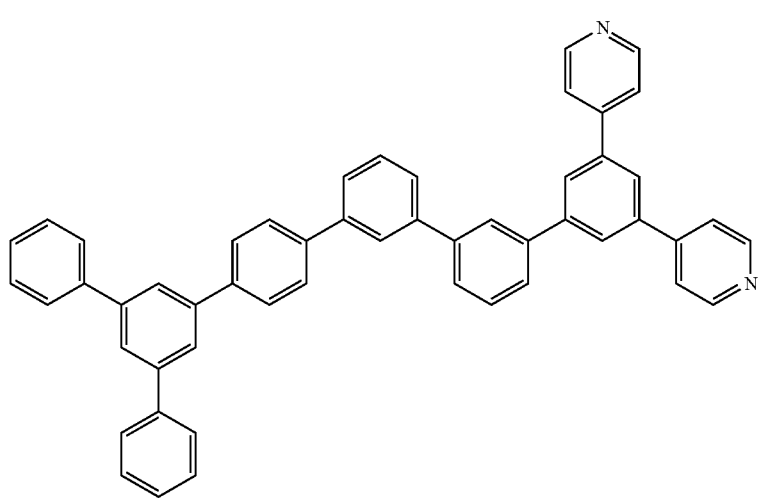
[6-153]

[6-154]

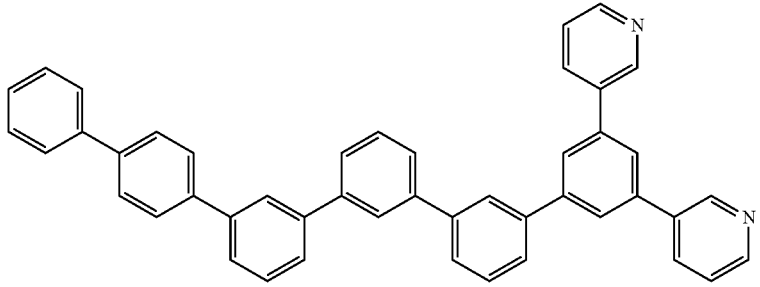

The composition may include the first compound for an organic optoelectric device and the second compound for an organic optoelectric device in a weight ratio of about 1:99 to 99:1.

The composition may be applied to an organic layer of an organic optoelectric device, and the first compound for an organic optoelectric device and the second compound for an organic optoelectric device may act as hosts.

The first compound for an organic optoelectric device may be a compound having relatively strong hole characteristics, while the second compound for an organic optoelectric device may be a compound having relatively strong electron characteristics, and thus, when the first and second compounds for an organic optoelectric device are used together, luminous efficiency and life-span characteristics may be further improved by increasing mobility and stability of charges.

The composition may further include one or more kinds of organic compounds in addition to the first compound for an organic optoelectric device and the second compound for an organic optoelectric device.

The composition may further include a dopant. The dopant may be a red, green, or blue dopant, for example a phosphorescent dopant.

The dopant is a material that is mixed with the first host compound and the second host compound in a small amount to cause light emission, and may be a material such as a metal complex that emits light by multiple excitation into a triplet or more. The dopant may be, for example an inorganic, organic, or organic/inorganic compound, and one or more kinds thereof may be used.

Examples of the dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by the following Chemical Formula Z, but is not limited thereto.

$L_2MX$             [Chemical Formula Z]

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd, or a combination thereof, and the L and X may be, for example a bidendate ligand.

The composition may be formed by a dry method, such as chemical vapor deposition (CVD), or a solution process.

Hereinafter, an organic optoelectric device including the compound for an organic optoelectric device or the composition is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device includes an anode and a cathode facing each other, and at least one organic layer between the anode and the cathode, wherein the organic layer includes the compound for an organic optoelectric device or the composition for an organic optoelectric device.

Herein, an organic light emitting diode as one example of an organic optoelectric device is described referring to drawings.

FIGS. 1 and 2 are cross-sectional views of each organic light emitting diode according to an embodiment.

Referring to FIG. 1, an organic light emitting diode 100 according to an embodiment includes an anode 120 and a cathode 110 facing each other and an organic layer 105 interposed between the anode 120 and the cathode 110.

The anode 120 may be made of a conductor having a large work function to help hole injection, and may be, for example, metal, metal oxide and/or a conductive polymer. The anode 120 may be, for example a metal such as nickel, platinum, vanadium, chromium, copper, zinc, or gold, or an alloy thereof; a metal oxide such as zinc oxide, indium oxide, indium tin oxide (ITO), indium zinc oxide (IZO), or the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, or polyaniline, but is not limited thereto.

The cathode 110 may be made of a conductor having a small work function to help electron injection, and may be, for example, metal, metal oxide, and/or a conductive polymer. The cathode 110 may be, for example, a metal or an alloy thereof such as magnesium, calcium, sodium, potassium, titanium, indium, yttrium, lithium, gadolinium, aluminum, silver, tin, lead, cesium, barium, or the like; a multi-layer structure material such as LiF/Al, $LiO_2$/Al, LiF/Ca, LiF/Al, or $BaF_2$/Ca, but is not limited thereto.

The organic layer 105 includes an emission layer 130 including the compound for an organic optoelectric device or the composition for an organic optoelectric device according to an embodiment.

The emission layer 130 may include, for example, the compound for an organic optoelectric device individually, a mixture of at least two of the compounds for an organic optoelectric device, or the composition for an organic optoelectric device.

In the emission layer 130, the first and second compounds for an organic optoelectric device may be included for example in a weight ratio of about 1:99 to about 99:1. The weight ratio may be about 10:90 to about 90:10, about 20:80 to about 80:20, about 30:70 to about 70:30, about 40:60 to about 60:40, and about 50:50. In addition, the first and second compounds for an organic optoelectric device may be mixed in a weight ratio of about 1:2, about 1:3, about 1:4, about 1:5, about 1:1, about 2:1, about 3:1, about 4:1, about 5:1, and the like. The mixing may be performed by first mixing two compounds and depositing the mixture, or simultaneously depositing each compound in each weight ratio.

When the compounds are included within the range, electron-injecting capability may be adjusted depending on a ratio of the two compounds and balanced with electron transport capability of the emission layer, and thus, electrons may not be accumulated on the interface of the emission layer.

The first compound for an organic optoelectric device having relatively strong hole characteristics and the second compound for an organic optoelectric device having relatively strong electron characteristics in the emission layer may be used together and may increase mobility and stability of charges.

For example, the first compound for an organic optoelectric device represented by Chemical Formula I-A or I-D or the second compound for an organic optoelectric device represented by Chemical Formula II-A or II-B may be used together. For example, the first compound for an organic optoelectric device represented by Chemical Formula Ia or Id and the second compound for an organic optoelectric device represented by Chemical Formula II-A1 or II-b1 may be used together.

Referring to FIG. 2, an organic light emitting diode 200 further includes a hole auxiliary layer 140 in addition to an emission layer 130. The hole auxiliary layer 140 may improve hole injection and/or hole mobility between the anode 120 and the emission layer 130 and may block electrons. The hole auxiliary layer 140 may include, for example at least one of a hole transport layer, a hole injection layer, and/or an electron blocking layer.

The hole auxiliary layer 140 may include the compound for an organic optoelectric device or the composition for an organic optoelectric device. For example, the hole auxiliary layer 140 may be positioned to be adjacent to the emission layer and include the compound for an organic optoelectric device or the composition for an organic optoelectric device.

In the present specification, when at least two hole transport layers (HTL) are formed, the hole transport layer (HTL) neighboring the emission layer is called a hole transport auxiliary layer.

An organic light emitting diode according to an embodiment may further include an electron transport layer (ETL), an electron injection layer (EIL), a hole injection layer (HIL) and the like as the organic layer 105 as shown in FIG. 1 or 2.

The organic light emitting diodes 100 and 200 may be manufactured by forming an anode or a cathode on a substrate, forming an organic layer in accordance with a dry coating method such as evaporation, sputtering, plasma plating, and ion plating; and forming a cathode or an anode thereon.

The organic light emitting diode may be applied to an organic light emitting diode (OLED) display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Compound for Organic Optoelectric Device

Hereinafter, starting materials and reaction materials used in Examples and Synthesis Examples were purchased from Sigma-Aldrich Co. Ltd. or TCI Inc. unless particularly mentioned otherwise.

Synthesis of First Compound for Organic Optoelectric Device

Synthesis Example 1

Synthesis of Compound 2-1

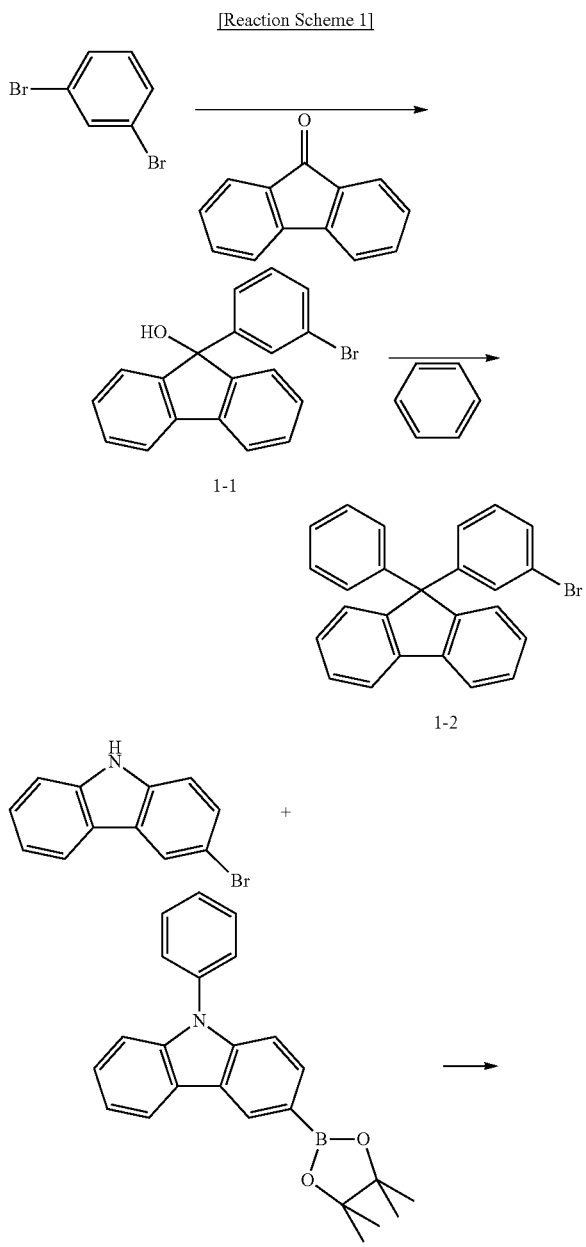

[Reaction Scheme 1]

-continued

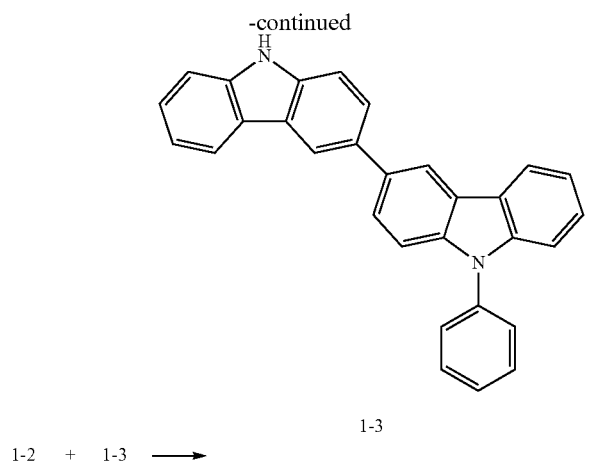

1-3

1-2 + 1-3 ⟶

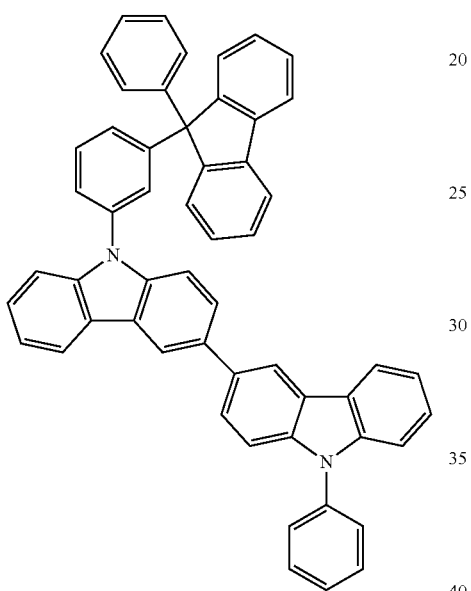

1st Step: Synthesis of Intermediate 1-1

29.98 g (127.09 mmol) of 1,3-dibromobenzene was dissolved in 500 mL of tetrahydrofuran under a nitrogen environment, and the solution was cooled down to −70° C. by using liquid nitrogen.

Next, 56 mL (139.80 mmol) of 2.5 M n-butyllithium (a hexane solvent) was slowly injected thereinto, and the mixture was agitated for 40 minutes. Then, 25 g (139.80 mmol) of 9-fluorenone dissolved in 50 mL of tetrahydrofuran was slowly injected thereinto after cooling down a reactor with liquid nitrogen. The reactor was heated up to room temperature, and then the mixture was agitated for 12 hours. When the reaction was complete, the reactant was poured into 500 mL of an ammonium chloride aqueous solution, and an organic layer was separated and then purified through column chromatography after removing a solvent therefrom, obtaining 35 g (82%) of an intermediate 1-1.

2nd Step: Synthesis of Intermediate 1-2

26.8 g (79.7 mmol) of the intermediate 1-1 was dissolved in 700 mL of benzene and then heated at 50° C. Then, 13 g (87.67 mmol) of trifluoromethanesulfonic acid was slowly injected thereto, and the mixture was agitated for 2 hours. The reactant was poured into a sodium bicarbonate aqueous solution for neutralization, and then an organic layer was separated therefrom and purified through column chromatography, obtaining 24 g (76%) of an intermediate 1-2.

3rd Step: Synthesis of Intermediate 1-3

26 g (104.9 mmol) of 3-bromocarbazole was dissolved in 400 mL of tetrahydrofuran under a nitrogen environment, 46.5 g (125.9 mmol) of 9-Phenyl-9H-carbazol-3-yl-3-boronic acid pinacol ester (Matrix Scientific) and 6.1 g (5.25 mmol) of tetrakis(triphenylphosphine)palladium were added thereto, and the mixture was agitated. Then, 43.5 g (314.75 mmol) of potassium carbonate saturated in water was added thereto, and the mixture was heated and refluxed at 80° C. for 24 hours. When the reaction was complete, water was added to the reaction solution, the mixture was extracted with dichloromethane, filtered after removing moisture with anhydrous $MgSO_4$ therefrom and concentrated under a reduced pressure. Then, a residue obtained therefrom was separated and purified through column chromatography, obtaining 33 g (77%) of an intermediate 1-3.

4th Step: Synthesis of Compound 2-1

8.86 g (21.68 mmol) of the intermediate 1-3, 9.48 g (23.85 mmol) of the intermediate 1-2, 0.62 g (1.08 mmol) of bisdibenzylidene acetonepalladium, 2.13 g (32.52 mmol) of sodium tert-butoxide, 2.104 g (4.34 (mmol) of tri-tert-butylphosphine (50%-toluene) and 90 mL of toluene were put in a reaction vessel and agitated under a nitrogen stream at 110° C. for 12 hours. When the reaction was complete, the reaction solution was filtered and then recrystallized with toluene, obtaining 13 g (83%) of a compound 2-1.

LC Mass (calcd.: 724.89 g/mol, found: M+H$^+$=725.69 g/mol).

Synthesis Example 2

Synthesis of Compound 2-6

[Reaction Scheme 2]

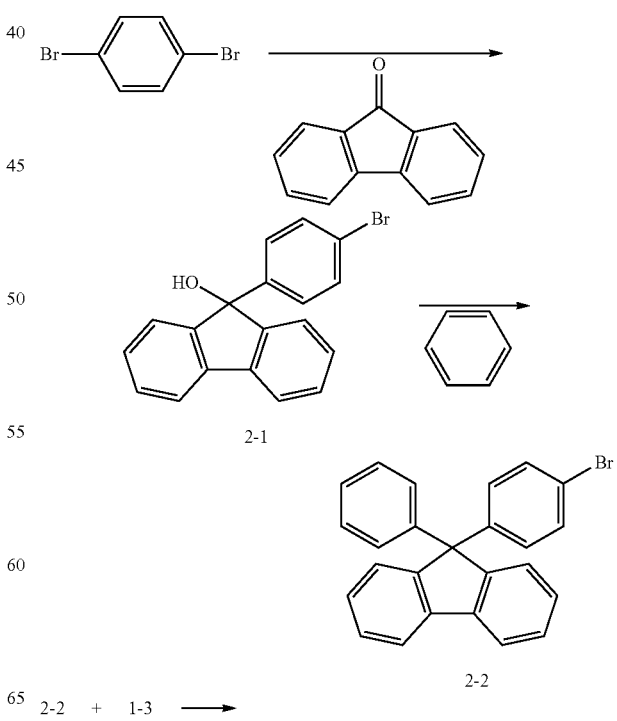

2-2 + 1-3 ⟶

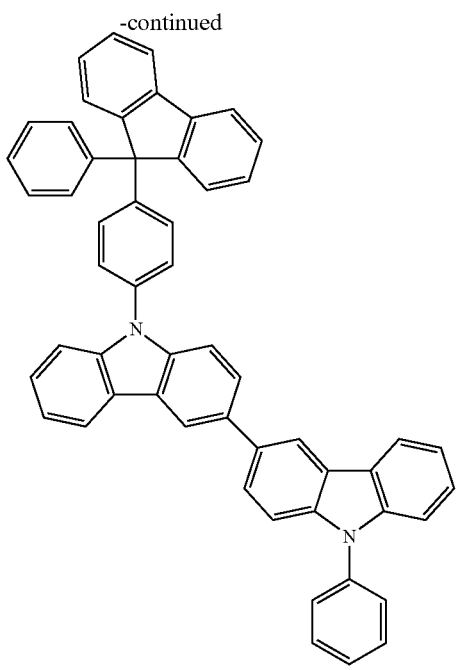

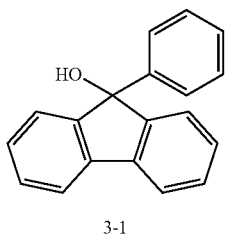

3-1

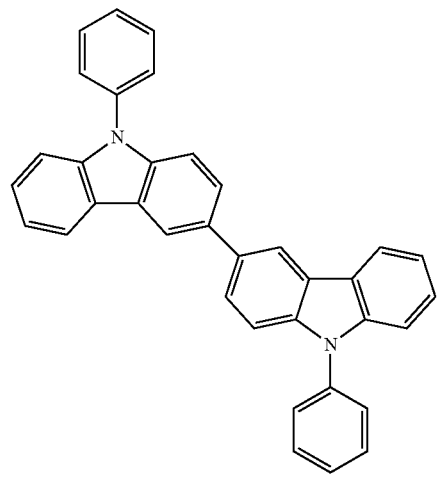

1<sup>st</sup> Step: Synthesis of Intermediate 2-1

29 g (81%) of an intermediate 2-1 was obtained according to the same synthesis method as the method of preparing the intermediate 1-1 by using 25 g (105.9 mmol) of 1,4-dibromobenzene, 46.6 mL (116.5 mmol) of 2.5 M n-butyllithium (a hexane solvent) and 21 g (116.50 mmol) of 9-fluorenone.

2<sup>nd</sup> Step: Synthesis of Intermediate 2-2

25 g (75%) of an intermediate 2-2 was obtained according to the same synthesis method as the method of preparing the intermediate 1-2 by using 28.3 g (83.90 mmol) of the intermediate 2-1 and 13.8 g (92.29 mmol) of trifluoromethanesulfonic acid.

3<sup>rd</sup> Step: Synthesis of Compound 2-6

13.5 g (79%) of a compound 2-6 was obtained according to the same synthesis method as Synthesis Example 1 by using 9.66 g (23.65 mmol) of the intermediate 1-3 and 10.336 g (26.01 mmol) of the intermediate 2-2.

LC Mass (calcd.: 724.89 g/mol, found: M+H$^+$=725.70 g/mol).

Synthesis Example 3

Synthesis of Compound 2-42

[Reaction Scheme 3]

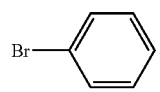 

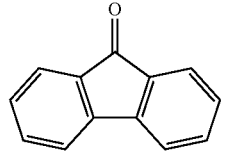

3-1 + 3-2 →

-continued

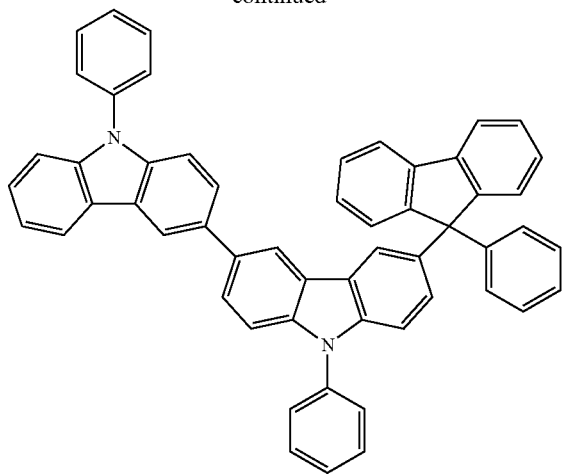

1st Step: Synthesis of Intermediate 3-1

31.2 g (73%) of an intermediate 3-1 was obtained according to the same synthesis method as the method of preparing the intermediate 1-1 by using 26 g (165.9 mmol) of bromobenzene, 73 mL (182.50 mmol) of 2.5 M n-butyllithium (a hexane solvent) and 32.8 g (182.50 mmol) of 9-fluorenone.

2nd Step: Synthesis of Intermediate 3-2

35 g (82%) of an intermediate 3-2 1 was obtained according to the same synthesis method as the method of preparing the intermediate 1-3 by using 28.5 g (88.44 mmol) of 3-bromo-9-phenylcarbazole and 45.720 g (123.8 mmol) of 9-Phenyl-9H-carbazol-3-yl-3-boronic acid pinacol ester (Matrix Scientific).

3rd Step: Synthesis of Compound 2-42

22.8 g (45.98 mmol) of the intermediate 3-2 and 11.8 g (45.98 mmol) of the intermediate 3-1 were dissolved in 450 mL of dichloromethane, and the solution was agitated at room temperature. Then, 3.2 g (22.99 mmol) of borontrifluoride (an ethyl ether complex) was slowly added thereto in a dropwise fashion. The mixture was agitated at room temperature for 2 hours, neutralized with a sodium bicarbonate aqueous solution, extracted with dichloromethane and then recrystallized with chlorobenzene, obtaining 24 g (72%) a compound 2-42.

LC Mass (calcd.: 724.89 g/mol, found: M+H$^+$=725.71 g/mol).

Comparative Synthesis Example 1

Synthesis of Compound a

[Reaction Scheme 4]

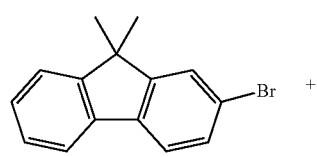

-continued

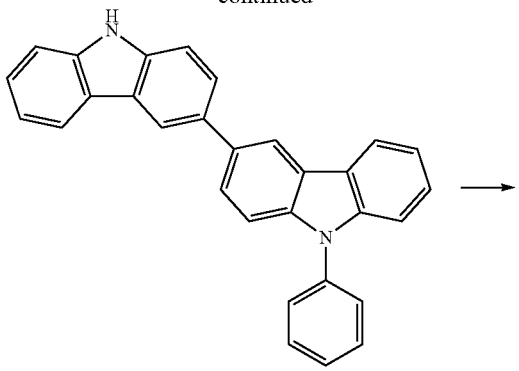

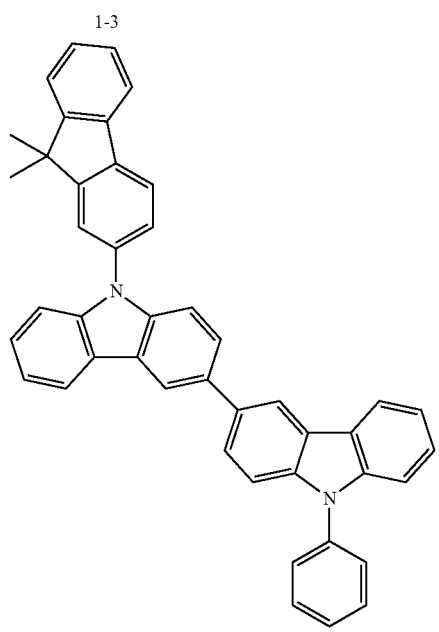

[Compound a]

12.5 g (80%) of a compound a was obtained according to the same method as Synthesis Example 1 by using 10.7 g (26.16 mmol) of the intermediate 1-3 and 8.6 g (31.4 mmol) of the 2-bromo-9,9-dimethylfluorene.

LC Mass (calcd.: 600.75 g/mol, found: M+H$^+$=601.64 g/mol).

Comparative Synthesis Example 2

Synthesis of Compound b

[Reaction Scheme 5]

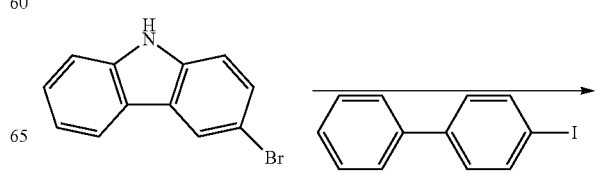

-continued

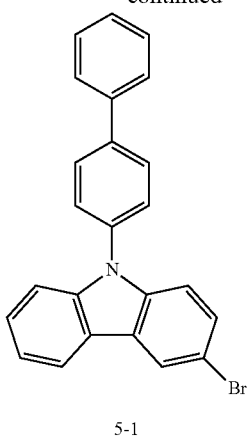

5-1

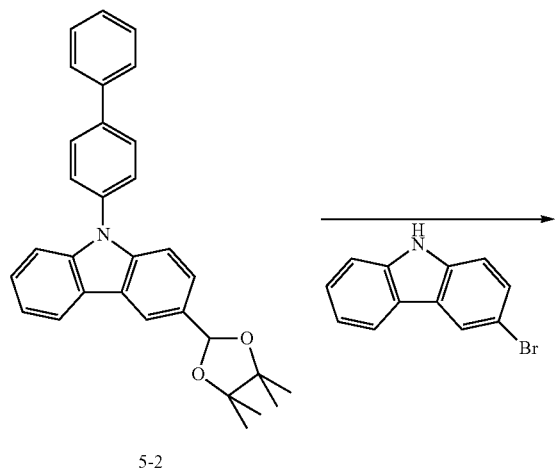

5-2

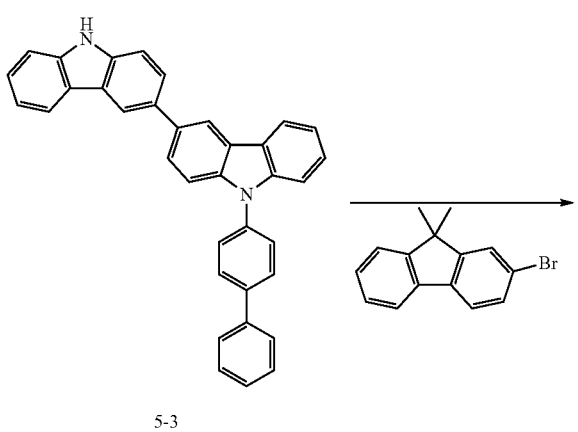

5-3

-continued

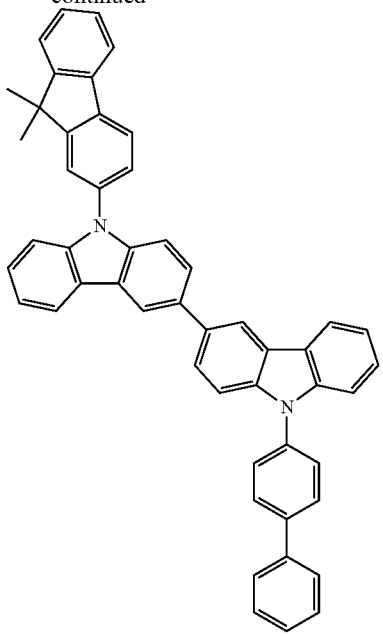

[Compound b]

1st Step: Synthesis of Intermediate 5-1

19 g (48%) of an intermediate 5-1 was obtained according to the same method as the synthesis method of Reaction Scheme 4 by using 24.7 g (100.4 mmol) of 3-bromocarbazole and 52.261 g (200.8 mmol) of 4-iodinebiphenyl.

2nd Step: Synthesis of Intermediate 5-2

12.8 g (44.7 mmol) of the intermediate 5-1 was dissolved in 300 mL of dimethyl formamide under a nitrogen environment, 13.6 g (53.6 mmol) of bis(pinacolato)diboron, 1.825 g (2.23 mmol) of (1,1'-bis(diphenylphosphine)ferrocene)dichloropalladium (II) and 6.6 g (67 mmol) of potassium acetate were added thereto, and the mixture was heated and refluxed at 150° C. for 24 hours. When the reaction was complete, water was added to the reaction solution, and the mixture was filtered and dried in a vacuum oven. Then, a residue obtained therefrom was separated and purified through column chromatography, obtaining 14 g (70%) of the intermediate 5-2.

3rd Step: Synthesis of Intermediate 5-3

12 g (84%) of an intermediate 5-3 was obtained according to the same method as the method of synthesizing the intermediate 1-3 by using 13.1 g (29.5 mmol) of the intermediate 5-2 and 8 g (32.43 mmol) of 3-bromocarbazole.

4th Step: Synthesis of Compound b 11.3 g (72%) of a compound b was obtained according to the same method as the synthesis method of Reaction Scheme 4 by using 11.25 g (23.33 mmol) of the intermediate 5-3 and 7 g (25.54 mmol) of 2-bromo-9,9-dimethylfluorene.

LC Mass (calcd.: 676.84 g/mol, found: M+H$^+$=677.75 g/mol).

Manufacture of Organic Light Emitting Diode

Example 1

An organic light emitting diode was manufactured by using 4,4'-di(9H-carbazol-9-yl)biphenyl (CBP) as a host and PhGD (illustrated below) as a dopant. As for an anode, a 1000 Å-thick ITO was used, while as for a cathode, a 1000

Å-thick aluminum (Al) was used. The organic light emitting diode is manufactured in a method of ultrasonic wave-cleaning an ITO glass substrate in acetone, isopropyl alcohol and pure water respectively for 15 minutes and then UV ozone cleaning it for 30 minutes. On the substrate, a 800 Å-thick hole transport layer (HTL) was formed by vacuum-depositing HT-1 to be 70 nm thick at a vacuum degree of 650×10$^{-7}$ Pa and a deposition rate ranging from 0.1 to 0.3 nm/s and depositing the compound 2-1 according to Synthesis Example 1 to form a 10 nm-thick hole transport auxiliary layer. Subsequently, a 300 Å-thick emission layer was formed by depositing 4,4'-di(9H-carbazol-9-yl)biphenyl (CBP) under the same vacuum deposition condition as above and herein, simultaneously depositing PhGD of a phosphorescent dopant. Herein, the phosphorescent dopant was deposited in an amount of 7 wt % based on 100 wt % of the emission layer by adjusting the deposition rate. On the emission layer, a 50 Å-thick hole blocking layer was formed by depositing bis(2-methyl-8-quinolinolate)-4-(phenylphenolato)aluminum (BAlq) under the same vacuum deposition condition as above. Subsequently, a 200 Å-thick electron transport layer (ETL) was formed by depositing Alq3 under the same deposition condition as above. On the electron transport layer (ETL), a cathode was formed by sequentially depositing LiF and Al, finally manufacturing an organic photoelectric device. The organic photoelectric device had a structure of ITO/HT-1 (70 nm)/the compound 2-1 (10 nm)/EML (CBP (93 wt %)+PhGD (7 wt %), 30 nm)/Balq (5 nm)/Alq3 (20 nm)/LiF (1 nm)/Al (100 nm).

Example 2

An organic light emitting diode was manufactured according to the same method as Example 1 except for using the compound 2-6 according to Synthesis Example 2 instead of the compound 2-1 according to Synthesis Example 1.

Example 3

An organic light emitting diode was manufactured according to the same method as Example 1 except for using the compound 2-42 according to Synthesis Example 3 instead of the compound 2-1 according to Synthesis Example 1.

Comparative Example 1

An organic light emitting diode was manufactured according to the same method as Example 1 except for using the compound a according to Comparative Synthesis Example 1 instead of the compound 2-1 according to Synthesis Example 1.

Comparative Example 2

An organic light emitting diode was manufactured according to the same method as Example 1 except for using the compound b according to Comparative Synthesis Example 2 instead of the compound 2-1 according to Synthesis Example 1.

Comparative Example 3

An organic light emitting diode was manufactured according to the same method as Example 1 except for using HT-1 instead of the compound 2-1 according to Synthesis Example 1.

The structures of the HT-1, BAlq, CBP, and PhGD used for manufacturing the organic light emitting diode were as follows.

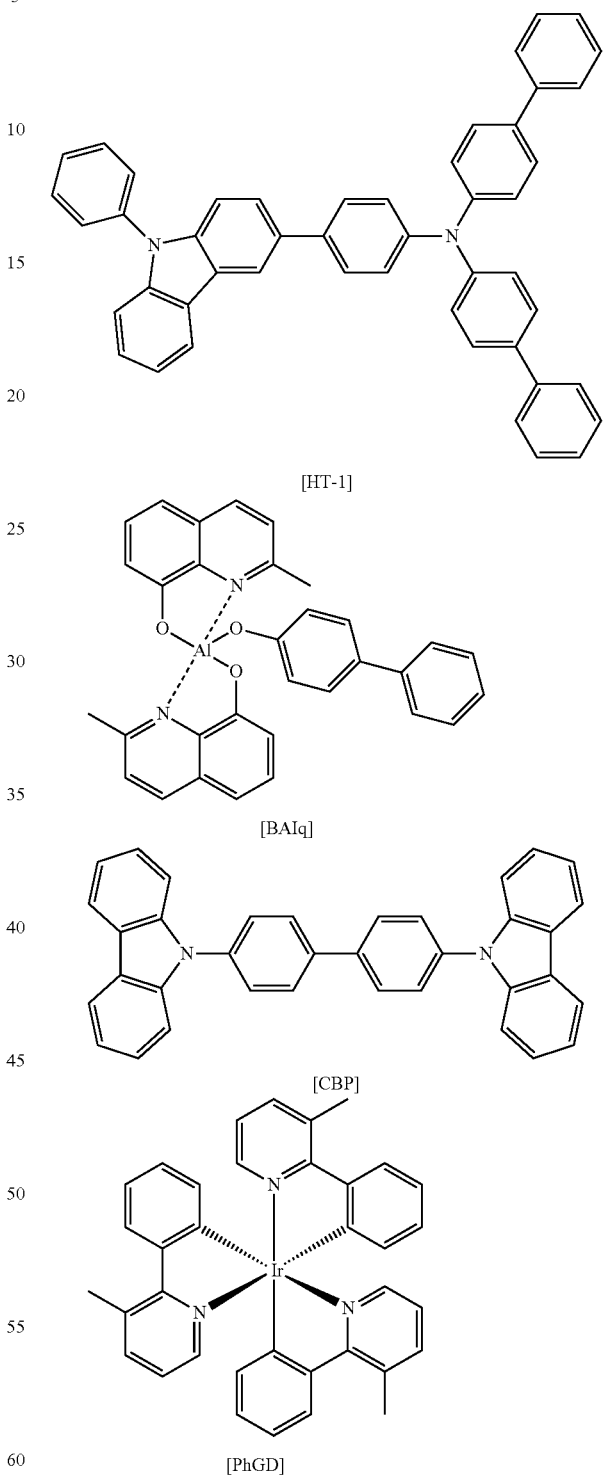

Evaluation

Current density and luminance changes depending on a voltage, luminous efficiency and life-span of each organic light emitting diode according to Examples 1 to 3 and Comparative Examples 1 to 3 were measured.

Specific measurement methods were as follows, and the results were provided in Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Life-span

The T90 life-span result was obtained by maintaining luminance (cd/m$^2$) of 3000 cd/m$^2$ and measuring time taken until current efficiency (cd/A) decreased down to 90%.

TABLE 1

| Nos. | Hole transport layer (HTL) | Color (EL color) | Efficiency (cd/A) | T90 life-span (h) At 3000 cd/m$^2$ |
|---|---|---|---|---|
| Example 1 | HT-1/compound 2-1 | Green | 42.3 | 230 |
| Example 2 | HT-1/compound 2-6 | Green | 40.7 | 225 |
| Example 3 | HT-1/compound 2-42 | Green | 40.2 | 223 |
| Comparative Example 1 | HT-1/compound a | Green | 36.8 | 185 |
| Comparative Example 2 | HT-1/compound b | Green | 37.5 | 190 |
| Comparative Example 3 | HT-1/HT-1 | Green | 35.2 | 180 |

Referring to the results of Table 1, Examples 1 to 3 using the compound according to an embodiment for a hole transport auxiliary layer showed improved luminous efficiency and life-span in a green phosphorescent organic light emitting diode compared with Comparative Example 3 using no hole transport auxiliary layer. In particular, an example embodiment showed at least greater than or equal to about 10% much improved luminous efficiency.

Analysis

The deposition process temperature and the glass transition temperature (Tg) of the compounds according to Synthesis Examples 1 to 3 and Comparative Synthesis Examples 1 to 2 were measured.

The temperatures were specifically measured in the following method, and the results are provided in Table 2.

Deposition Process Temperature (° C.)

The deposition process temperature indicates a temperature at which a compound for a hole transport auxiliary layer was deposited to be 1 Å thick per 1 second (Å/sec) during the manufacture of the organic light emitting diode of Synthesis Example 1.

Glass Transition Temperature (Tg)

An energy input difference was measured as a function of a temperature by using a DSC1 equipment made by Mettler Toledo International Inc., while temperature of a sample and a reference was changed.

TABLE 2

| Nos. | Molecular weight | Deposition temperature (° C.) | Tg (° C.) |
|---|---|---|---|
| Synthesis Example 1 | 724.89 | 220 | 149 |
| Synthesis Example 2 | 724.89 | 230 | 161 |
| Synthesis Example 3 | 724.89 | 231 | 172 |
| Comparative Synthesis Example 1 | 600.75 | 223 | 132 |
| Comparative Synthesis Example 2 | 676.84 | 238 | 146 |

Referring to Table 2, the compounds according to an embodiment showed a similar or the same deposition process temperature to or as those of the compounds according to Comparative Synthesis Examples 1 to 2 as an absolute value but a lower process temperature based on their molecular weight. In other words, the compounds having a low process temperature based on their molecular weight had a very commercially advantageous condition when used to manufacture an organic light emitting diode. Without being bound by theory, this is believed to be because the compound had non-planarity due to a phenyl group substituted at No. 9 of fluorine and thus, was suppressed from an interaction among molecules. In addition, the compounds according to an embodiment had a higher glass transition temperature than the compounds according to Comparative Synthesis Examples 1 and 2. Without being bound by theory, it is believed that the compounds having a high glass transition temperature prevented degradation of a device due to Joule's heat during the operation and realized a device having a stable long life-span.

Luminous efficiency and life-span are significant factors in terms of commercialization of a device. Based on the results of Examples, the results of the Examples are sufficient to commercialize the device. In addition, the compounds had a low process temperature and thus, decreased time for manufacturing the device and also, had a high glass transition temperature and contributed to realizing a device having a stable long life-span.

Synthesis of Second Compound for Organic Optoelectric Device

Synthesis Example 4

Synthesis of Compound 4-10

A compound 4-10 was synthesized through the following synthesis method and the like.

1$^{st}$ Step: Synthesis of Intermediate 1-2

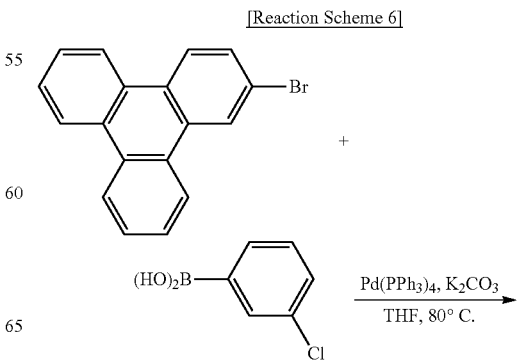

[Reaction Scheme 6]

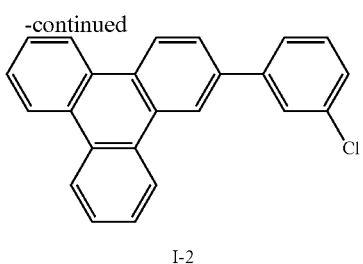

I-2

32.7 g (107 mmol) of 2-bromotriphenylene was dissolved in 300 ml of tetrahydrofuran under a nitrogen environment, 20 g (128 mmol) of 3-chlorophenylboronic acid and 1.23 g (1.07 mmol) of tetrakis(triphenylphosphine)palladium were added thereto, and the mixture was agitated. Then, 36.8 g (267 mmol) of potassium carbonate saturated in water was heated and refluxed at 80° C. for 24 hours. When the reaction was complete, water was added to the reaction solution, and the mixture was extracted with dichloromethane and then filtered after removing moisture with anhydrous MgSO$_4$ and concentrated under a reduced pressure. Then, a residue obtained therefrom was separated and purified through column chromatography, obtaining 22.6 g (63%) of the compound I-2.

2$^{nd}$ Step: Synthesis of Intermediate I-3

[Reaction Scheme 7]

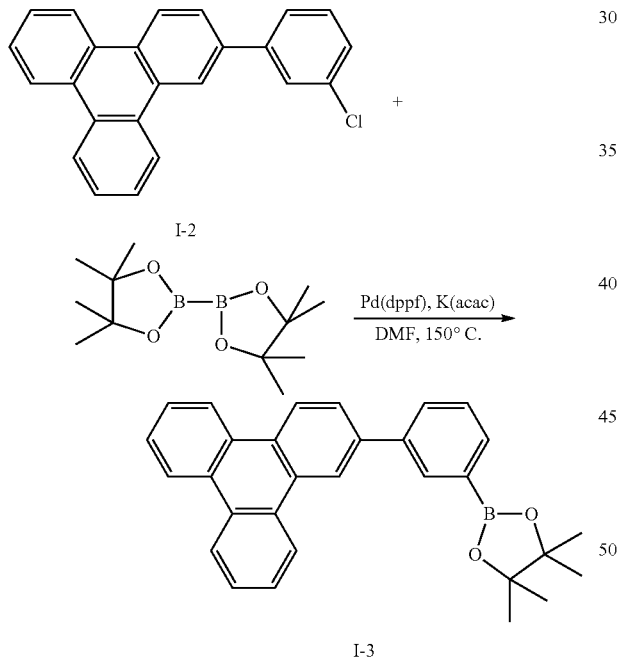

I-3

22.6 g (66.7 mmol) of the compound I-2 was dissolved in 300 ml of dimethyl formamide under a nitrogen environment, 25.4 g (100 mmol) of bis(pinacolato)diboron, 0.54 g (0.67 mmol) of (1,1'-bis(diphenylphosphine)ferrocene)dichloropalladium (II) and 16.4 g (167 mmol) of potassium acetate were added thereto, and the mixture was heated and refluxed at 150° C. for 48 hours. When the reaction was complete, water was added to the reaction solution, the mixture was filtered and then dried in a vacuum oven. Then, a residue obtained therefrom was separated and purified through column chromatography, obtaining 18.6 g (65%) of a compound I-3.

3$^{rd}$ Step: Synthesis of Intermediate I-6

[Reaction Scheme 8]

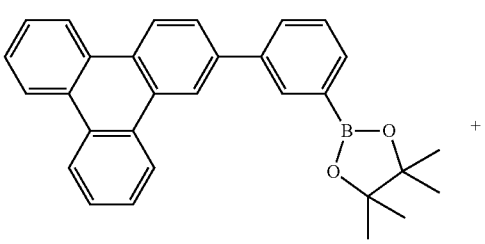

I-3

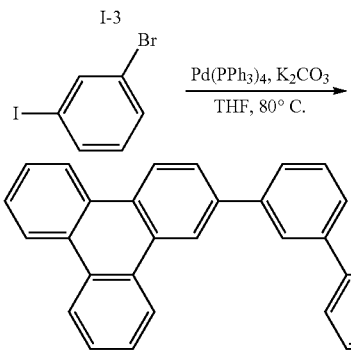

I-6

50 g (116 mmol) of the compound I-3 was dissolved in 500 ml of tetrahydrofuran under a nitrogen environment, 39.4 g (139 mmol) of 1-bromo-3-iodobenzene and 1.34 g (1.16 mmol) of tetrakis(triphenylphosphine)palladium were added thereto, and the mixture was agitated. Then, 40.1 g (290 mmol) of potassium carbonate saturated in water was added thereto, and the mixture was heated and refluxed at 80° C. for 12 hours. When the reaction was complete, water was added to the reaction solution, and the mixture was extracted with dichloromethane and then filtered after removing moisture with anhydrous MgSO$_4$ and concentrated under a reduced pressure. Then, a residue obtained therefrom was separated and purified through column chromatography, obtaining 42.6 g (80%) of a compound I-6.

4$^{th}$ Step: Synthesis of Intermediate I-7

[Reaction Scheme 9]

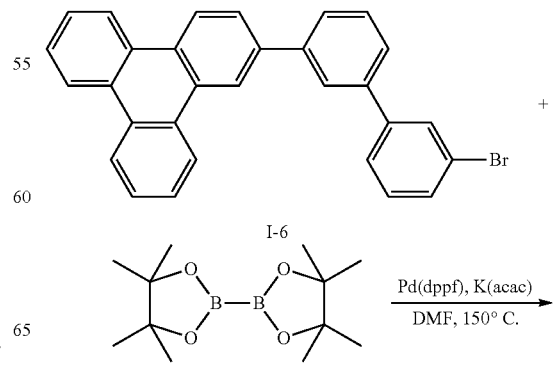

I-6

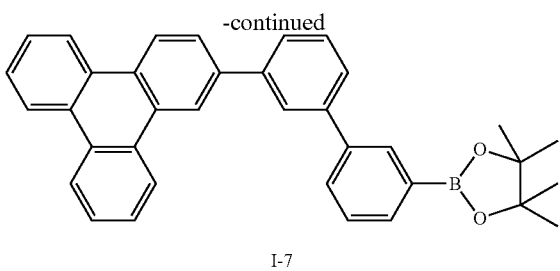

40 g (87.1 mmol) of the compound I-6 was dissolved in 300 ml of dimethyl formamide under a nitrogen environment, 26.5 g (104 mmol) of bis(pinacolato)diboron, 0.71 g (0.87 mmol) of (1,1'-bis(diphenylphosphine)ferrocene)dichloropalladium (II), and 21.4 g (218 mmol) of potassium acetate were added thereto, and the mixture was heated and refluxed at 150° C. for 26 hours. When the reaction was complete, water was added to the reaction solution, and the mixture was filtered and dried in a vacuum oven. Then, a residue obtained therefrom was separated and filtered through column chromatography, obtaining 34 g (77%) of the compound I-7.

5$^{th}$ Step: Synthesis of Compound 4-10

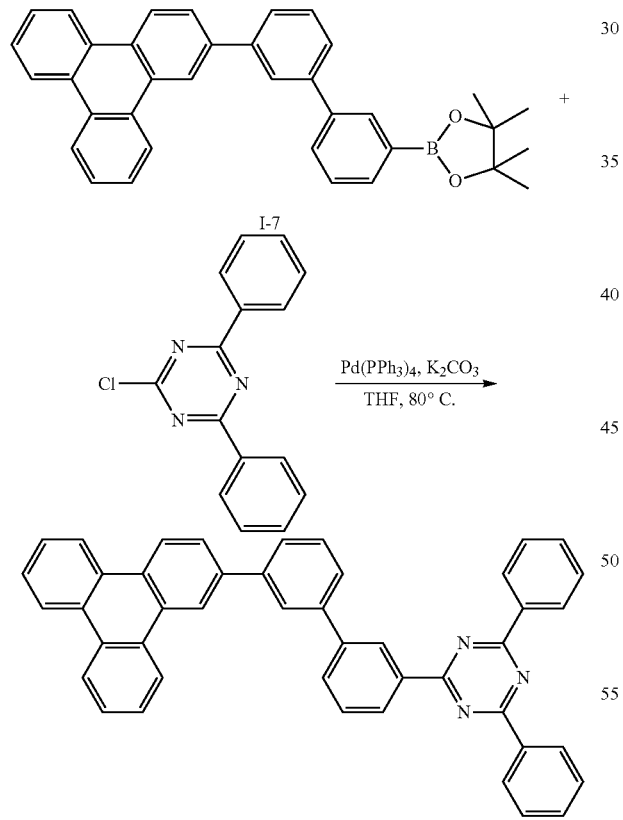

20 g (39.5 mmol) of the compound 1-7 was dissolved in 200 ml of tetrahydrofuran under a nitrogen environment, 10.6 g (39.5 mmol) of 2-chloro-4,6-diphenyl-1,3,5-triazine and 0.46 g (0.4 mmol) of tetrakis(triphenylphosphine)palladium were added thereto, and the mixture was agitated. Then, 13.6 g (98.8 mmol) of potassium carbonate saturated in water was heated and refluxed at 80° C. for 23 hours. When the reaction was complete, water was added to the reaction solution, and the mixture was extracted with dichloromethane and then filtered after removing moisture with anhydrous MgSO$_4$ and concentrated under a reduced pressure. Then, a residue obtained therefrom was separated and purified through column chromatography, obtaining 17.9 g (74%) of the compound 4-10.

LC Mass (calcd.: 611.73 g/mol, found: M+H$^+$=612.54 g/mol).

Synthesis Example 5

Synthesis of Compound 6-1

A compound 6-1 was synthesized through the following synthesis method.

1$^{st}$ Step: Synthesis of Intermediate II-1

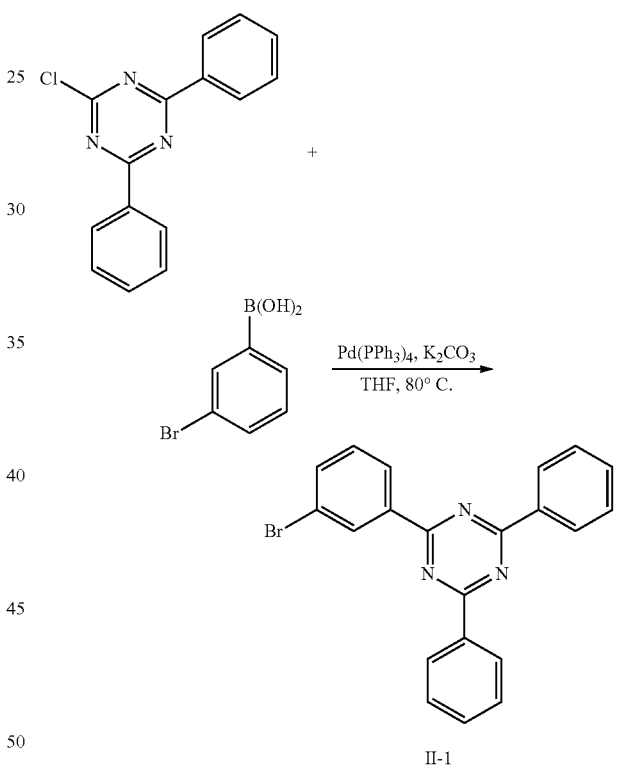

50 g (187 mmol) of the compound, 2-chloro-4,6-diphenyl-1,3,5-triazine was dissolved in 1 L of THF (tetrahydrofuran) under a nitrogen environment, 45 g (224.12 mmol) of (3-bromophenyl)boronic acid and 2.1 g (1.87 mmol) of tetrakis(triphenylphosphine)palladium were added thereto, and the mixture was agitated. Then, 64 g (467 mmol) of potassium carbonate saturated in water was added thereto, and the resulting mixture was heated and refluxed at 80° C. for 12 hours. When the reaction was complete, water was added to the reaction solution, and the mixture was extracted with dichloromethane (DCM) and then filtered after removing moisture with anhydrous MgSO$_4$ and concentrated under a reduced pressure. Then, the obtained residue was separated and purified through flash column chromatography, obtaining 69 g (95%) of the compound II-1.

Synthesis of Intermediate II-2

[Reaction Scheme 12]

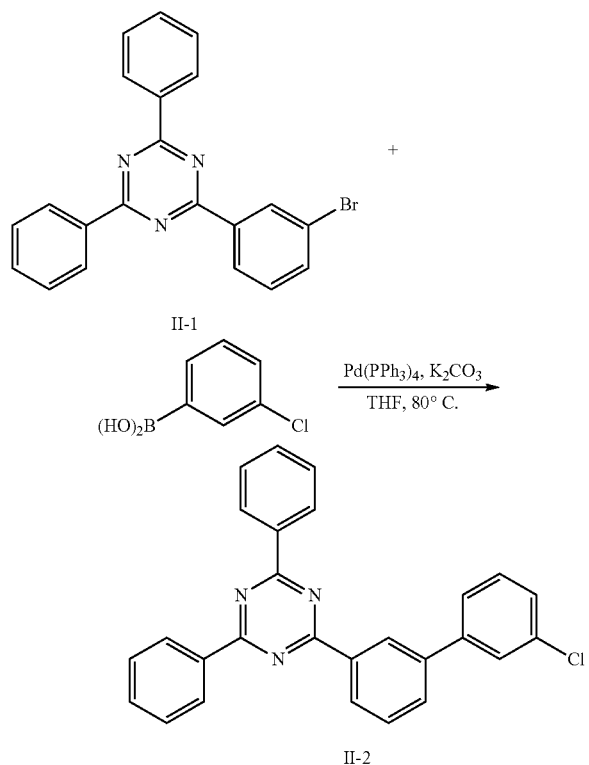

50 g (128 mmol) of the compound II-1 was dissolved in 1 L of THF under a nitrogen environment, 24 g (155 mmol) of (3-chlorophenyl)boronic acid and 1.5 g (1.3 mmol) of tetrakis(triphenylphosphine)palladium were added thereto, and the mixture was agitated. Then, 44 g (320 mmol) of potassium carbonate saturated in water was added thereto, and the resulting mixture was heated and refluxed at 80° C. for 12 hours. When the reaction was complete, water was added to the reaction solution, and the mixture was extracted with dichloromethane (DCM) and then filtered after removing moisture with anhydrous MgSO$_4$ and concentrated under a reduced pressure. Then, the obtained residue was separated and purified through flash column chromatography, obtaining 51 g (95%) of the compound II-2.

3$^{rd}$ Step: Synthesis of Intermediate II-3

[Reaction Scheme 13]

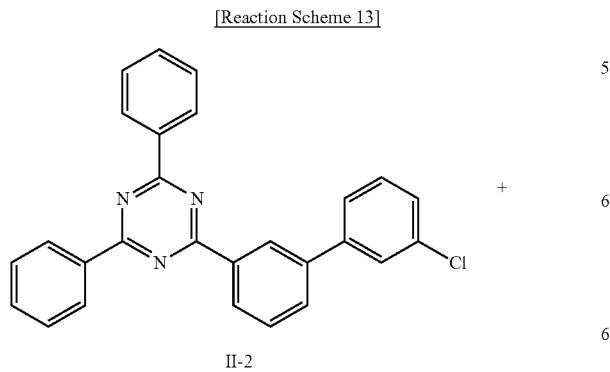

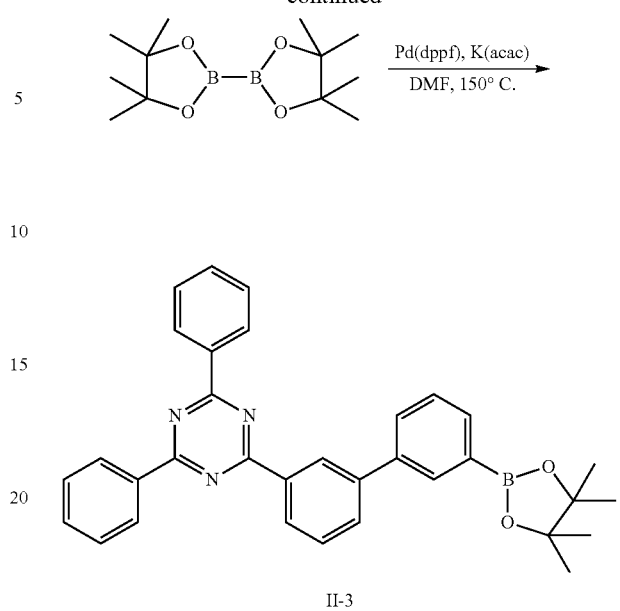

100 g (238 mmol) of the compound II-2 was dissolved in 1 L of dimethylformamide (DMF) under a nitrogen environment, 72.5 g (285 mmol) of bis(pinacolato)diboron, 2 g (2.38 mmol) of (1,1'-bis(diphenylphosphine)ferrocene)dichloropalladium (II) and 58 g (595 mmol) of potassium acetate were added thereto, and the mixture was heated and refluxed at 150° C. for 48 hours. When the reaction was complete, water was added to the reaction solution, and the mixture was filtered and dried in a vacuum oven. The obtained residue was separated and purified through flash column chromatography, obtaining 107 g (88%) of the compound II-3.

4$^{th}$ Step: Synthesis of Intermediate II-4

[Reaction Scheme 14]

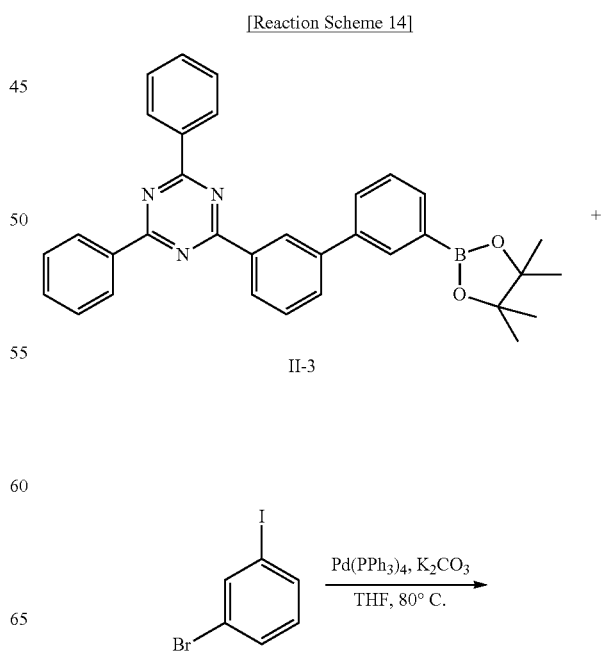

-continued

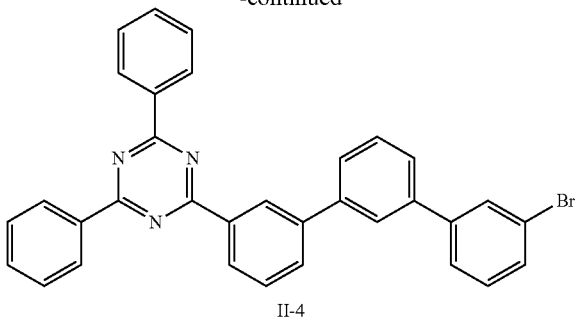

II-4

50 g (98 mmol) of the compound II-3 was dissolved in 1 L of THF under a nitrogen environment, 33 g (117 mmol) of 1-bromo-3-iodobenzene and 1 g (0.98 mmol) of tetrakis(triphenylphosphine)palladium were added thereto, and the mixture was agitated. Then, 34 g (245 mmol) of potassium carbonate saturated in water was added thereto, and the mixture was heated and refluxed at 80° C. for 12 hours. When the reaction was complete, water was added to the reaction solution, and the mixture was extracted with dichloromethane (DCM) and then filtered after removing moisture with anhydrous $MgSO_4$ and concentrated under a reduced pressure. The obtained residue was separated and purified through flash column chromatography, obtaining 50 g (95%) of the compound II-4.

5$^{th}$ Step: Synthesis of Intermediate II-5

[Reaction Scheme 15]

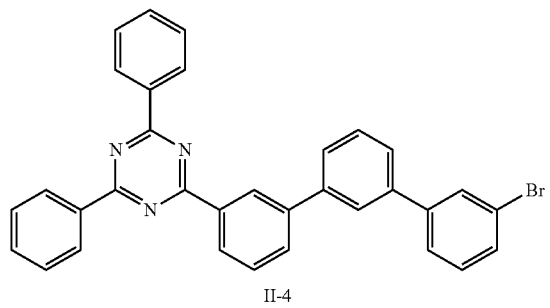

II-4

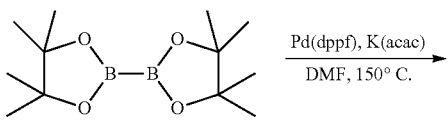

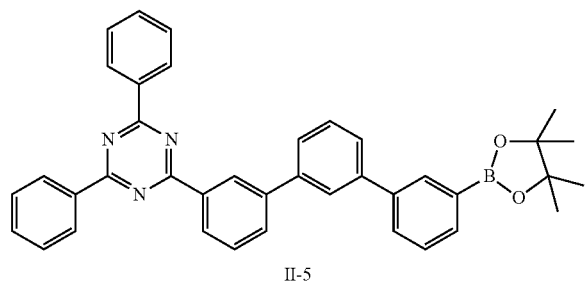

II-5

100 g (185 mmol) of the compound II-4 was dissolved in 1 L of dimethylformamide (DMF) under a nitrogen environment, 56 g (222 mmol) of bis(pinacolato)diboron, 1.5 g (1.85 mmol) of (1,1'-bis(diphenylphosphine)ferrocene)dichloropalladium (II) and 45 g (595 mmol) of potassium acetate were added thereto, and the mixture was heated and refluxed at 150° C. for 5 hours. When the reaction was complete, water was added to the reaction solution, and the mixture was filtered and dried in a vacuum oven. The obtained residue was separated and purified through flash column chromatography, obtaining 95 g (88%) of the compound II-5.

6$^{th}$ Step: Synthesis of Compound 6-1

[Reaction Scheme 16]

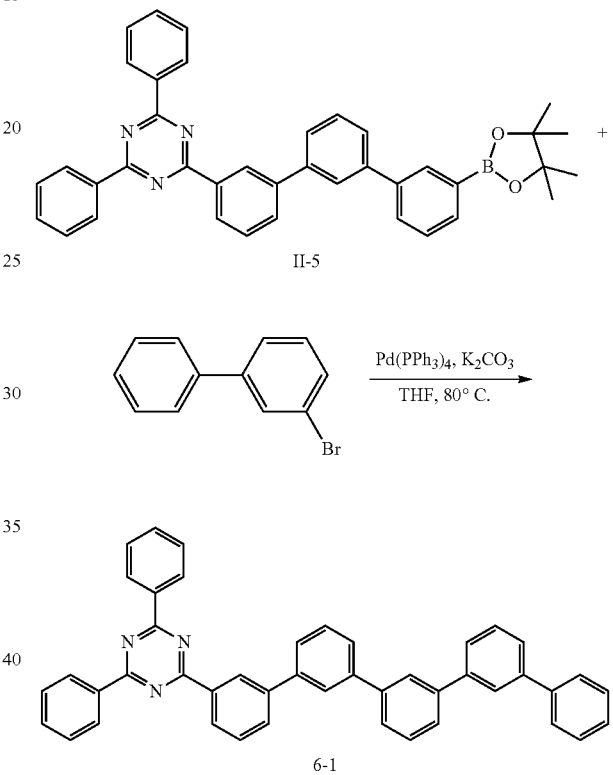

20 g (34 mmol) of the compound II-5 was dissolved in 0.2 L of tetrahydrofuran (THF) under a nitrogen environment, 9.5 g (40 mmol) of 3-bromo-1,1'-biphenyl and 0.39 g (0.34 mmol) of tetrakis(triphenylphosphine)palladium were added thereto, and the mixture was agitated. Then, 12 g (85 mmol) of potassium carbonate saturated in water was added thereto, and the mixture was heated and refluxed at 80° C. for 20 hours. When the reaction was complete, water was added to the reaction solution, and the mixture was extracted with dichloromethane (DCM) and then filtered after removing moisture with anhydrous $MgSO_4$ and concentrated under a reduced pressure. The obtained residue was separated and purified through flash column chromatography, obtaining 24 g (70%) of the compound 6-1.

LC Mass (calcd.: 613.75 g/mol, found: M+H$^+$=614.62 g/mol).

Synthesis Example 6

Synthesis of Compound 6-5

[Reaction Scheme 17]

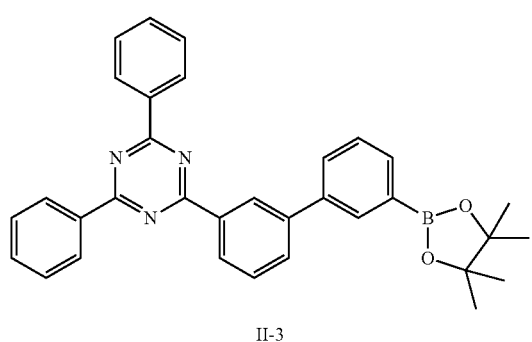

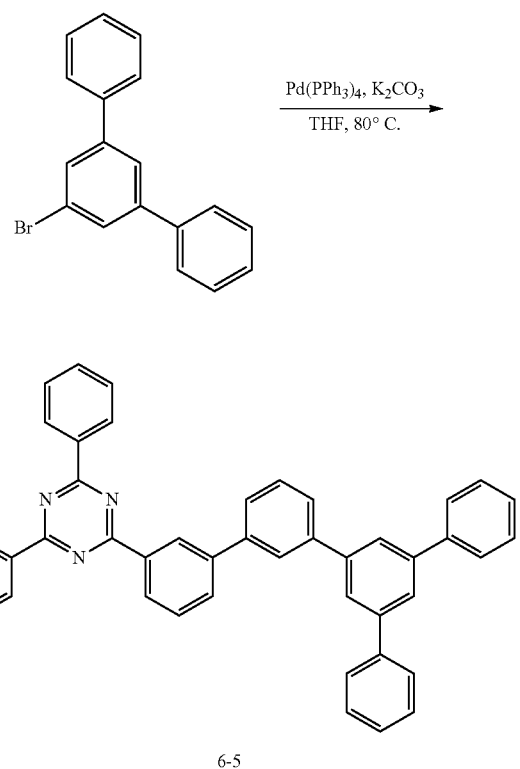

20 g (39.1 mmol) of the compound II-3 was dissolved in 0.2 L of tetrahydrofuran (THF) under a nitrogen environment, 14.5 g (47 mmol) of 5"-bromo-1,1':3',1"-terphenyl and 0.45 g (0.39 mmol) of tetrakis(triphenylphosphine) palladium were added thereto, and the mixture was agitated. Then, 9.7 g (99 mmol) of potassium carbonate saturated in water was added thereto, and the resulting mixture was heated and refluxed at 80° C. for 20 hours. When the reaction was complete, water was added to the reaction solution, and the mixture was extracted with dichloromethane (DCM) and then filtered after removing moisture with anhydrous MgSO$_4$ and concentrated under a reduced pressure. The obtained residue was separated and purified through flash column chromatography, obtaining 20 g (83%) of the compound 6-5.

LC Mass (calcd.: 613.75 g/mol, found: M+H$^+$=614.63 g/mol).

Synthesis Example 7

Synthesis of Compound 6-7

[Reaction Scheme 18]

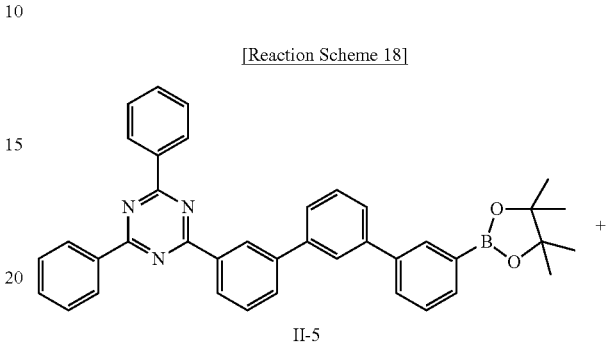

20 g (34 mmol) of the compound II-5 was dissolved in 0.2 L of tetrahydrofuran (THF) under a nitrogen environment, 12.6 g (40 mmol) of 5'-bromo-1,1':3',1"-terphenyl and 0.40 g (0.34 mmol) of tetrakis(triphenylphosphine)palladium were added thereto, and the mixture was agitated. Then, 12 g (85 mmol) of potassium carbonate saturated in water was heated and refluxed at 80° C. for 20 hours. When the reaction was complete, water was added to the reaction solution, and the mixture was extracted with dichloromethane (DCM) and then filtered after removing moisture with anhydrous MgSO$_4$ and concentrated under a reduced pressure. The obtained residue was separated and purified through flash column chromatography, obtaining 19 g (80%) of the compound 6-7.

LC Mass (calcd.: 689.84 g/mol, found: M+H$^+$=690.72 g/mol).

Synthesis Example 8

Synthesis of Compound 6-90

1st Step: Synthesis of Intermediate I-17

[Reaction Scheme 19]

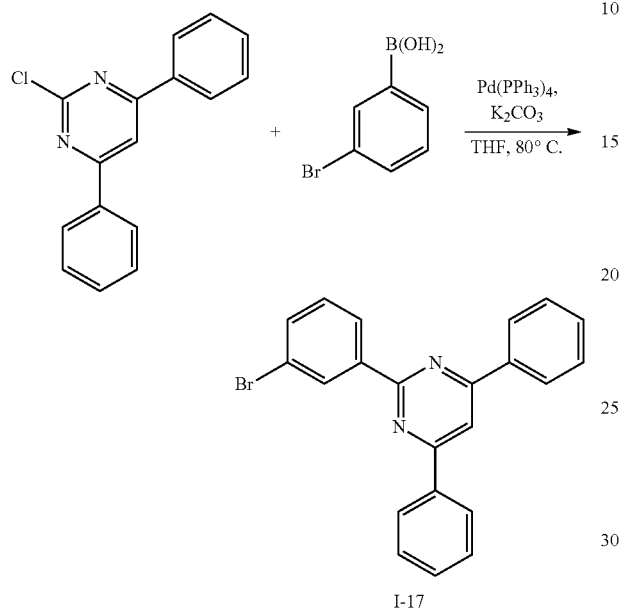

I-17

50 g (187 mmol) of the compound, 2-chloro-4,6-diphenylpyrimidine was dissolved in 1 L of THF under a nitrogen environment, 37 g (155 mmol) of (3-bromophenyl)boronic acid and 2.1 g (1.8 mmol) of tetrakis(triphenylphosphine)palladium were added thereto, and the mixture was agitated. Then, 64 g (467 mmol) of potassium carbonate saturated in water was added thereto, and the resulting mixture was heated and refluxed at 80° C. for 12 hours. When the reaction was complete, water was added to the reaction solution, and the mixture was extracted with dichloromethane (DCM) and then filtered after removing moisture with anhydrous MgSO₄ and concentrated under a reduced pressure. The obtained residue was separated and purified through flash column chromatography, obtaining 66 g (92%) of the compound I-17.

2nd Step: Synthesis of Intermediate I-18

[Reaction Scheme 20]

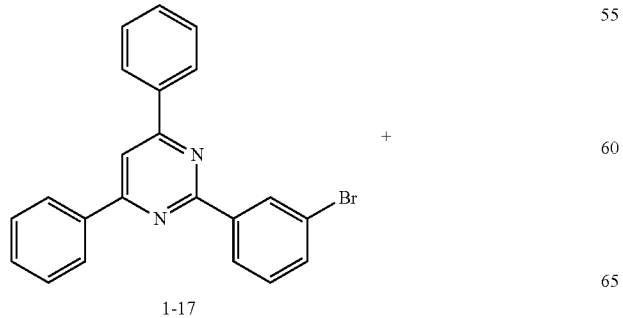

1-17

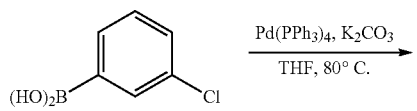

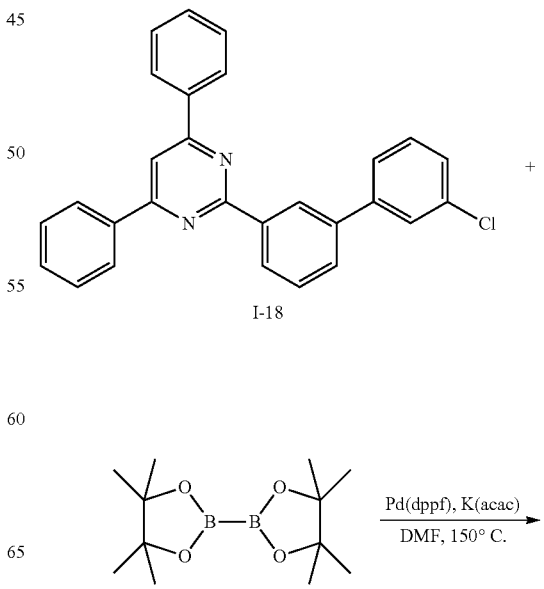

1-18

50 g (129 mmol) of the compound I-17 was dissolved in 1 L of THF under a nitrogen environment, 24 g (155 mmol) of (3-chlorophenyl)boronic acid and 1.5 g (1.3 mmol) of tetrakis(triphenylphosphine)palladium were added thereto, and the mixture was agitated. Then, 45 g (322 mmol) of potassium carbonate was added thereto, and the mixture was heated and refluxed at 80° C. for 12 hours. When the reaction was complete, water was added to the reaction solution, and the mixture was extracted with dichloromethane (DCM) and then filtered after removing moisture with anhydrous MgSO₄ and concentrated under a reduced pressure. The obtained residue was separated and purified through flash column chromatography, obtaining 50 g (92%) of the compound I-18.

3rd Step: Synthesis of Intermediate I-19

[Reaction Scheme 21]

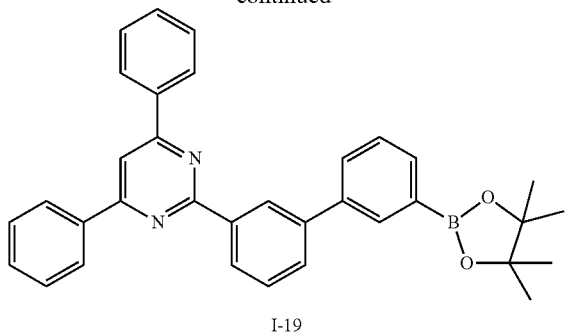

I-19

100 g (239 mmol) of the compound I-18 was dissolved in 1 L of dimethylformamide (DMF) under a nitrogen environment, 72.5 g (287 mmol) of bis(pinacolato)diboron, 2 g (2.38 mmol) of (1,1'-bis(diphenylphosphine)ferrocene)dichloropalladium (II) and 58 g (595 mmol) of potassium acetate were added thereto, and the mixture was heated and refluxed at 150° C. for 48 hours. When the reaction was complete, water was added to the reaction solution, and the mixture was filtered and dried in a vacuum oven. The obtained residue was separated and purified through flash column chromatography, obtaining 105 g (86%) of the compound I-19.

4$^{th}$ Step: Synthesis of Intermediate I-20

50 g (98 mmol) of the compound I-19 was dissolved in 1 L of THF under a nitrogen environment, 33 g (117 mmol) of 1-bromo-3-iodobenzene and 1 g (0.98 mmol) of tetrakis(triphenylphosphine)palladium were added thereto, and the mixture was agitated. Then, 34 g (245 mmol) of potassium carbonate saturated in water was heated and refluxed at 80° C. for 12 hours. When the reaction was complete, water was added to the reaction solution, and the mixture was extracted with dichloromethane (DCM) and then filtered after removing moisture with anhydrous MgSO$_4$ and concentrated under a reduced pressure. The obtained residue was separated and purified through flash column chromatography, obtaining 50 g (95%) of the compound I-20.

5$^{th}$ Step: Synthesis of Intermediate I-21

[Reaction Scheme 23]

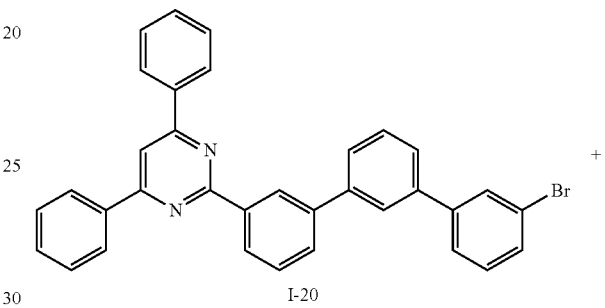

[Reaction Scheme 22]

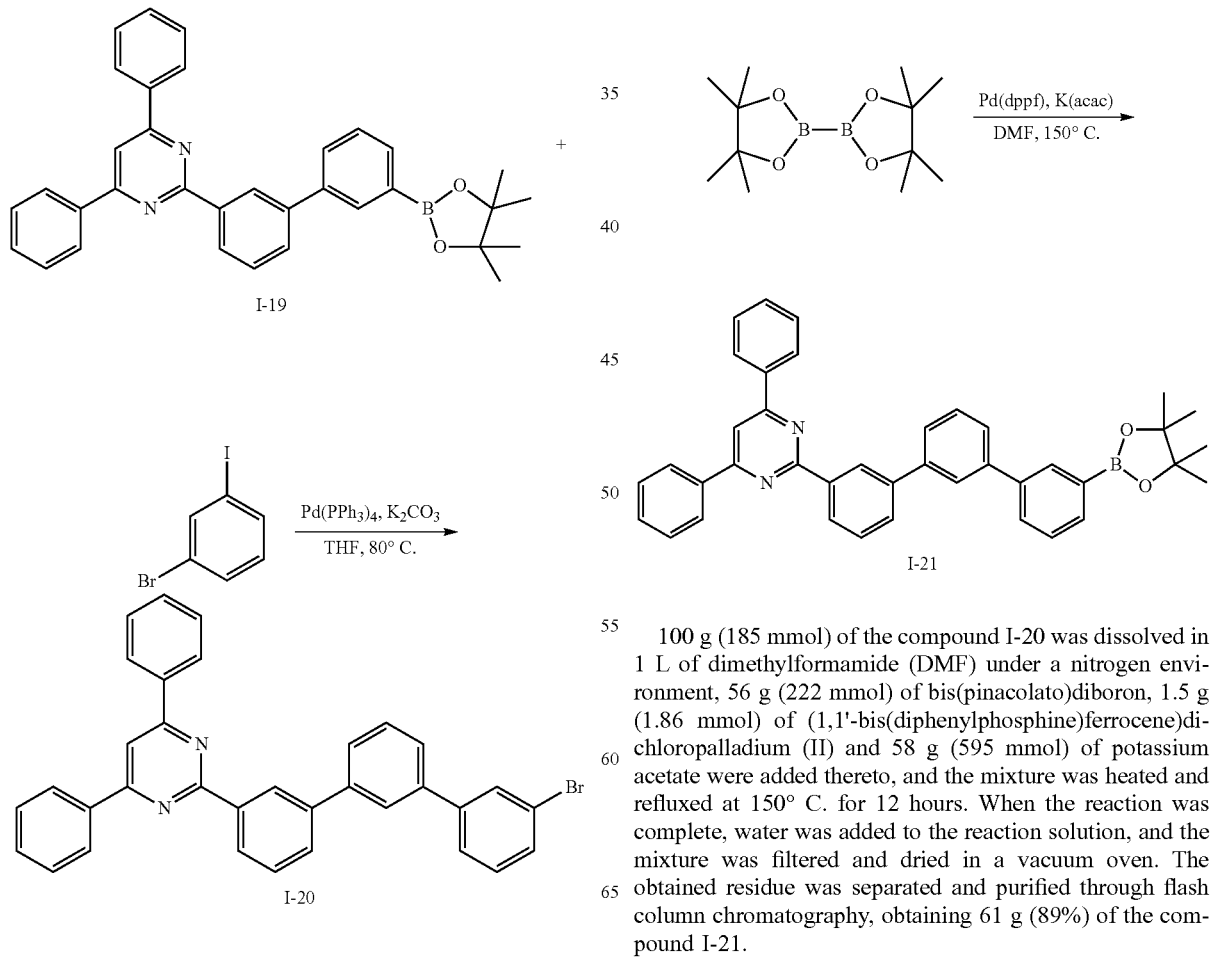

100 g (185 mmol) of the compound I-20 was dissolved in 1 L of dimethylformamide (DMF) under a nitrogen environment, 56 g (222 mmol) of bis(pinacolato)diboron, 1.5 g (1.86 mmol) of (1,1'-bis(diphenylphosphine)ferrocene)dichloropalladium (II) and 58 g (595 mmol) of potassium acetate were added thereto, and the mixture was heated and refluxed at 150° C. for 12 hours. When the reaction was complete, water was added to the reaction solution, and the mixture was filtered and dried in a vacuum oven. The obtained residue was separated and purified through flash column chromatography, obtaining 61 g (89%) of the compound I-21.

6<sup>th</sup> Step: Synthesis of Compound 6-90

[Reaction Scheme 24]

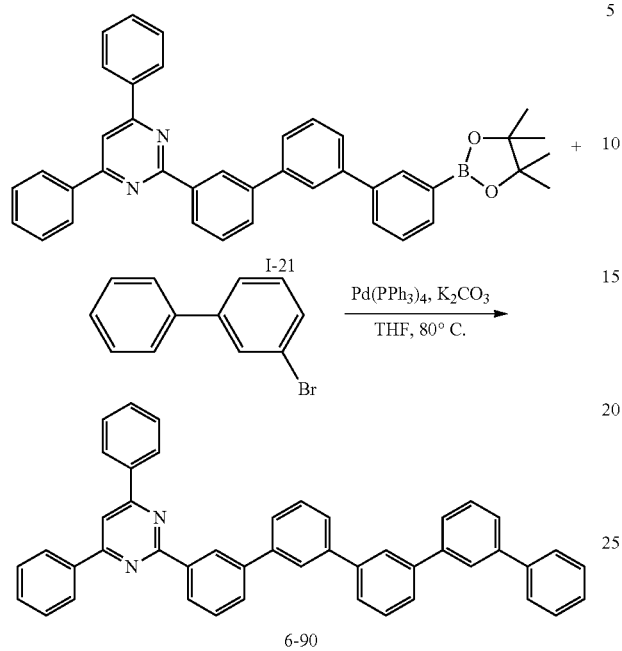

6-90

20 g (34 mmol) of the compound I-21 was dissolved in 0.2 L of tetrahydrofuran (THF) in a nitrogen environment, 9.5 g (40 mmol) of 3-bromo-1,1'-biphenyl and 0.39 g (0.34 mmol) of tetrakis(triphenylphosphine)palladium were added thereto, and the mixture was agitated. Then, 12 g (85 mmol) of potassium carbonate was added thereto, and the resulting mixture was heated and refluxed at 80° C. for 20 hours. When the reaction was complete, water was added to the reaction solution, and the mixture was extracted with dichloromethane (DCM) and then filtered after removing moisture with anhydrous MgSO₄ and concentrated under a reduced pressure. The obtained residue was separated and purified through flash column chromatography, obtaining 16 g (75%) of the compound 6-90.

LC Mass (calcd.: 612.76 g/mol, found: M+H⁺=613.68 g/mol).

Synthesis Example 9

Synthesis of Compound 6-9

1<sup>st</sup> Step: Synthesis of Intermediate I-10

[Reaction Scheme 25]

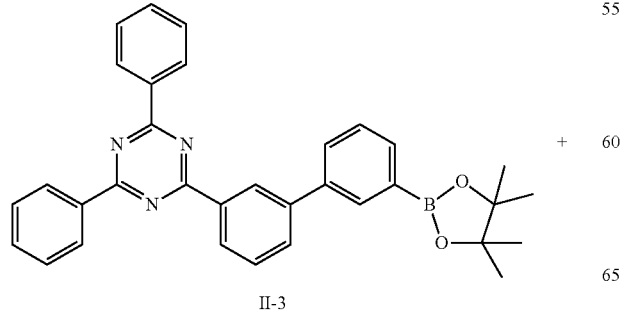

II-3

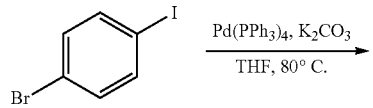

-continued

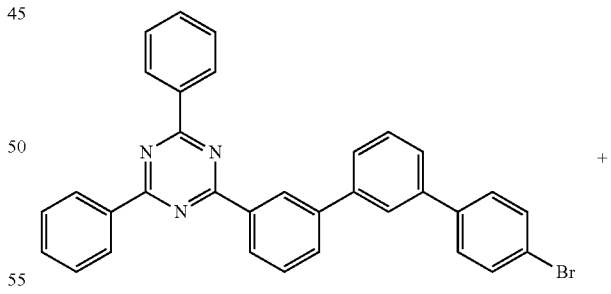

I-10

50 g (98 mmol) of the compound II-3 was dissolved in 1 L of THF under a nitrogen environment, 33 g (117 mmol) of 1-bromo-4-iodobenzene and 1 g (0.98 mmol) of tetrakis(triphenylphosphine)palladium were added thereto, and the mixture was agitated. Then, 34 g (245 mmol) of potassium carbonate saturated in water was added thereto, and the resulting mixture was heated and refluxed at 80° C. for 12 hours. When the reaction was complete, water was added to the reaction solution, and the mixture was extracted with dichloromethane (DCM) and then filtered after removing moisture with anhydrous MgSO₄ and concentrated under a reduced pressure. The obtained residue was separated and purified through flash column chromatography, obtaining 50 g (95%) of the compound I-10.

2<sup>nd</sup> Step: Synthesis of Intermediate I-11

[Reaction Scheme 26]

I-10

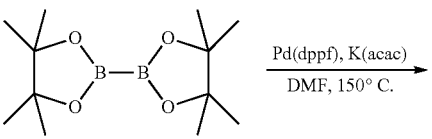

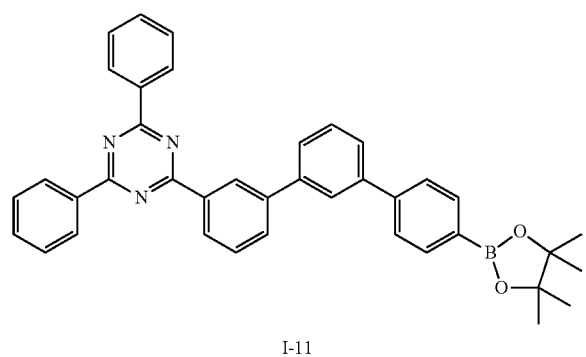

I-11

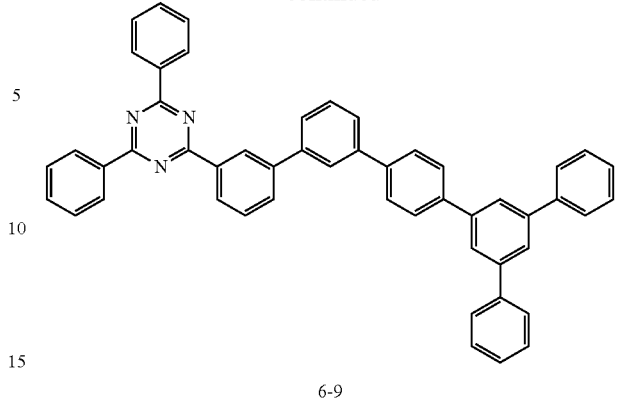

6-9

100 g (185 mmol) of the compound I-10 was dissolved in 1 L of dimethylformamide (DMF) under a nitrogen environment, 56 g (222 mmol) of bis(pinacolato)diboron, 1.5 g (1.85 mmol) of (1,1'-bis(diphenylphosphine)ferrocene)dichloropalladium (II) and 45 g (595 mmol) of potassium acetate were added thereto, and the mixture was heated and refluxed at 50° C. for 5 hours. When the reaction was complete, water was added to the reaction solution, and the mixture was filtered and dried in a vacuum oven. The obtained residue was separated and purified through flash column chromatography, obtaining 95 g (88%) of the compound I-11.

3$^{rd}$ Step: Synthesis of Compound 6-9

[Reaction Scheme 27]

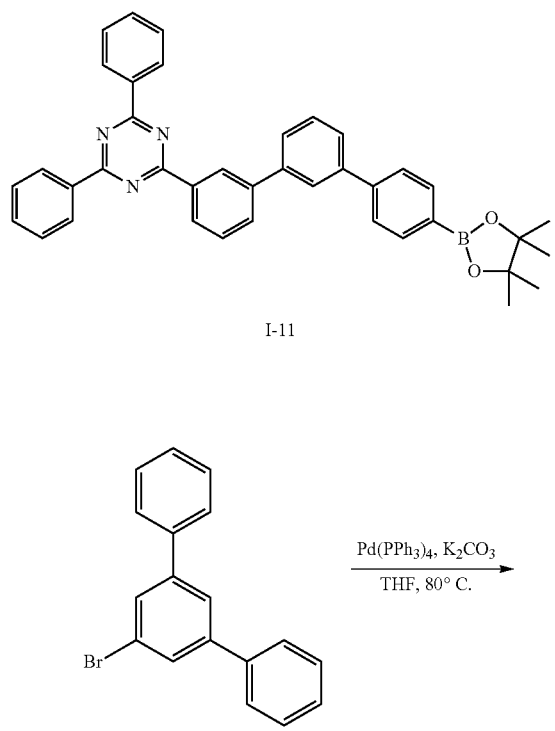

20 g (34 mmol) of the compound I-11 was dissolved in 0.2 L of tetrahydrofuran (THF) under a nitrogen environment, 12.6 g (40 mmol) of 5'-bromo-1,1':3',1''-terphenyl and 0.40 g (0.34 mmol) of tetrakis(triphenylphosphine)palladium were added thereto, and the mixture was agitated. Then, 12 g (85 mmol) of potassium carbonate saturated in water was heated and refluxed at 80° C. for 20 hours. When the reaction was complete, water was added to the reaction solution, and the mixture was extracted with dichloromethane (DCM) and then filtered and concentrated under a reduced pressure after removing moisture with anhydrous MgSO$_4$. The obtained residue was separated and purified through flash column chromatography, obtaining 20 g (85%) of the compound 6-9.

LC Mass (calcd.: 689.84 g/mol, found: M+H$^+$=690.71 g/mol).

Manufacture of Organic Light Emitting Diode

Example 4

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then moved to a vacuum depositor. This ITO transparent electrode was used as an anode, a 700 Å-thick hole injection layer (HIL) was formed by vacuum-depositing the compound A on the ITO substrate, and a hole transport layer (HTL) was formed by depositing the compound B to be 50 Å thick on the injection layer and the compound C to be 1020 Å thick. On the hole transport layer (HTL), a 400 Å-thick emission layer was formed by vacuum-depositing both the compound 2-1 according to Synthesis Example 1 and the compound 4-10 according to Synthesis Example 4 as a host doped with 10 wt % of tris(2-phenylpyridine)iridium (III) [Ir(ppy)$_3$]. Herein, the compound 2-1 and the compound 4-10 were used in a ratio of 1:1.

Subsequently, on the emission layer, a 300 Å-thick electron transport layer (ETL) were formed by simultaneously vacuum-depositing the compound D and Liq in a ratio of 1:1, and a cathode was formed by sequentially vacuum-depositing Liq to be 15 Å thick and Al to be 1200 Å thick on the electron transport layer (ETL), manufacturing an organic light emitting diode.

The organic light emitting diode had a five-layered organic thin film structure specifically as follows.

A structure of ITO/compound A 700 Å/compound B 50 Å/compound C 1020 Å/EML [compound 2-1: compound 4-10:Ir(ppy)$_3$=X:X:10%]400 Å/compound D:Liq 300 Å/Liq 15 Å/Al 1200 Å. (X=a weight ratio)

The compound A: N4,N4'-diphenyl-N4,N4'-bis (9-phenyl-9H-carbazol-3-yl)biphenyl-4,4'-diamine The compound B: 1,4,5,8,9,11-hexaazatriphenylene-hexacarbonitrile (HAT-CN), The compound C: N-(biphenyl-4-yl)-9,9-dimethyl-N-(4-(9-phenyl-9H-carbazol-3-yl)phenyl)-9H-fluoren-2-amine The compound D: 8-(4-(4,6-di(naphthalen-2-yl)-1,3,5-triazin-2-yl)phenyl)quinoline Example 5

An organic light emitting diode was manufactured according to the same method as Example 4 except for using the compound 2-1 of Synthesis Example 1 and the compound 6-1 of Synthesis Example 5 in a ratio of 1:1.

Example 6

An organic light emitting diode was manufactured according to the same method as Example 4 except for using the compound 2-1 of Synthesis Example 1 and the compound 6-5 of Synthesis Example 6 in a ratio of 1:1.

Example 7

An organic light emitting diode was manufactured according to the same method as Example 4 except for using the compound 2-1 of Synthesis Example 1 and the compound 6-7 of Synthesis Example 7 in a ratio of 1:1.

Example 8

An organic light emitting diode was manufactured according to the same method as
Example 4 except for using the compound 2-1 of Synthesis Example 1 and the compound 6-90 of Synthesis Example 8 in a ratio of 1:1.

Example 9

An organic light emitting diode was manufactured according to the same method as Example 4 except for using the compound 2-6 of Synthesis Example 2 and the compound 4-10 of Synthesis Example 4 in a ratio of 1:1.

Example 10

An organic light emitting diode was manufactured according to the same method as Example 4 except for using the compound 2-6 of Synthesis Example 2 and the compound 6-5 of Synthesis Example 6 in a ratio of 1:1.

Example 11

An organic light emitting diode was manufactured according to the same method as Example 4 except for using the compound 2-42 of Synthesis Example 3 and the compound 4-10 of Synthesis Example 4 in a ratio of 1:1.

Example 12

An organic light emitting diode was manufactured according to the same method as Example 4 except for using the compound 2-42 of Synthesis Example 3 and the compound 6-1 of Synthesis Example 5 in a ratio of 1:1.

Example 13

An organic light emitting diode was manufactured according to the same method as Example 4 except for using the compound 2-42 of Synthesis Example 3 and the compound 6-5 of Synthesis Example 6 in a ratio of 1:1.

Comparative Example 4

An organic light emitting diode was manufactured according to the same method as Example 4 except for using CBP as a single host instead of two hosts of the compounds according to Synthesis Examples 1 and 4.

Reference Example 1

An organic light emitting diode was manufactured according to the same method as Example 4 except for using the compound 2-1 according to Synthesis Example 1 instead of the two hosts of the compounds according to Synthesis Examples 1 and 4.

Reference Example 2

An organic light emitting diode was manufactured according to the same method as Example 4 except for using the compound 6-7 according to Synthesis Example 7 instead of the two hosts of the compounds according to Synthesis Examples 1 and 4.

Evaluation

Luminous efficiency and life-span characteristics of each organic light emitting diode according to Examples 4 to 13 and Comparative Example 4, Reference Examples 1 and 2 were measured.

Specific measurement methods were as follows, and the results are provided in Table 3.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Life-Span

The life span result was obtained by measuring time taken until current efficiency (cd/A) decreased down to 97%, while the luminance (cd/m$^2$) was maintained at 6000 cd/m$^2$.

TABLE 3

| | First host | Second host | First host:Second host | Luminous efficiency (cd/A) | Life-span T97 (h) |
|---|---|---|---|---|---|
| Ex. 4 | Synth. Ex. 1 (cmpd 2-1) | Synth. Ex. 4 (cmpd 4-10) | 1:1 | 47.0 | 76 |

TABLE 3-continued

| | First host | Second host | First host:Second host | Luminous efficiency (cd/A) | Life-span T97 (h) |
|---|---|---|---|---|---|
| Ex. 5 | Synth. Ex. 1 (cmpd 2-1) | Synth. Ex. 5 (cmpd 6-1) | 1:1 | 46.5 | 80 |
| Ex. 6 | Synth. Ex. 1 (cmpd 2-1) | Synth. Ex. 6 (cmpd 6-5) | 1:1 | 46.8 | 65 |
| Ex. 7 | Synth. Ex. 1 (cmpd 2-1) | Synth. Ex. 7 (cmpd 6-7) | 1:1 | 45.5 | 68 |
| Ex. 8 | Synth. Ex. 1 (cmpd 2-1) | Synth. Ex. 8 (cmpd 6-90) | 1:1 | 46.9 | 60 |
| Ex. 9 | Synth. Ex. 2 (cmpd 2-6) | Synth. Ex. 4 (cmpd 4-10) | 1:1 | 46.8 | 72 |
| Ex. 10 | Synth. Ex. 2 (cmpd 2-6) | Synth. Ex. 6 (cmpd 6-5) | 1:1 | 45.4 | 61 |
| Ex. 11 | Synth. Ex. 3 (cmpd 2-42) | Synth. Ex. 4 (cmpd 4-10) | 1:1 | 46.6 | 67 |
| Ex. 12 | Synth. Ex. 3 (cmpd 2-42) | Synth. Ex. 5 (cmpd 6-1) | 1:1 | 46.1 | 70 |
| Ex. 13 | Synth. Ex. 3 (cmpd 2-42) | Synth. Ex. 6 (cmpd 6-5) | 1:1 | 46.3 | 69 |
| Comp. Ex. 4 | CBP | | — | 31.5 | 0.5 |
| Ref. Ex. 1 | Synth. Ex. 1 (cmpd 2-1) | | — | 3.5 | 1 |
| Ref. Ex. 2 | Synth. Ex. 7 (cmpd 6-7) | | — | 34.6 | 48 |

Referring to Table 3, the organic light emitting diodes according to Examples 4 to 13 showed remarkably improved luminous efficiency and life-span characteristics compared with the organic light emitting diodes according to Comparative Example 4 and Reference Examples 1 and 2.

By way of summation and review, examples of an organic optoelectric device may be an organic photoelectric device, an organic light emitting diode, an organic solar cell, and an organic photo conductor drum.

Of these, an organic light emitting diode (OLED) has drawn attention due to demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport layer, an electron injection layer, and a hole blocking layer in order increase efficiency and stability of an organic light emitting diode.

Performance of an organic light emitting diode may be affected by characteristics of the organic layer, and among them, may be significantly affected by characteristics of an organic material of the organic layer.

For example, development for an organic material capable of increasing hole and electron mobility and simultaneously increasing electrochemical stability may be important in the case that the organic light emitting diode is applied to a large-size flat panel display.

As described above, embodiments may provide a compound for an organic optoelectric device realizing an organic optoelectric device having high efficiency and long life-span.

As described above, embodiments may provide a composition for an organic optoelectric device including the compound for an organic optoelectric device.

As described above, embodiments may provide an organic optoelectric device including the compound for an organic optoelectric device.

As described above, embodiments may provide a display device including the organic optoelectric device.

According to embodiments, an organic optoelectric device having high efficiency and long life-span may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS 100, 200: organic light emitting diode
105: organic layer
110: cathode
120: anode
130: emission layer
140: hole auxiliary layer

What is claimed is:
1. A compound for an organic optoelectric device, the compound represented by a combination of Chemical Formula I-1 and Chemical Formula I-2 linked together:

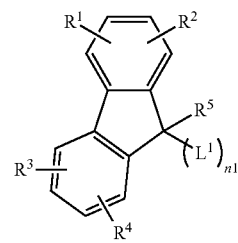

[Chemical Formula I-1]

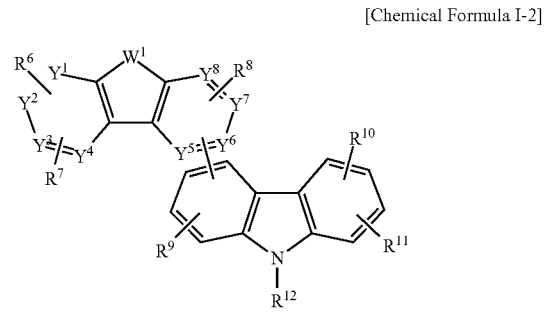

[Chemical Formula I-2]

wherein, in Chemical Formulae I-1 and I-2,
$Y^1$ to $Y^8$ are independently C or $CR^a$,
$W^1$ is N or $NR^b$,
one of $Y^1$ to $Y^8$ and $W^1$ of Chemical Formula I-2 is linked to $L^1$ of Chemical Formula I-1,
$R^1$ to $R^{12}$, $R^a$ and $R^b$ are each independently hydrogen, deuterium, a substituted or unsubstituted C1 to C30 alkyl group, a substituted or unsubstituted C6 to C30 aryl group, or a combination thereof, $L^1$ is a single bond, a substituted or unsubstituted C6 to C30 arylene group, or a combination thereof, and n1 is an integer of 1 to 3, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

2. The compound for an organic optoelectric device as claimed in claim 1, wherein the compound is represented by Chemical Formulae I-A to I-E:

[Chemical Formula I-A]

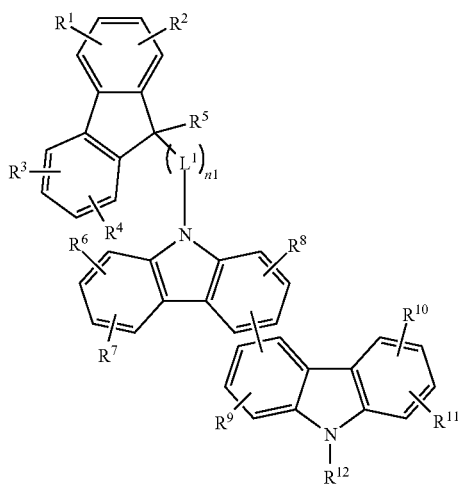

[Chemical Formula I-B]

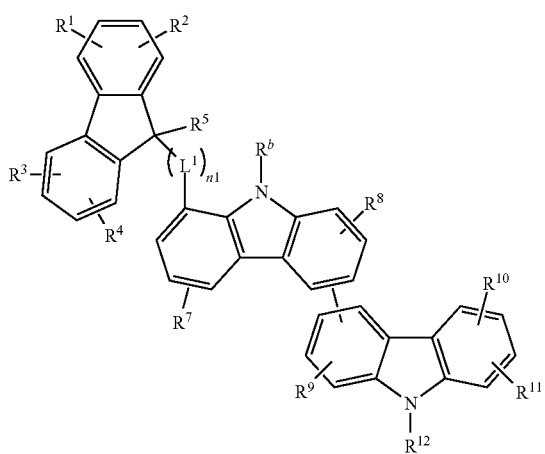

[Chemical Formula I-C]

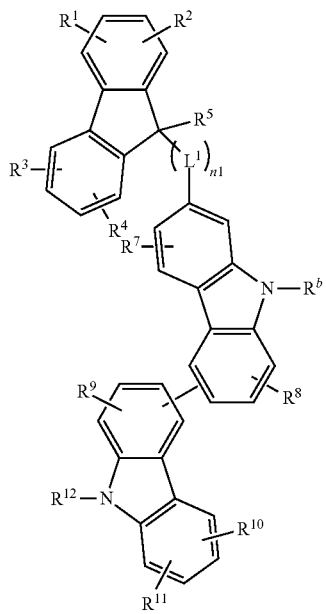

[Chemical Formula I-D]

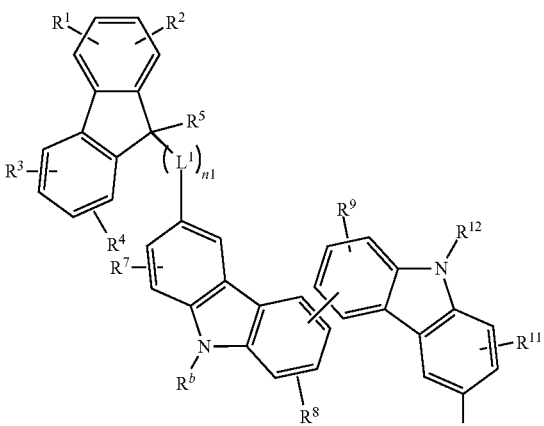

[Chemical Formula I-E]

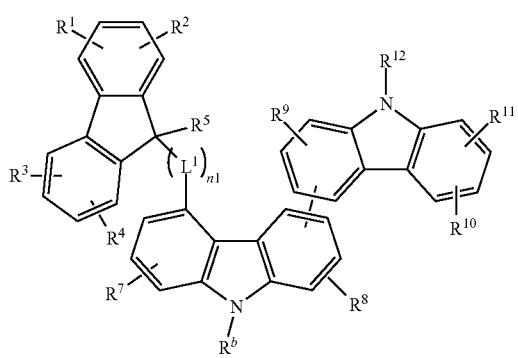

wherein, in Chemical Formulae I-A to I-E, $R^1$ to $R^{12}$ and $R^b$ are each independently hydrogen, deuterium, a substituted or unsubstituted C1 to C30 alkyl group, a substituted or unsubstituted C6 to C30 aryl group, or a combination thereof, $L^1$ is a single bond, a substituted or unsubstituted C6 to C30 arylene group, or a combination thereof, and n1 is an integer of 1 to 3, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

3. The compound for an organic optoelectric device as claimed in claim 1, wherein the Chemical Formula I-2 is represented by one of Chemical Formulae I-2a to I-2h:

[Chemical Formula I-2a]

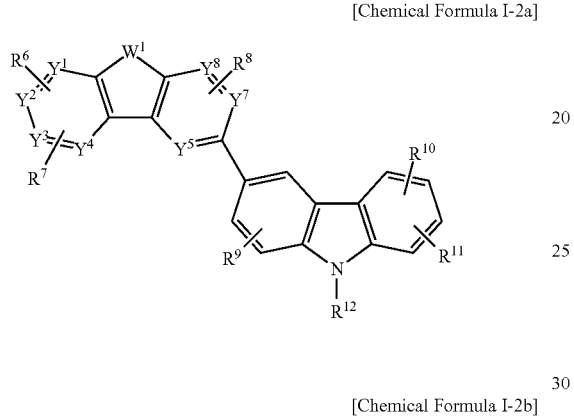

[Chemical Formula I-2b]

[Chemical Formula I-2c]

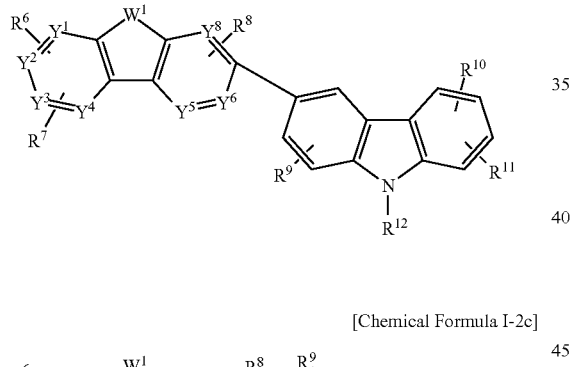

[Chemical Formula I-2d]

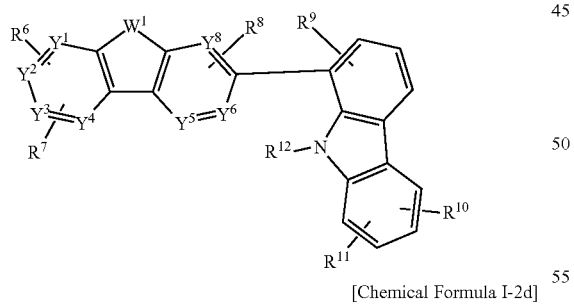

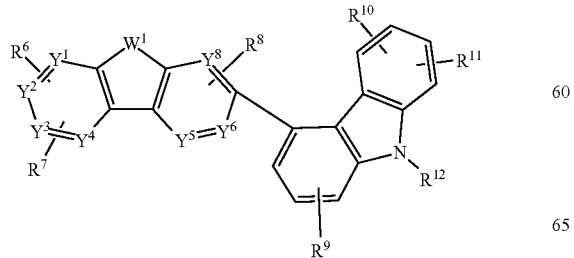

[Chemical Formula I-2e]

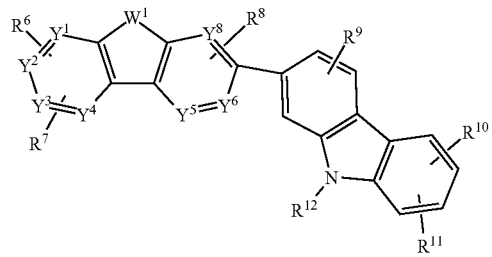

[Chemical Formula I-2f]

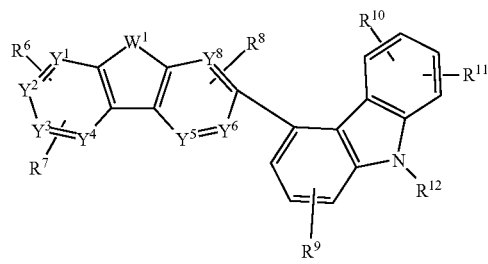

[Chemical Formula I-2g]

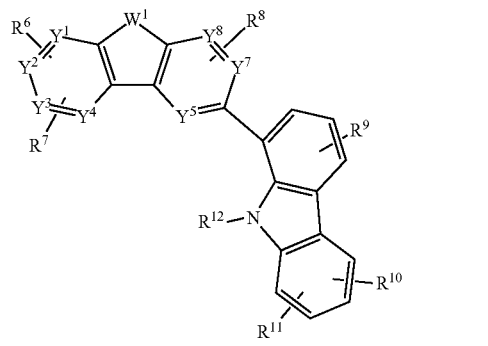

[Chemical Formula I-2h]

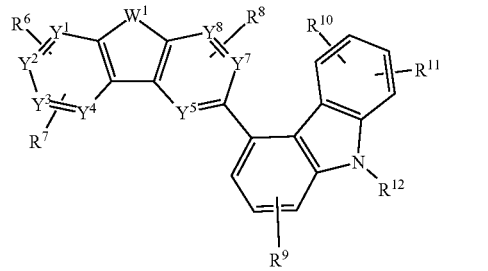

wherein, in Chemical Formulae I-2a to I-2h,
$Y^1$ to $Y^8$ are independently C or $CR^a$,
$W^1$ is N or $NR^b$,
one of $Y^1$ to $Y^8$ and $W^1$ is linked to $L^1$ of Chemical Formula I-1,
$R^6$ to $R^{12}$, $R^a$ and $R^b$ are each independently hydrogen, deuterium, a substituted or unsubstituted C1 to C30 alkyl group, a substituted or unsubstituted C6 to C30 aryl group, or a combination thereof, and
wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

4. The compound for an organic optoelectric device as claimed in claim 1, wherein the compound is represented by Chemical Formulae I a to I e:

[Chemical Formula I a]

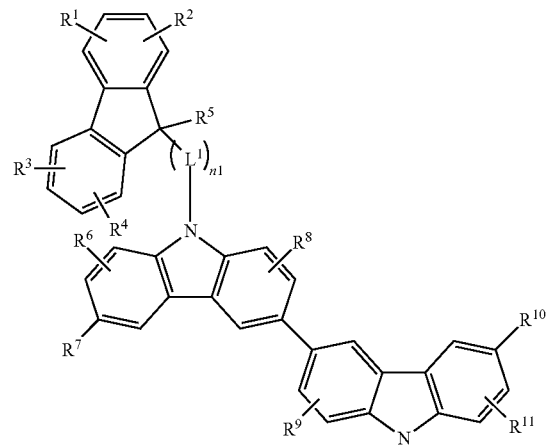

[Chemical Formula I b]

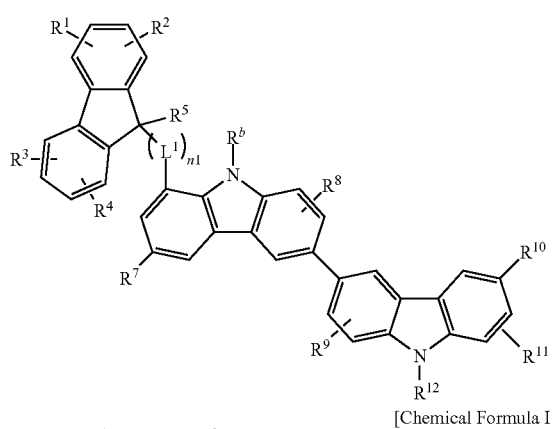

[Chemical Formula I c]

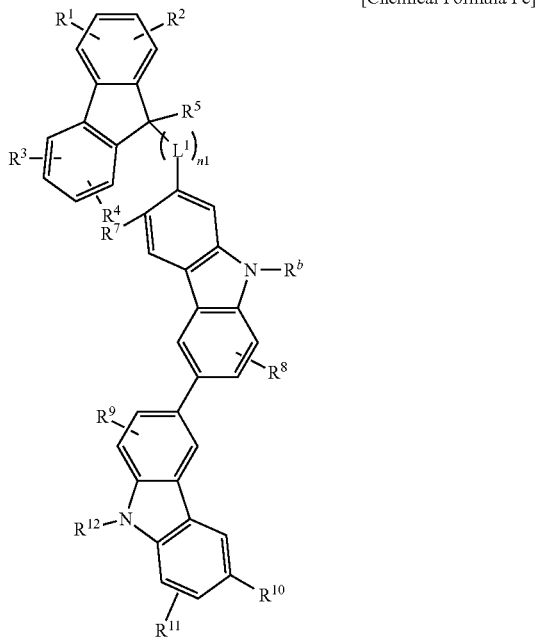

[Chemical Formula I d]

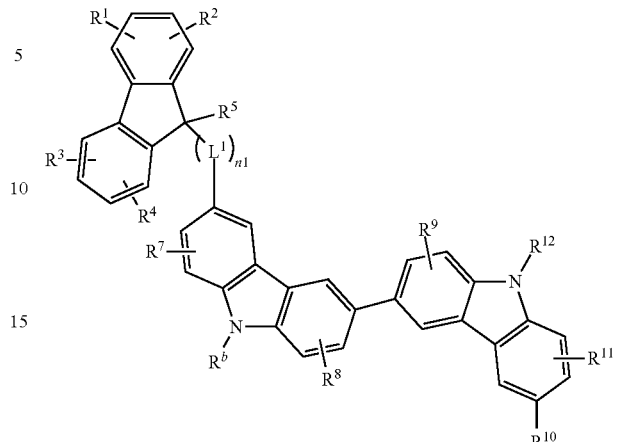

[Chemical Formula I e]

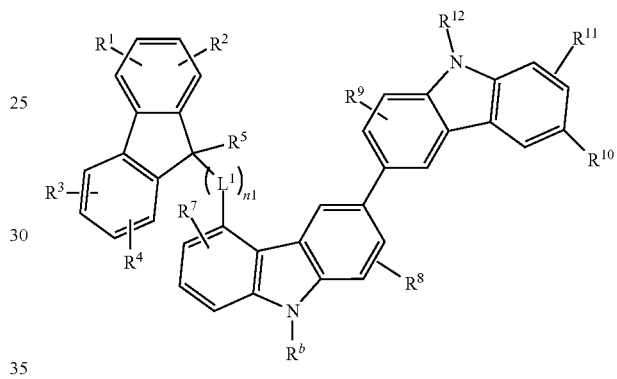

wherein, in Chemical Formulae I a to I e, $R^1$ to $R^{12}$ and $R^b$ are each independently hydrogen, deuterium, a substituted or unsubstituted C1 to C30 alkyl group, a substituted or unsubstituted C6 to C30 aryl group, or a combination thereof, $L^1$ is a single bond, a substituted or unsubstituted C6 to C30 arylene group, or a combination thereof, and n1 is an integer of 1 to 3, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

5. The compound for an organic optoelectric device as claimed in claim 1, wherein the $L^1$ is a substituted or unsubstituted phenylene listed in Group 1:

[Group 1]

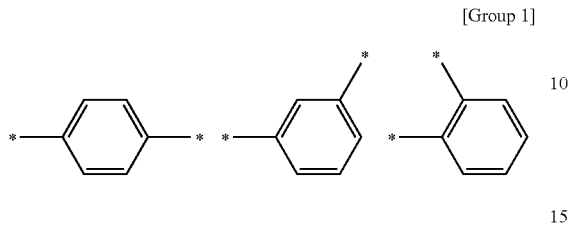

wherein, in Group 1, indicates a linking point, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C1 to C20 alkoxy group, a fluoro group, a C1 to C10 trifluoroalkyl group, or a cyano group.

6. The compound for an organic optoelectric device as claimed in claim 1, wherein the compound is listed in Group 2:

[Group 2]

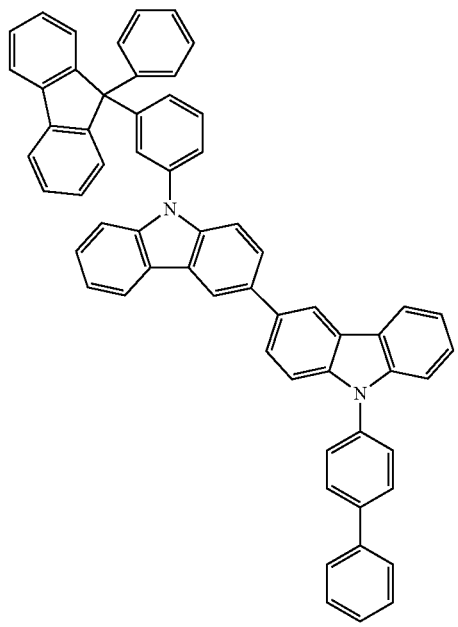

[2-2]

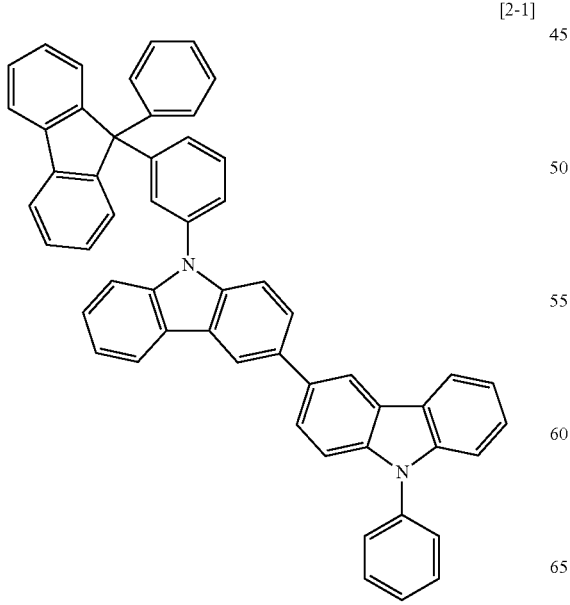

[2-1]

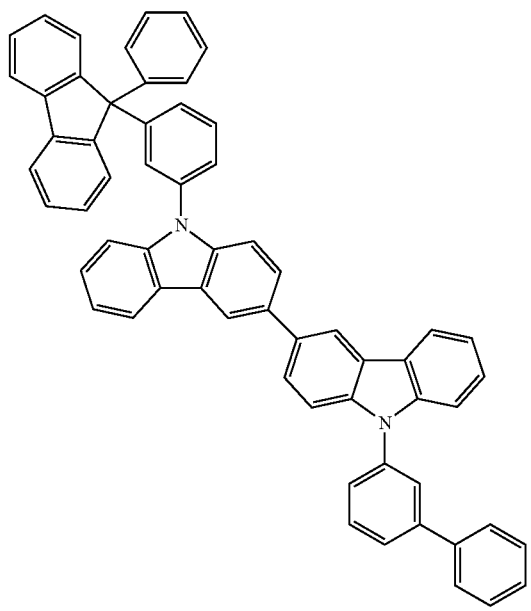

[2-3]

[2-4]
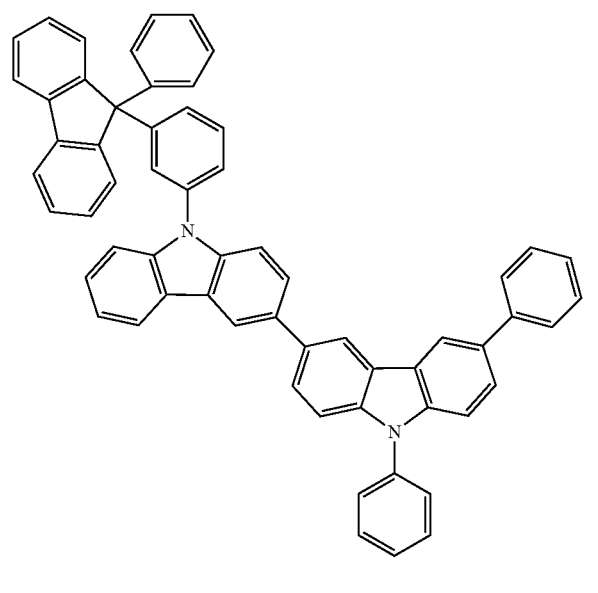
[2-6]
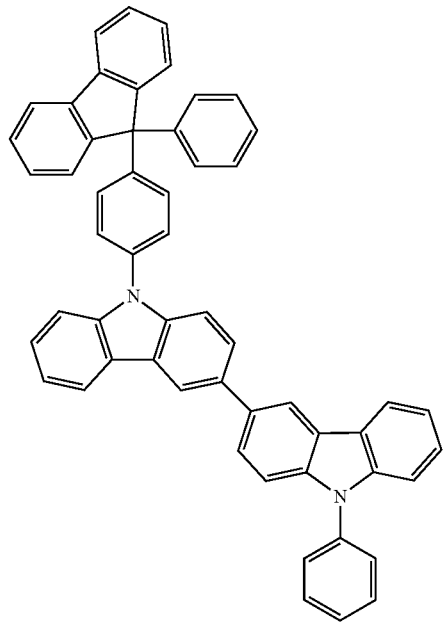
[2-5]
[2-7]
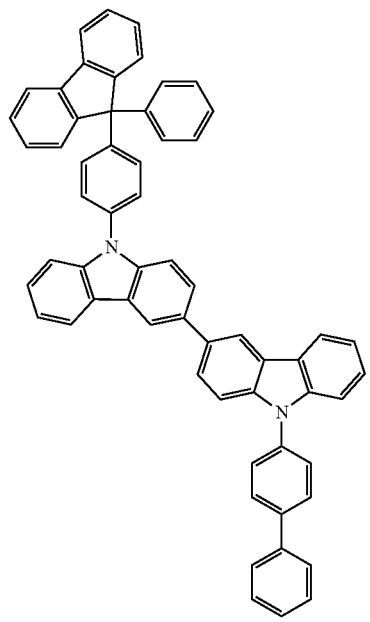

[2-8]
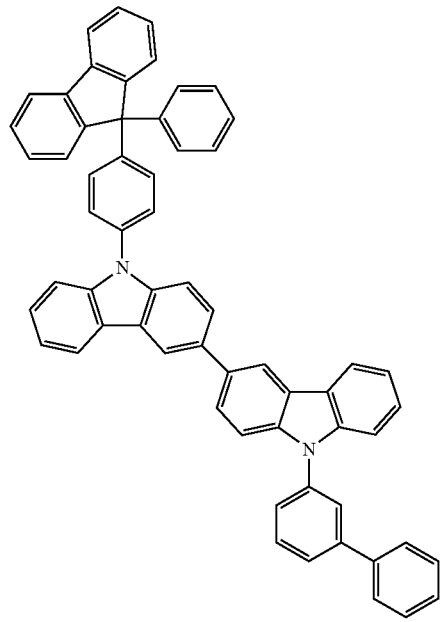
[2-9]
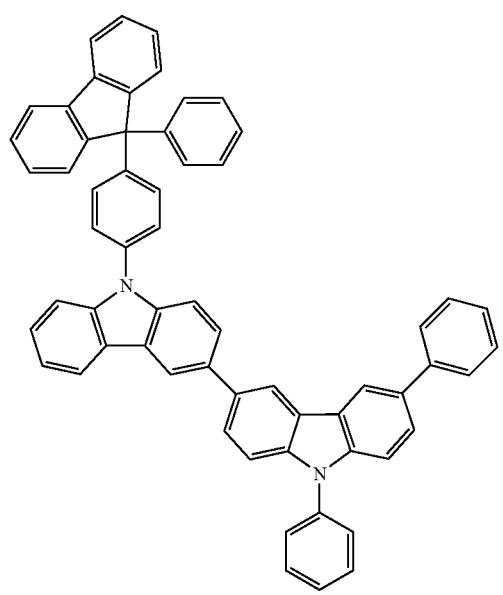
[2-10]
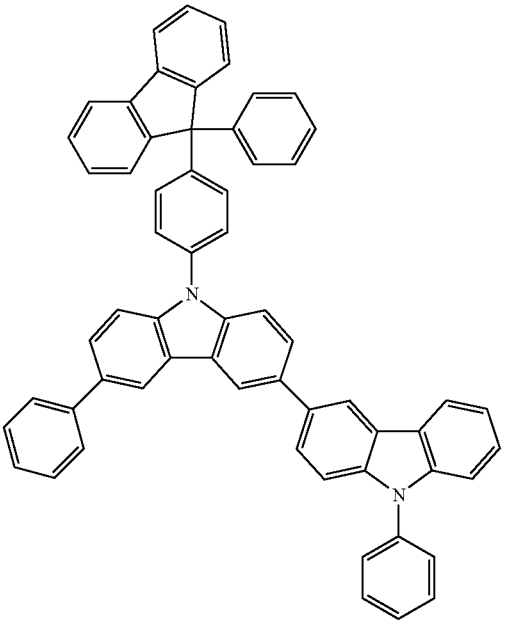
[2-11]
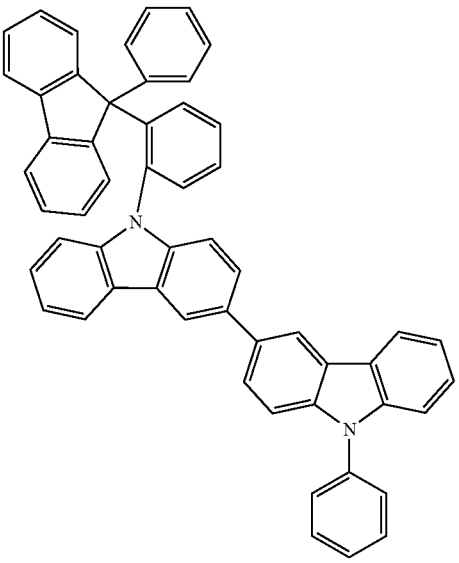

-continued
[2-12]
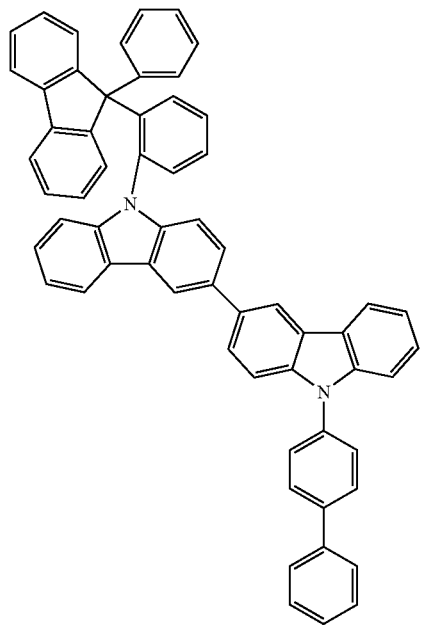
[2-13]
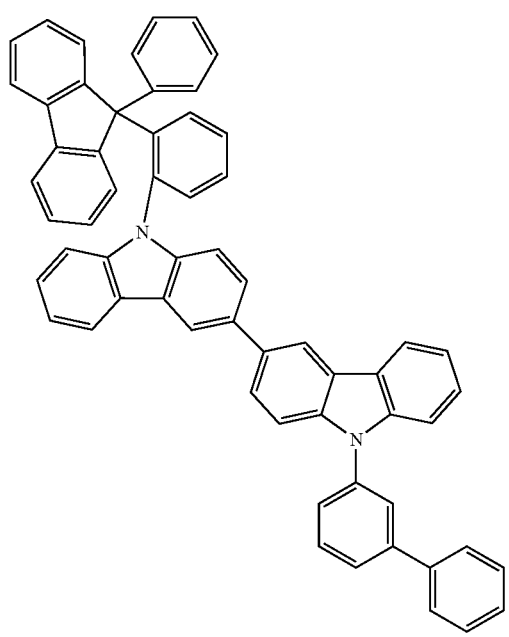
[2-14]
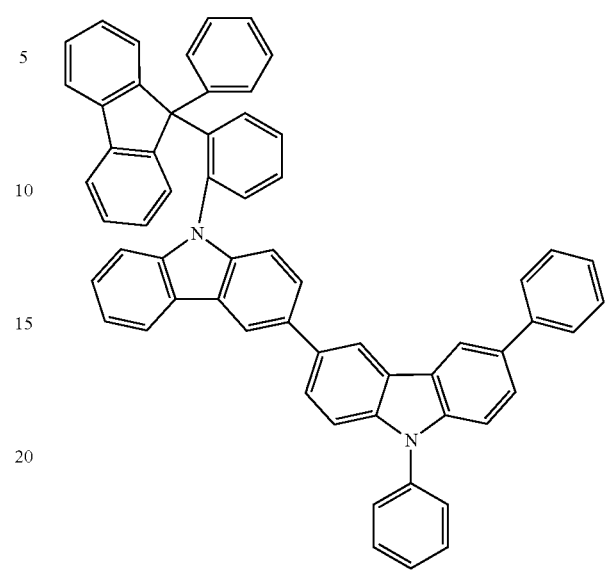
[2-15]
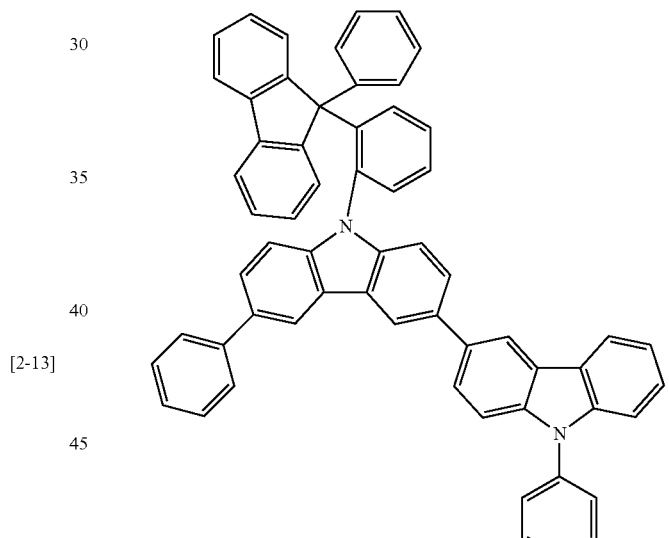
[2-16]
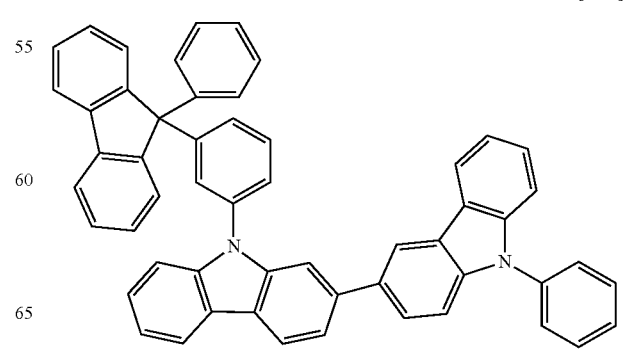

[2-17]
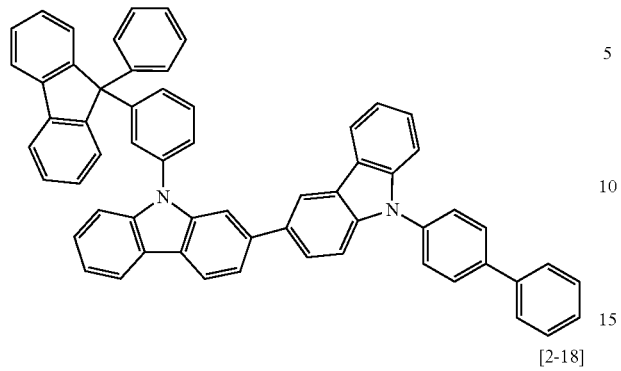
[2-18]
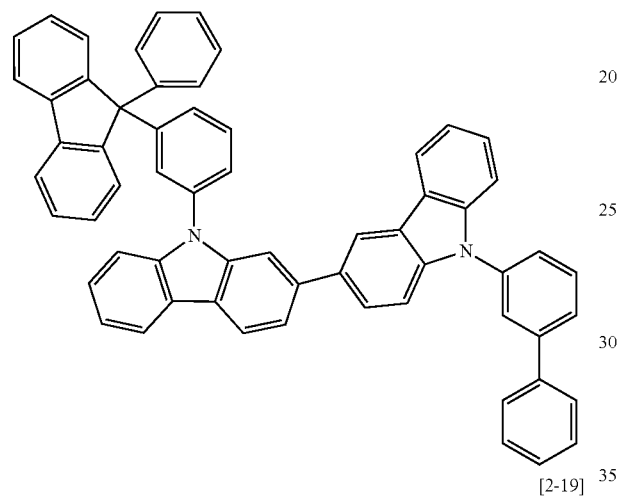
[2-19]
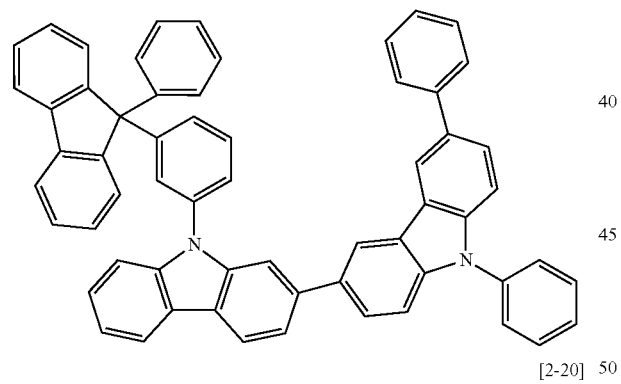
[2-20]
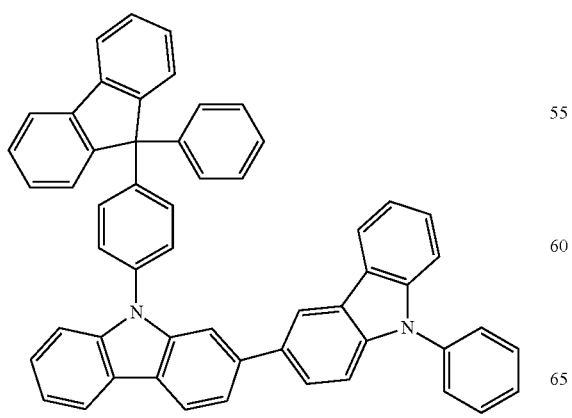
[2-21]
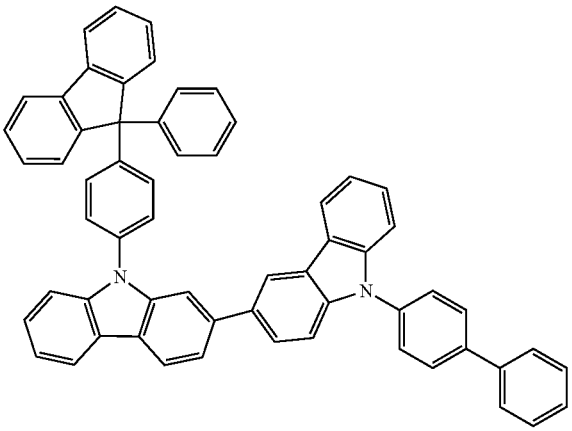
[2-22]
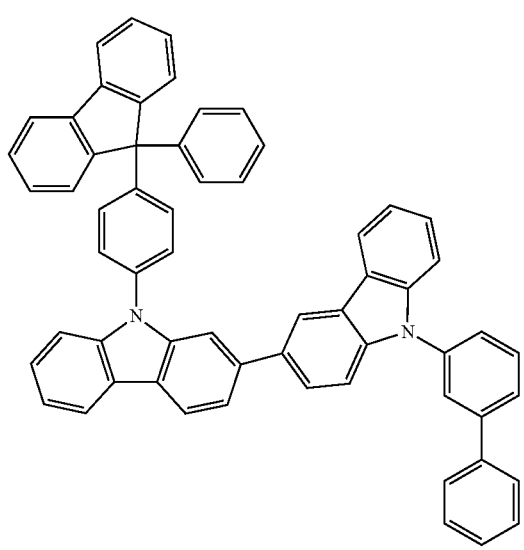
[2-23]
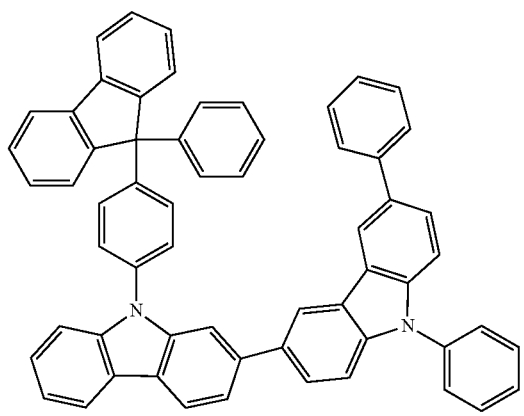

[2-24]
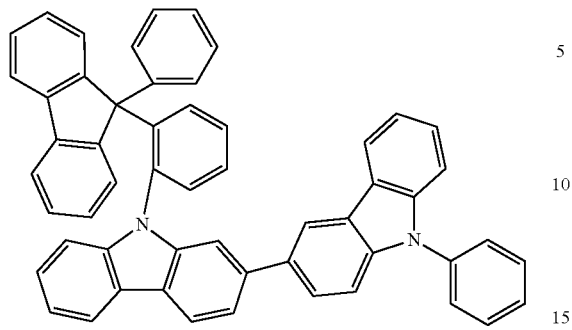
[2-25]
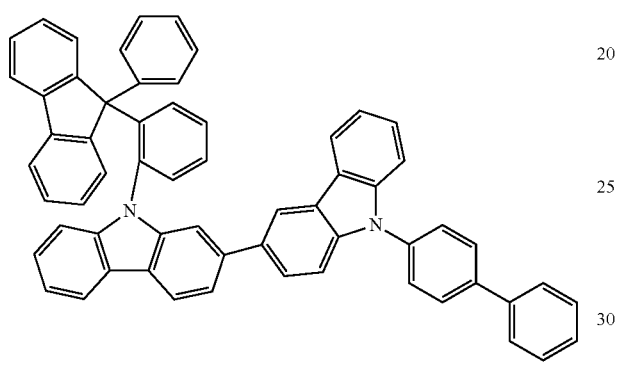
[2-26]
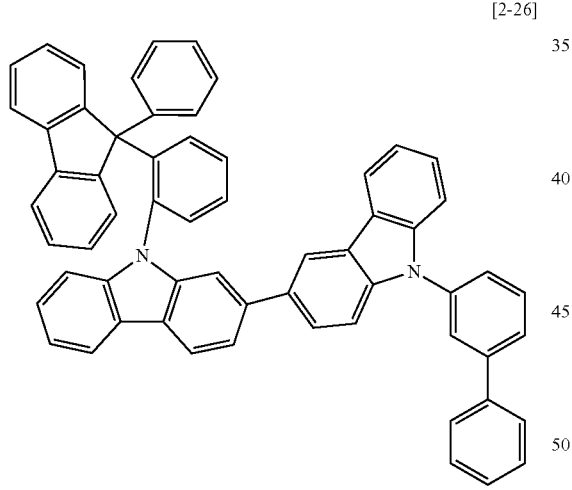
[2-27]
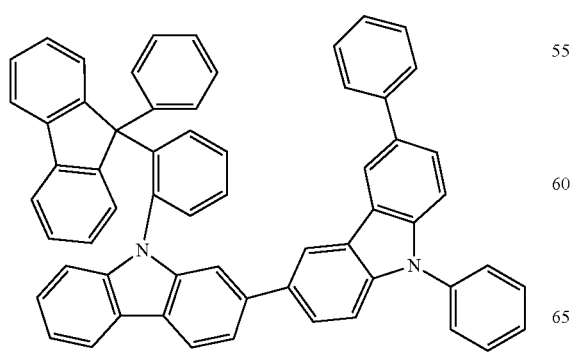
[2-28]
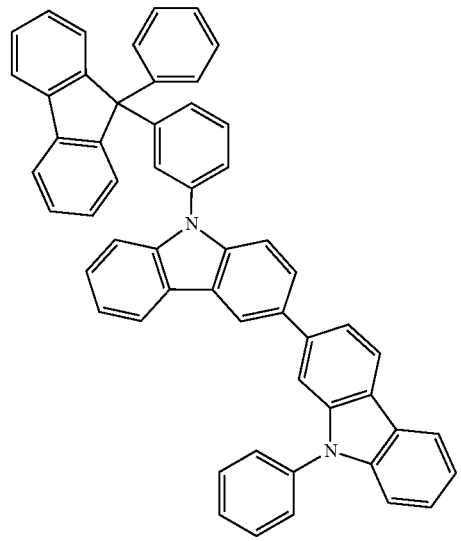
[2-29]
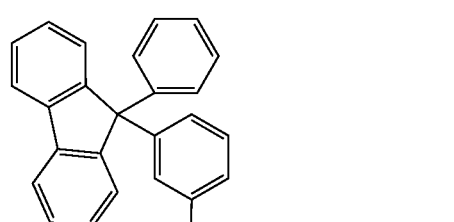

[2-30]
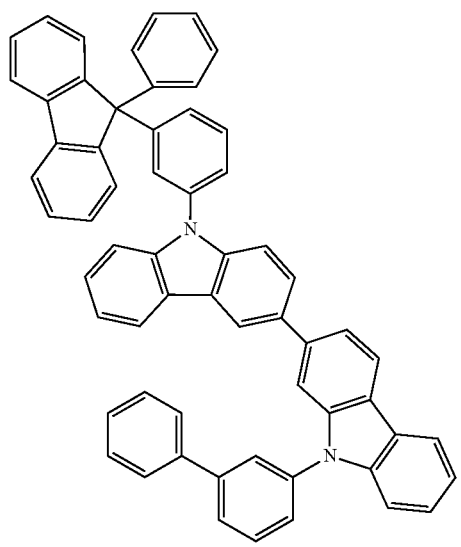
[2-31]
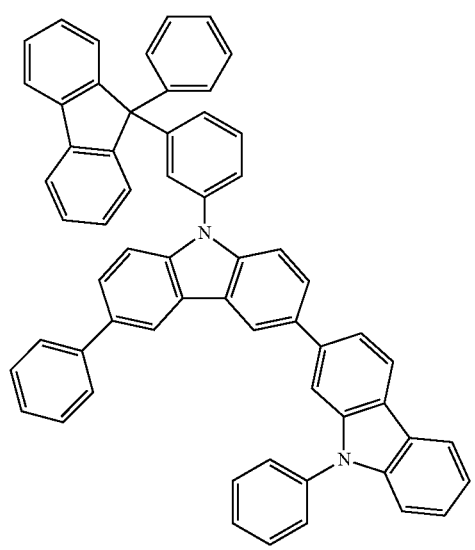
[2-32]
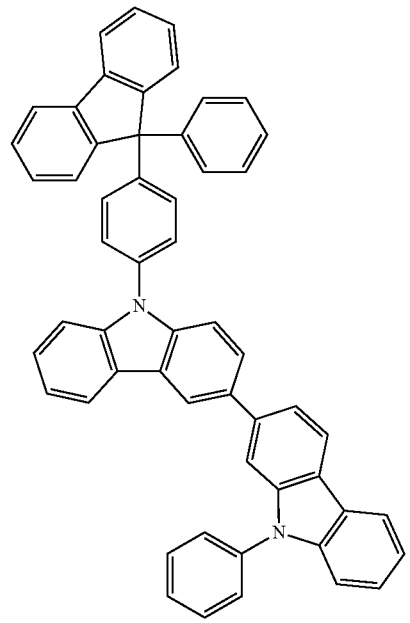
[2-33]
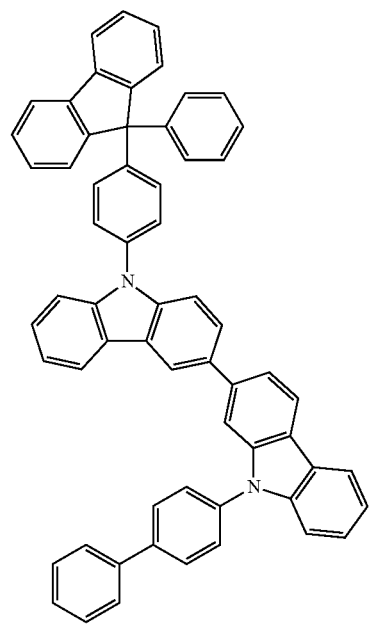

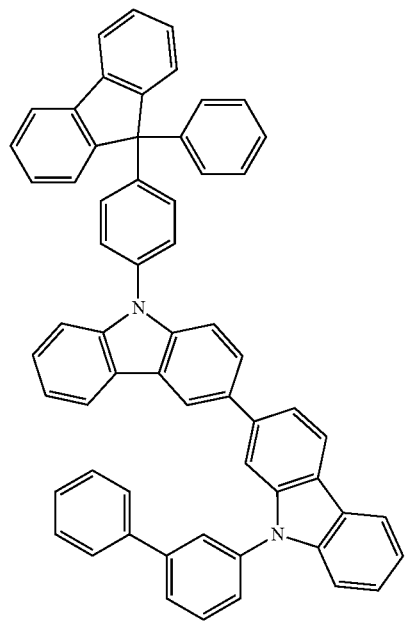
[2-34]
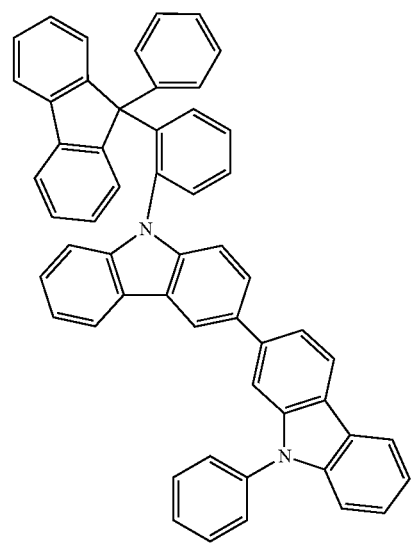
[2-36]
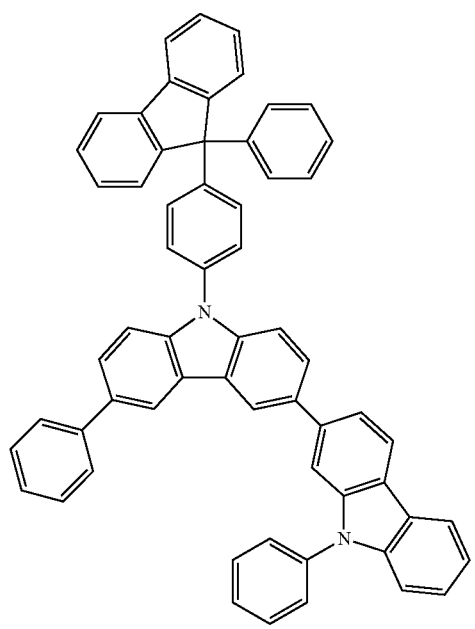
[2-35]
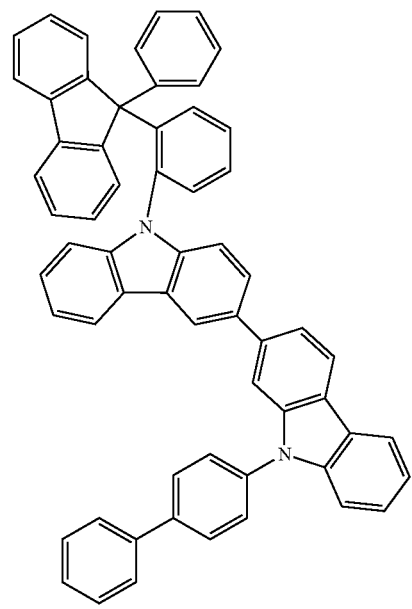
[2-37]

[2-38]
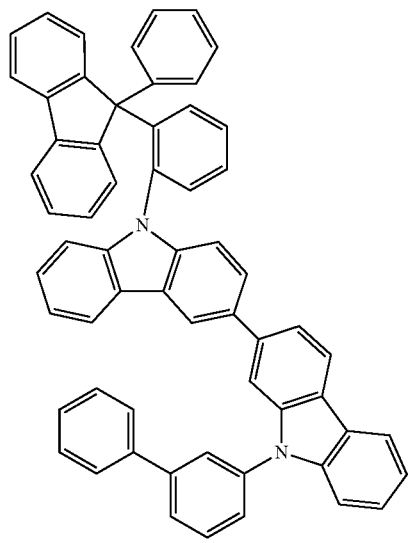
[2-39]
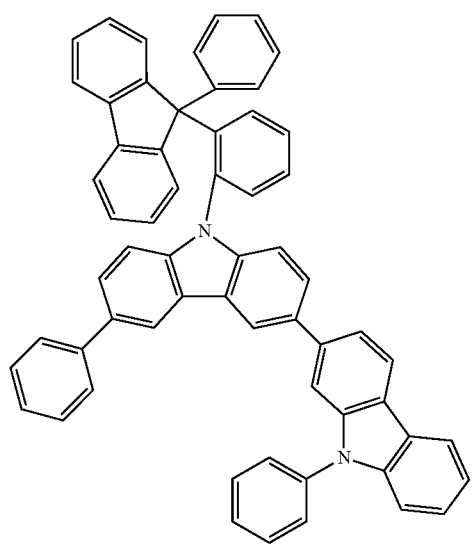
[2-40]
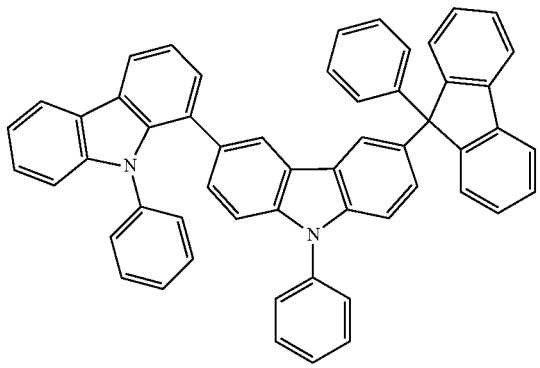
[2-41]
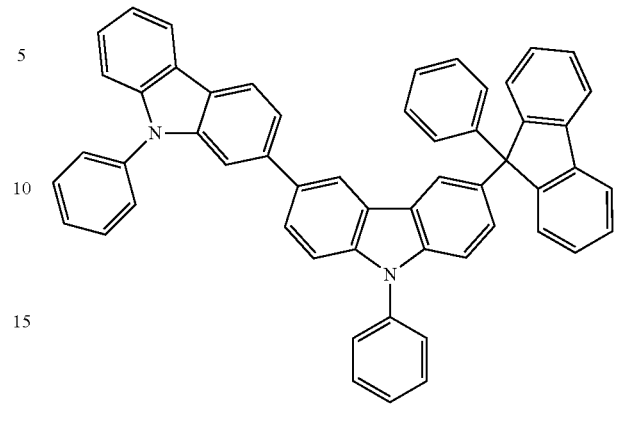
[2-42]
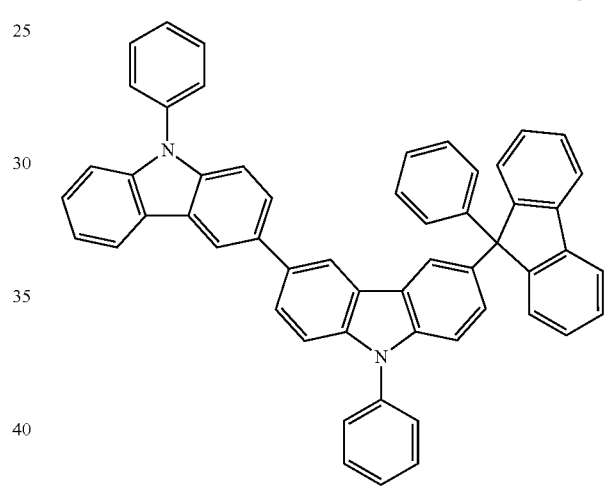
[2-43]
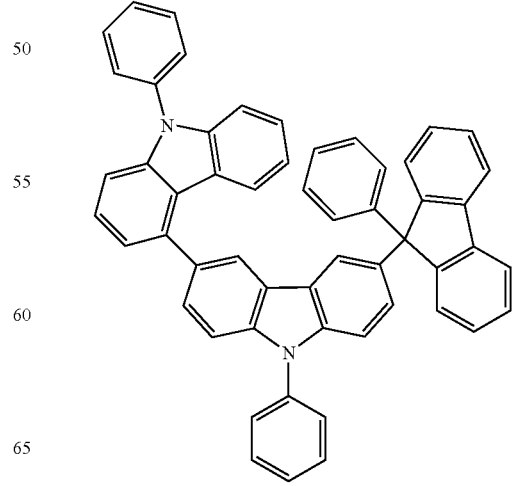

-continued
[2-44]
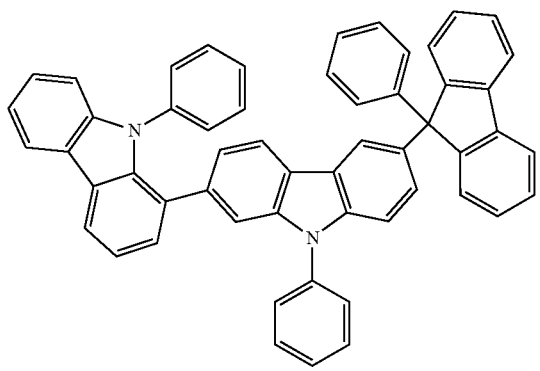
[2-45]
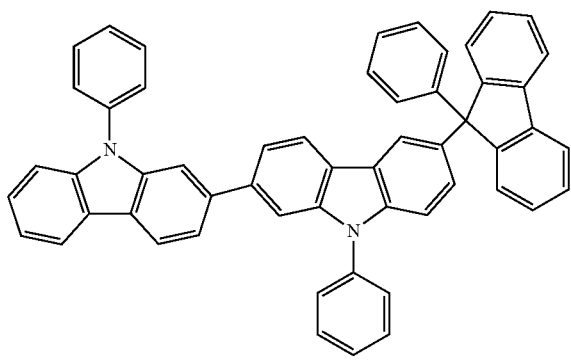
[2-46]
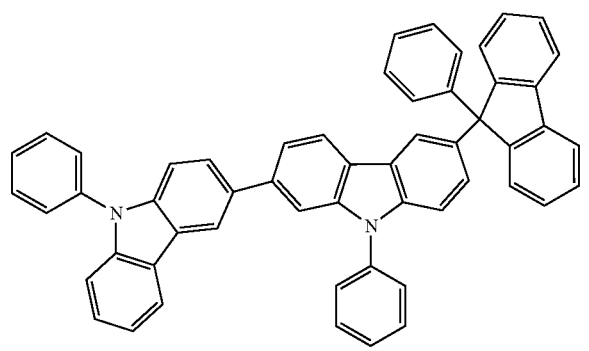
[2-47]
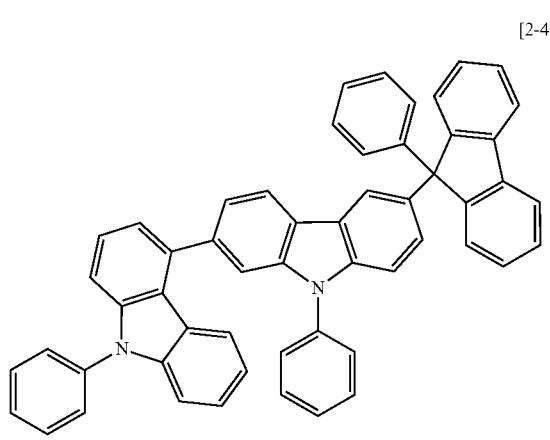
-continued
[2-48]
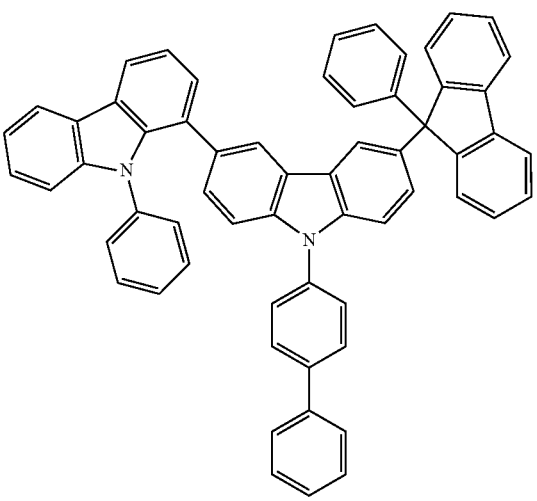
[2-49]
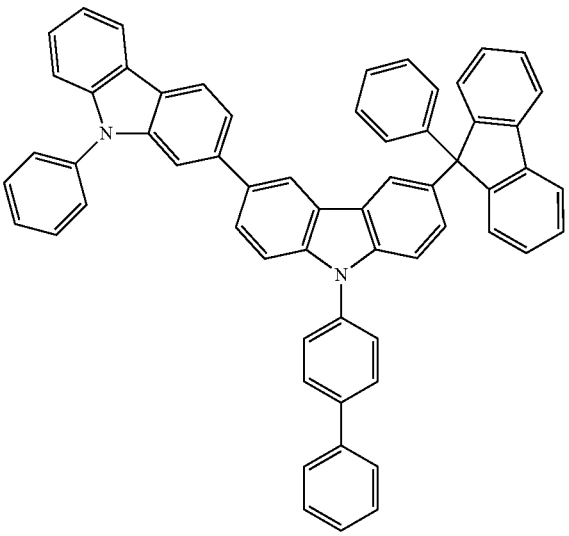

[2-50]
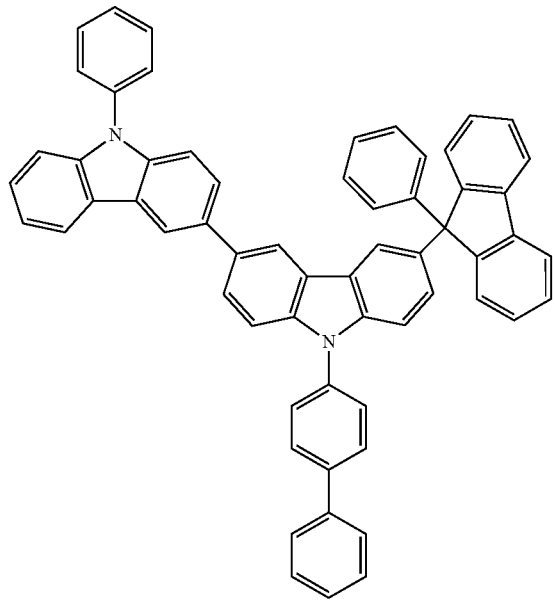
[2-51]
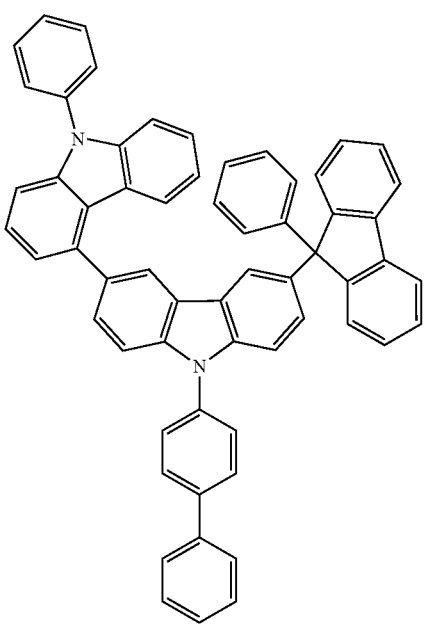
[2-52]
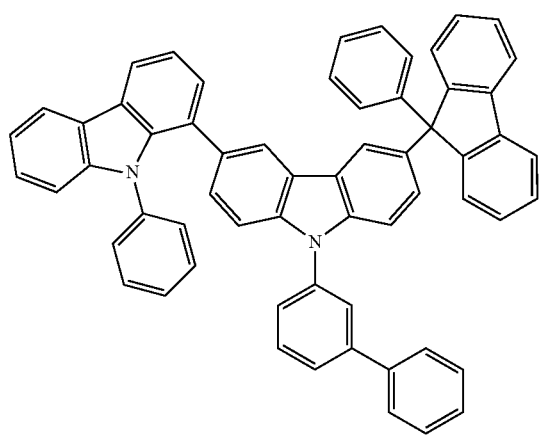
[2-53]
[2-54]
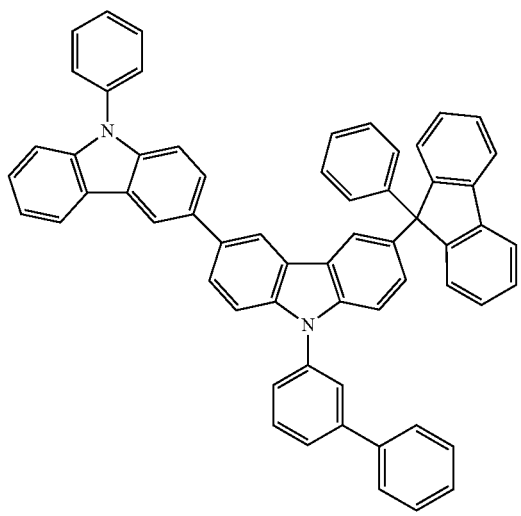

[2-55]
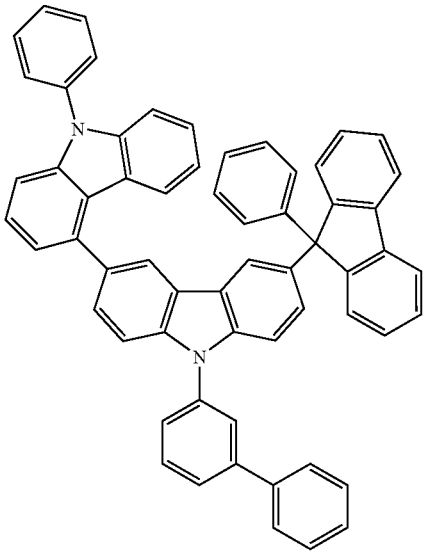
[2-58]
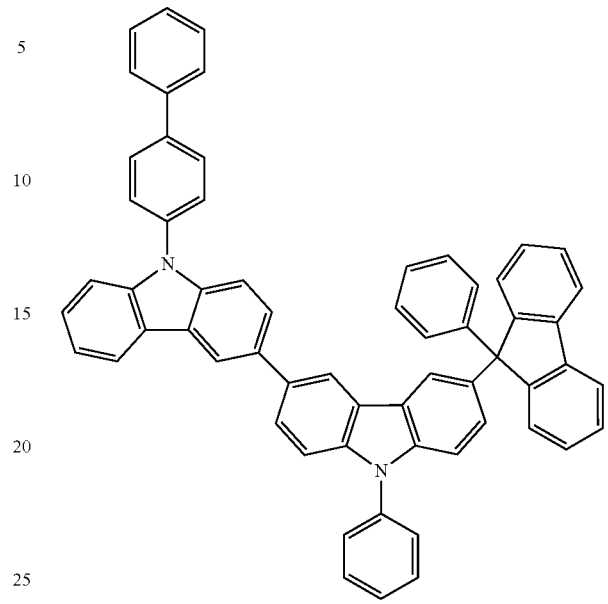
[2-56]
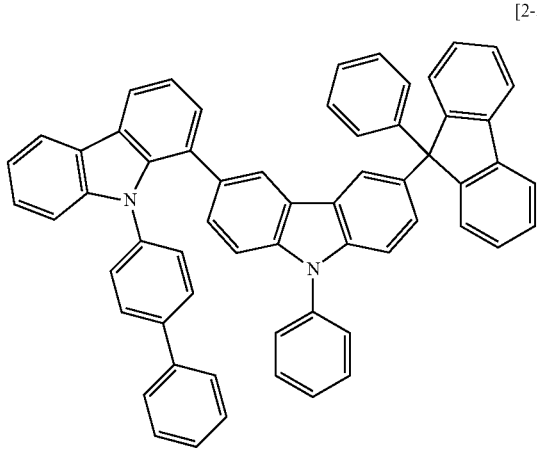
[2-59]
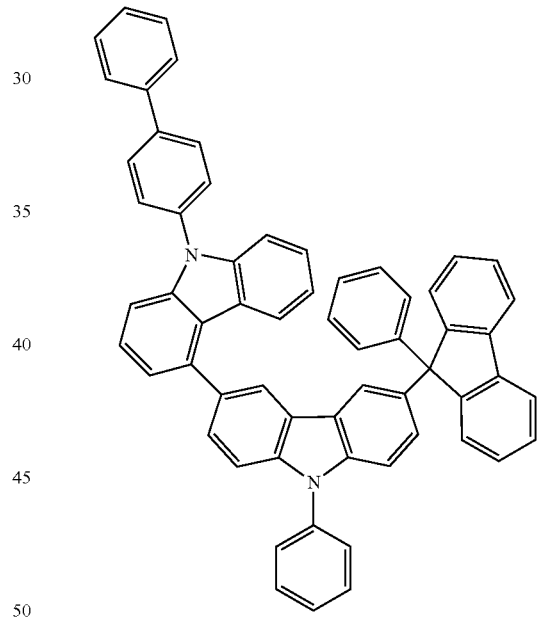
[2-57]
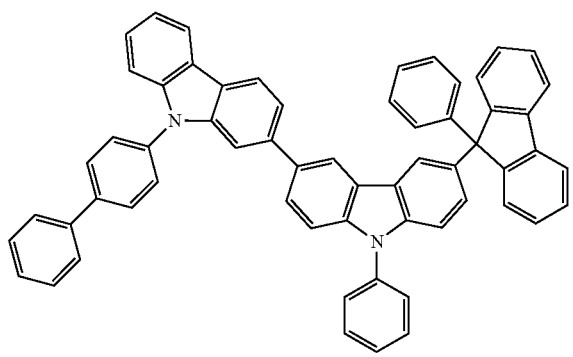
[2-60]
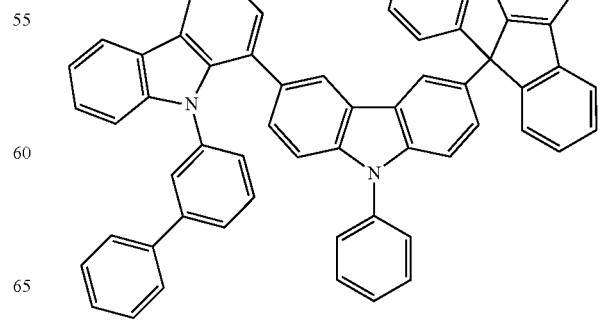

[2-61]
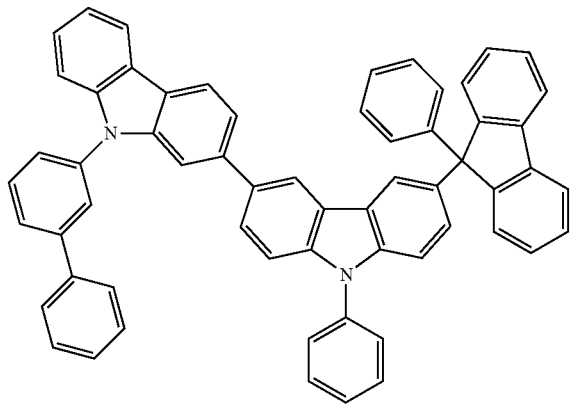
[2-62]
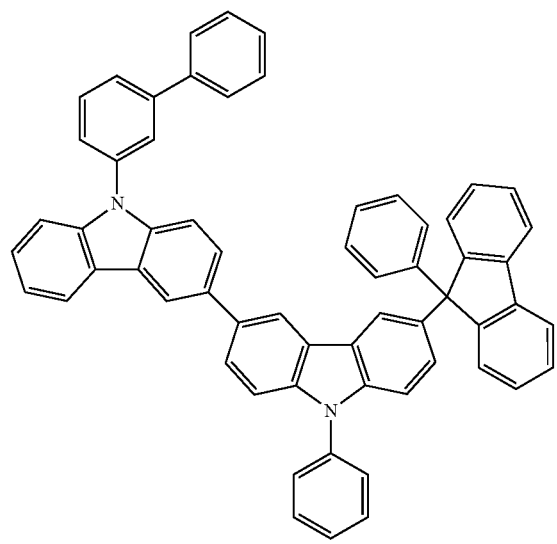
[2-63]
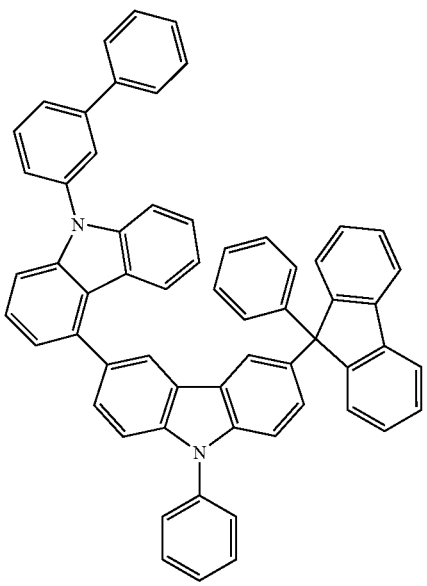
[2-64]
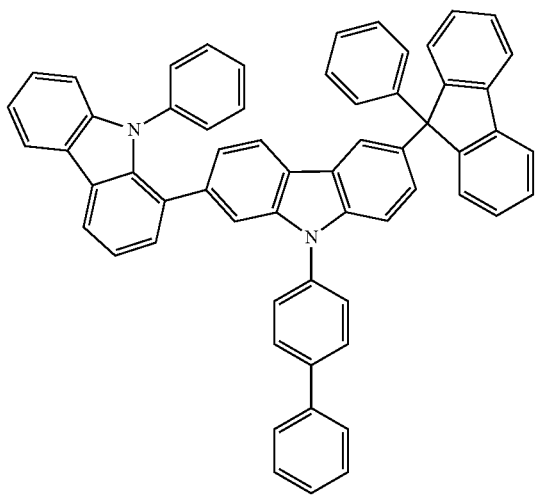
[2-65]
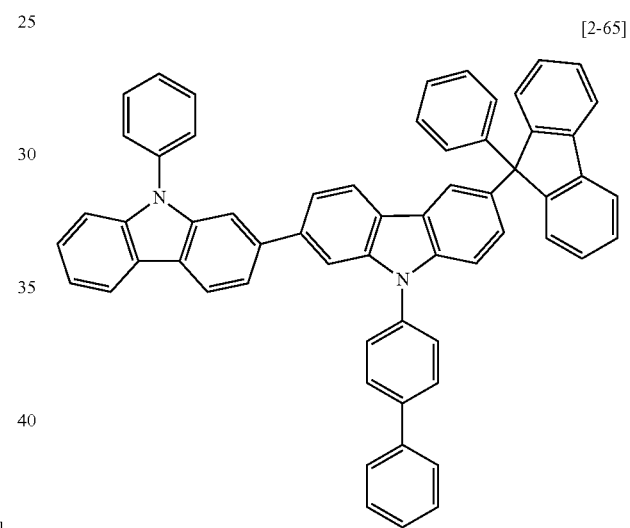
[2-66]
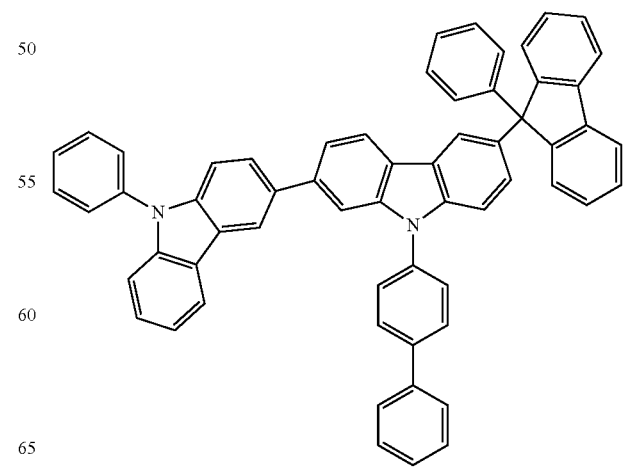

[2-67]
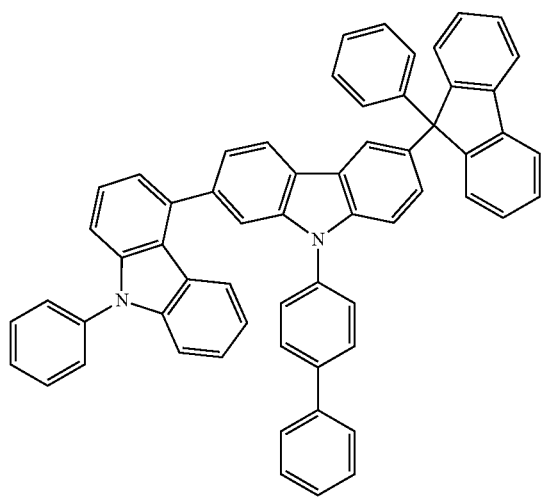
[2-68]
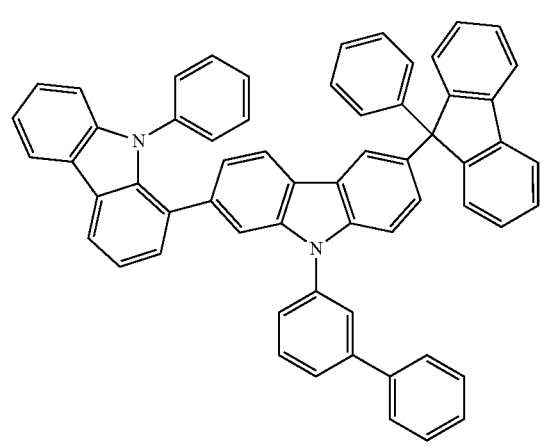
[2-69]
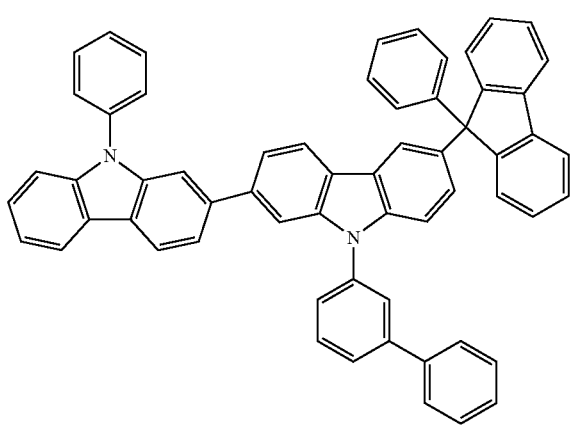
[2-70]
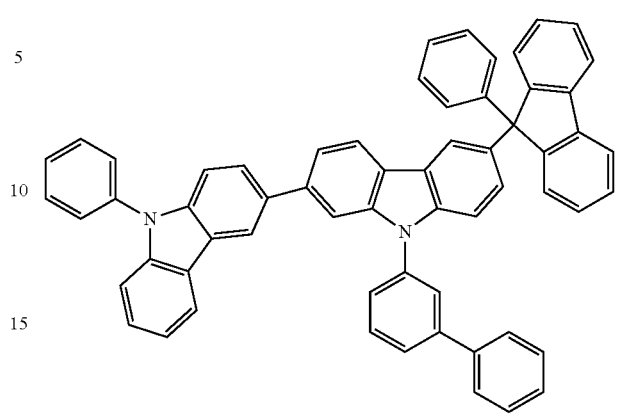
[2-71]
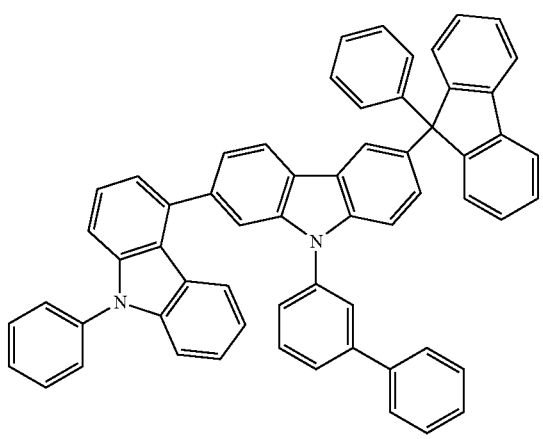
[2-72]
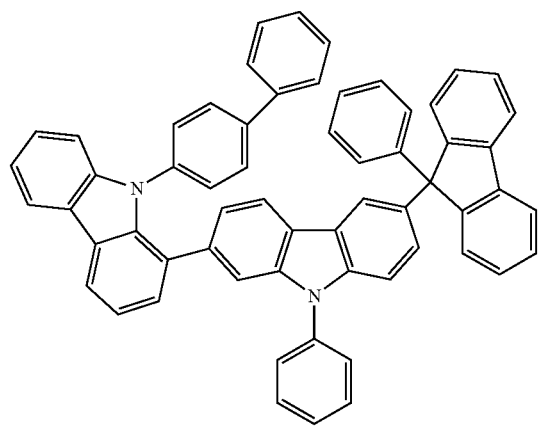

[2-73]
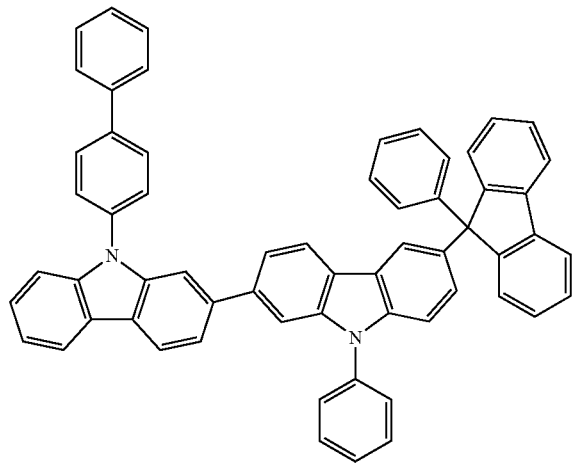
[2-76]
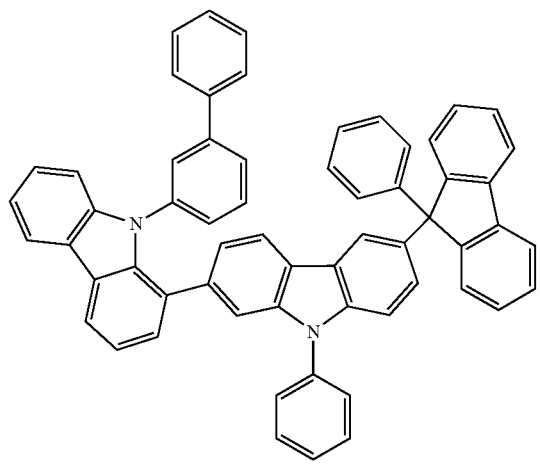
[2-74]
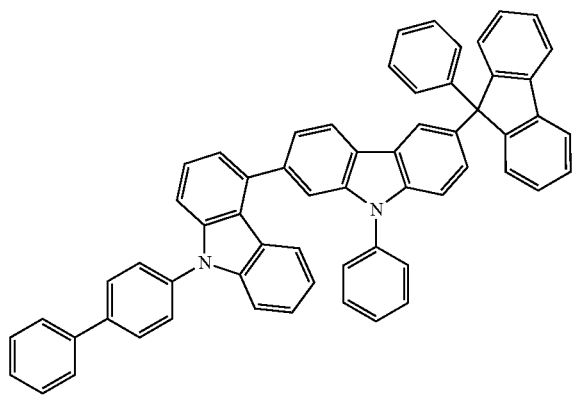
[2-77]
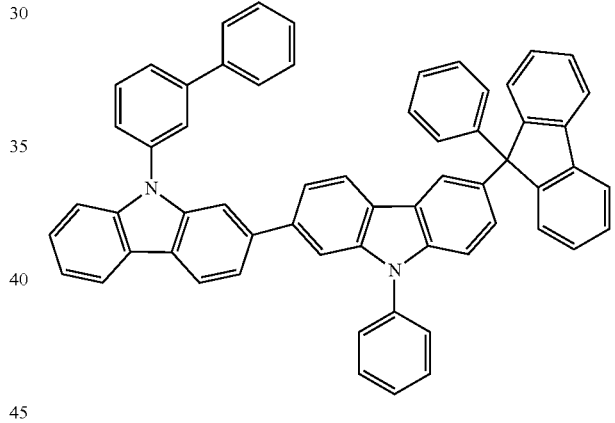
[2-75]
[2-78]
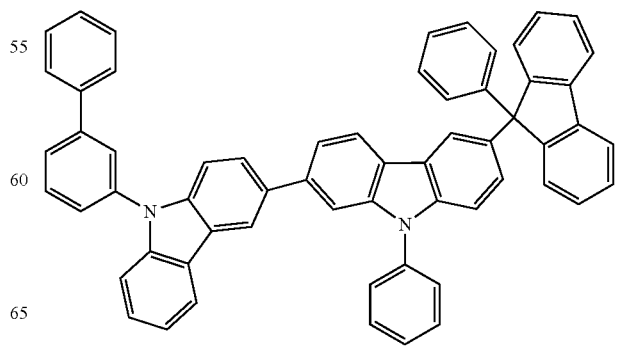

-continued

[2-79]

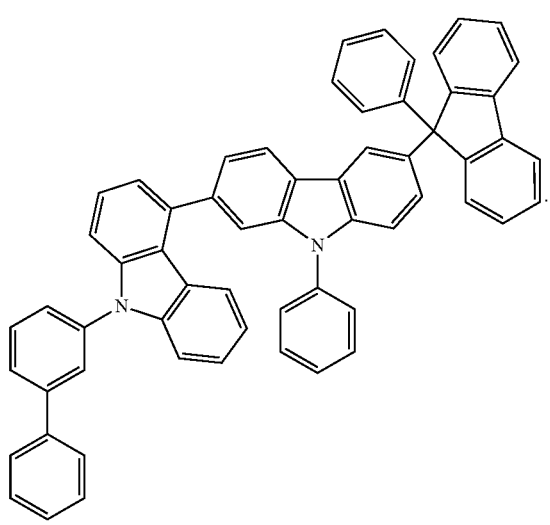

7. A composition for an organic optoelectric device, the composition comprising
a first compound, the first compound being the compound for an organic optoelectric device as claimed in claim 1, and
at least one second compound for an organic optoelectric device having a moiety represented by Chemical Formula II

[Chemical Formula II]

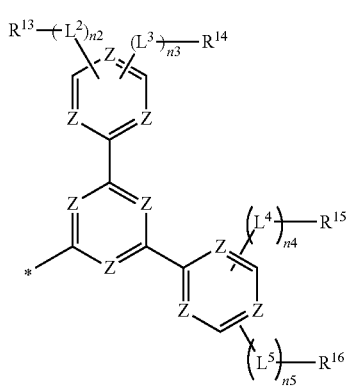

wherein, in Chemical Formula II,
each Z is independently N, C or CR$^c$, provided that at least one of Z is N,
R$^{13}$ to R$^{16}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, L$^2$ to L$^5$ are each independently a single bond, a substituted or unsubstituted C6 to C30 arylene group, a substituted or unsubstituted C2 to C30 heteroarylene group, or a combination thereof,
n2 to n5 are each independently one of integers of 0 to 5, and
indicates a linking point,
wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

8. The composition for an organic optoelectric device as claimed in claim 7, wherein the second compound for an organic optoelectric device is represented by Chemical Formula II-A, or Chemical Formula II-B:

[Chemical Formula II-A]

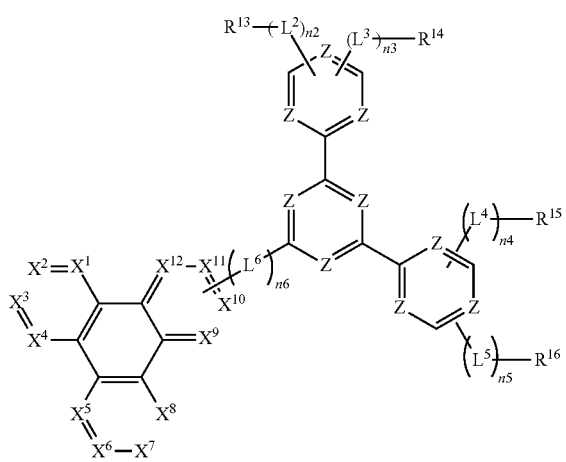

[Chemical Formula II-B]

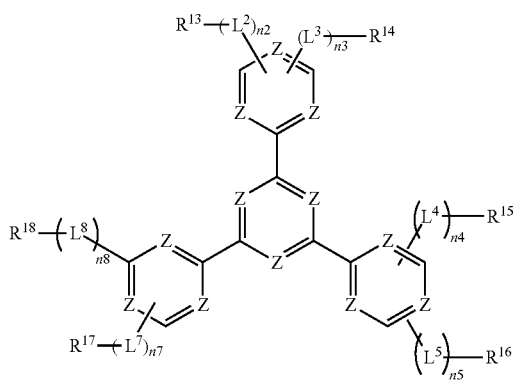

wherein, in Chemical Formulae II-A and II-B,
each Z is independently N, C or CR$^c$, provided that at least one of Z is N,
X$^1$ to X$^{12}$ are each independently N, C or CR$^d$,
L$^2$ to L$^8$ are each independently a single bond, a substituted or unsubstituted C6 to C30 arylene group, a substituted or unsubstituted C2 to C30 heteroarylene group, or a combination thereof, n2 to n8 are each independently one of integers of 0 to 5, and R$^{13}$ to R$^{18}$, R$^c$ and R$^d$ are independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

9. The composition for an organic optoelectric device as claimed in claim 8, wherein the second compound for an organic optoelectric device represented by Chemical Formula II-A is represented by Chemical Formula II-A1 or Chemical Formula II-A2:

[Chemical Formula II-A1]

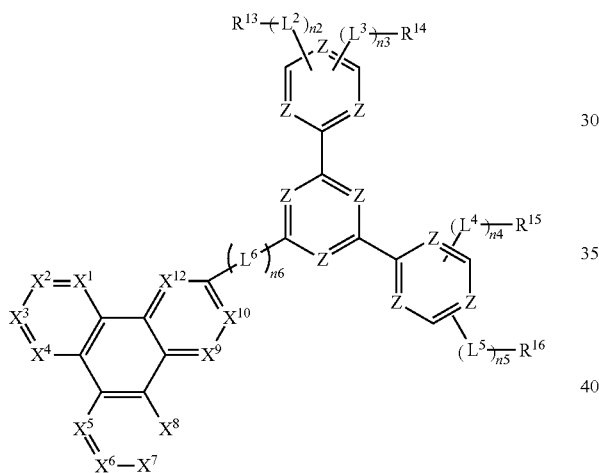

[Chemical Formula II-A2]

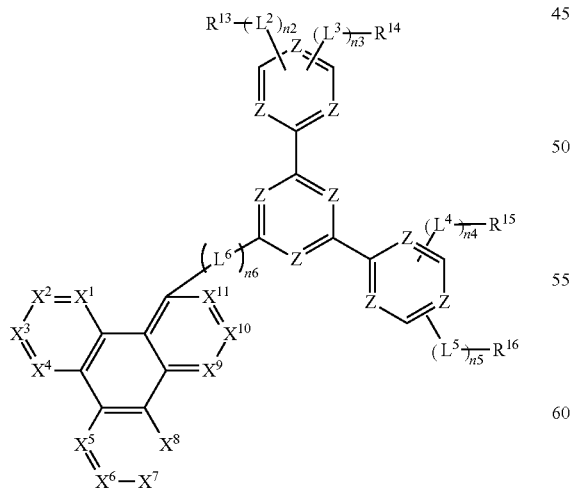

wherein in Chemical Formula II-A 1 and II-A2,
each Z is independently N, C or CR$^c$, provided that at least one of Z is N, X$^1$ to X$^{12}$ are each independently N or CR$^d$, R$^{13}$ to R$^{16}$, R$^c$ and R$^d$ are each independently hydrogen, deuterium, a substituted or unsubstituted C1 to C10 alkyl group, a substituted or unsubstituted C6 to C12 aryl group, or a combination thereof, n2 to n6 are each independently 0 or 1, n2+n3+n4+n5+n6≥1, L$^2$ to L$^5$ are each independently a single bond, a substituted or unsubstituted C6 to C30 arylene group, a substituted or unsubstituted C2 to C30 heteroarylene group, or a combination thereof, and L$^6$ is a substituted or unsubstituted phenylene group having a kink structure, a substituted or unsubstituted biphenylene group having a kink structure or a substituted or unsubstituted terphenylene group having a kink structure listed in Group 3, wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group,

[Group 3]

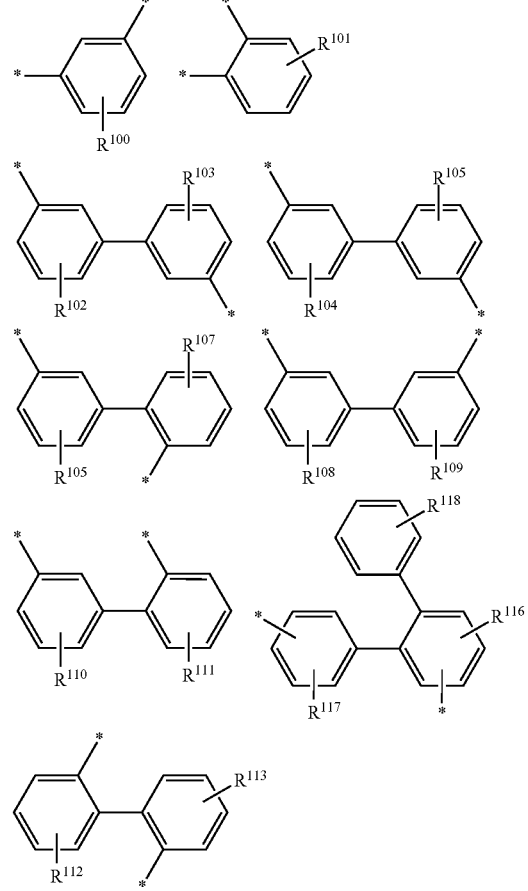

-continued

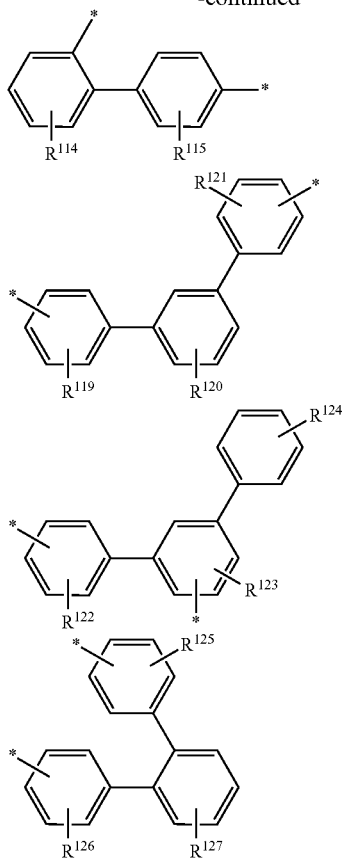

wherein in Group 3,
$R^{100}$ to $R^{127}$ are each independently hydrogen, deuterium, a C1 to C10 alkyl group, a C3 to C30 cycloalkyl group, a C3 to C30 heterocycloalkyl group, a C6 to C30 aryl group, a C2 to C30 heteroaryl group, an amine group, a C6 to C30 arylamine group, a C2 to C30 heteroarylamine group, a C1 to C30 alkoxy group, a halogen, a halogen-containing group, a cyano group, a hydroxyl group, an amino group, a nitro group, a carboxyl group, a ferrocenyl group or a combination thereof.

10. The composition for an organic optoelectric device as claimed in claim 8, wherein the second compound for an organic optoelectric device represented by Chemical Formula II-A is one of compounds of Group 4:

[Group 4]

[4-1]

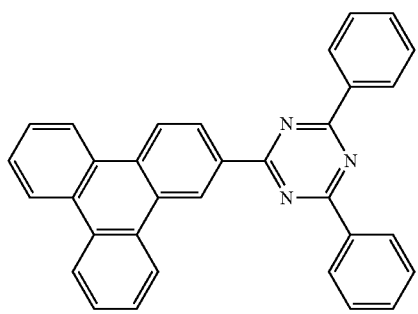

[4-2]

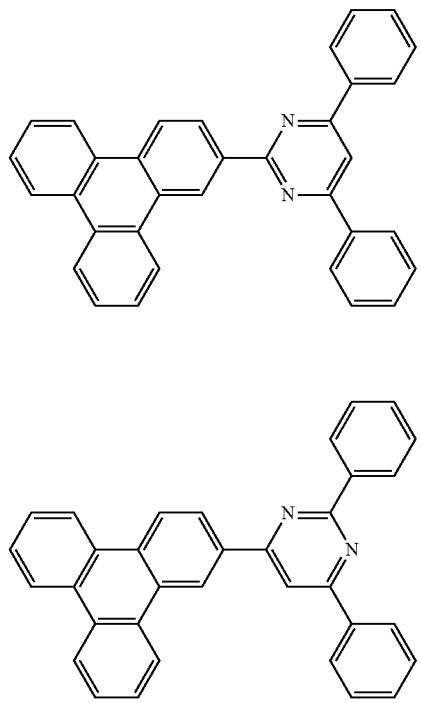

[4-3]

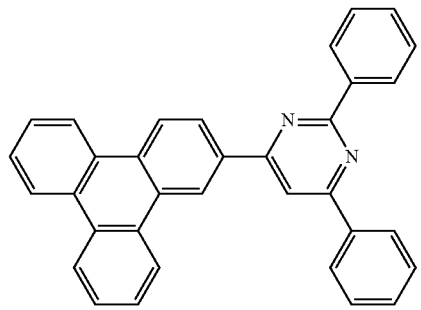

[4-4]

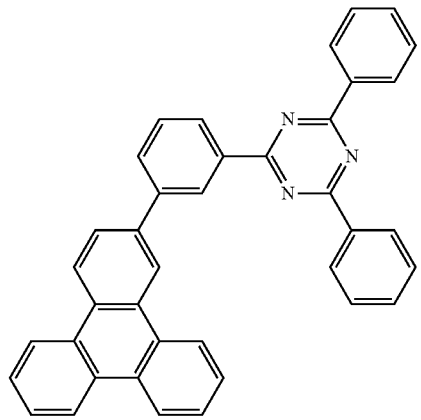

[4-5]

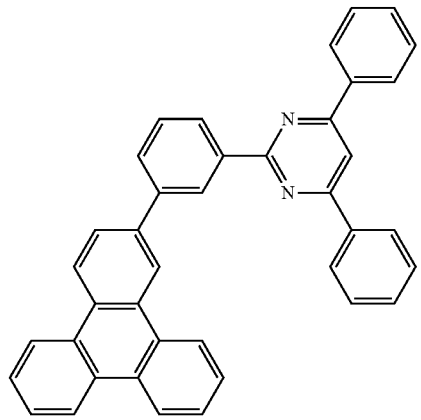

[4-6]
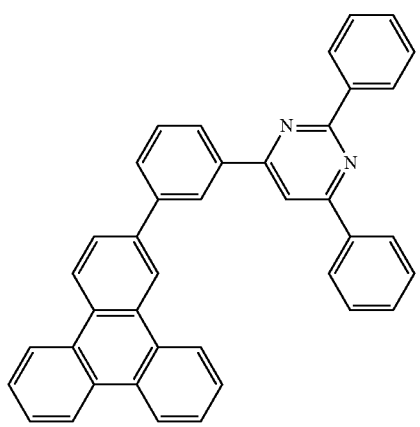
[4-9]
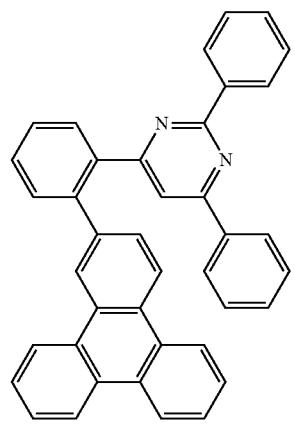
[4-7]
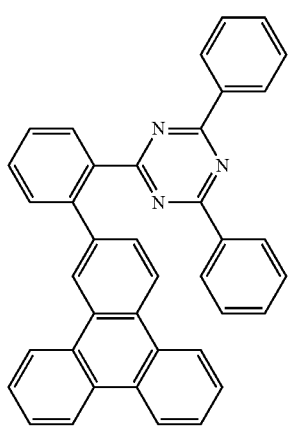
[4-10]
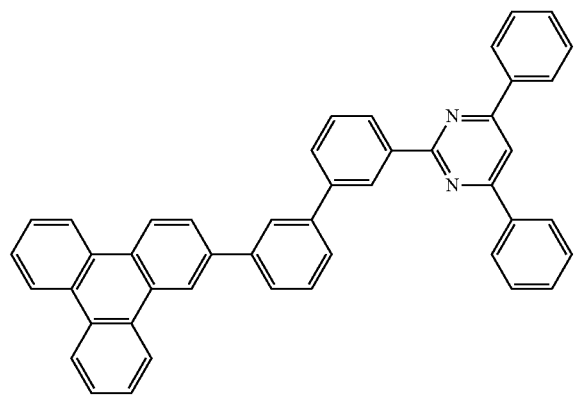
[4-8]
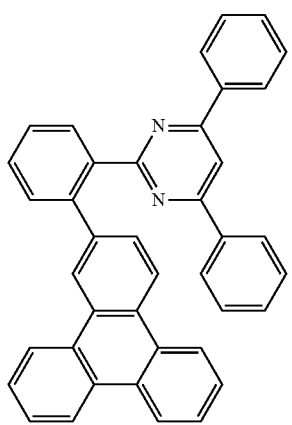
[4-11]

[4-12]
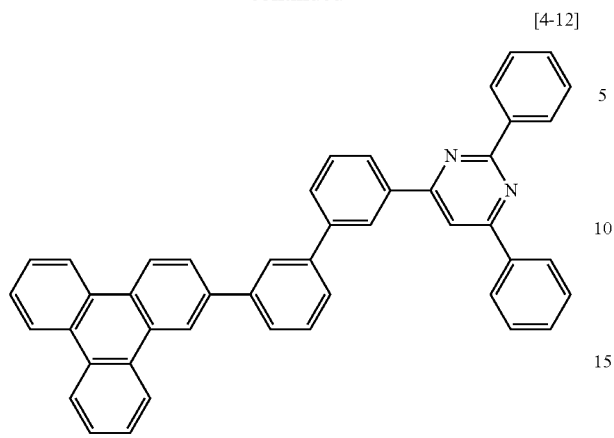
[4-13]
[4-14]
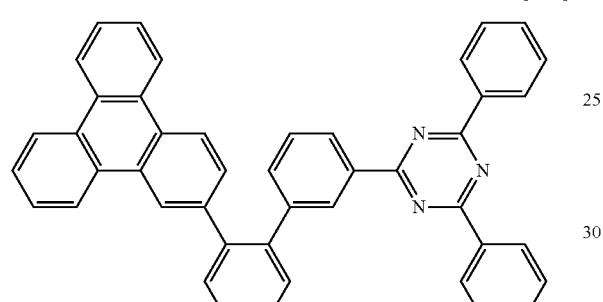
[4-15]
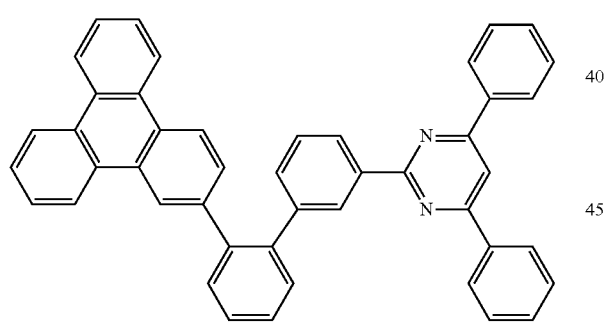
[4-16]
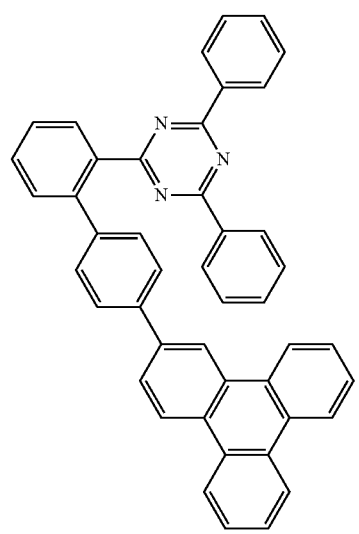
[4-17]
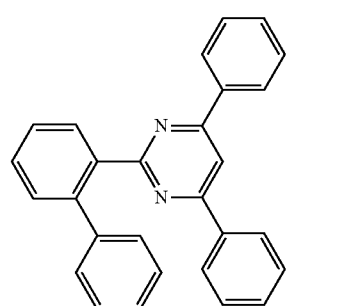
[4-18]
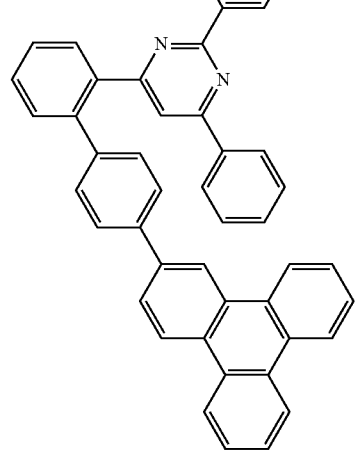
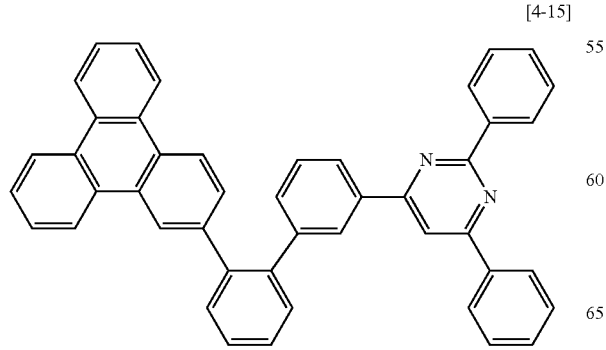

[4-19]
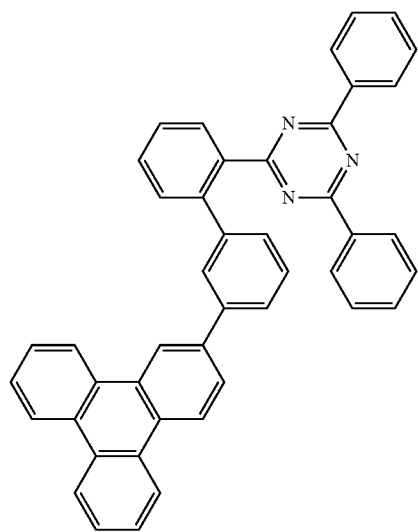
[4-20]
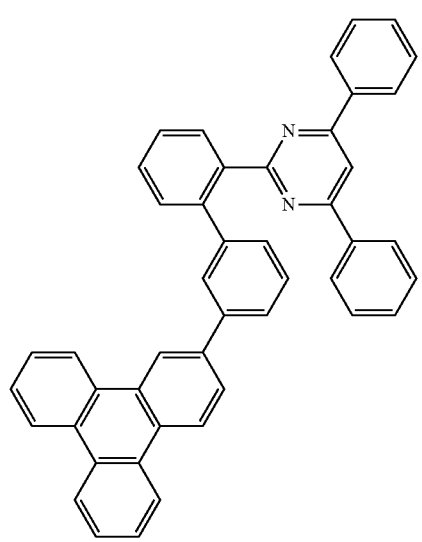
[4-21]
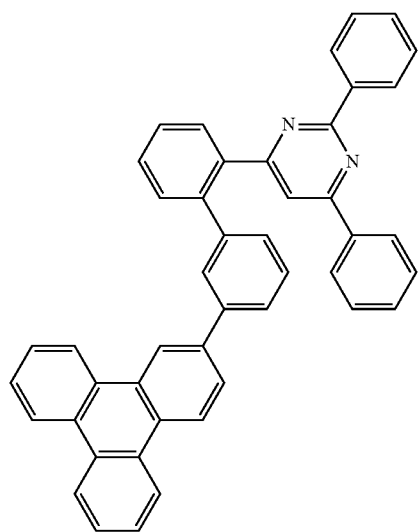
[4-22]
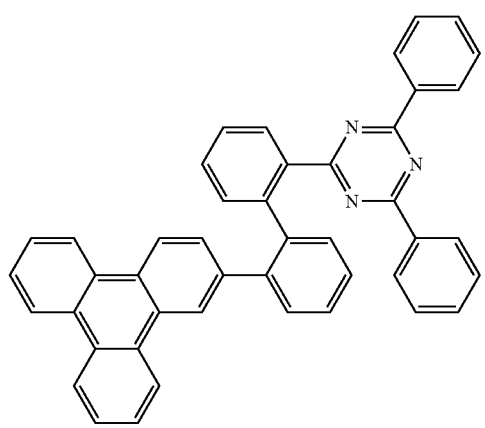
[4-23]
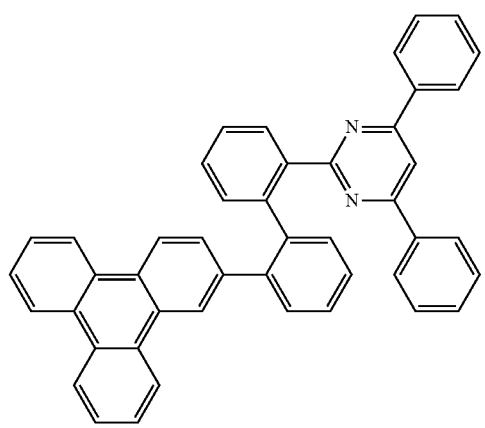
[4-24]
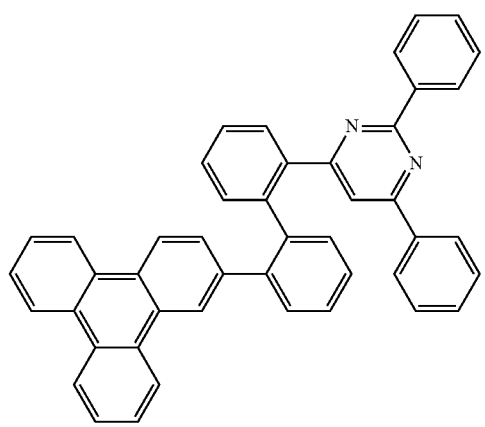
[4-25]
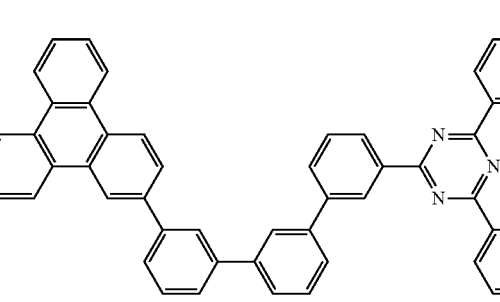

227
-continued
[4-26]
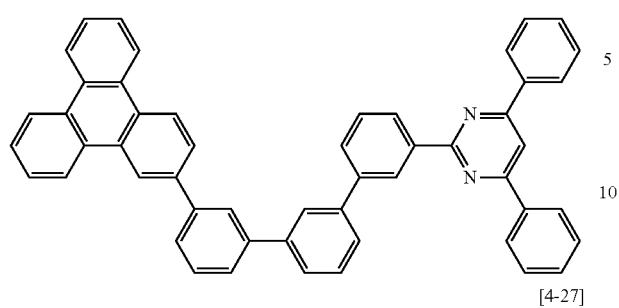
[4-27]
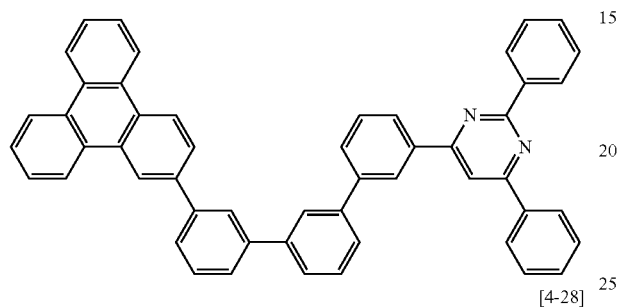
[4-28]
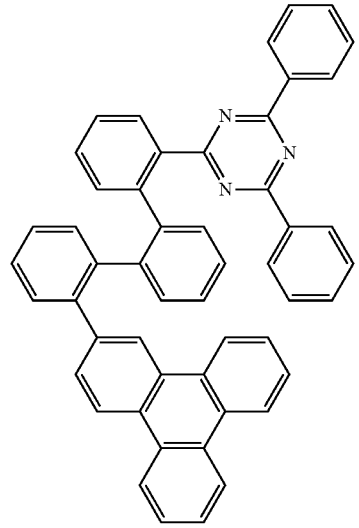
[4-29]
228
-continued
[4-30]
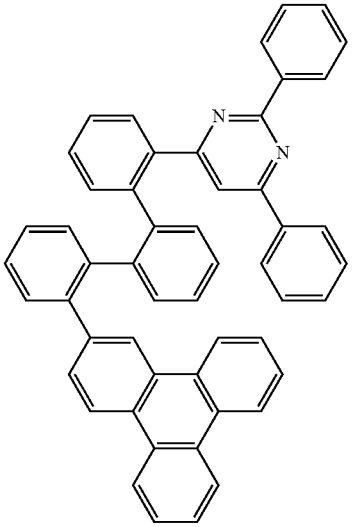
[4-31]
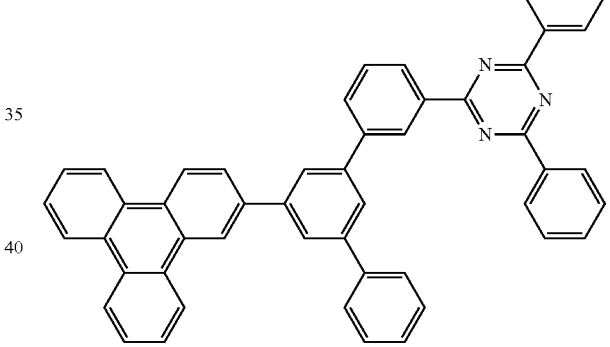
[4-32]
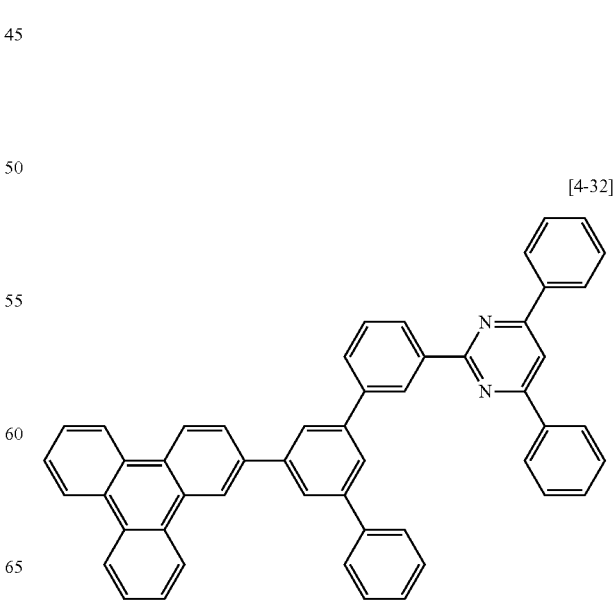

[4-33]
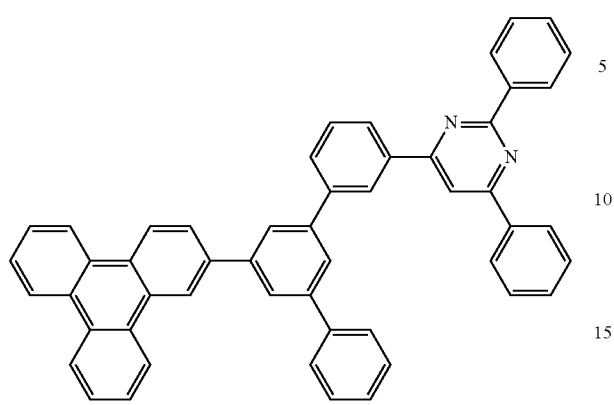
[4-37]
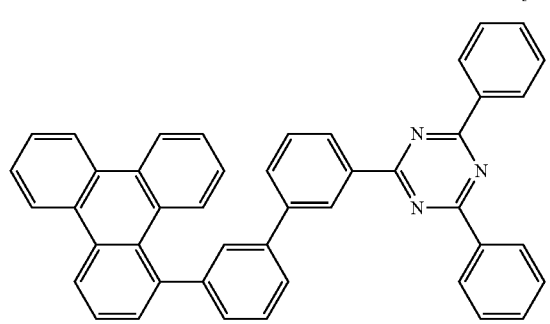
[4-34]
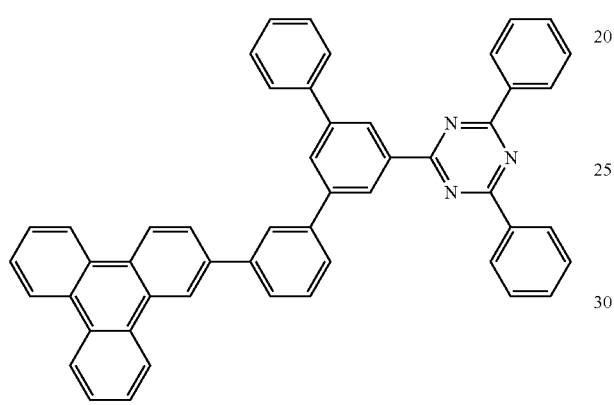
[4-35]
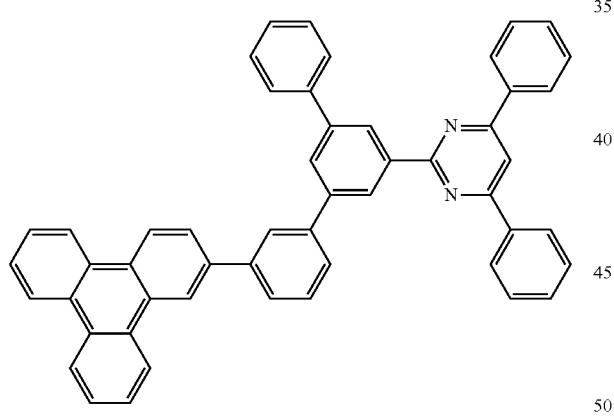
[4-38]
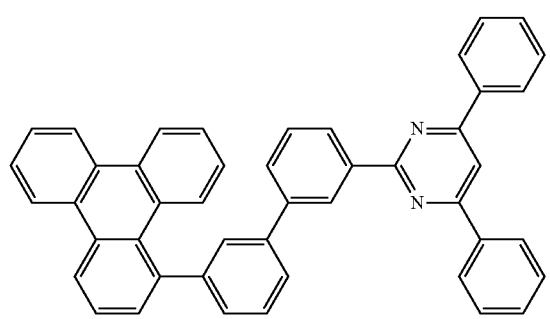
[4-36]
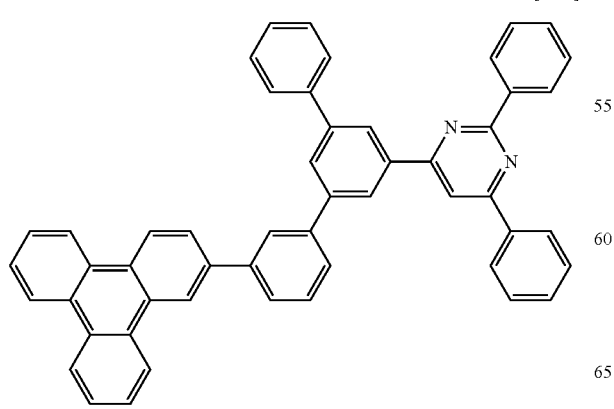
[4-39]
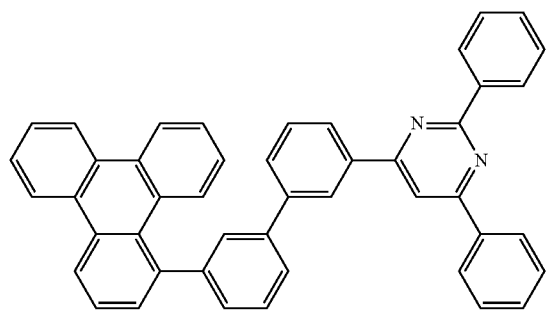

-continued
[4-40]
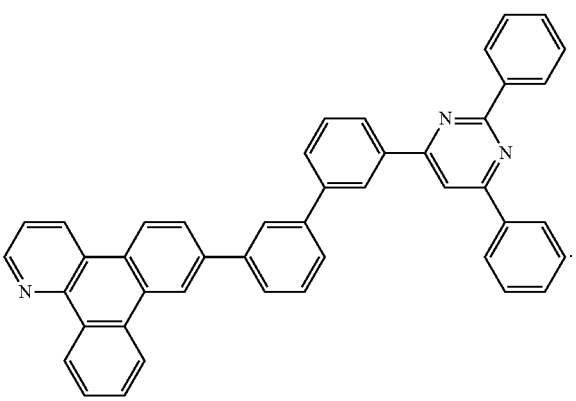
[4-42]
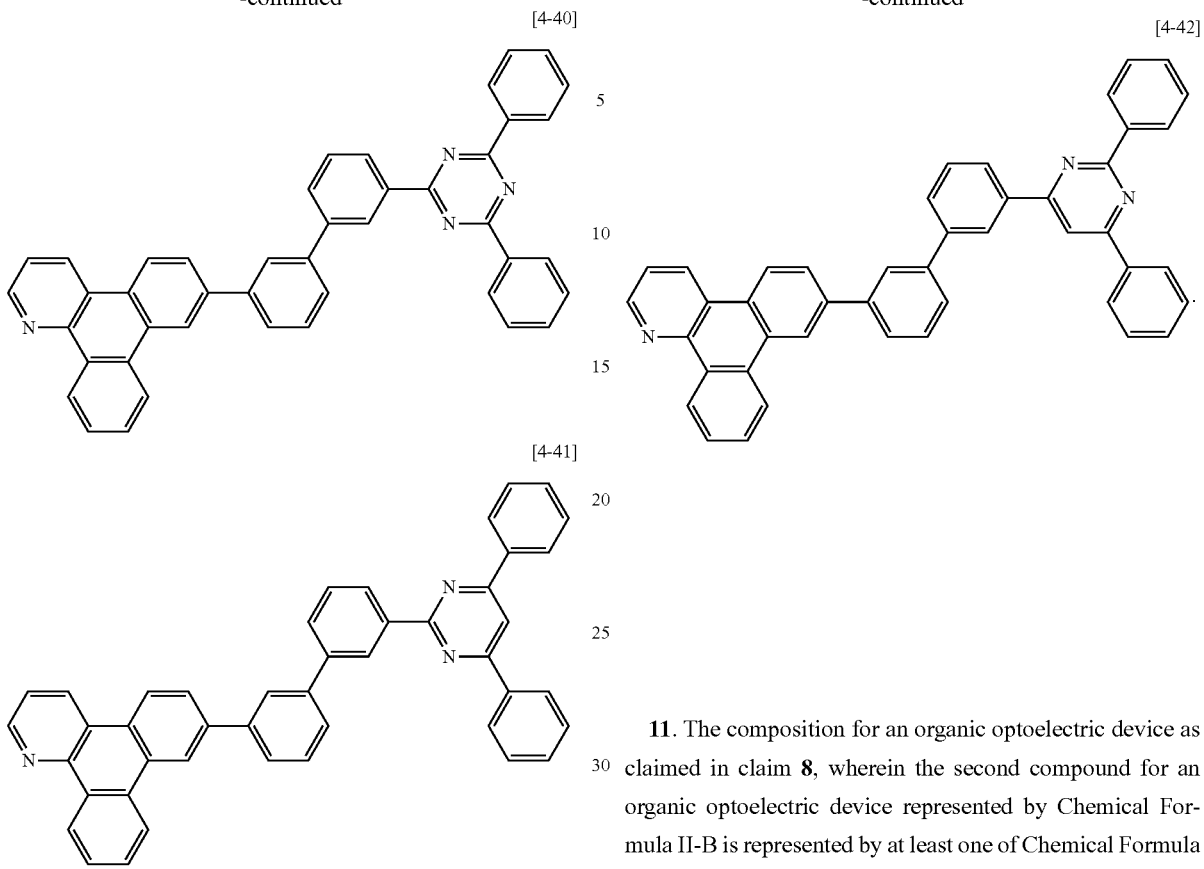
[4-41]
11. The composition for an organic optoelectric device as claimed in claim 8, wherein the second compound for an organic optoelectric device represented by Chemical Formula II-B is represented by at least one of Chemical Formula II-b1 to Chemical Formula II-b7:
[Chemical Formula II-b1]
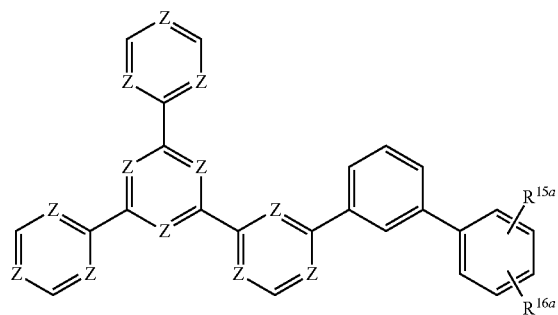
[Chemical Formula II-b2]
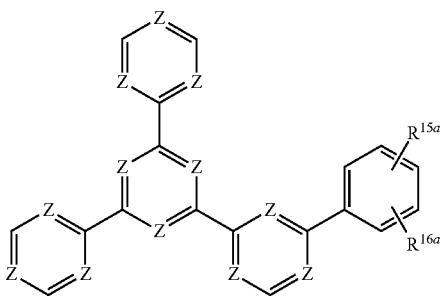
[Chemical Formula II-b3]
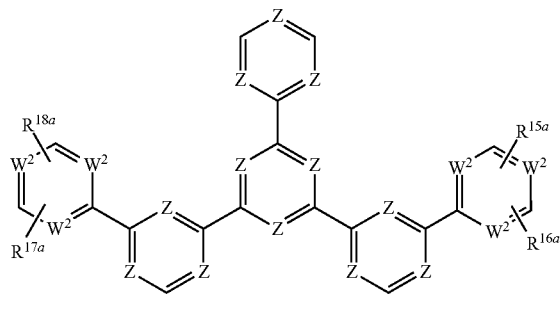
[Chemical Formula II-b4]
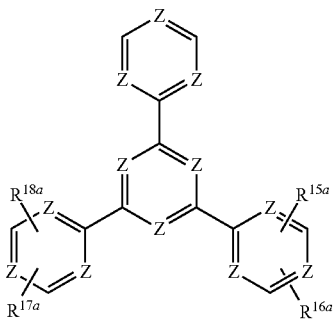

[Chemical Formula II-b5]

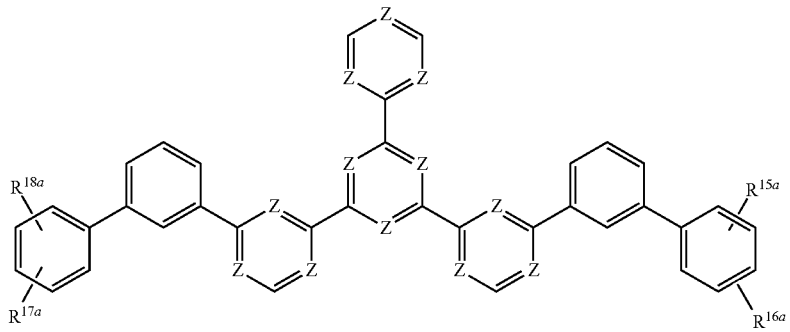

[Chemical Formula II-b6]

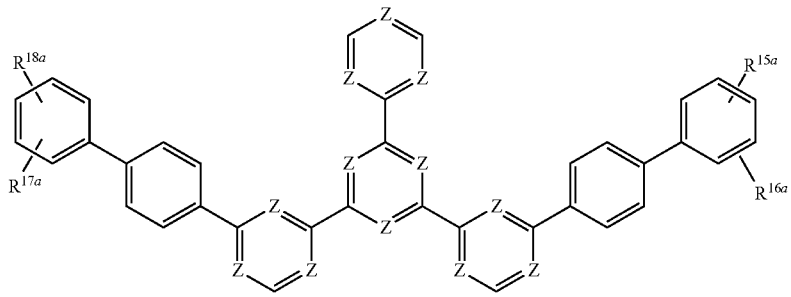

[Chemical Formula II-b7]

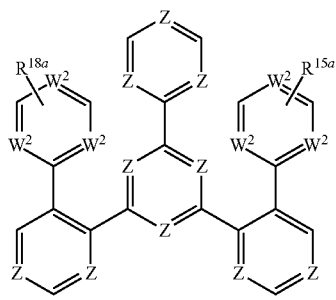

wherein, in Chemical Formulae II-b1 to II-b7,
each Z is independently N, C or CR$^e$, provided that at least one of Z is N,
each W$^2$ is independently N, C or CR$^e$, and
R$^{15a}$ to R$^{18a}$, R$^c$ and R$^e$ are each independently hydrogen, deuterium, a substituted or unsubstituted C1 to C10 alkyl group, a substituted or unsubstituted C6 to C30 aryl group, a substituted or unsubstituted C3 to C30 heteroaryl group, or a combination thereof,
wherein "substituted" refers to that at least one hydrogen is replaced by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

12. The composition for an organic optoelectric device as claimed in claim 8, wherein the second compound for an organic optoelectric device represented by Chemical Formula II-B is one of compounds of Group 6:

[Group 6]
[6-1]
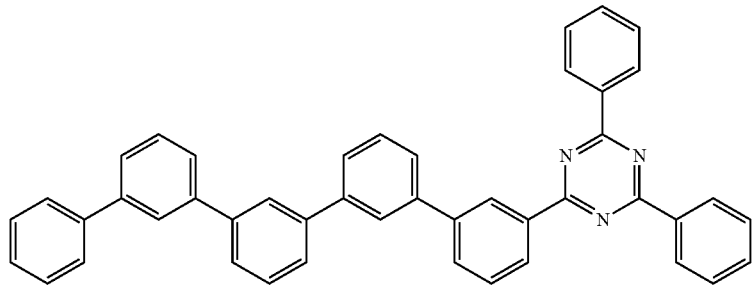
[6-2]
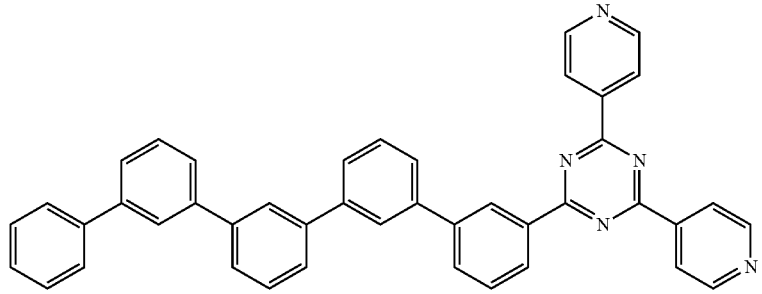
[6-3]
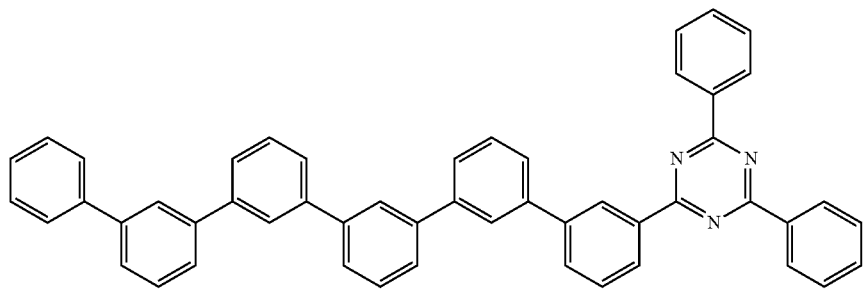
[6-4]
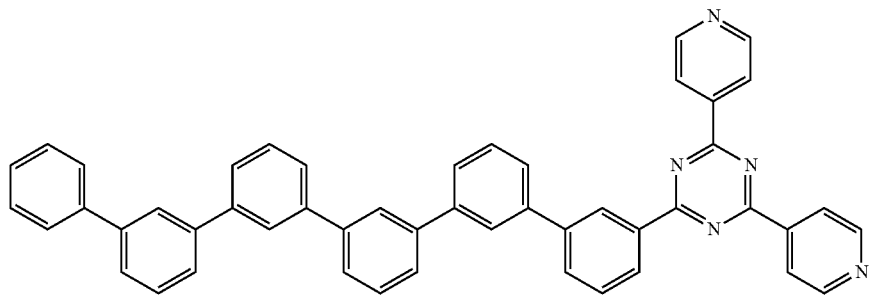
[6-5] [6-6]
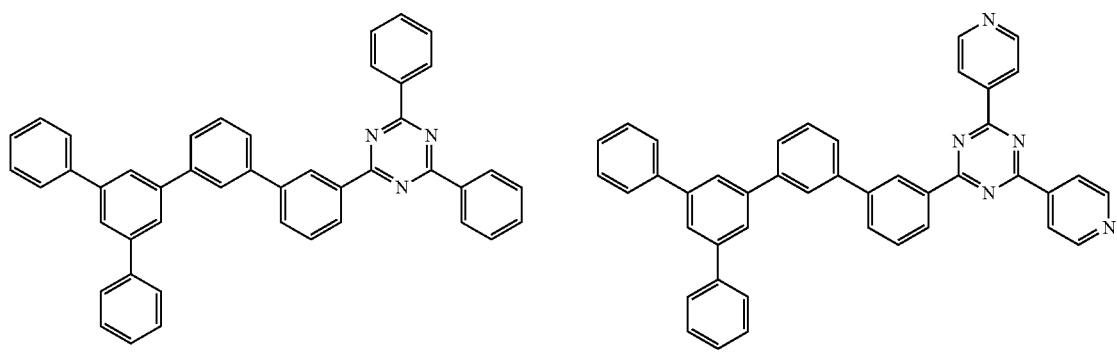

-continued
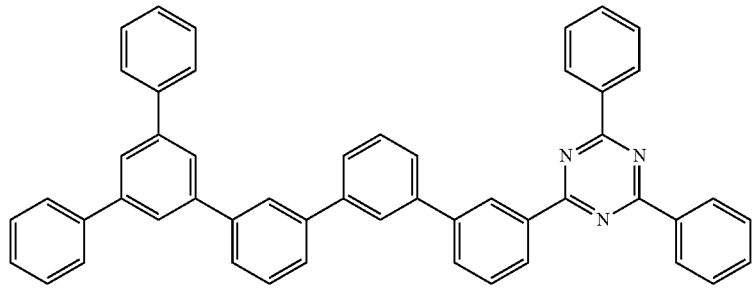
[6-7]
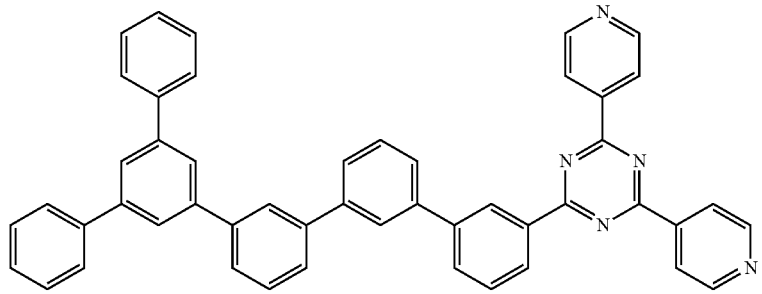
[6-8]
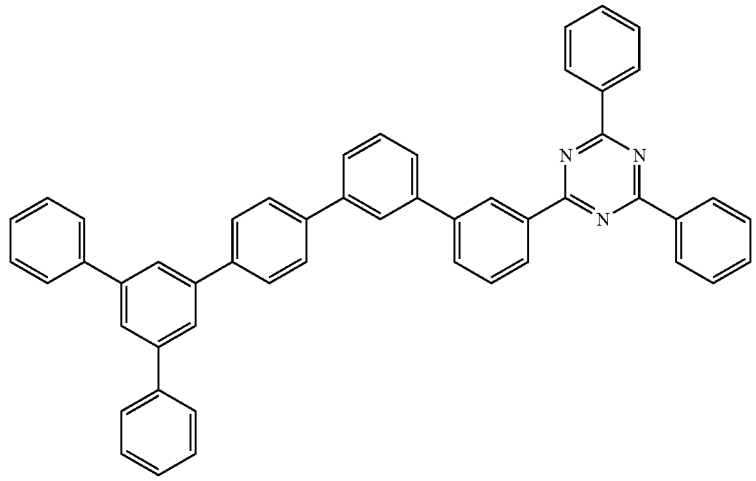
[6-9]
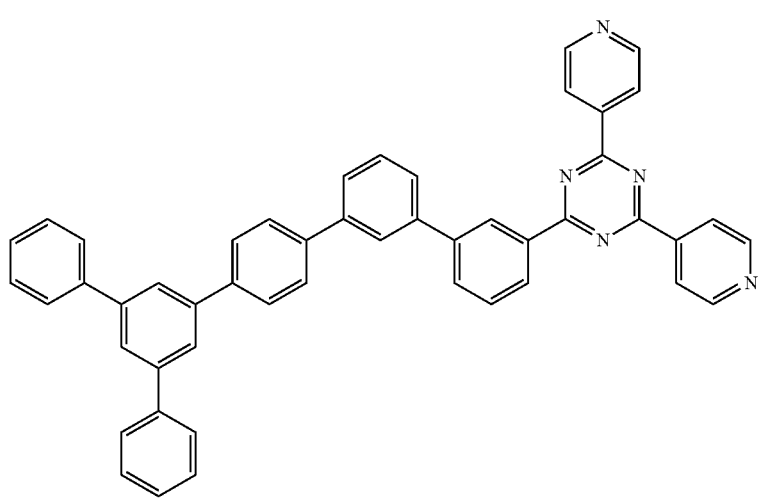
[6-10]

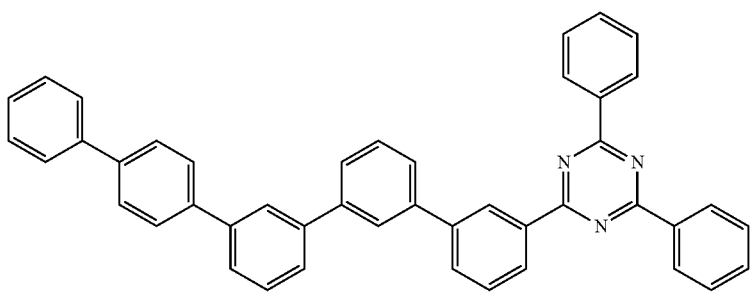
[6-11]
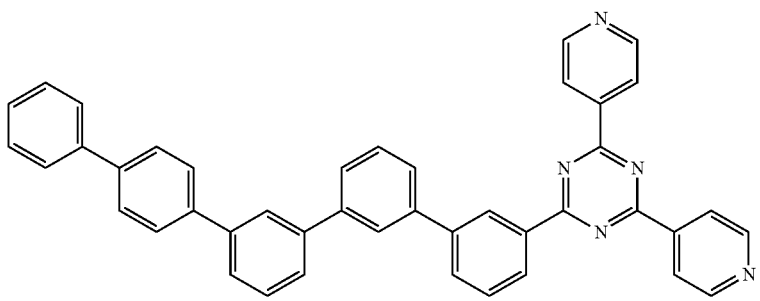
[6-12]
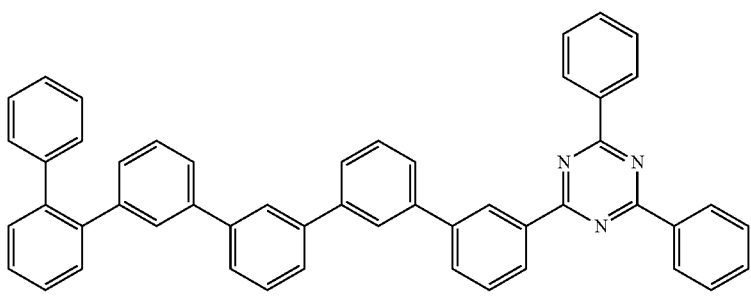
[6-13]
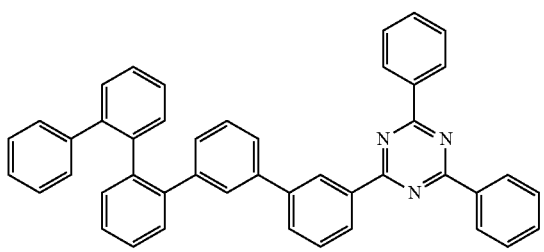
[6-14]
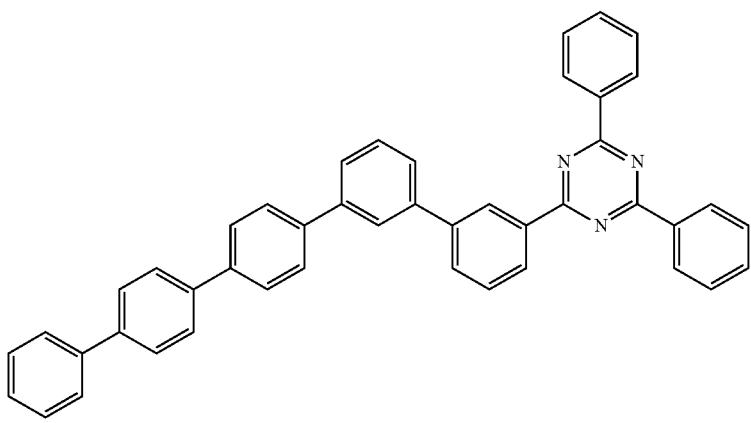
[6-15]

-continued
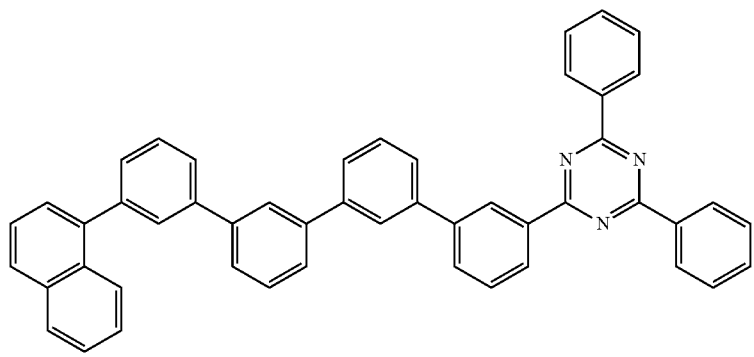
[6-16]
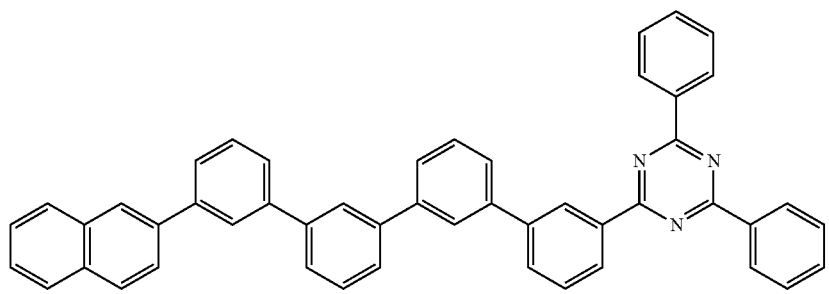
[6-17]
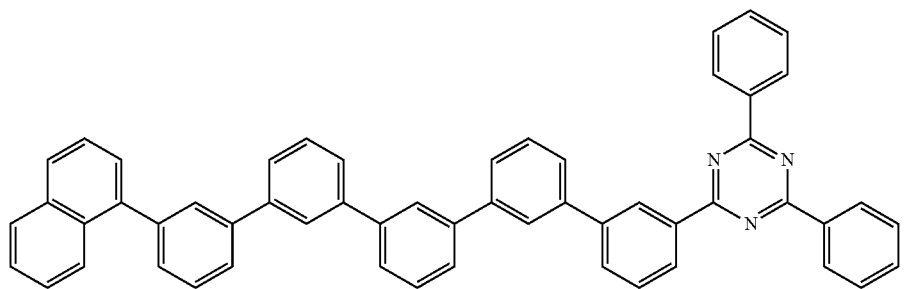
[6-18]
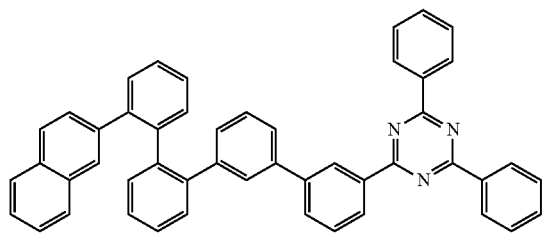
[6-19]
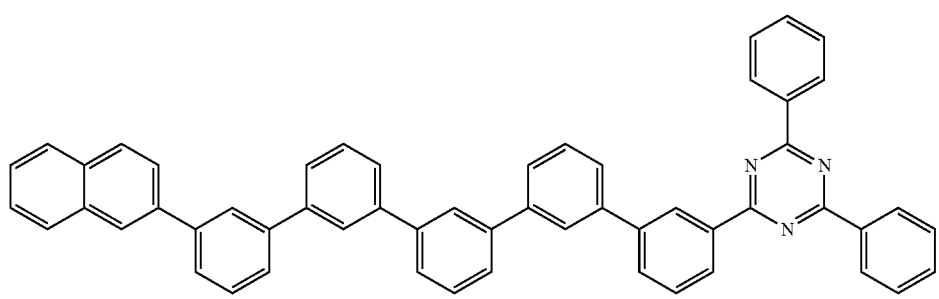
[6-20]

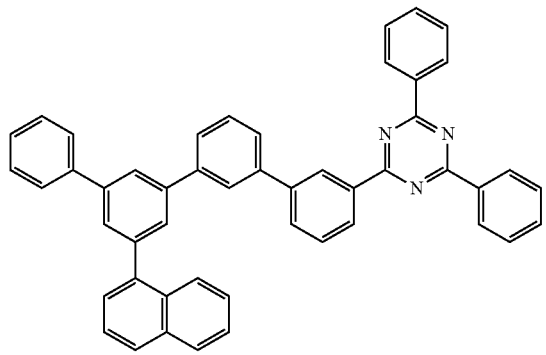
[6-21]
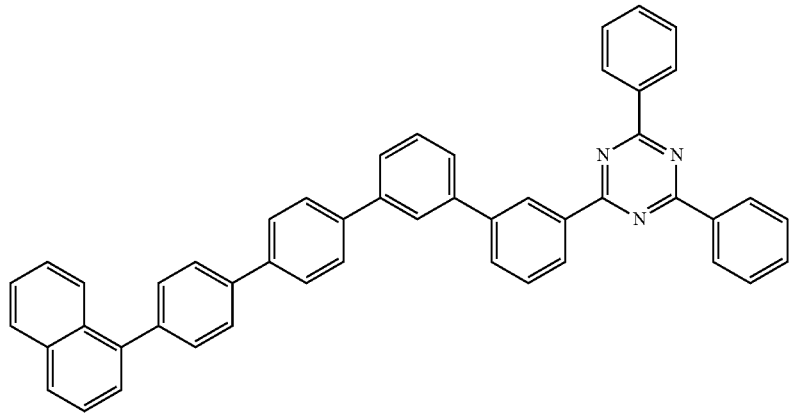
[6-22]
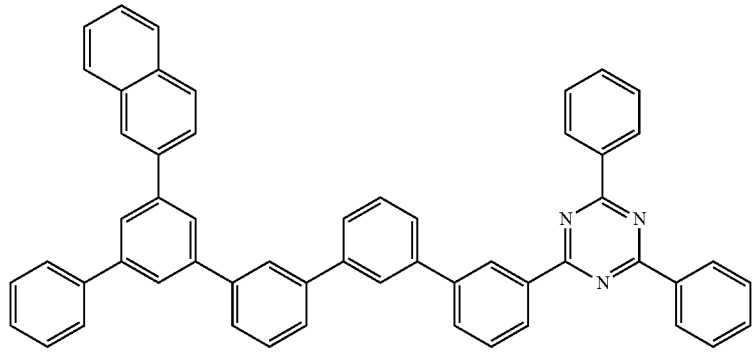
[6-23]
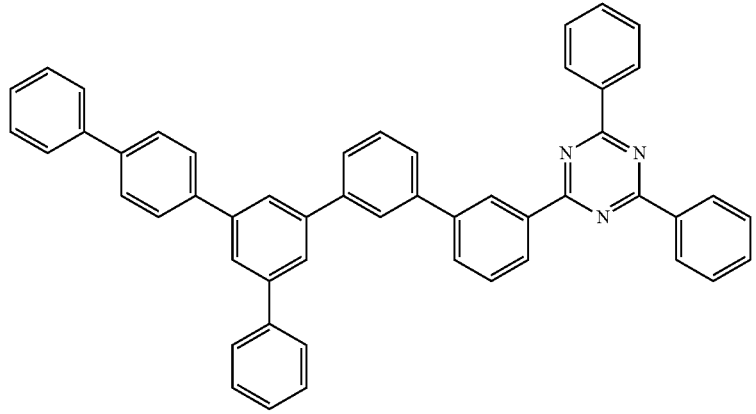
[6-24]

[6-25]
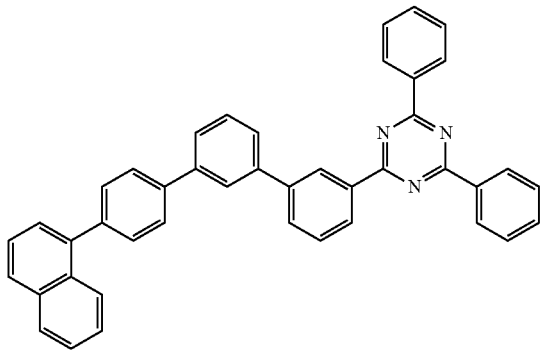
[6-26]
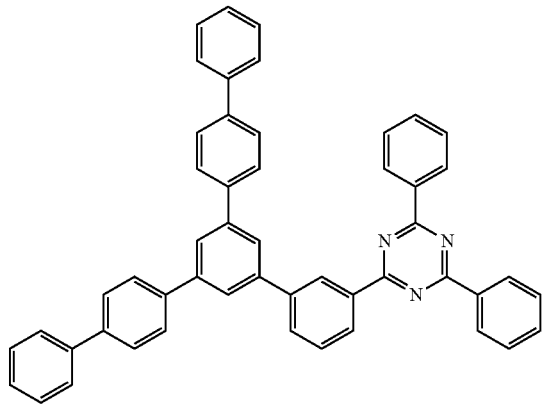
[6-27]
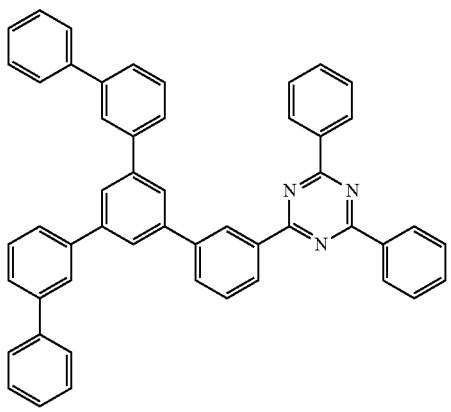
[6-28]
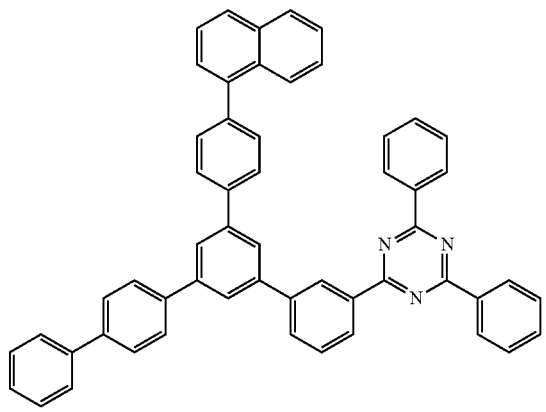
[6-29]
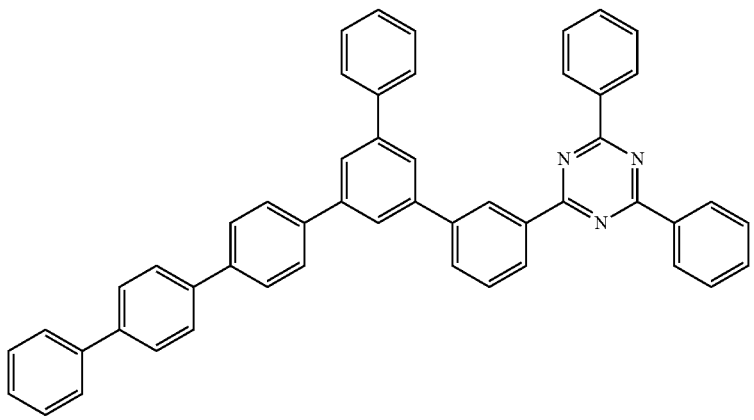

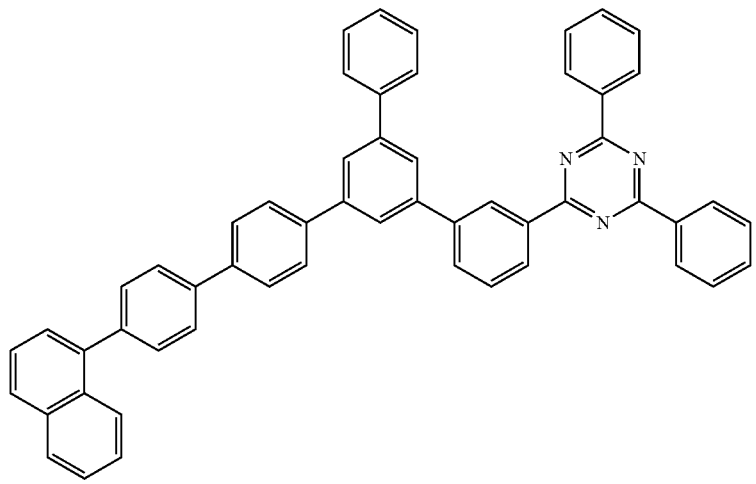
[6-30]
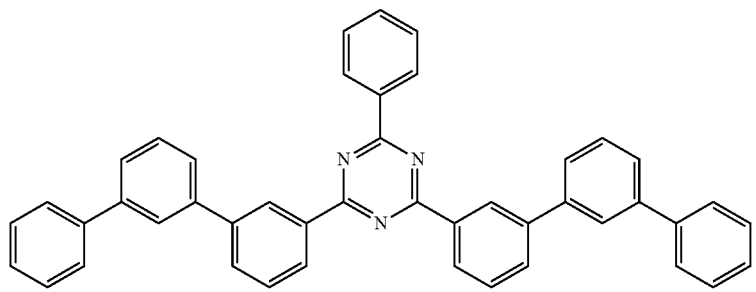
[6-31]
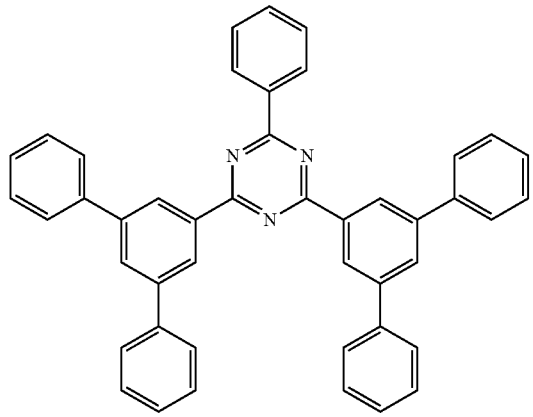
[6-32]
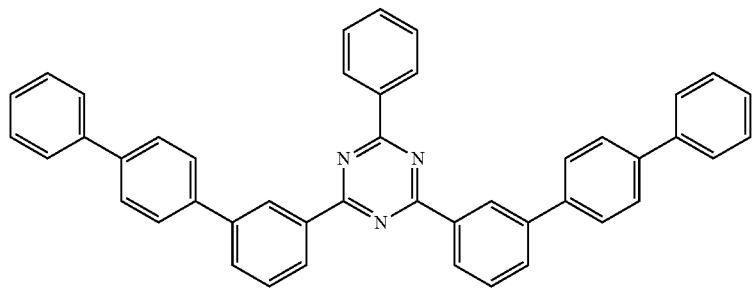
[6-33]

[6-34]
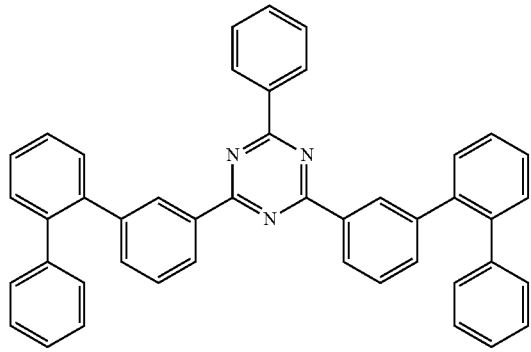
[6-35]
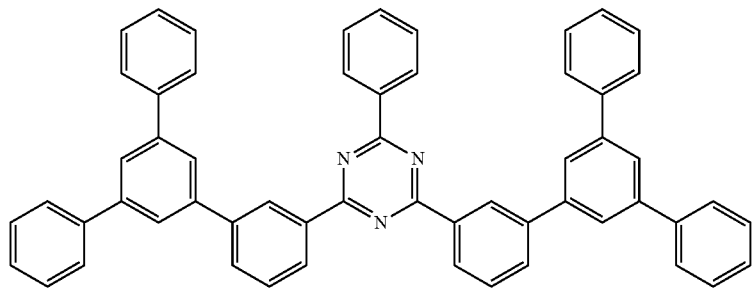
[6-36]
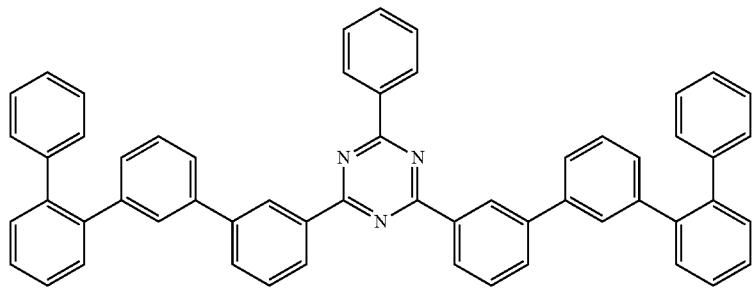
[6-37]
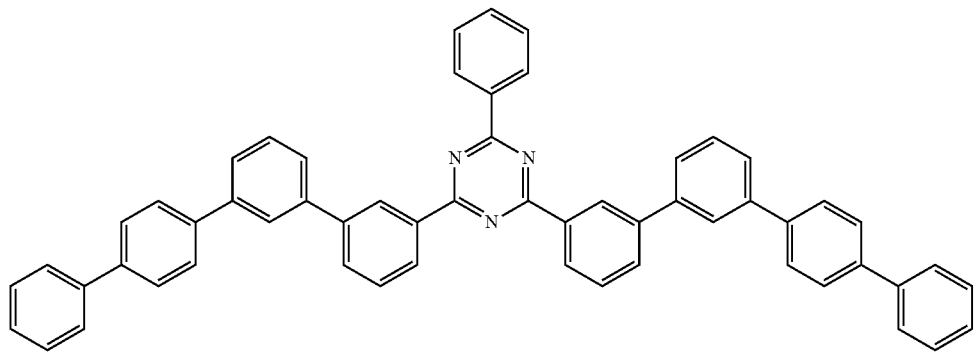

[6-38]
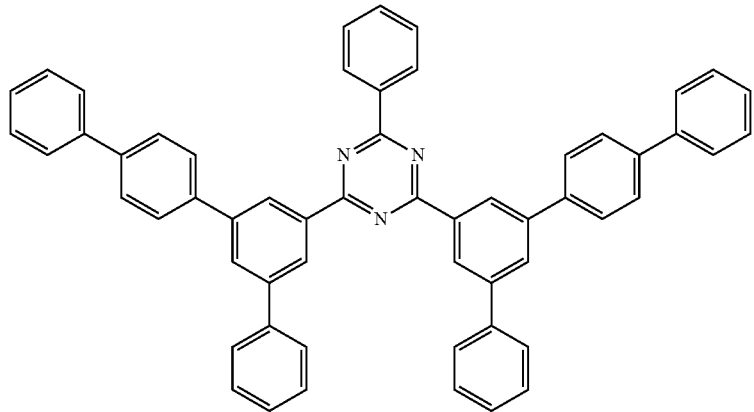
[6-39]
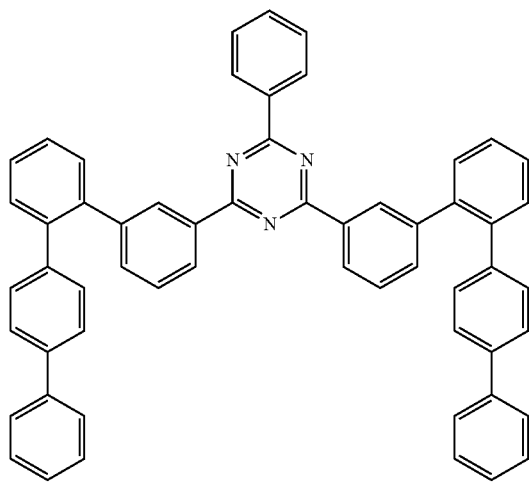
[6-40]
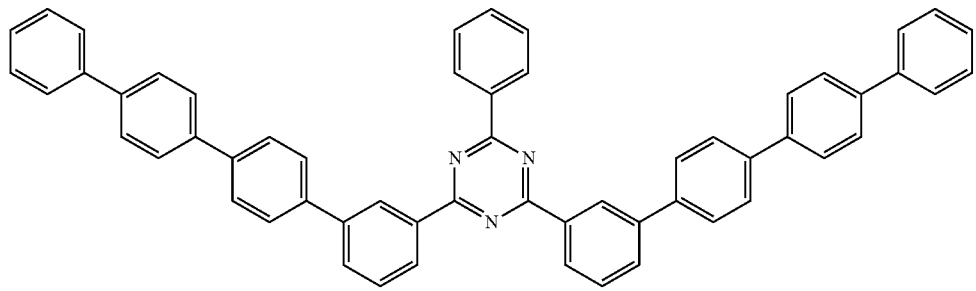

-continued
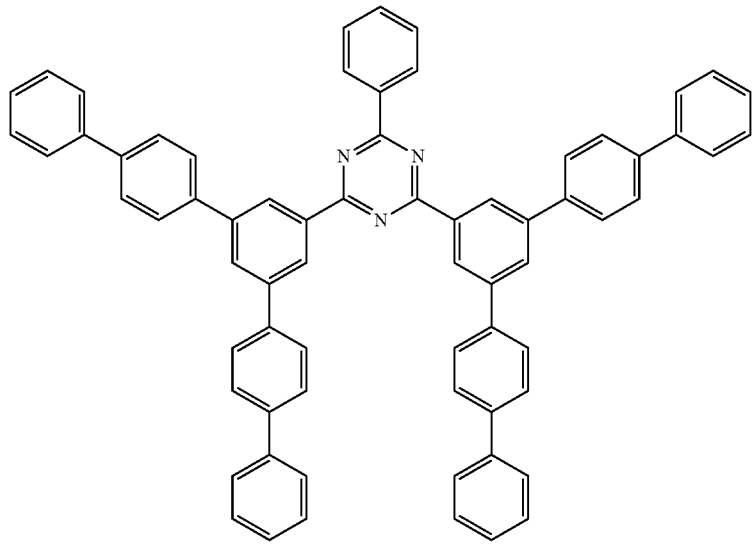
[6-41]
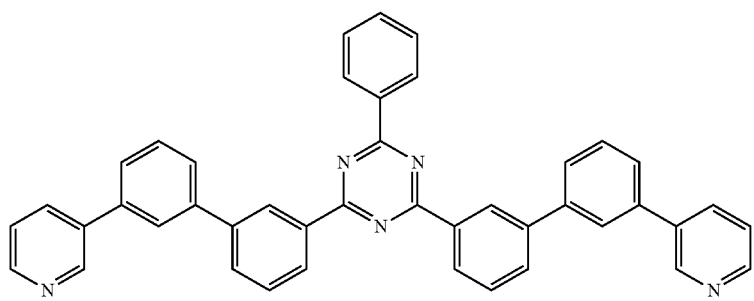
[6-42]
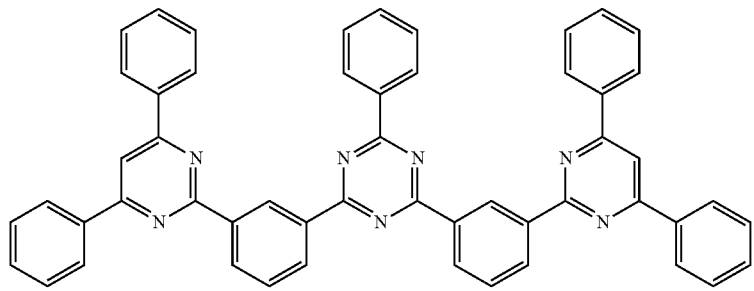
[6-43]
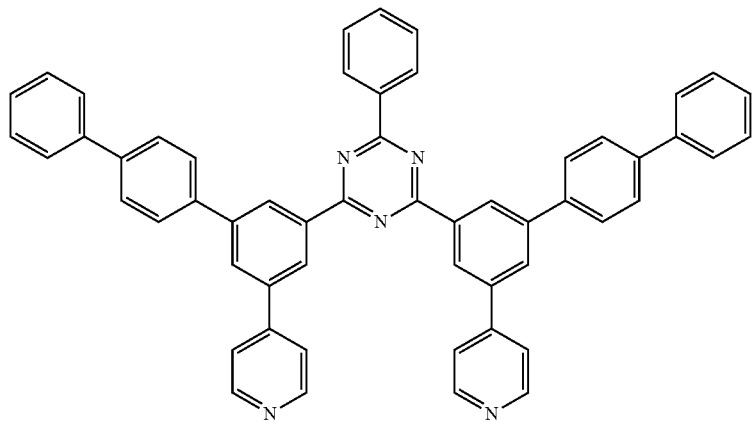
[6-44]

[6-45]
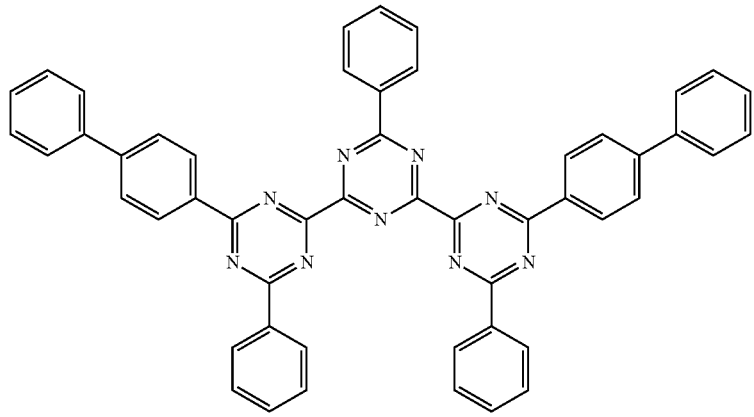
[6-46]
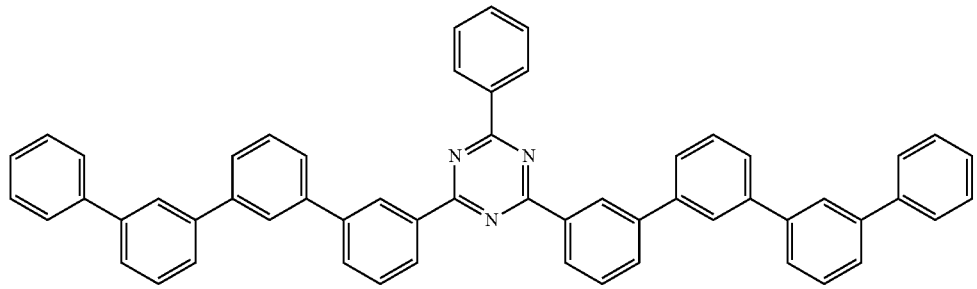
[6-47]
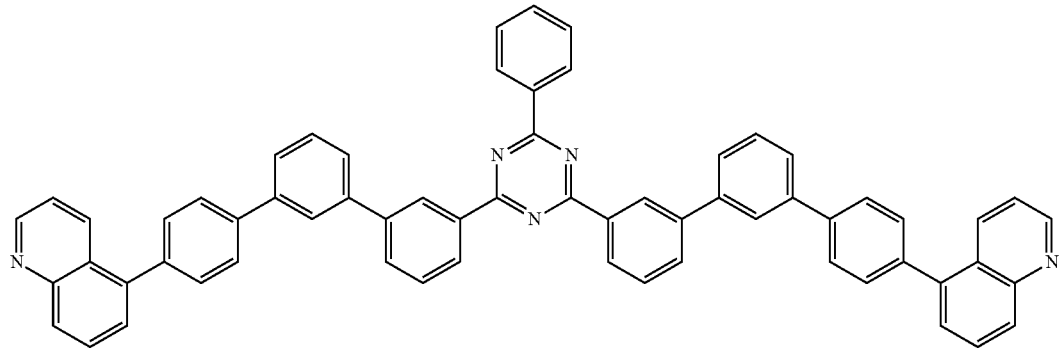
[6-48]
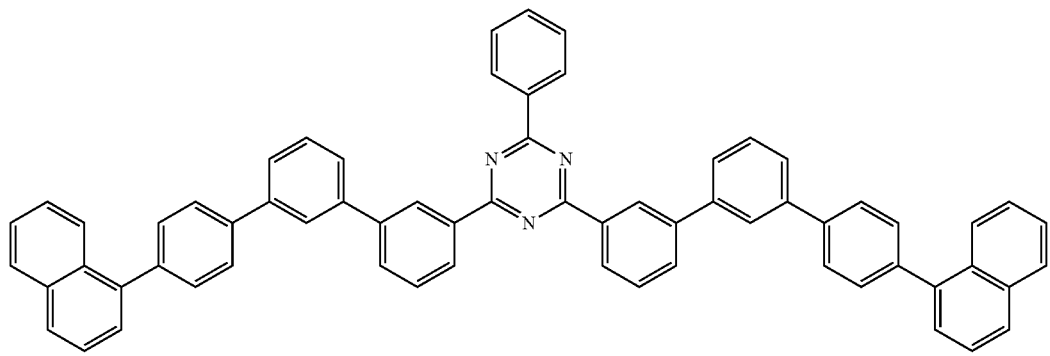

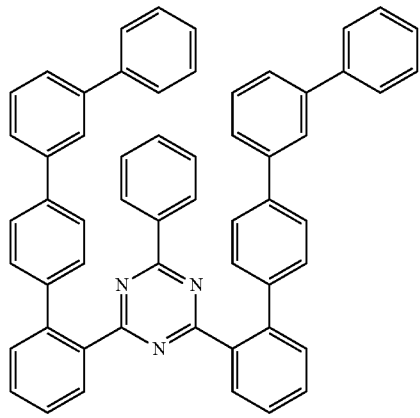
[6-49]
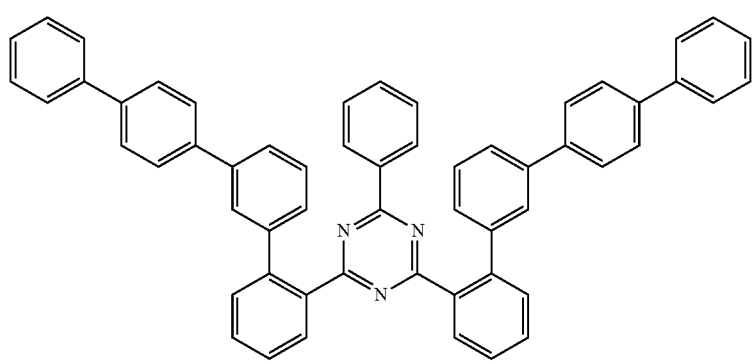
[6-50]
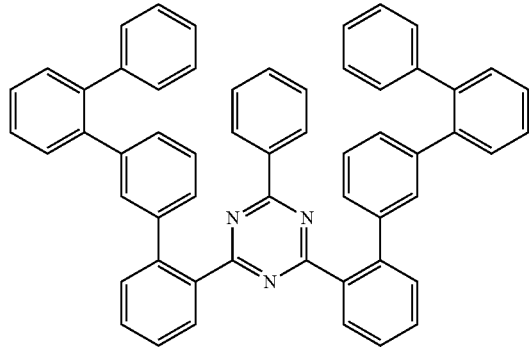
[6-51]
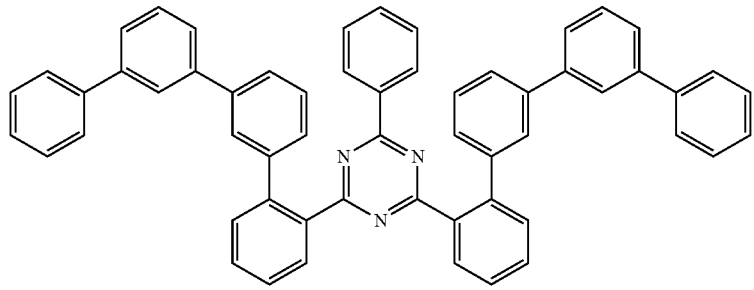
[6-52]

-continued
[6-53]
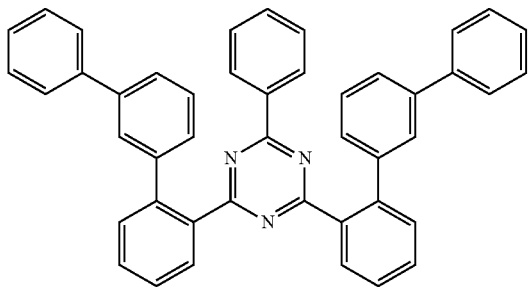
[6-54]
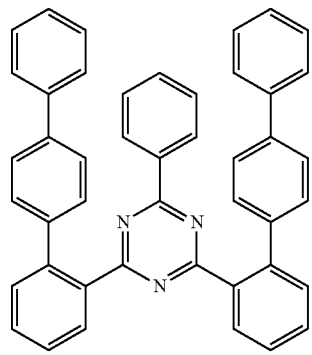
[6-55]
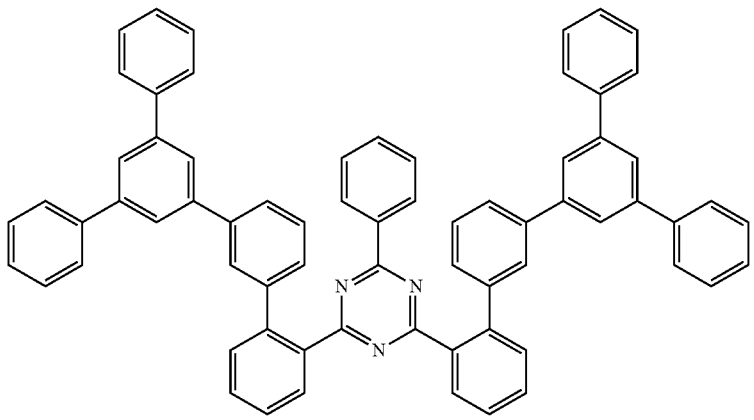
[6-56]
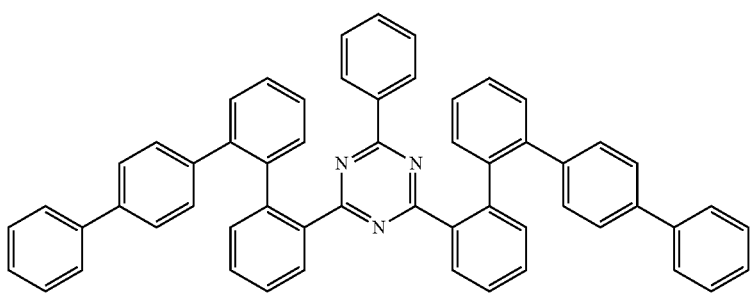
[6-57]
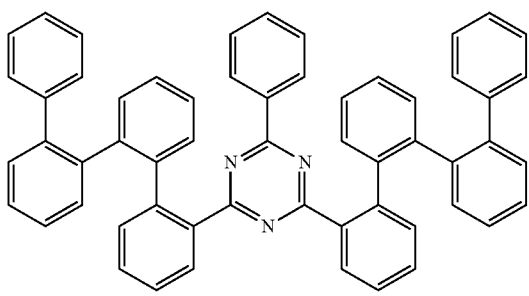
[6-58]
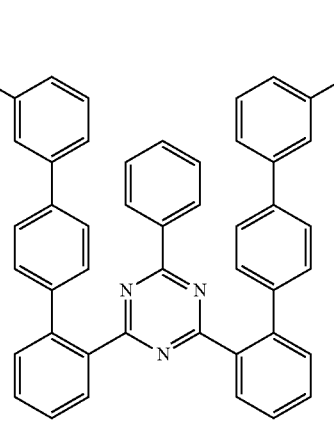

[6-59]
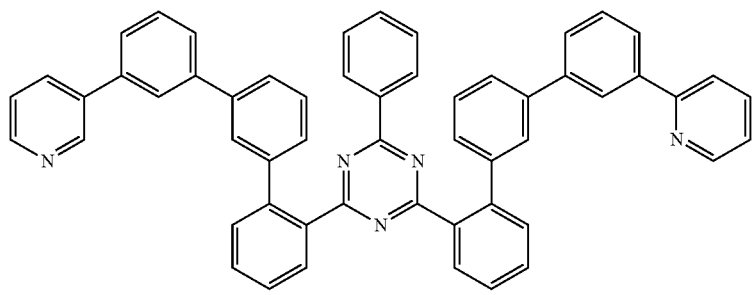
[6-60]
[6-61]
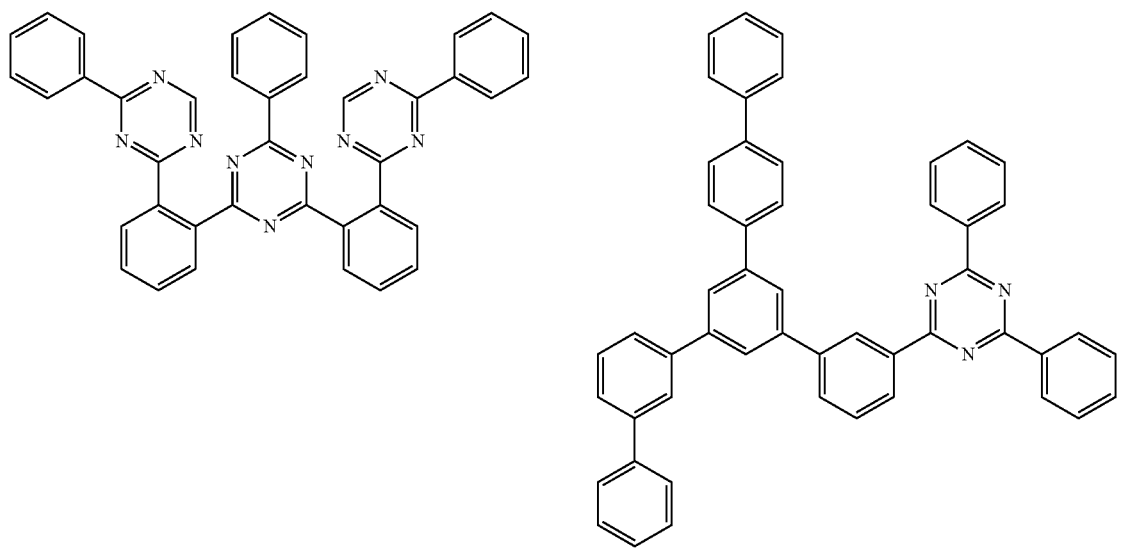
[6-62]
[6-63]
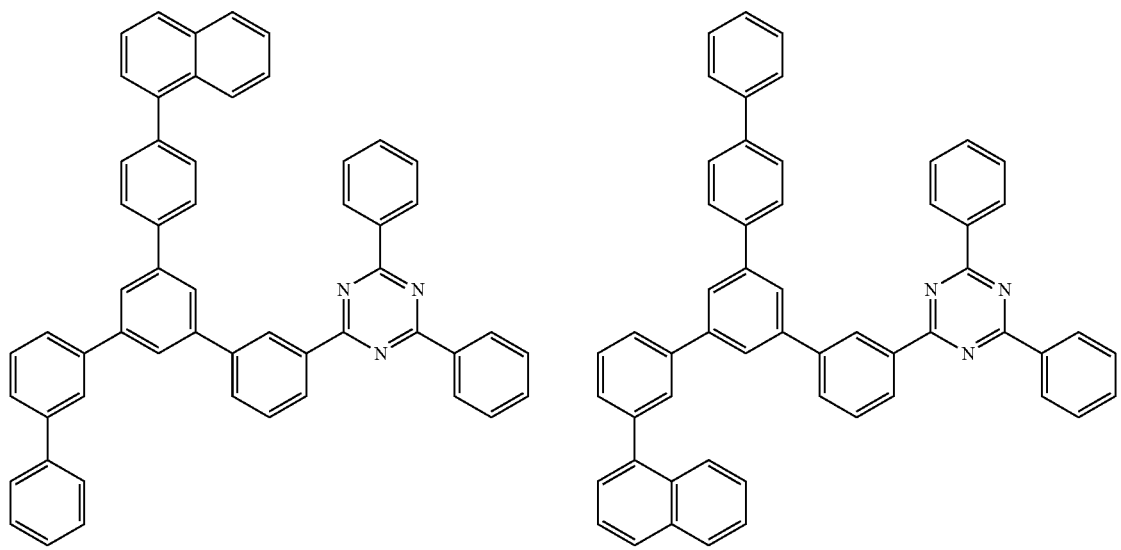

-continued
[6-64]
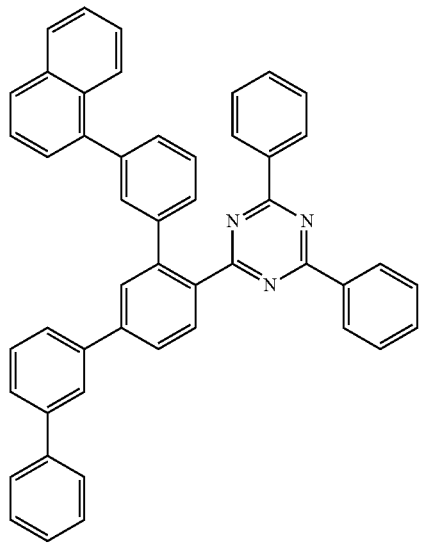
[6-65]
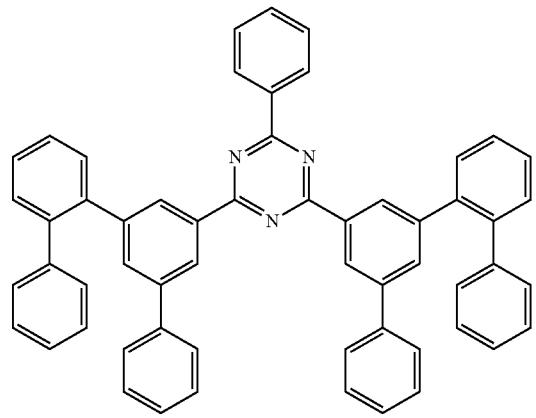
[6-66]
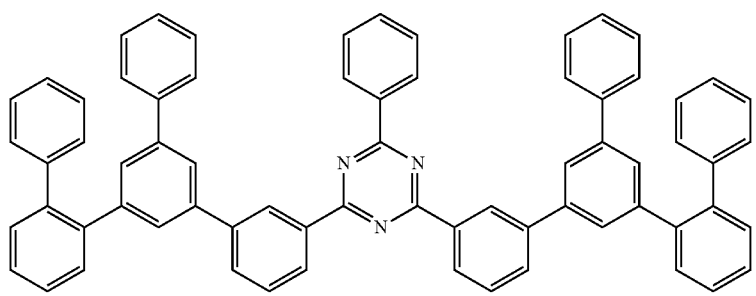
[6-67]
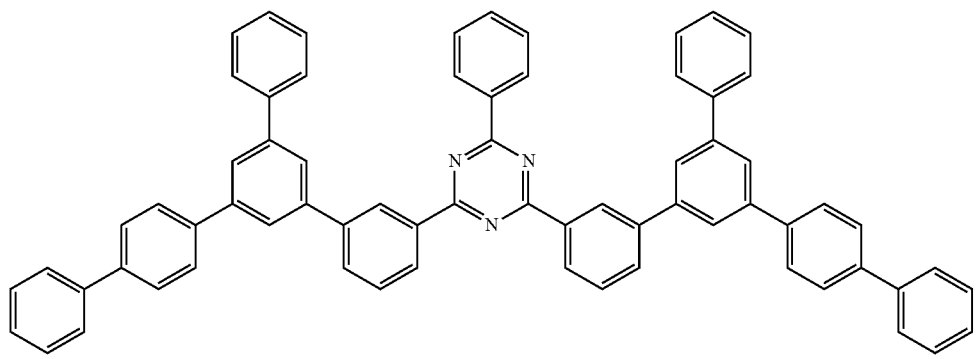
[6-68]
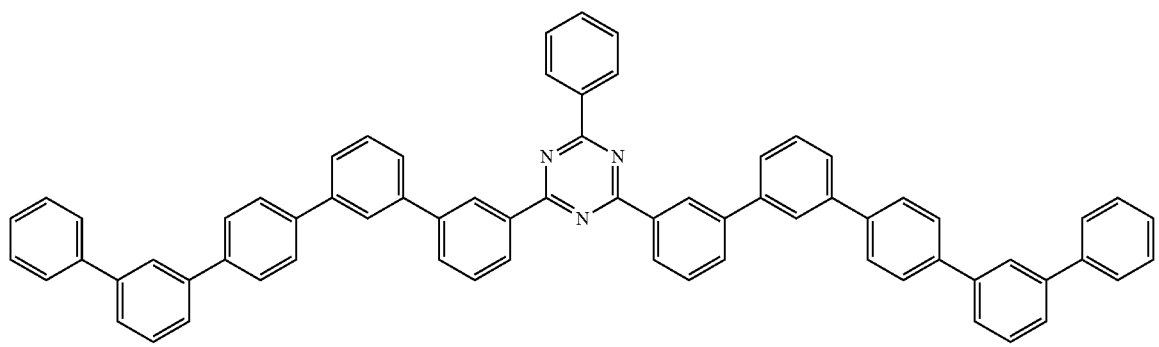

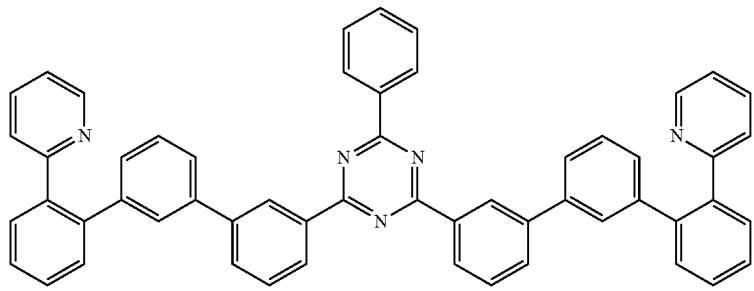
[6-69]
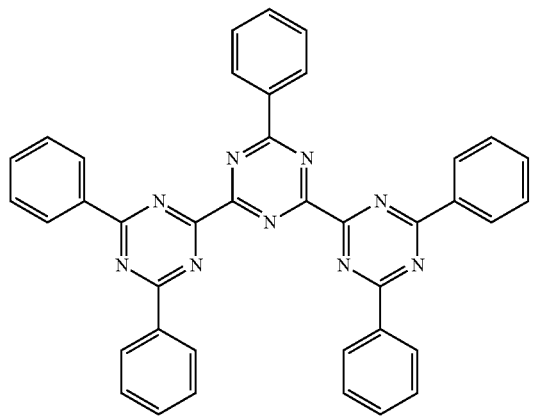
[6-70]
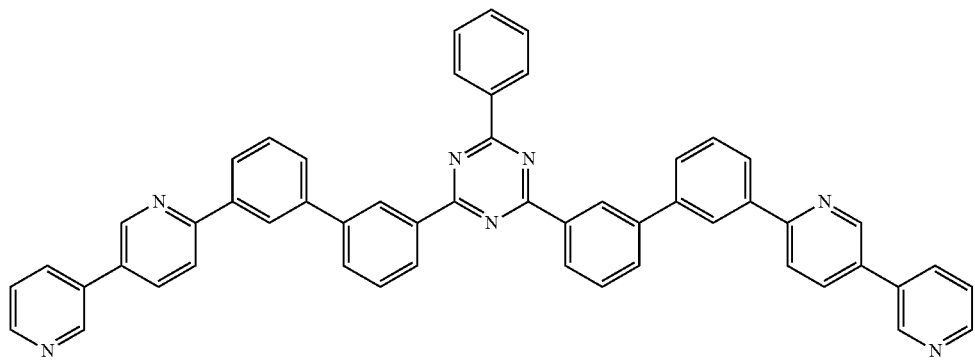
[6-71]
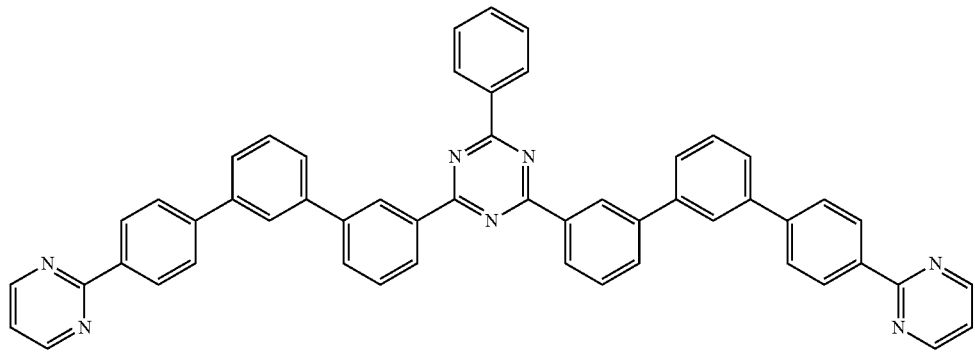
[6-72]

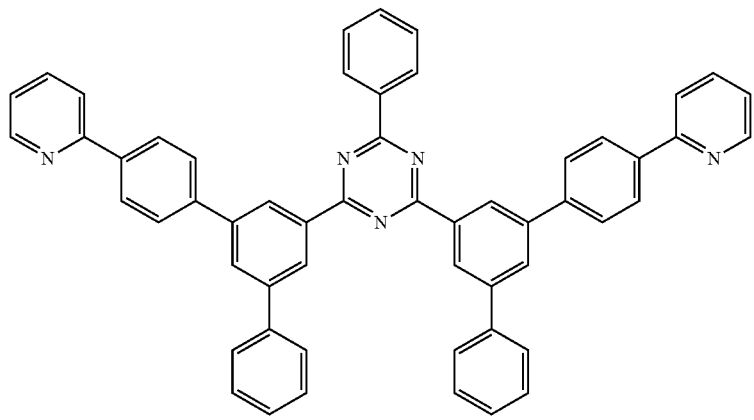
[6-73]
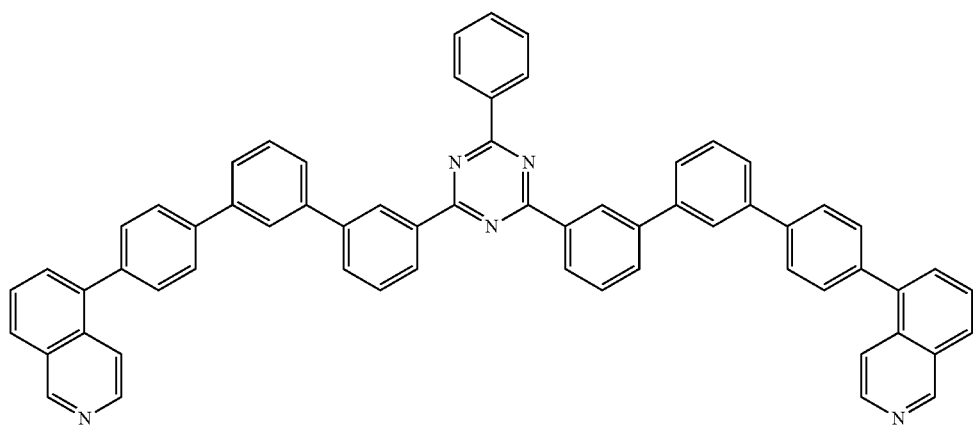
[6-74]
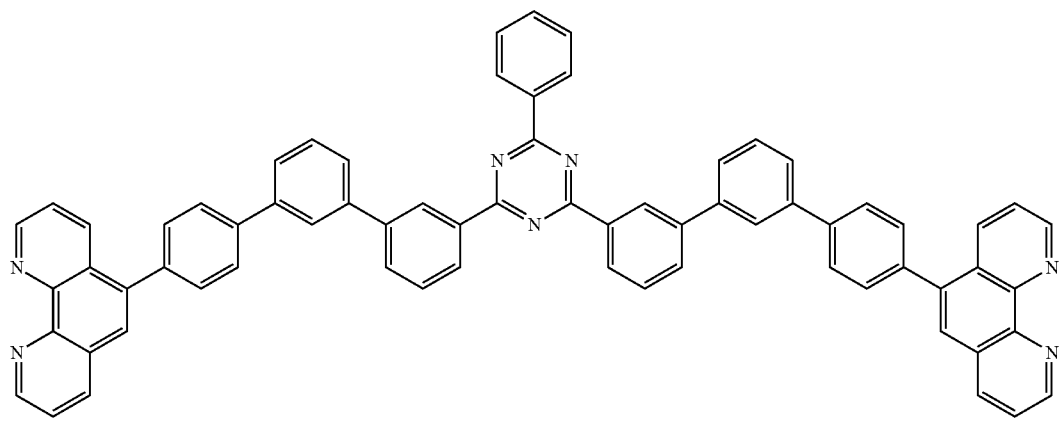
[6-75]

[6-76]
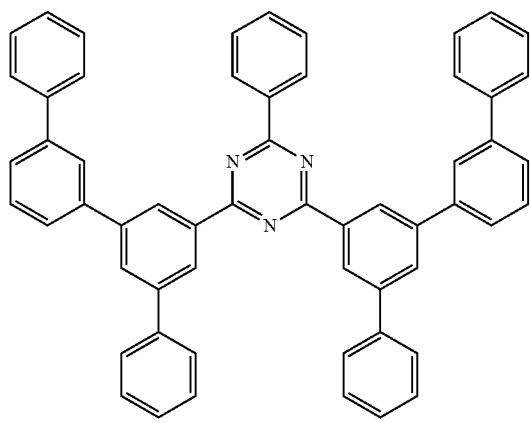
[6-77]
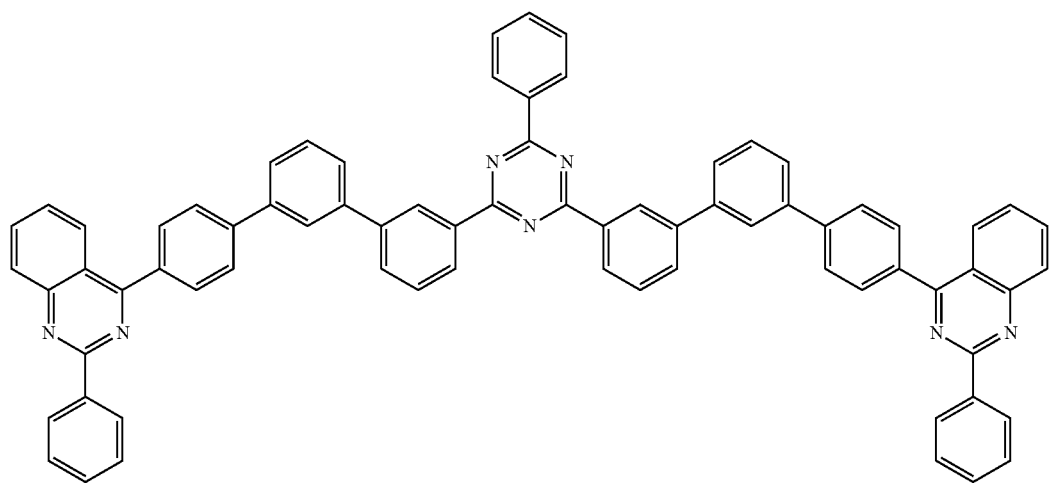
[6-78]
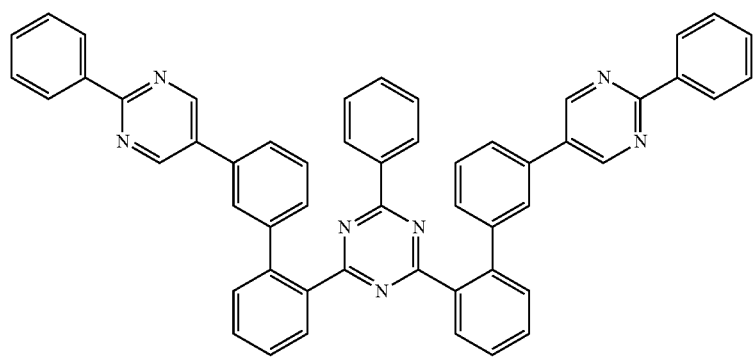

-continued
[6-79]
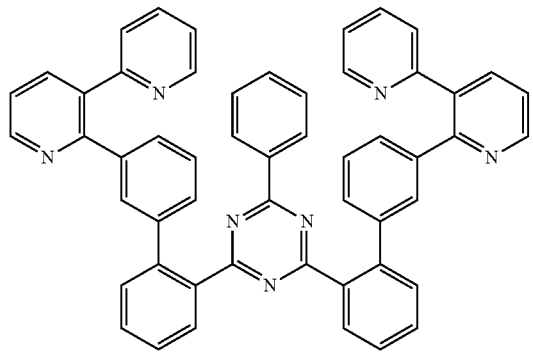
[6-80]
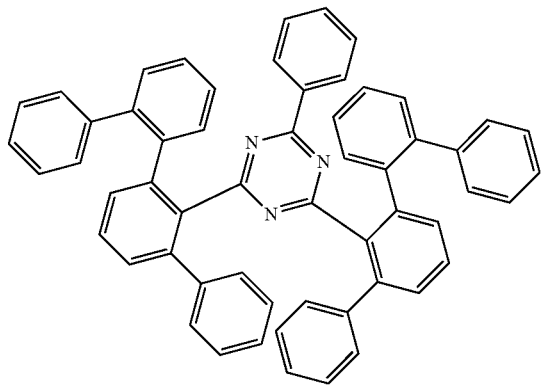
[6-81]
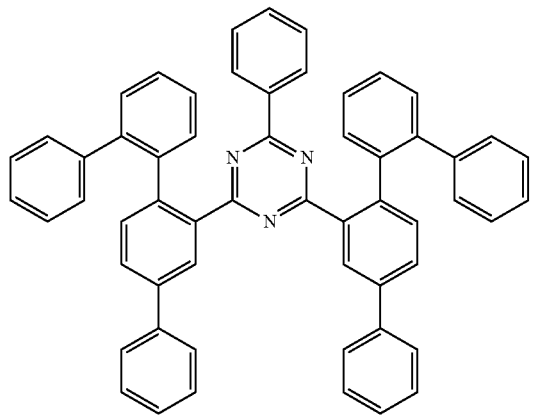
[6-82]
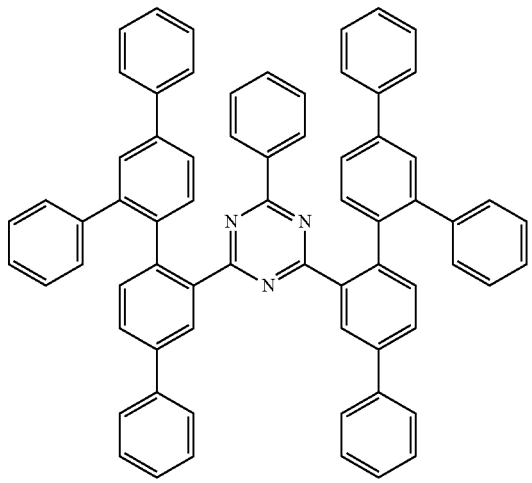
[6-83]
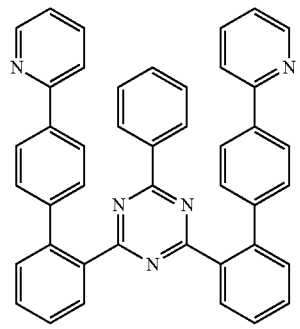
[6-84]
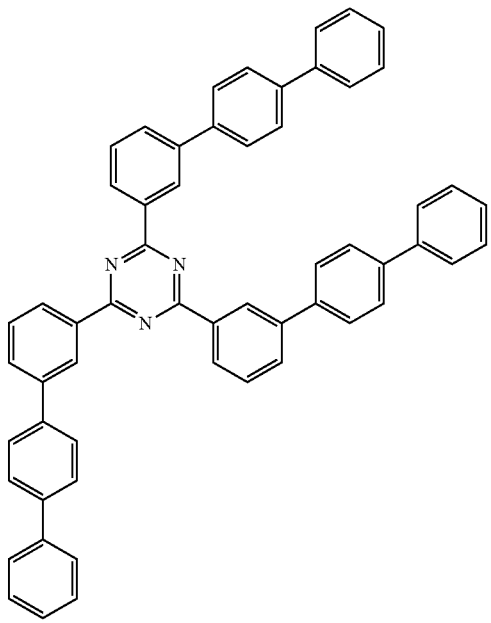

[6-85]
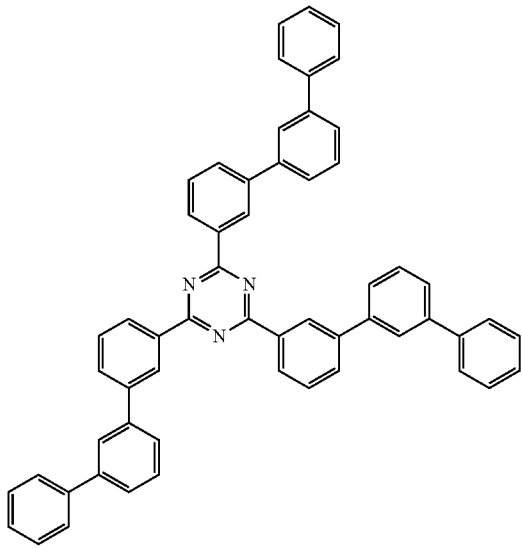
[6-86]
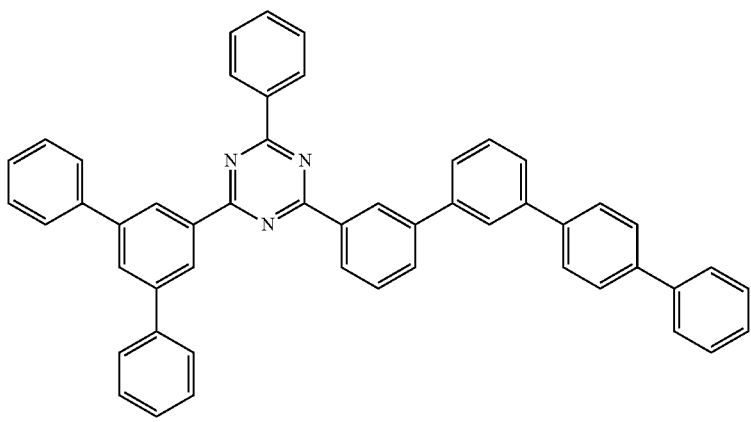
[6-87]
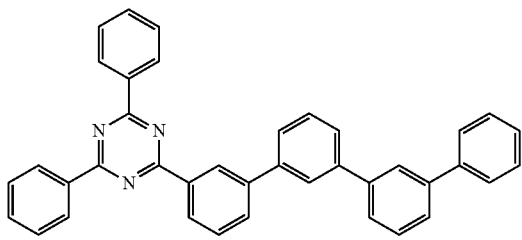
[6-88]
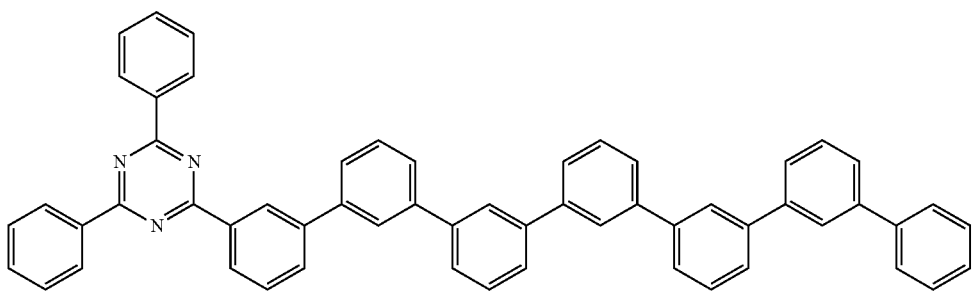

-continued
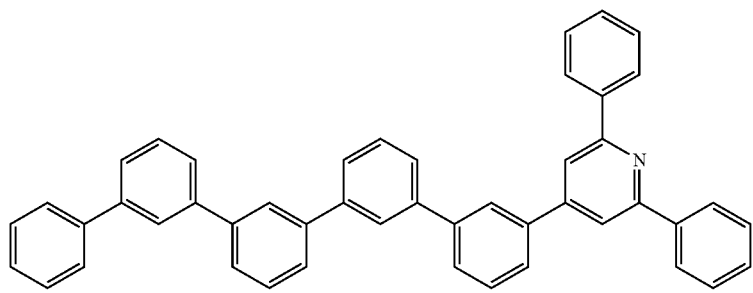
[6-89]
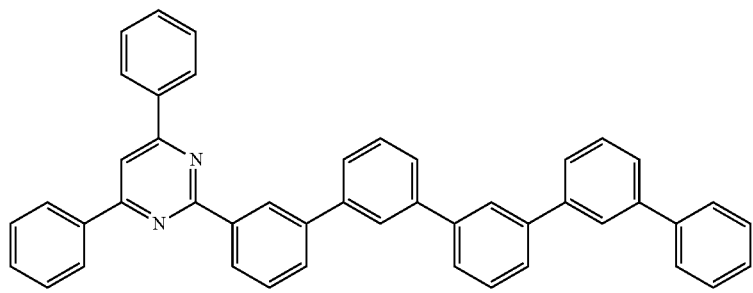
[6-90]
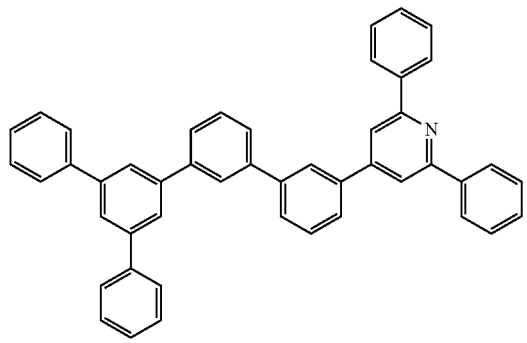
[6-91]
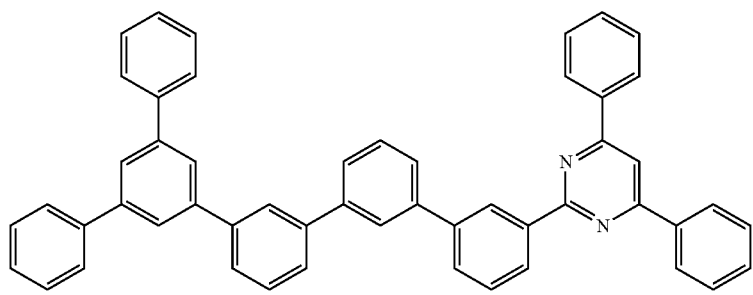
[6-92]

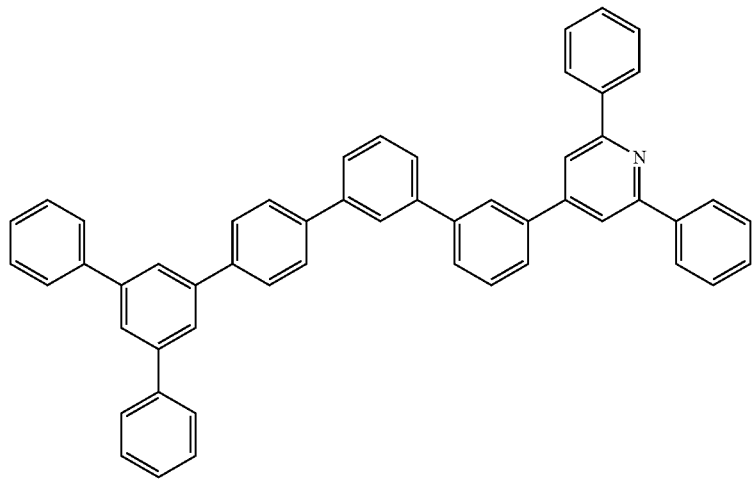
[6-93]
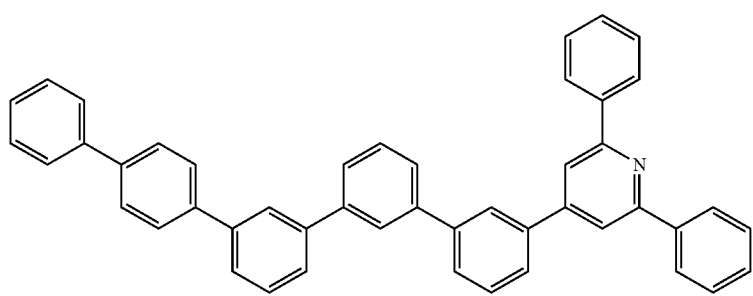
[6-94]
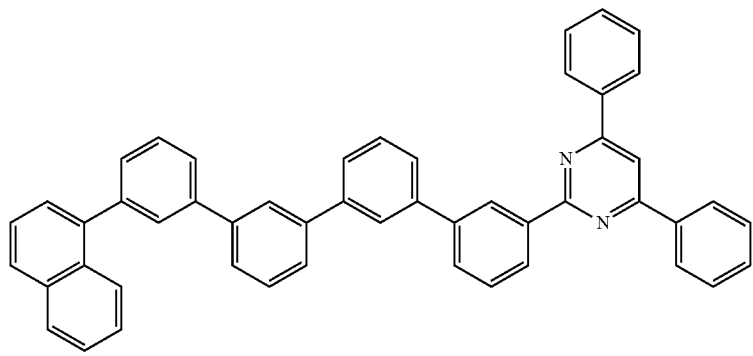
[6-95]
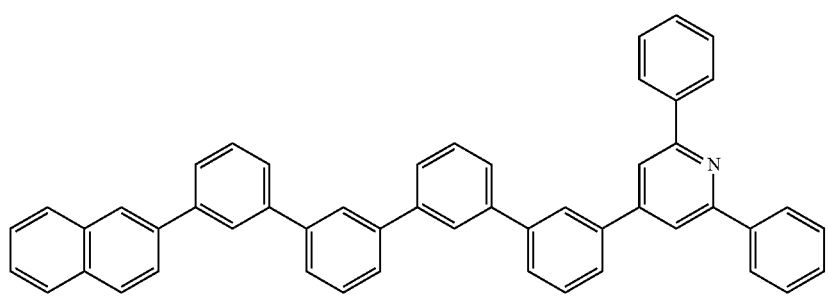
[6-96]

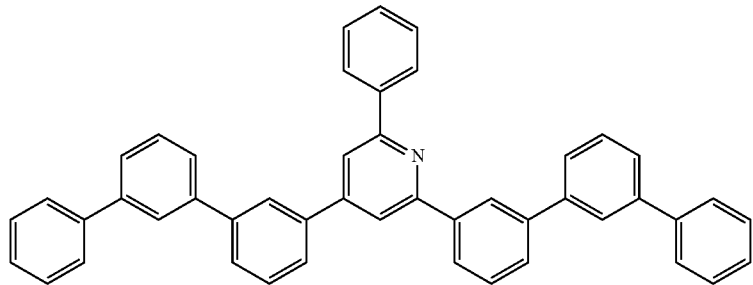
[6-97]
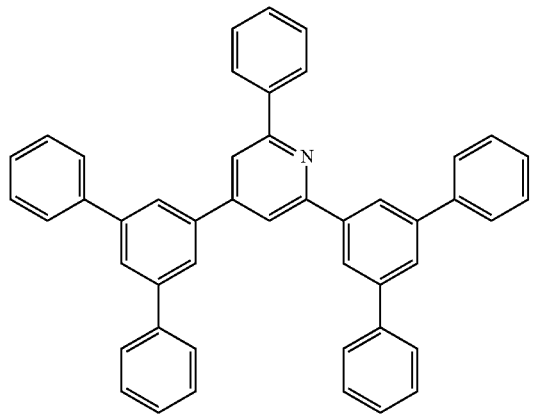
[6-98]
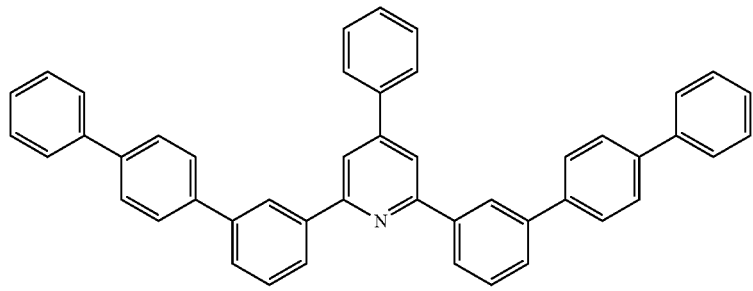
[6-99]
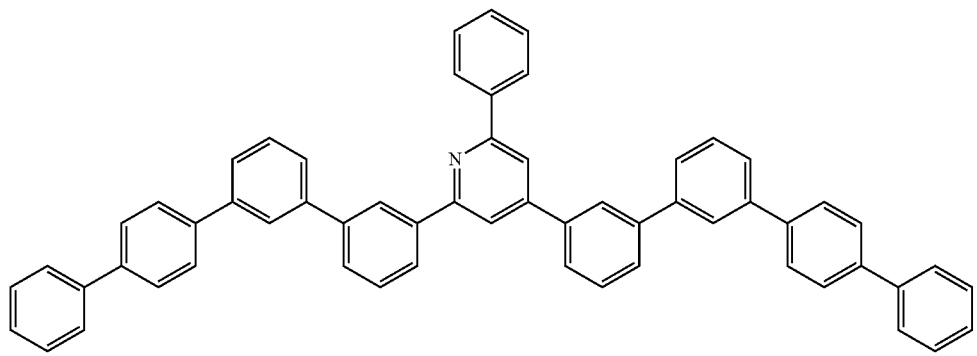
[6-100]

[6-101]
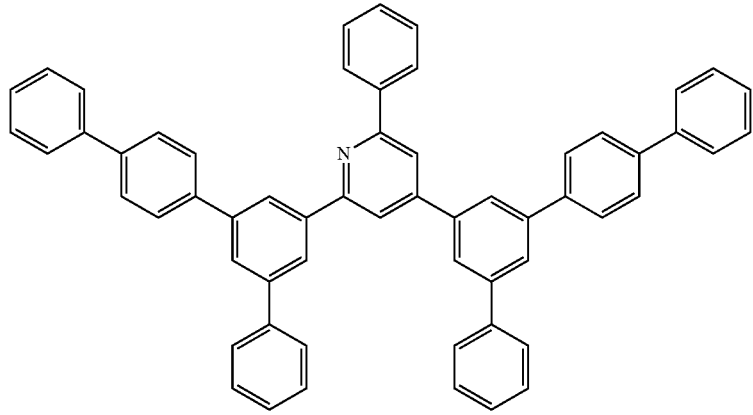
[6-102]
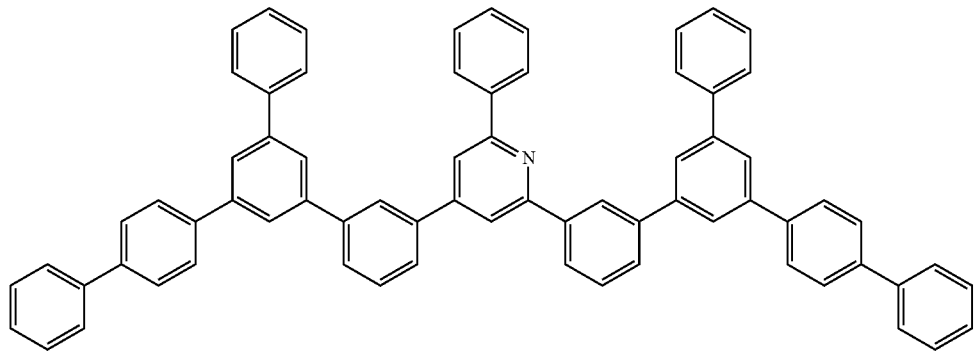
[6-103]
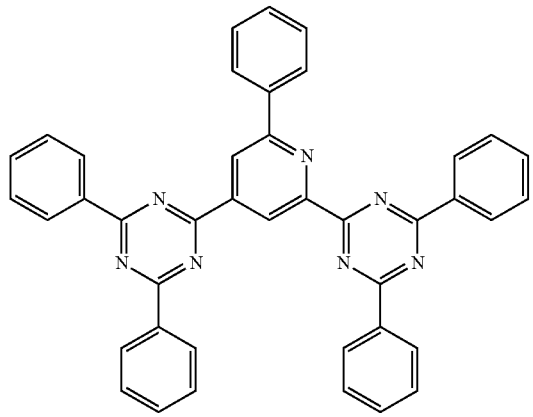
[6-104]
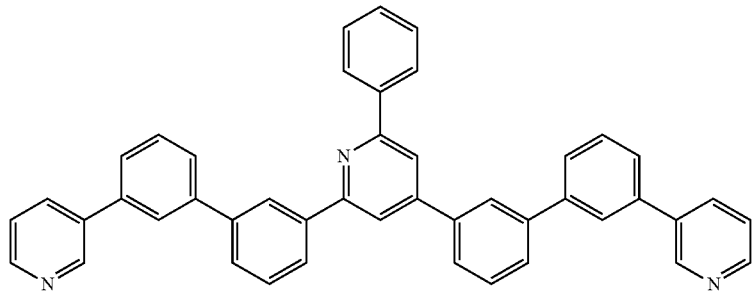

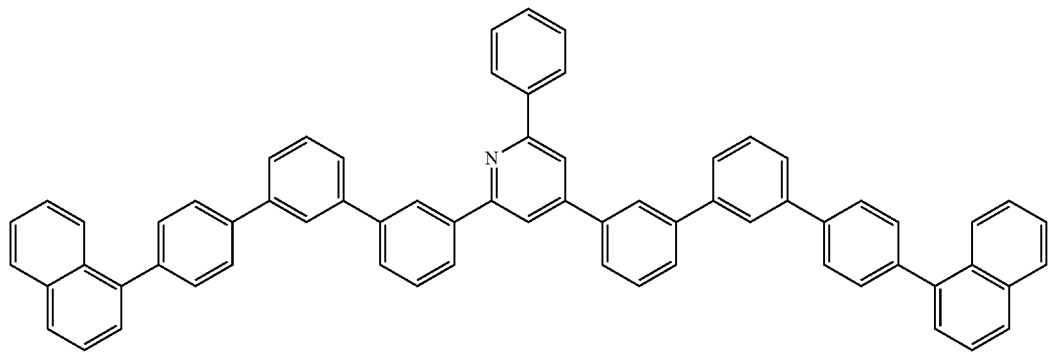
[6-105]
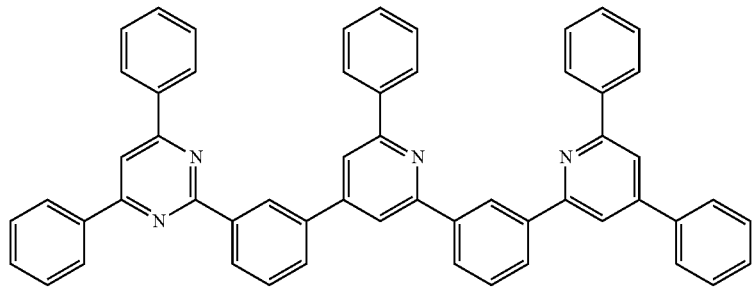
[6-106]
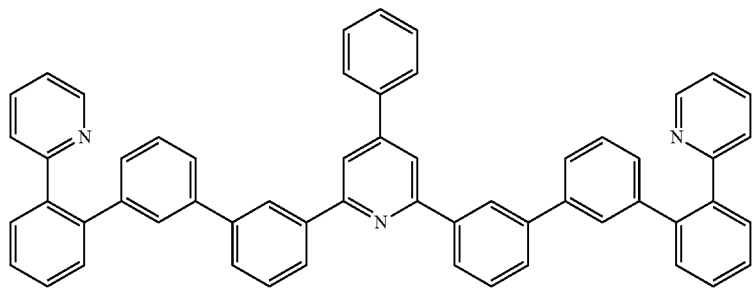
[6-107]
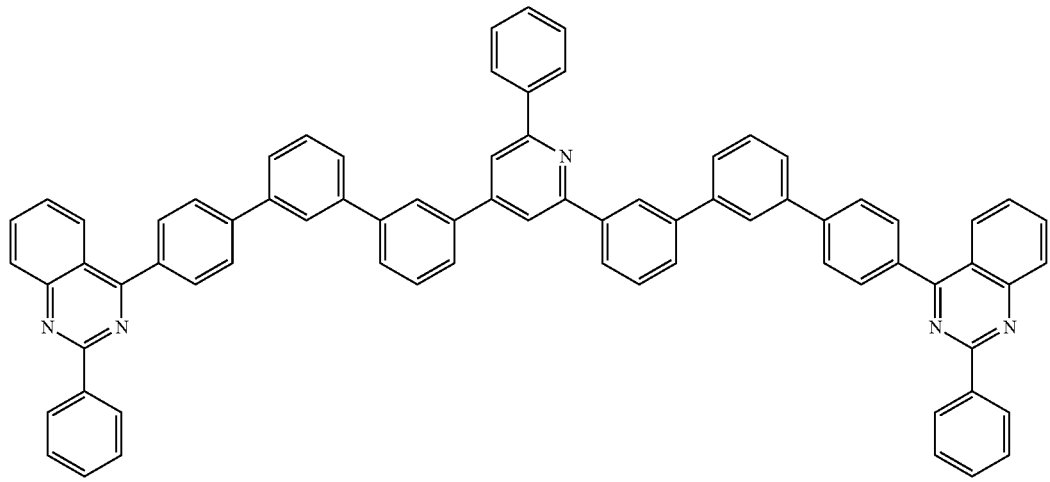
[6-108]

[6-109]
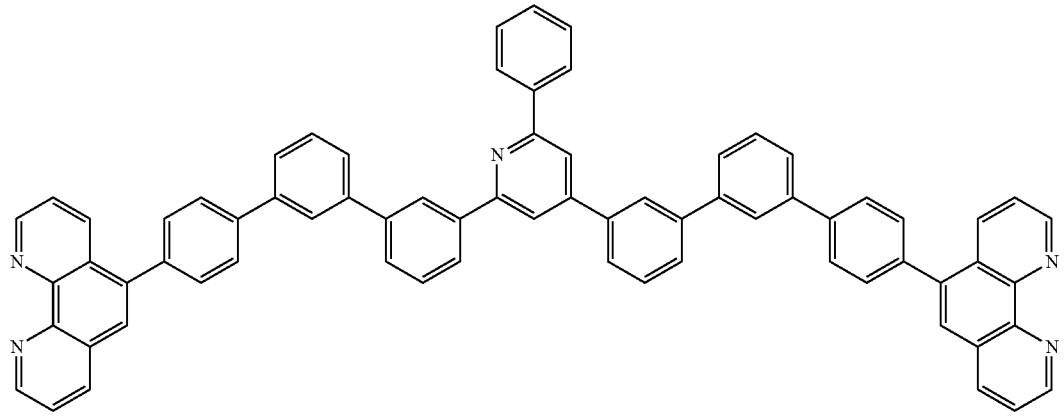
[6-110]
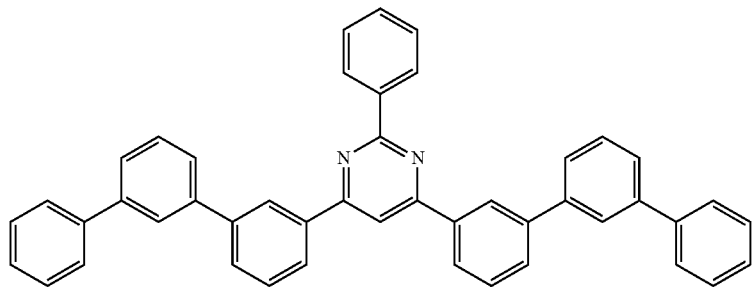
[6-111]
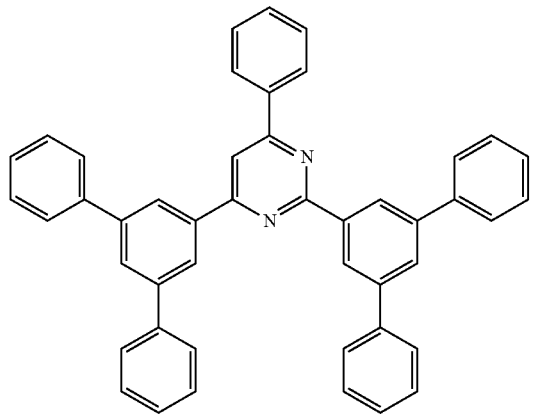
[6-112]
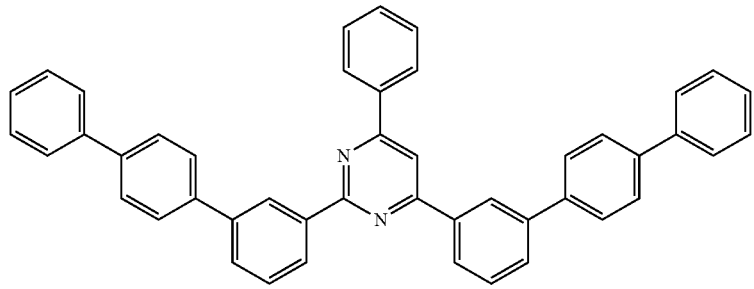

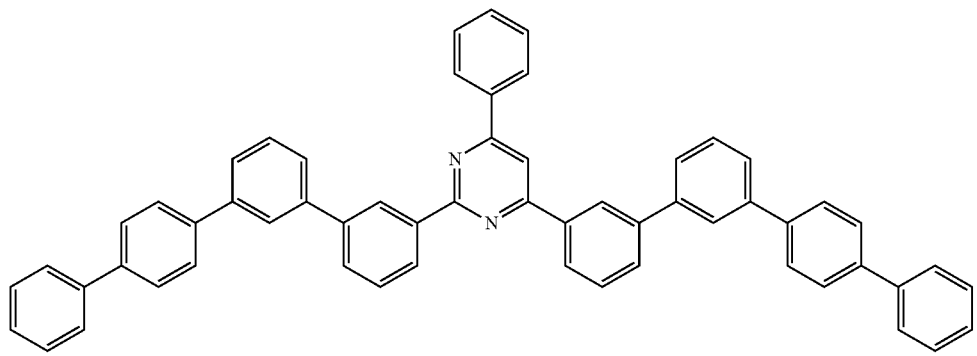
[6-113]
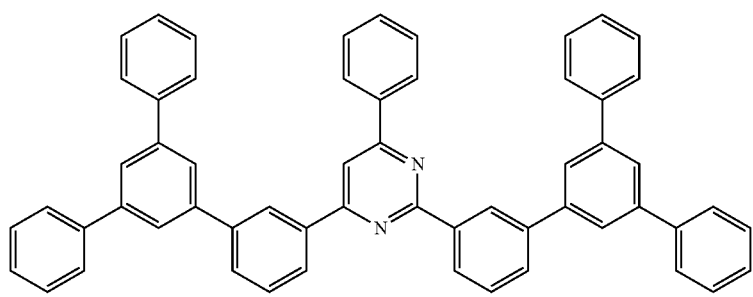
[6-114]
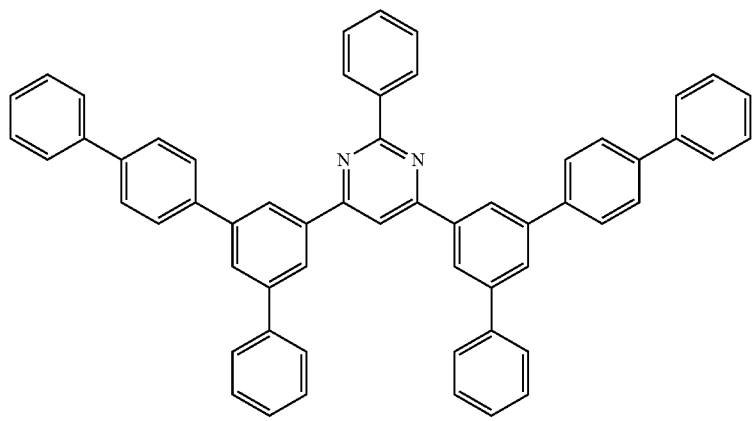
[6-115]
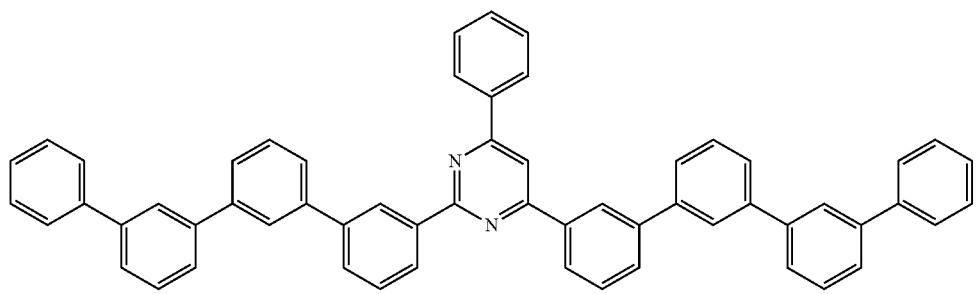
[6-116]

-continued
[6-117]
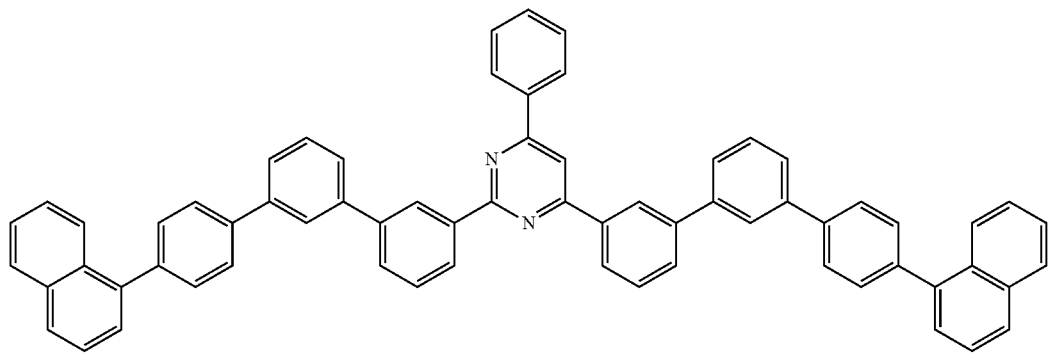
[6-118]
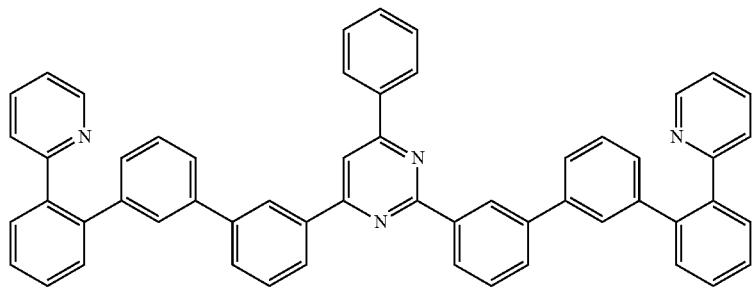
[6-119]
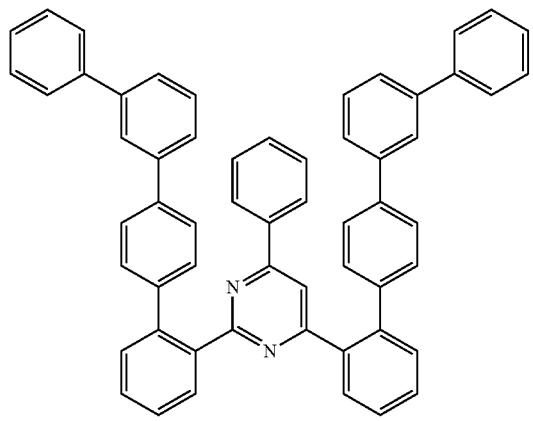
[6-120]
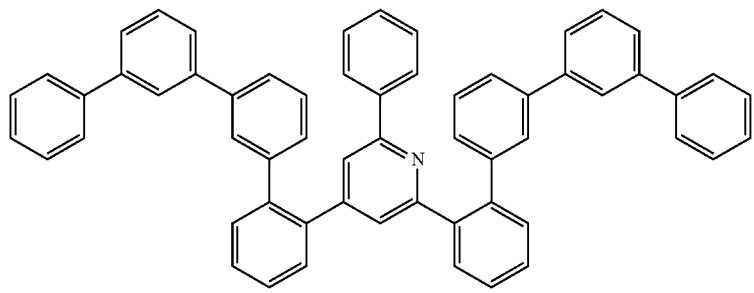

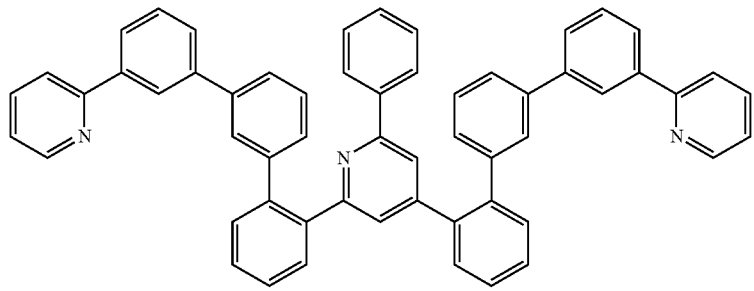
[6-121]
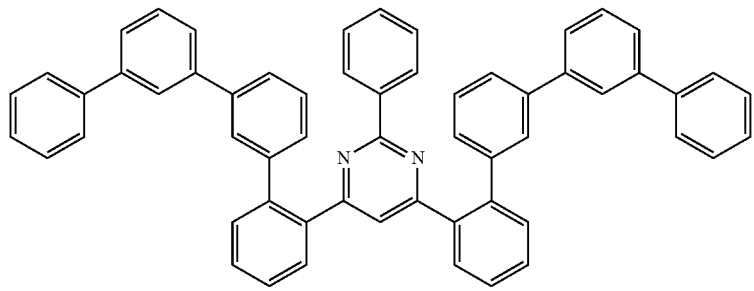
[6-122]
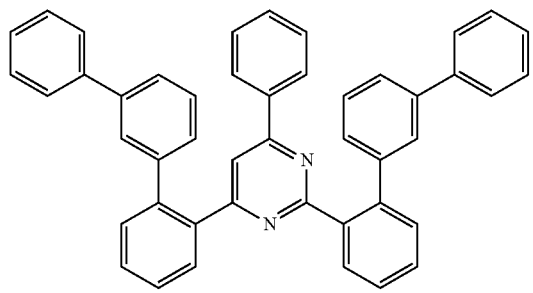
[6-123]
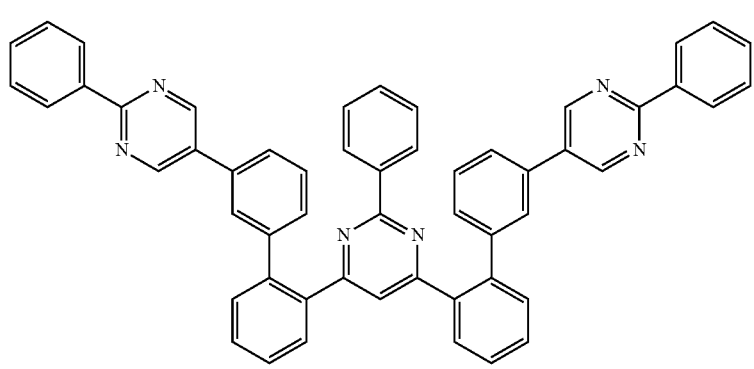
[6-124]
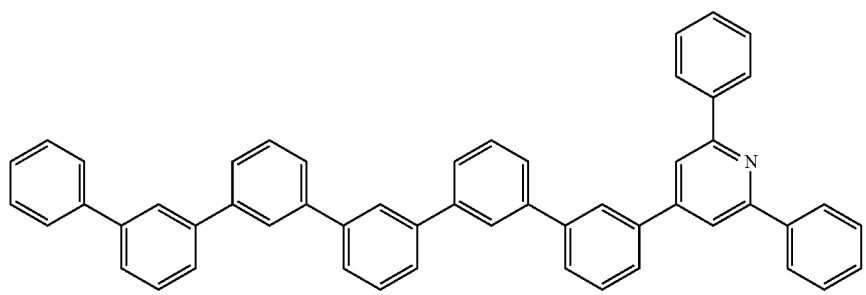
[6-125]

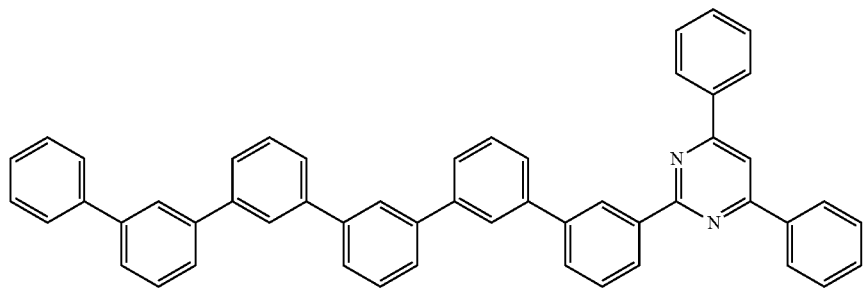
[6-126]
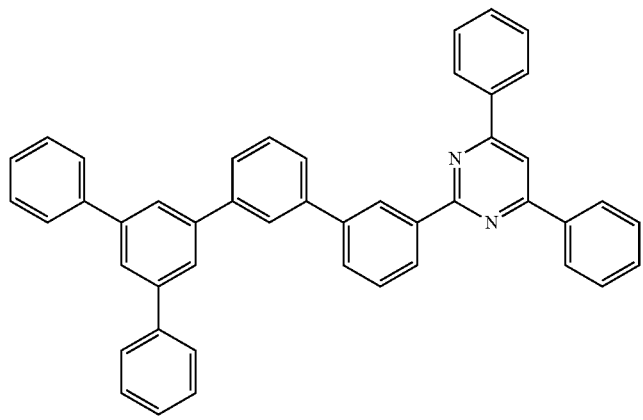
[6-127]
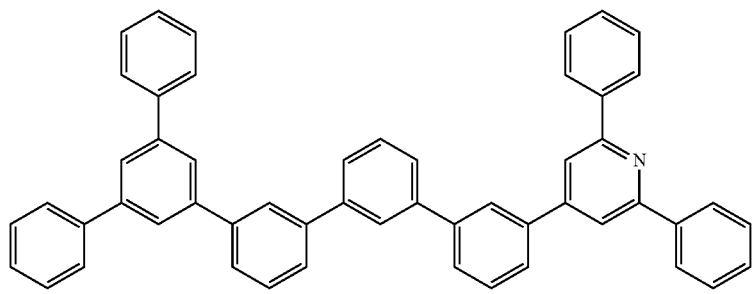
[6-128]
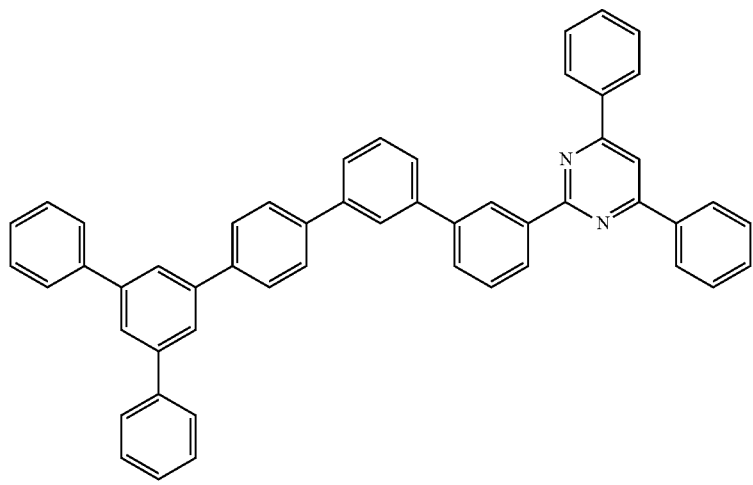
[6-129]

-continued
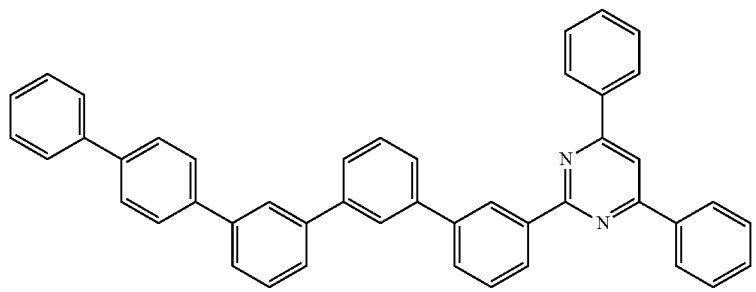
[6-130]
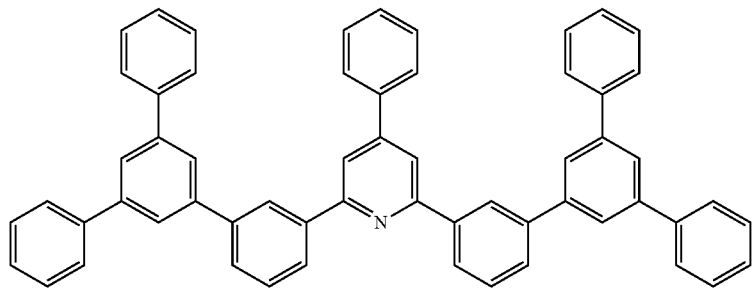
[6-131]
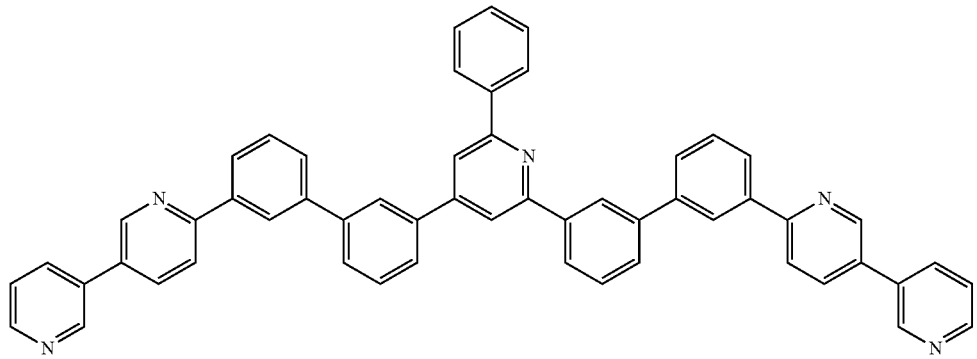
[6-132]
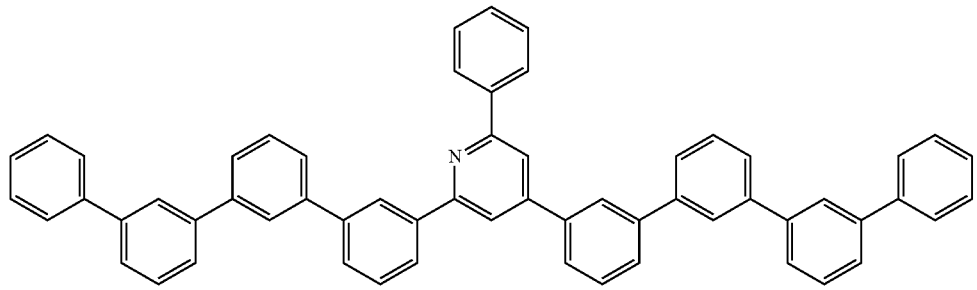
[6-133]
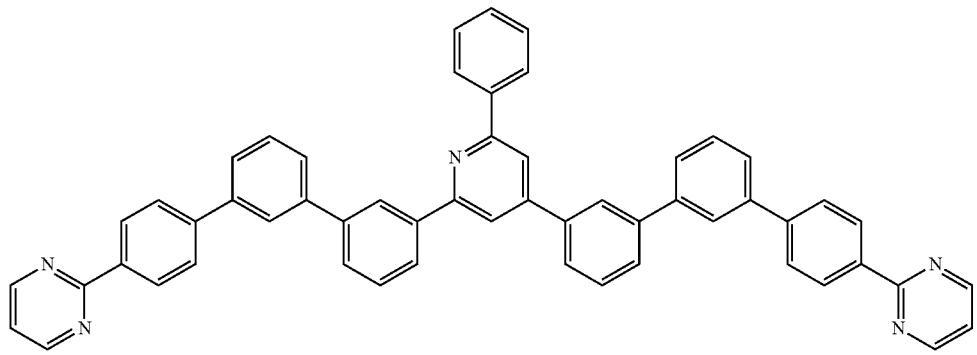
[6-134]

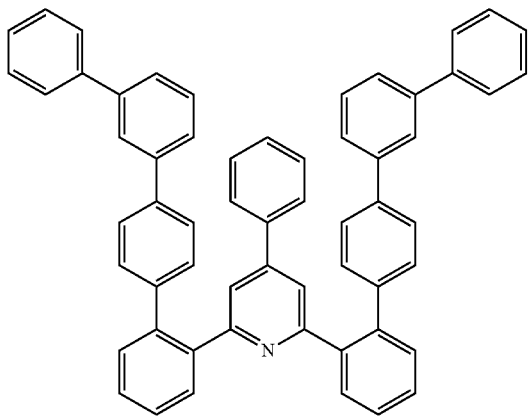
[6-135]
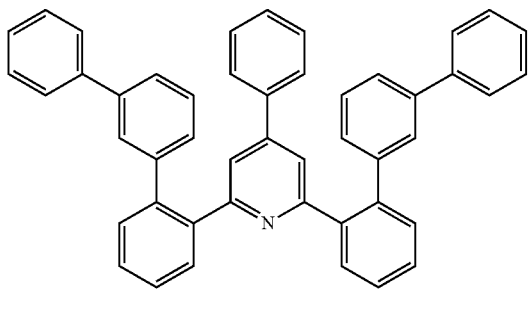
[6-136]
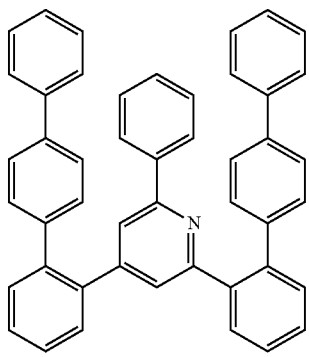
[6-137]
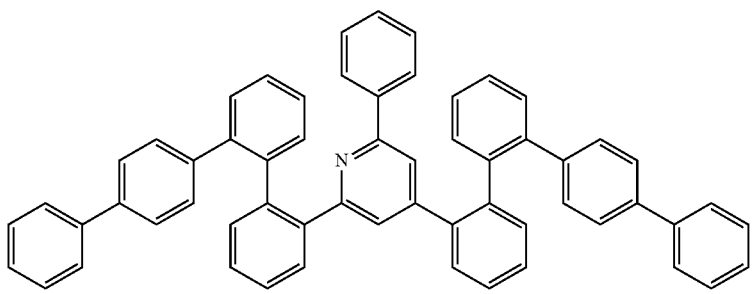
[6-138]
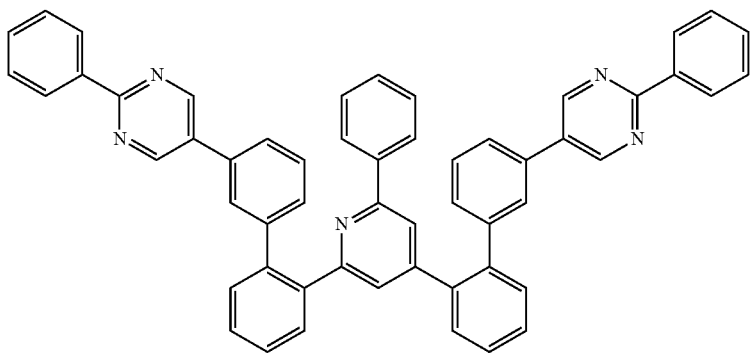
[6-139]

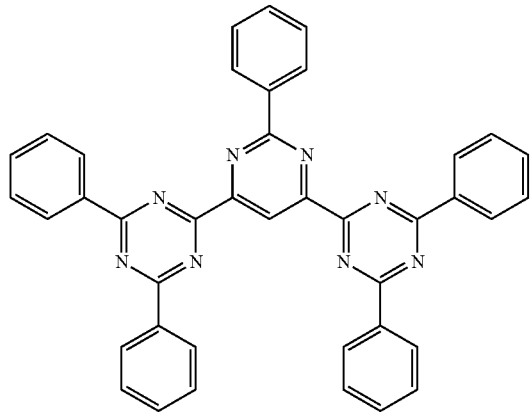
[6-140]
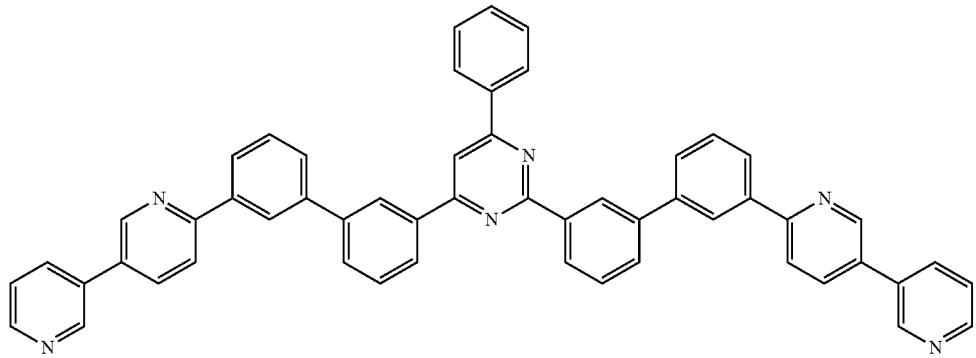
[6-141]
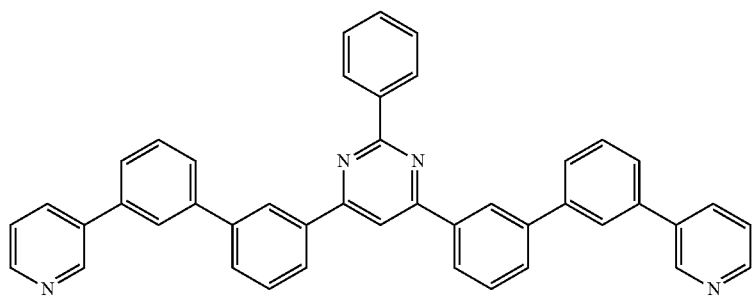
[6-142]
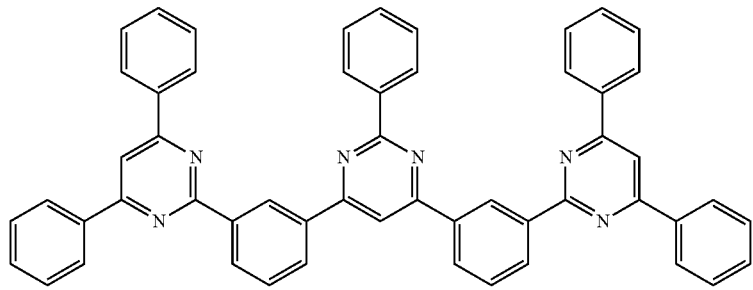
[6-143]

[6-144]
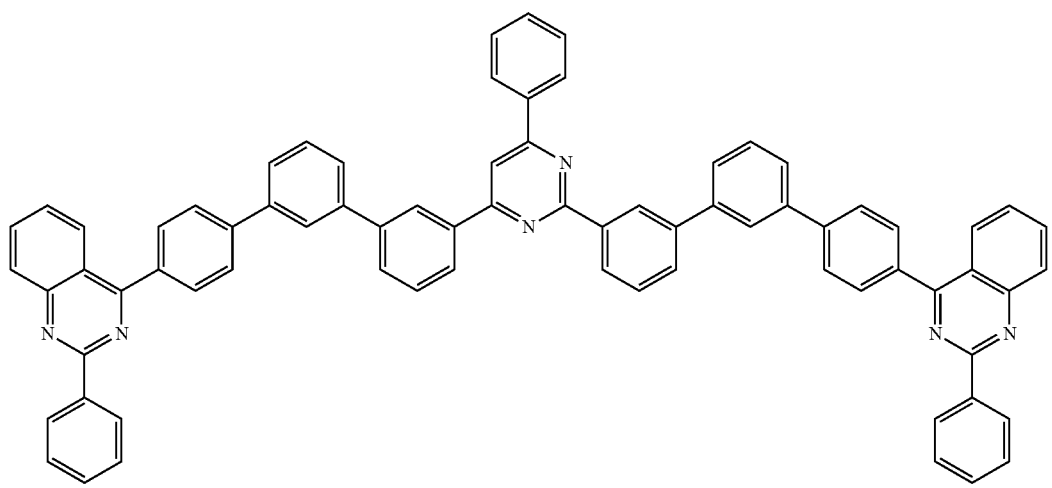
[6-145]
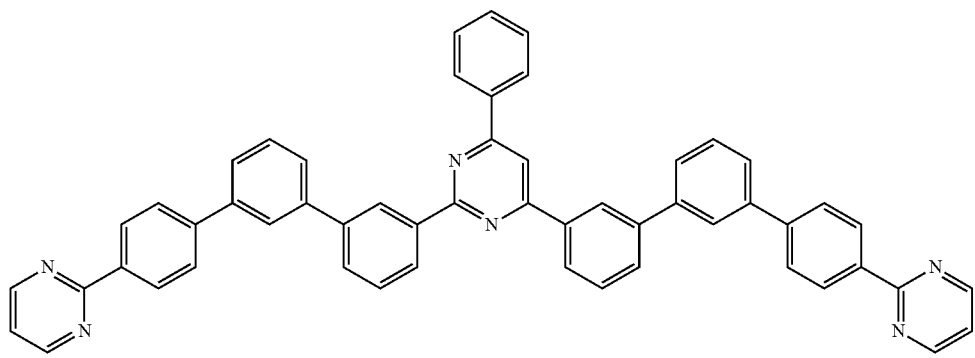
[6-146]
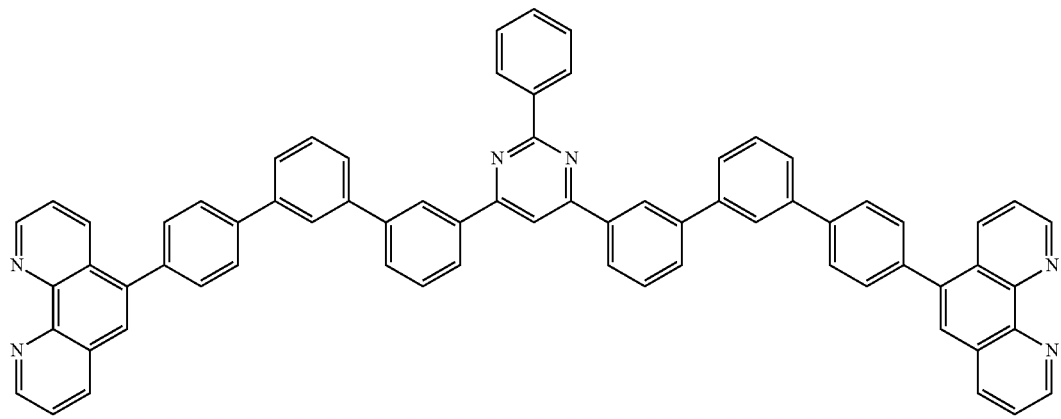
[6-147]
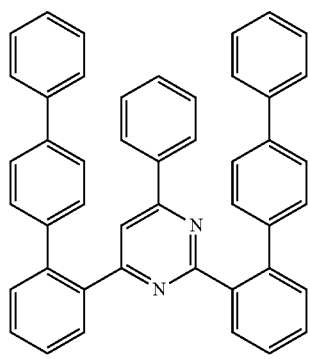

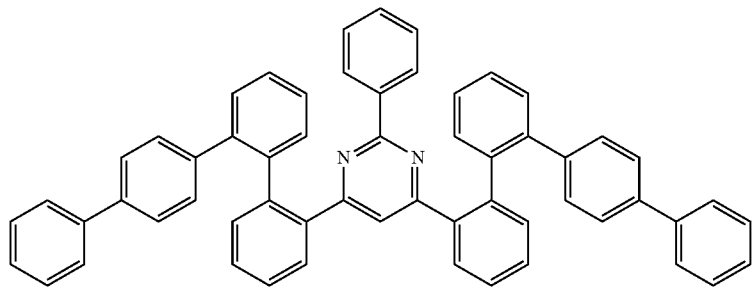
[6-148]
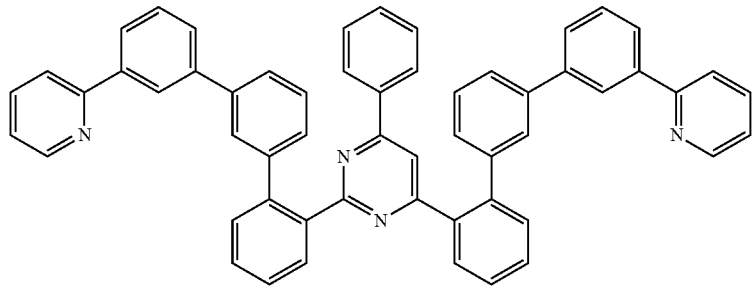
[6-149]
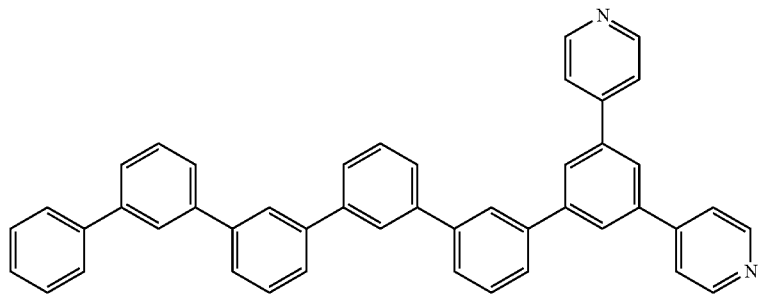
[6-150]
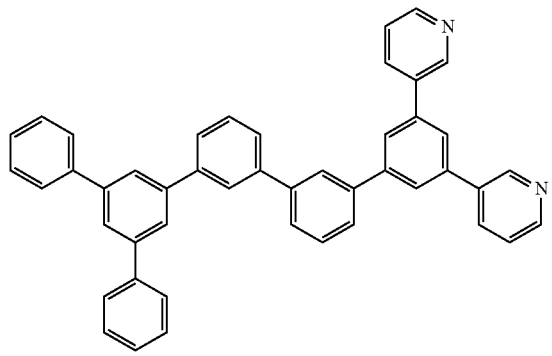
[6-151]
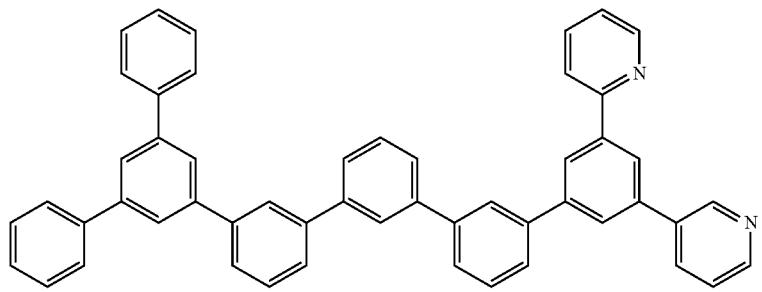
[6-152]

-continued

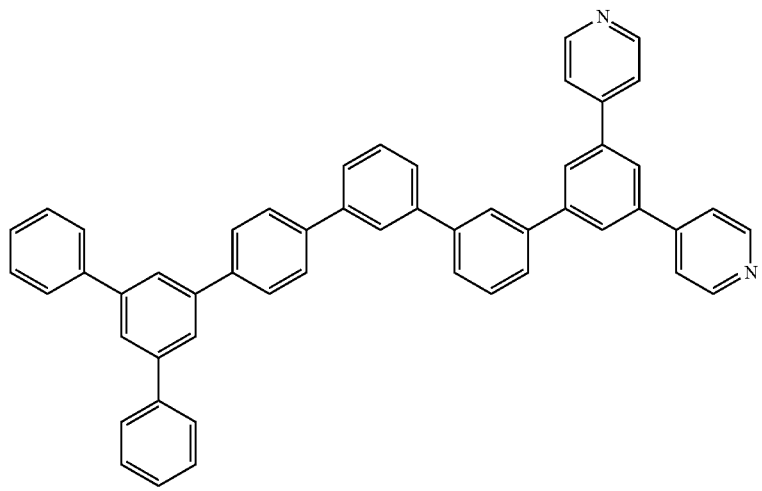

[6-153]

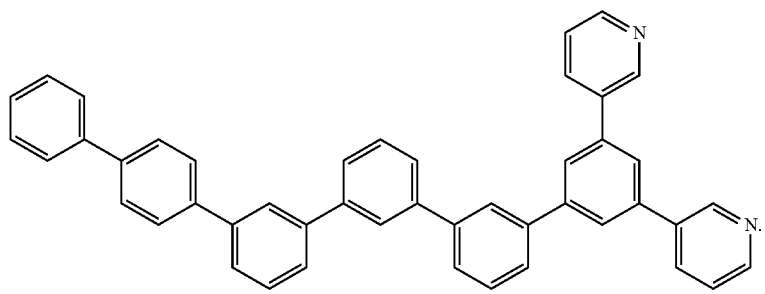

[6-154]

13. The composition for an organic optoelectric device as claimed in claim 7, wherein the composition further comprises a phosphorescent dopant.

14. An organic optoelectric device comprising
an anode and a cathode facing each other, and
at least one organic layer between the anode and the cathode,
wherein the organic layer includes the compound for an organic optoelectric device as claimed in claim 1.

15. The organic optoelectric device as claimed in claim 14, wherein the organic layer comprises an emission layer,
the emission layer comprises the compound for an organic optoelectric device.

16. The organic optoelectric device as claimed in claim 15, wherein:
the compound for an organic optoelectric device is a host of the emission layer, or
the organic layer further comprises a hole transport auxiliary layer, and the compound for an organic optoelectric device is in the hole transport auxiliary layer.

17. A display device comprising the organic optoelectric device as claimed in claim 14.

18. An organic optoelectric device comprising
an anode and a cathode facing each other, and
at least one organic layer between the anode and the cathode,
wherein the organic layer includes the composition for an organic optoelectric device as claimed in claim 7.

19. A display device comprising the organic optoelectric device as claimed in claim 18.

* * * * *